(12) United States Patent
Han et al.

(10) Patent No.: US 10,647,705 B2
(45) Date of Patent: May 12, 2020

(54) SUBSTITUTED BIARYL COMPOUNDS AS INDOLEAMINE 2,3-DIOXYGENASE (IDO) INHIBITORS

(71) Applicant: Merck Sharp & Dohme Corp., Rahway, NJ (US)

(72) Inventors: Yongxin Han, Needham, MA (US); Abdelghani Achab, Melrose, MA (US); Yongqi Deng, Newton, MA (US); Xavier Fradera, Brookline, MA (US); Craig Gibeau, Holliston, MA (US); Brett A. Hopkins, Stoughton, MA (US); Derun Li, West Roxbury, MA (US); Kun Liu, Needham, MA (US); Meredeth A. McGowan, Boston, MA (US); Nunzio Sciammetta, Sudbury, MA (US); David Sloman, Brookline, MA (US); Catherine White, Newton Center, MA (US); Hongjun Zhang, Boston, MA (US); Hua Zhou, Acton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/186,769

(22) Filed: Nov. 12, 2018

(65) Prior Publication Data

US 2019/0144433 A1 May 16, 2019

Related U.S. Application Data

(60) Provisional application No. 62/585,737, filed on Nov. 14, 2017.

(51) Int. Cl.
| | |
|---|---|
| *C07D 405/10* | (2006.01) |
| *A61K 31/4523* | (2006.01) |
| *A61K 45/06* | (2006.01) |
| *C07D 471/04* | (2006.01) |
| *A61K 31/437* | (2006.01) |
| *A61K 31/506* | (2006.01) |
| *A61K 31/4155* | (2006.01) |
| *C07D 305/08* | (2006.01) |
| *A61K 31/337* | (2006.01) |
| *C07D 417/10* | (2006.01) |
| *A61K 31/427* | (2006.01) |
| *A61K 31/41* | (2006.01) |
| *A61K 31/4245* | (2006.01) |
| *A61K 31/4184* | (2006.01) |
| *C07D 405/14* | (2006.01) |
| *A61K 31/444* | (2006.01) |

(Continued)

(52) U.S. Cl.
CPC .......... *C07D 405/10* (2013.01); *A61K 31/337* (2013.01); *A61K 31/41* (2013.01); *A61K 31/4155* (2013.01); *A61K 31/4184* (2013.01); *A61K 31/427* (2013.01); *A61K 31/4245* (2013.01); *A61K 31/437* (2013.01); *A61K 31/444* (2013.01); *A61K 31/4418* (2013.01); *A61K 31/4427* (2013.01); *A61K 31/4523* (2013.01); *A61K 31/4965* (2013.01); *A61K 31/501* (2013.01); *A61K 31/506* (2013.01); *A61K 31/513* (2013.01); *A61K 45/06* (2013.01); *A61P 31/00* (2018.01); *A61P 35/00* (2018.01); *A61P 37/00* (2018.01); *C07D 209/46* (2013.01); *C07D 213/56* (2013.01); *C07D 231/12* (2013.01); *C07D 241/12* (2013.01); *C07D 263/32* (2013.01); *C07D 305/08* (2013.01); *C07D 401/04* (2013.01); *C07D 401/12* (2013.01); *C07D 405/04* (2013.01); *C07D 405/14* (2013.01); *C07D 413/04* (2013.01); *C07D 413/10* (2013.01); *C07D 413/14* (2013.01); *C07D 417/10* (2013.01); *C07D 417/14* (2013.01); *C07D 471/04* (2013.01)

(58) Field of Classification Search
CPC .......................... C07D 401/12; C07D 405/10
See application file for complete search history.

(56) References Cited

U.S. PATENT DOCUMENTS

| | | |
|---|---|---|
| 5,086,054 A | 2/1992 | Parish |
| 8,436,011 B2 | 5/2013 | Sanofi |

(Continued)

FOREIGN PATENT DOCUMENTS

| | | |
|---|---|---|
| EP | 647612 A1 | 4/1995 |
| EP | 757037 A2 | 2/1997 |

(Continued)

*Primary Examiner* — Rei Tsang Shiao
(74) *Attorney, Agent, or Firm* — Yong Zhao; Anna L. Cocuzzo

(57) ABSTRACT

Disclosed herein is a compound of formula (I), or a pharmaceutically acceptable salt thereof:

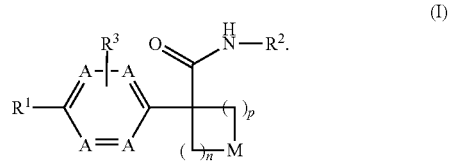

Also disclosed herein are uses of a compound disclosed herein in the potential treatment or prevention of an IDO-associated disease or disorder. Also disclosed herein are compositions comprising a compound disclosed herein. Further disclosed herein are uses of a composition in the potential treatment or prevention of an IDO-associated disease or disorder.

16 Claims, No Drawings

(51) Int. Cl.

| | | |
|---|---|---|
| A61K 31/513 | (2006.01) | |
| C07D 413/04 | (2006.01) | |
| C07D 401/04 | (2006.01) | |
| C07D 213/56 | (2006.01) | |
| A61K 31/4418 | (2006.01) | |
| C07D 417/14 | (2006.01) | |
| A61K 31/501 | (2006.01) | |
| C07D 241/12 | (2006.01) | |
| A61K 31/4965 | (2006.01) | |
| A61K 31/4427 | (2006.01) | |
| C07D 263/32 | (2006.01) | |
| A61P 37/00 | (2006.01) | |
| C07D 231/12 | (2006.01) | |
| A61P 35/00 | (2006.01) | |
| C07D 413/10 | (2006.01) | |
| C07D 401/12 | (2006.01) | |
| C07D 405/04 | (2006.01) | |
| A61P 31/00 | (2006.01) | |
| C07D 209/46 | (2006.01) | |
| C07D 413/14 | (2006.01) | |

(56) References Cited

U.S. PATENT DOCUMENTS

| | | |
|---|---|---|
| 8,524,910 B2 | 9/2013 | Hadida |
| 8,563,573 B2 | 10/2013 | Ruah |
| 9,073,895 B2 * | 7/2015 | Berry .................. C07D 239/42 |
| 2004/0186103 A1 | 9/2004 | Marzabadi et al. |
| 2007/0071813 A1 | 3/2007 | Ahmed |
| 2009/0246137 A1 | 10/2009 | Hadida |
| 2010/0105663 A1 | 4/2010 | Siegel |
| 2010/0197688 A1 | 8/2010 | Nantermet et al. |
| 2012/0270869 A1 | 10/2012 | Hadida Ruah |
| 2014/0275023 A1 | 9/2014 | Namdev |
| 2016/0159773 A1 | 6/2016 | Saitoh et al. |

FOREIGN PATENT DOCUMENTS

| | | |
|---|---|---|
| EP | 1997005868 A1 | 2/1997 |
| FR | 2933700 A1 | 1/2010 |
| GB | 2470833 A | 12/2010 |
| GB | 2493914 A | 2/2013 |
| WO | 1993013073 A1 | 7/1993 |
| WO | 2000059874 A1 | 10/2000 |
| WO | 2002048114 A1 | 6/2002 |
| WO | 2003004474 A1 | 1/2003 |
| WO | 2004056744 A1 | 7/2004 |
| WO | 2005056529 A1 | 6/2005 |
| WO | 2006016219 A2 | 2/2006 |
| WO | WO2006012227 A2 | 2/2006 |
| WO | WO2006133559 A1 | 12/2006 |
| WO | 2007099326 A1 | 9/2007 |
| WO | 2007113548 A1 | 10/2007 |
| WO | 2007113565 A1 | 10/2007 |
| WO | 2007117715 A2 | 10/2007 |
| WO | 2008073936 A1 | 6/2008 |
| WO | 2008127399 A2 | 10/2008 |
| WO | 2010028174 A1 | 3/2010 |
| WO | 2010028179 A1 | 3/2010 |
| WO | 2011041461 A2 | 4/2011 |
| WO | 2011082270 A2 | 7/2011 |
| WO | 2012059541 A1 | 5/2012 |
| WO | 2012082817 A1 | 6/2012 |
| WO | 2015016206 A1 | 2/2015 |
| WO | WO2017076742 A1 | 5/2017 |
| WO | WO2017192844 A1 | 11/2017 |

* cited by examiner

SUBSTITUTED BIARYL COMPOUNDS AS INDOLEAMINE 2,3-DIOXYGENASE (IDO) INHIBITORS

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt thereof:

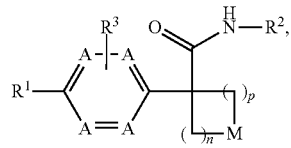

(I)

wherein:
n is selected from 1, 2 and 3;
p is selected from 0, 1 and 2;
each occurrence of A is independently selected from —CH= and —N=, provided that at least one A is —CH=;
M is selected from —O—, —S—, and —CR$^a$R$^b$—, each of R$^a$ and R$^b$ is independently selected from H, halogen, —OH and —C$_{1-8}$ alkyl; or alternatively, R$^a$ and R$^b$ together with the carbon to which they are attached form a C$_{3-4}$ carbocyclic ring, optionally substituted with 1-2 substituents independently selected from halogen and C$_{1-4}$ alkyl;
R$^1$ is selected from:
(1) aryl, and
(2) heterocyclyl;
wherein the aryl of (1) is optionally substituted with 1-3 substituents independently selected from:
(a) halogen,
(b) —C$_{3-8}$ cycloalkyl, optionally substituted with —OH,
(c) —CN,
(d) oxo,
(e) —O—C$_{1-8}$ alkyl, optionally substituted with 1-5 halogens,
(f) —O—C$_{3-8}$ cycloalkyl,
(g) —C$_{1-8}$ alkyl, optionally substituted with 1-4 substituents independently selected from halogen, —OH, —NH$_2$, NHC(O)R$^c$ and —S(O)$_2$—C$_{1-8}$ alkyl, wherein R$^c$ is selected from —C$_{1-8}$ alkyl and —C$_{3-8}$ cycloalkyl,
(h) —NH—S(O)$_2$—R$^c$, wherein R$^c$ is selected from —C$_{1-8}$ alkyl and —C$_{3-8}$ cycloalkyl,
(i) —C(O)—R$^e$, R$^e$ is selected from —OH and —C$_{1-8}$ alkyl,
(j) aryl, optionally substituted with 1-3 halogens and
(k) heterocyclyl, optionally substituted with 1-3 substituents independently selected from halogen and —C$_{1-8}$ alkyl; and
wherein the heterocyclyl of (2) is optionally substituted with 1-3 substituents independently selected from:
(a) halogen,
(b) —C$_{3-8}$ cycloalkyl, optionally substituted with —OH,
(c) —CN,
(d) oxo,
(e) —O—C$_{1-8}$ alkyl, optionally substituted with 1-5 halogens,
(f) —O—C$_{3-8}$ cycloalkyl,
(g) —C$_{1-8}$ alkyl, optionally substituted with 1-4 substituents independently selected from halogen, —OH, —NH$_2$, NHC(O)R$^c$ and —S(O)$_2$—C$_{1-8}$ alkyl, wherein R$^c$ is selected from —C$_{1-8}$ alkyl and —C$_{3-8}$ cycloalkyl,
(h) —NH—S(O)$_2$—R$^c$, wherein R$^c$ is selected from —C$_{1-8}$ alkyl and —C$_{3-8}$ cycloalkyl,
(i) —C(O)—R$^f$, R$^f$ is selected from —OH, —NH$_2$ and —NH—C$_{1-8}$ alkyl,
(j) aryl, optionally substituted with 1-3 halogens, and
(k) heterocyclyl, optionally substituted with 1-3 substituents independently selected from halogen and —C$_{1-8}$ alkyl;
R$^2$ is selected from:
(1) C$_{1-8}$ alkyl,
(2) C$_{3-8}$ carbocyclyl,
(3) aryl, and
(4) heterocyclyl;
wherein the C$_{1-8}$ alkyl of (1) is optionally substituted with 1-3 substituents independently selected from:
(a) halogen,
(b) —C$_{3-8}$ cycloalkyl,
(c) —O—C$_{1-8}$ alkyl, and
(d) heterocyclyl; and
wherein each of the C$_{3-8}$ carbocyclyl of (2), the aryl of (3), and the heterocyclyl of (4) is optionally substituted with 1-3 substituents independently selected from:
(a) halogen,
(b) —C$_{3-8}$ cycloalkyl,
(c) —CN,
(d) —O—C$_{1-8}$ alkyl, optionally substituted with 1-3 halogens and (e) —C$_{1-8}$ alkyl, optionally substituted with 1-3 substituents independently selected from halogen, —OH and —NH$_2$; and R$^3$ is selected from H, halogen and —C$_{1-8}$ alkyl, optionally substituted with —OH.

In one embodiment of the compound of formula (I), or a pharmaceutically acceptable salt thereof:
n is selected from 1 and 2;
p is selected from 0 and 1;
M is selected from —O— and —CR$^a$R$^b$—, each of R$^a$ and R$^b$ is independently selected from H and halogen; or alternatively, R$^a$ and R$^b$ together with the carbon to which they are attached form a C$_{3-4}$ cycloalkyl ring;
R$^1$ is selected from:
(1) aryl, and
(2) heterocyclyl;
wherein the aryl of (1) is optionally substituted with 1-3 substituents independently selected from:
(a) halogen,
(b) —C$_{3-6}$ cycloalkyl, optionally substituted with —OH,
(c) —CN,
(d) —O—C$_{1-6}$ alkyl, optionally substituted with 1-3 halogens,
(e) —O—C$_{3-6}$ cycloalkyl,
(f) —C$_{1-6}$ alkyl, optionally substituted with 1-4 substituents independently selected from halogen and —OH, and
(g) —C(O)—R$^e$, R$^e$ is selected from —OH and —C$_{1-6}$ alkyl;
wherein the heterocyclyl of (2) is optionally substituted with 1-3 substituents independently selected from:
(a) halogen,
(b) —C$_{3-6}$ cycloalkyl, optionally substituted with —OH,
(c) —CN,
(d) oxo,
(e) —O—C$_{1-6}$ alkyl, optionally substituted with 1-3 halogens,
(f) —O—C$_{3-6}$ cycloalkyl,
(g) —C$_{1-6}$ alkyl, optionally substituted with 1-4 substituents independently selected from halogen, —OH, and —NH$_2$,
(h) —C(O)—R$^f$, R$^f$ is selected from —OH, —NH$_2$ and —NH—C$_{1-6}$ alkyl,
(i) phenyl, optionally substituted with 1-3 halogens;
R$^2$ is selected from:
(1) C$_{1-6}$ alkyl, optionally substituted with 1-3 halogens,
(2) C$_{3-6}$ cycloalkyl,
(3) aryl, and
(4) a 4-7 membered mono-cyclic heterocyclyl;
wherein each of the C$_{3-6}$ cycloalkyl of (2), the aryl of (3), and the heterocyclyl of (4) is optionally substituted with 1-3 substituents independently selected from:
(a) halogen,
(b) —C$_{3-6}$ cycloalkyl,
(c) —CN,
(d) —O—C$_{1-6}$ alkyl, optionally substituted with 1-3 halogens and
(e) —C$_{1-6}$ alkyl, optionally substituted with 1-3 substituents independently selected from halogen and —OH; and R$^3$ is selected from H, halogen and —C$_{1-6}$ alkyl, optionally substituted with —OH.

In one embodiment of the compound of formula (I), or a pharmaceutically acceptable n is 1;
p is 1;
each A group is —CH═;
or alternatively, one A group is —N═ and the three other A groups are each —CH═;
or alternatively, two A groups are each —N═ and the two other A groups are each —CH═; and
M is selected from —O—, —CH$_2$—, —CHF, —CF$_2$— and

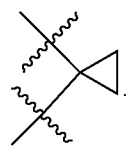

In one embodiment of the compound of formula (I), or a pharmaceutically acceptable salt thereof, R$^3$ is selected from H, halogen and —CH$_2$—OH.

In one embodiment of the compound of formula (I), or a pharmaceutically acceptable salt thereof:
R$^1$ is selected from:
(1) phenyl,
(2) a 4-7 membered mono-cyclic heterocyclyl selected from a saturated, a partially unsaturated and an aromatic ring containing one to four heteroatoms independently selected from N, O and S, and
(3) a 7-10 membered fused bicyclic heterocyclyl containing one to three heteroatoms independently selected from N, O and S in either of the rings;
wherein the phenyl of (1) is optionally substituted with 1-3 substituents independently selected from:
(a) halogen,
(b) —C$_{3-6}$ cycloalkyl, optionally substituted with —OH,
(c) —CN,
(d) —O—C$_{1-6}$ alkyl, optionally substituted with 1-3 halogens,
(e) —O—C$_{3-6}$ cycloalkyl,
(f) —C$_{1-6}$ alkyl, optionally substituted with 1-4 substituents independently selected from halogen and —OH, and
(g) —C(O)—R$^e$, R$^e$ is selected from —OH and —C$_{1-6}$ alkyl; and
wherein each of the mono-cyclic heterocyclyl of (2) and the fused bicyclic heterocyclyl of (3) is optionally substituted with 1-3 substituents independently selected from:
(a) halogen,
(b) —C$_{3-6}$ cycloalkyl optionally substituted with —OH,
(c) —CN,
(d) oxo,
(e) —O—C$_{1-6}$ alkyl, optionally substituted with 1-3 halogens,
(f) —O—C$_{3-6}$ cycloalkyl,
(g) —C$_{1-6}$ alkyl, optionally substituted with 1-4 substituents independently selected from halogen, —OH, and —NH$_2$,
(h) —C(O)—R$^f$, R$^f$ is selected from —OH, —NH$_2$ and —NH—C$_{1-6}$ alkyl,
(i) phenyl, optionally substituted with 1-3 halogens.

In one embodiment of the compound of formula (I), or a pharmaceutically acceptable salt thereof:
R$^1$ is selected from:
(1) phenyl;

(2) a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl; and
(3) a fused bicyclic heterocyclyl selected from 3a,4,5,6,7,7a-hexahydro-1H-benzo[d]imidazolyl, imidazol[4,5-b]pyridinyl, imidazol[4,5-c]pyridinyl, indolyl, isoindolinyl;

wherein the phenyl of (1) is optionally substituted with 1-3 substituents independently selected from:
(a) halogen,
(b) cyclopropyl, optionally substituted with —OH,
(c) cyclobutyl, optionally substituted with —OH,
(d) —O—$C_{1-4}$ alkyl, optionally substituted with 1-3 halogens,
(e) —O-cyclopropyl,
(f) —$C_{1-4}$ alkyl optionally substituted with 1-4 substituents independently selected from halogen and —OH, and
(g) —C(O)—$C_{1-4}$ alkyl; and wherein each of the mono-cyclic heterocyclyl of (2) and the fused bicyclic heterocyclyl of (3) is optionally substituted with 1-3 substituents independently selected from:
(a) halogen,
(b) cyclopropyl, optionally substituted with —OH,
(c) cyclobutyl, optionally substituted with —OH,
(d) —CN,
(e) oxo,
(f) —O—$C_{1-4}$ alkyl, optionally substituted with 1-3 halogens,
(g) —O-cyclopropyl,
(h) —$C_{1-4}$ alkyl, optionally substituted with 1-4 substituents independently selected from halogen and —OH, and
(i) phenyl, optionally substituted with 1-3 halogens.

In one embodiment of the compound of formula (I), or a pharmaceutically acceptable salt thereof:
$R^2$ is selected from:
(1) $C_{1-6}$ alkyl, optionally substituted with 1-3 halogens,
(2) $C_{3-6}$ cycloalkyl,
(3) phenyl, and
(4) a 5-6 membered mono-cyclic heterocyclyl;
wherein each of the $C_{3-6}$ cycloalkyl of (2), the phenyl of (3), and the heterocyclyl of (4) is optionally substituted with 1-3 substituents independently selected from:
(a) halogen,
(b) —$C_{3-6}$ cycloalkyl,
(c) —CN,
(d) —O—$C_{1-6}$ alkyl, optionally substituted with 1-3 halogens and
(e) —$C_{1-6}$ alkyl, optionally substituted with 1-3 substituents independently selected from halogen and —OH.

In one embodiment of the compound of formula (I), or a pharmaceutically acceptable salt thereof:
$R^2$ is selected from:
(1) $C_{1-4}$ alkyl,
(2) $C_{3-6}$ cycloalkyl,
(3) phenyl, and
(4) a 5-6 membered mono-cyclic heterocyclyl selected from oxazolyl, pyridinyl, and thiazolyl;
wherein each of the $C_{3-6}$ cycloalkyl of (2), the phenyl of (3), and the heterocyclyl of (4) is optionally substituted with 1-3 substituents independently selected from:
(a) halogen,
(b) —CN,
(c) —O—$C_{1-4}$ alkyl, optionally substituted with 1-3 halogens and
(e) —$C_{1-4}$ alkyl, optionally substituted with 1-3 halogens.

In one embodiment of the compound of formula (I), or a pharmaceutically acceptable salt thereof:
n is 1;
p is 1;
each A group is —CH=;
or alternatively, one A group is —N= and the three other A groups are each —CH=;
or alternatively, two A groups are —N= and the two other A groups are each —CH=;
M is selected from —O—, —$CH_2$—, —CHF, —$CF_2$— and

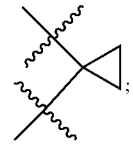 [SMILES: *C1(*)CC1]

$R^1$ is selected from:
(1) phenyl;
(2) a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl; and
(3) a fused bicyclic heterocyclyl selected from 3a,4,5,6,7,7a-hexahydro-1H-benzo[d]imidazolyl, imidazol[4,5-b]pyridinyl, imidazol[4,5-c]pyridinyl, indolyl, isoindolinyl;
wherein the phenyl of (1) is optionally substituted with 1-3 substituents independently selected from:
(a) halogen,
(b) cyclopropyl, optionally substituted with —OH,
(c) cyclobutyl, optionally substituted with —OH,
(d) —O—$C_{1-4}$ alkyl, optionally substituted with 1-3 halogens,
(e) —O-cyclopropyl,
(f) —$C_{1-4}$ alkyl, optionally substituted with 1-4 substituents independently selected from halogen and —OH, and
(g) —C(O)—$C_{1-4}$ alkyl; and
wherein each of the mono-cyclic heterocyclyl of (2) and the fused bicyclic heterocyclyl of (3) is optionally substituted with 1-3 substituents independently selected from:
(a) halogen,
(b) cyclopropyl, optionally substituted with —OH,
(c) cyclobutyl, optionally substituted with —OH,
(d) —CN,
(e) oxo,
(f) —O—$C_{1-4}$ alkyl, optionally substituted with 1-3 halogens,
(g) —O-cyclopropyl,
(h) —$C_{1-4}$ alkyl, optionally substituted with 1-4 substituents independently selected from halogen and —OH, and
(i) phenyl, optionally substituted with 1-3 halogens;
$R^2$ is selected from:
(1) $C_{1-4}$ alkyl,
(2) $C_{3-6}$ cycloalkyl,
(3) phenyl, and
(4) a 5-6 membered mono-cyclic heterocyclyl selected from oxazolyl, pyridinyl, and thiazolyl;

wherein each of the $C_{3-6}$ cycloalkyl of (2), the phenyl of (3), and the heterocyclyl of (4) is optionally substituted with 1-3 substituents independently selected from:
(a) halogen,
(b) —CN,
(c) —O—$C_{1-4}$ alkyl, optionally substituted with 1-3 halogens and
(e) —$C_{1-4}$ alkyl, optionally substituted with 1-3 halogens; and $R^3$ is selected from H, halogen and —$CH_2$—OH.

In one embodiment of the compound of formula (I), or a pharmaceutically acceptable salt thereof:
each A group is —CH═;
M is —O—;
$R^1$ is selected from:
(1) phenyl; and
(2) a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl;
wherein the phenyl of (1) is optionally substituted with 1-3 substituents independently selected from:
(a) halogen,
(b) cyclopropyl, optionally substituted with —OH,
(c) —O—$C_{1-4}$ alkyl, optionally substituted with 1-3 halogens,
(d) —O-cyclopropyl, and
(e) —$C_{1-4}$ alkyl, optionally substituted with 1-4 substituents independently selected from halogen and —OH, and
wherein the mono-cyclic heterocyclyl of (2) is optionally substituted with 1-3 substituents independently selected from:
(a) halogen,
(b) —CN,
(c) —O—$C_{1-4}$ alkyl, optionally substituted with 1-3 halogens,
(d) —O-cyclopropyl,
(e) —$C_{1-4}$ alkyl, optionally substituted with 1-4 substituents independently selected from halogen and —OH;
$R^2$ is selected from:
(1) phenyl, and
(2) pyridinyl;
wherein each of the phenyl of (1) and the pyridinyl of (2) is optionally substituted with 1-3 halogens; and
$R^3$ is H.

In one embodiment of the compound of formula (I), or a pharmaceutically acceptable salt thereof, the compound is of formula (Ia):

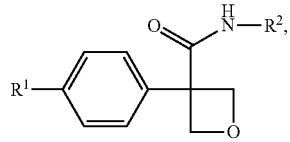

(Ia)

wherein:
$R^1$ is selected from:
(1) phenyl; and
(2) a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl;
wherein the phenyl of (1) is optionally substituted with 1-3 substituents independently selected from:
(a) halogen,
(b) cyclopropyl, optionally substituted with —OH,
(c) cyclobutyl, optionally substituted with —OH,
(d) —O—$C_{1-4}$ alkyl, optionally substituted with 1-3 halogens,
(e) —O-cyclopropyl, and
(f) —$C_{1-4}$ alkyl, optionally substituted with 1-4 substituents independently selected from halogen and —OH, and
(g) —C(O)—$C_{1-4}$ alkyl; and
wherein the mono-cyclic heterocyclyl of (2) is optionally substituted with 1-3 substituents independently selected from:
(a) halogen,
(b) —O—$C_{1-4}$ alkyl, optionally substituted with 1-3 halogens,
(c) —O-cyclopropyl, and
(d) —$C_{1-4}$ alkyl, optionally substituted with 1-4 substituents independently selected from halogen and —OH; and
$R^2$ is selected from:
(1) phenyl, and
(2) pyridinyl;
wherein each of the phenyl of (1) and the pyridinyl of (2) is optionally substituted with 1-3 halogens.

In one embodiment of the compound of formula (Ia), or a pharmaceutically acceptable salt thereof:
$R^1$ is pyridinyl, optionally substituted with 1-3 substituents independently selected from:
(a) halogen,
(b) —$CH_3$,
(c) —$CHF_2$,
(d) —$CF_3$, and
(e) —$C(CH_3)_2OH$; and
$R^2$ is phenyl, optionally substituted with 1-3 halogens.

In one embodiment of the compound of formula (I), or a pharmaceutically acceptable salt thereof, the compound is of a formula selected from (Ii), (Ij) and (Ik):

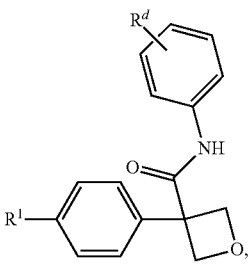

(Ii)

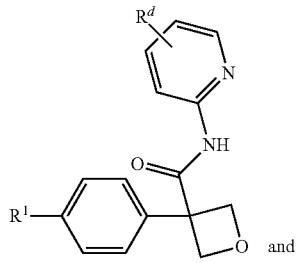

(Ij)

and (Ik)

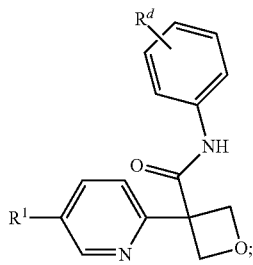

wherein:
R¹ is selected from:
(1) phenyl; and
(2) a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl;
wherein the phenyl of (1) is optionally substituted with 1-3 substituents independently selected from:
(a) halogen,
(b) cyclopropyl, optionally substituted with —OH,
(c) —O—$C_{1-4}$ alkyl, optionally substituted with 1-3 halogens,
(d) —O-cyclopropyl, and
(e) —$C_{1-4}$ alkyl, optionally substituted with 1-4 substituents independently selected from halogen and —OH, and
wherein the mono-cyclic heterocyclyl of (2) is optionally substituted with 1-3 substituents independently selected from:
(a) halogen,
(b) —CN,
(c) —O—$C_{1-4}$ alkyl, optionally substituted with 1-3 halogens,
(d) —O-cyclopropyl,
(e) —$C_{1-4}$ alkyl, optionally substituted with 1-4 substituents independently selected from halogen and —OH; and
$R^d$ is selected from:
(a) halogen,
(b) —CN,
(c) —O—$C_{1-3}$ alkyl, optionally substituted with 1-3 halogens and
(d) $C_{1-3}$ alkyl, optionally substituted with 1-3 halogens.

In one embodiment of the compound of formula (Ii), (Ij) or (Ik), or a pharmaceutically acceptable salt thereof:
R¹ is pyridinyl, optionally substituted with 1-3 substituents independently selected from:
(a) halogen,
(b) —$CH_3$,
(c) —$CHF_2$,
(d) —$CF_3$, and
(e) —$C(CH_3)_2OH$; and
$R^d$ is selected from:
(a) halogen,
(b) —CN,
(c) —$CH_3$, and
(d) —$CF_3$.

In one embodiment of a compound of formula (I), or a pharmaceutically acceptable salt thereof:
n is selected from 1, 2 and 3;
p is selected from 0, 1 and 2;
M is selected from —O—, —S— and —$CR^aR^b$—, each of $R^a$ and $R^b$ is independently selected from H, halogen, —OH and —$C_{1-6}$ alkyl; or alternatively, $R^a$ and $R^b$ together with the carbon to which they are attached form a $C_{3-4}$ cycloalkyl ring, optionally substituted with 1-2 substituents independently selected from halogen and $C_{1-4}$ alkyl;
R¹ is selected from:
(1) aryl and
(2) heterocyclyl;
wherein the aryl of (1) is optionally substituted with 1-3 substituents independently selected from:
(a) halogen,
(b) —$C_{3-8}$ cycloalkyl optionally substituted with —OH,
(c) —CN,
(d) oxo,
(e) —O—$C_{1-8}$ alkyl optionally substituted with 1-5 halogens,
(f) —O—$C_{3-8}$ cycloalkyl,
(g) —$C_{1-8}$ alkyl optionally substituted with 1-4 substituents independently selected from halogen, —OH, —$NH_2$, NHC(O)$R^c$ and —$S(O)_2$—$C_{1-8}$ alkyl, wherein $R^c$ is selected from —$C_{1-8}$ alkyl and —$C_{3-8}$ cycloalkyl,
(h) —NH—$S(O)_2$—$R^c$, wherein $R^c$ is selected from —$C_{1-8}$ alkyl and —$C_{3-8}$ cycloalkyl,
(i) —C(O)—OH,
(j) aryl optionally substituted with 1-3 halogens and
(k) heterocyclyl optionally substituted with 1-3 substituents independently selected from halogen and —$C_{1-8}$ alkyl;
wherein the heterocyclyl of (2) is substituted with 1-3 substituents independently selected from:
(a) halogen,
(b) —$C_{3-8}$ cycloalkyl optionally substituted with —OH,
(c) —CN,
(d) oxo,
(e) —O—$C_{1-8}$ alkyl substituted with 1-5 halogens,
(f) —O—$C_{3-8}$ cycloalkyl,
(g) —$C_{1-8}$ alkyl substituted with 1-4 substituents independently selected from halogen, —$NH_2$, NHC(O)$R^c$ and —$S(O)_2$—$C_{1-8}$ alkyl, wherein $R^c$ is selected from —$C_{1-8}$ alkyl and —$C_{3-8}$ cycloalkyl,
(h) —NH—$S(O)_2$—$R^c$, wherein $R^c$ is selected from —$C_{1-8}$ alkyl and —$C_{3-8}$ cycloalkyl,
(i) —C(O)—OH,
(j) aryl optionally substituted with 1-3 halogens and
(k) heterocyclyl optionally substituted with 1-3 substituents independently selected from halogen and —$C_{1-8}$ alkyl;
R² is selected from:
(1) $C_{1-8}$ alkyl,
(2) $C_{3-8}$ carbocyclyl,
(3) aryl and
(4) heterocyclyl;
wherein the $C_{1-8}$ alkyl of (1) is optionally substituted with 1-3 substituents independently selected from:
(a) halogen,
(b) —$C_{3-8}$ cycloalkyl,
(c) —O—$C_{1-8}$ alkyl, and
(d) heterocyclyl; and
wherein each of the $C_{3-8}$ carbocyclyl of (2), aryl of (3), and heterocyclyl of (4) is optionally substituted with 1-3 substituents independently selected from:
(a) halogen,
(b) —$C_{3-8}$ cycloalkyl,
(c) —CN, (d) —O—$C_{1-8}$ alkyl optionally substituted with 1-3 halogens and (e) —$C_{1-8}$ alkyl optionally substituted with 1-3 substituents independently selected from halogen, —OH and —$NH_2$; and $R^3$ is selected from H, halogen and —$C_{1-8}$ alkyl.

In one embodiment of a compound of formula (I), or a pharmaceutically acceptable salt thereof:

$R^1$ is selected from:
(1) phenyl,
(2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl, and
(3) bicyclic heterocyclyl selected from 3a,4,5,6,7,7a-hexahydro-1H-benzo[d]imidazolyl, indolyl, 1,2,3-thiadizolyl, 1H-benzo[d]imidazolyl, 3H-imidazo[4,5-c]pyridinyl, 3H-imidazo[4,5-b]pyridinyl, imidazo-[1,2-a]pyridinyl, and imidazole-[1,2-b]pyridazinyl;

wherein the phenyl of (1) is optionally substituted with 1-3 substituents independently selected from:
(a) halogen,
(b) $C_{3-4}$ cycloalkyl optionally substituted with —OH,
(c) —CN,
(d) oxo,
(e) —O—$C_{1-4}$ alkyl optionally substituted with 1-5 halogens,
(f) —O-cyclopropyl,
(g) —$C_{1-4}$ alkyl optionally substituted with 1-4 substituents independently selected from halogen, —OH, —$NH_2$, NHC(O)$C_{1-3}$ alkyl and —$S(O)_2$—$C_{1-4}$ alkyl,
(h) —NH—$S(O)_2$—$R^c$, wherein $R^c$ is selected from methyl, ethyl, propyl and cyclopropyl,
(i) —C(O)—OH,
(j) phenyl optionally substituted with 1-3 halogens and
(k) oxadiazolyl optionally substituted with methyl or ethyl; and wherein the mono-cyclic heterocyclyl of (2) and bicyclic heterocyclyl of (3) is substituted with 1-3 substituents independently selected from:
(a) halogen,
(b) $C_{3-4}$ cycloalkyl optionally substituted with —OH,
(c) —CN,
(d) oxo,
(e) —O—$C_{1-4}$ alkyl substituted with 1-5 halogens,
(f) —O-cyclopropyl,
(g) —$C_{1-4}$ alkyl substituted with 1-4 substituents independently selected from halogen, —$NH_2$, NHC(O) $C_{1-3}$ alkyl and —$S(O)_2$—$C_{1-4}$ alkyl,
(h) —NH—$S(O)_2$—$R^c$, wherein $R^c$ is selected from methyl, ethyl, propyl and cyclopropyl,
(i) —C(O)—OH,
(j) phenyl optionally substituted with 1-3 halogens and
(k) oxadiazolyl optionally substituted with methyl or ethyl.

In one embodiment of a compound of formula (I), or a pharmaceutically acceptable salt thereof:

$R^1$ is selected from:
(1) phenyl; and
(2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl;

wherein the phenyl of (1) is optionally substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl optionally substituted with 1-5 halogens,
(e) —O-cyclopropyl, and
(f) —$C_{1-4}$ alkyl optionally substituted with 1-4 substituents independently selected from halogen, —OH and —$NH_2$; and wherein the mono-cyclic heterocyclyl of (2) is substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl substituted with 1-5 halogens,
(e) —O-cyclopropyl, and
(f) —$C_{1-4}$ alkyl substituted with 1-4 substituents independently selected from halogen and —$NH_2$.

In one embodiment of a compound of formula (I), or a pharmaceutically acceptable salt thereof:

$R^2$ is selected from:
(1) phenyl,
(2) pyridinyl and
(3) pyrimidinyl;

wherein each of the phenyl of (1), pyridinyl of (2) and pyrimidinyl of (3) is optionally substituted with 1-3 substituents independently selected from:
(a) halogen,
(b) —CN,
(c) —O—$C_{1-4}$ alkyl optionally substituted with 1-3 halogens and
(d) $C_{1-4}$ alkyl optionally substituted with 1-3 halogens.

In one embodiment of a compound of formula (I), or a pharmaceutically acceptable salt thereof:

$R^2$ is selected from:
(1) phenyl,
(2) pyridinyl and wherein each of the phenyl of (1) and pyridinyl of (2) is optionally substituted with 1-3 substituents independently selected from:
(a) halogen,
(b) —CN,
(c) —O—$CHF_2$,
(d) —O—$CF_3$,
(e) —$CH_3$,
(f) —$CH_2F$,
(g) —$CHF_2$, and
(h) —$CF_3$.

In one embodiment of a compound of formula (I), or a pharmaceutically acceptable salt thereof:

n is 1;

p is 1;

each A group is —CH═; or alternatively, one A group is —N═ and three other A groups are each —CH═;

M is selected from —O—, —$CH_2$—, —$CF_2$— and

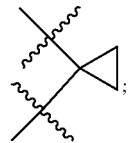 [SMILES: *C1(*)CC1]

$R^1$ is selected from:
 (1) phenyl,
 (2) pyridinyl, and
 (3) pyrimidinyl;
 wherein the phenyl of (1) is optionally substituted with 1-3 substituents independently selected from:
  (a) halogen,
  (b) cyclopropyl optionally substituted with —OH,
  (c) cyclobutyl optionally substituted with —OH,
  (d) —O—CH$_3$,
  (e) —O—CH$_2$CH$_3$,
  (f) —O—CF$_3$,
  (g) —O—CHF$_2$,
  (h) —O—CF$_2$CF$_3$,
  (i) —CH$_3$,
  (j) —CH$_2$F,
  (k) —CHF$_2$,
  (l) —CF$_3$,
  (m) —CH$_2$CF$_3$,
  (n) —CH$_2$OH,
  (o) —CH$_2$CH$_3$,
  (p) —CH(CH$_3$)OH,
  (q) —CH$_2$CH$_2$OH,
  (r) —CH(CHF$_2$)OH,
  (s) —C(CH$_3$)$_2$OH,
  (t) —C(CF$_3$)$_2$OH,
  (u) —O-cyclopropyl, and
  (v) —O-cyclobutyl;
 wherein each of the pyridinyl of (2) and pyrimidinyl of (3) is substituted with 1-3 substituents independently selected from:
  (a) halogen,
  (b) cyclopropyl optionally substituted with —OH,
  (c) cyclobutyl optionally substituted with —OH,
  (d) —O—CF$_3$,
  (e) —O—CHF$_2$,
  (f) —O—CF$_2$CF$_3$,
  (g) —CH$_2$F,
  (h) —CHF$_2$,
  (i) —CF$_3$,
  (j) —CH$_2$CF$_3$,
  (k) —CH(CHF$_2$)OH,
  (l) —C(CF$_3$)$_2$OH,
  (m) —O-cyclopropyl, and
  (n) —O-cyclobutyl;
$R^2$ is selected from:
 (1) phenyl, and
 (2) pyridinyl;
 wherein each of the phenyl of (1) and pyridinyl of (2) is optionally substituted with 1-3 substituents independently selected from:
  (a) halogen,
  (b) —CN,
  (c) —O—CHF$_2$,
  (d) —O—CF$_3$,
  (e) —CH$_3$,
  (f) —CH$_2$F,
  (g) —CHF$_2$, and
  (h) —CF$_3$; and
$R^3$ is H.

In one embodiment of a compound of formula (I), or a pharmaceutically acceptable salt thereof:
n is 1;
p is 1;
each A group is —CH═; or alternatively, one A group is —N═ and three other A groups are each —CH═;

M is selected from —O—, —CH$_2$—, —CF$_2$— and

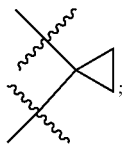 [SMILES: *C1(*)CC1]

$R^1$ is selected from:
 (1) phenyl and
 (2) pyridinyl;
 wherein the phenyl of (1) is optionally substituted with 1-3 substituents independently selected from:
  (a) halogen,
  (b) cyclopropyl optionally substituted with —OH,
  (c) —O—CH$_3$,
  (d) —O—CF$_3$,
  (e) —O—CHF$_2$,
  (f) —CHF$_2$,
  (g) —CF$_3$,
  (h) —CH$_2$CF$_3$,
  (i) —CH$_2$OH,
  (j) —CH$_2$CH$_3$,
  (k) —CH(CH$_3$)OH,
  (l) —CH$_2$CH$_2$OH,
  (m) —CH(CHF$_2$)OH,
  (n) —C(CH$_3$)$_2$OH,
  (o) —C(CF$_3$)$_2$OH, and
  (p) —O-cyclopropyl;
 wherein the pyridinyl of (2) is substituted with 1-3 substituents independently selected from:
  (a) halogen,
  (b) cyclopropyl optionally substituted with —OH,
  (c) —O—CF$_3$,
  (d) —O—CHF$_2$,
  (e) —CHF$_2$,
  (f) —CF$_3$,
  (g) —CH$_2$CF$_3$,
  (h) —CH(CHF$_2$)OH,
  (i) —C(CF$_3$)$_2$OH, and
  (j) —O-cyclopropyl;
$R^2$ is selected from:
 (1) phenyl, and
 (2) pyridinyl;
 wherein each of the phenyl of (1) and pyridinyl of (2) is optionally substituted with 1-3 substituents independently selected from:
  (a) halogen,
  (b) —CN,
  (c) —O—CHF$_2$,
  (d) —O—CF$_3$,
  (e) —CHF$_2$, and
  (f) —CF$_3$; and
$R^3$ is H.

In one embodiment of a compound of formula (I), or a pharmaceutically acceptable salt thereof:
n is 1;
p is 1;
each A group is —CH═; or alternatively, one A group is —N═ and three other A groups are each —CH═;

M is selected from —O—, —CH$_2$—, —CF$_2$— and

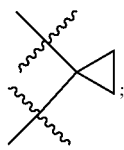 [SMILES: *C1(*)CC1]
;

R$^1$ is selected from:
(1) phenyl and
(2) pyridinyl;
wherein each of the phenyl of (1) and pyridinyl of (2) is optionally substituted with 1-3 substituents independently selected from:
(a) halogen,
(b) cyclopropyl optionally substituted with —OH,
(c) —O—CH$_3$,
(d) —O—CF$_3$,
(e) —O—CHF$_2$,
(f) —CHF$_2$,
(g) —CF$_3$,
(h) —CH$_2$CF$_3$,
(i) —CH$_2$OH,
(j) —CH$_2$CH$_3$,
(k) —CH(CH$_3$)OH,
(l) —CH$_2$CH$_2$OH,
(m) —CH(CHF$_2$)OH,
(n) —C(CH$_3$)$_2$OH,
(o) —C(CF$_3$)$_2$OH, and
(p) —O-cyclopropyl; and
R$^2$ is phenyl, optionally substituted with 1-3 substituents independently selected from:
(a) halogen,
(b) —CN,
(c) —O—CHF$_2$,
(d) —O—CF$_3$,
(e) —CH$_3$,
(f) —CH$_2$F,
(g) —CHF$_2$ and
(h) —CF$_3$; and
R$^3$ is H.

In one embodiment of a compound of formula (I), or a pharmaceutically acceptable salt thereof:
n is 1;
p is 1;
each A group is —CH═; or alternatively, one A group is —N═ and three other A groups are each —CH═;
M is selected from —O—, —CH$_2$—, —CF$_2$— and

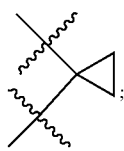 [SMILES: *C1(*)CC1]
;

R$^1$ is selected from:
(1) phenyl and
(2) pyridinyl;
wherein each of the phenyl of (1) and pyridinyl of (2) is substituted with 1-3 substituents independently selected from:
(a) halogen,
(b) cyclopropyl optionally substituted with —OH,
(c) —O—CH$_3$,
(d) —O—CF$_3$,
(e) —O—CHF$_2$,
(f) —CHF$_2$,
(g) —CF$_3$,
(h) —CH$_2$CF$_3$,
(i) —CH$_2$OH,
(j) —CH(CH$_3$)OH,
(k) —CH$_2$CH$_2$OH,
(l) —CH(CHF$_2$)OH,
(m) —C(CH$_3$)$_2$OH and
(n) —C(CF$_3$)$_2$OH; and
R$^2$ is phenyl, optionally substituted with 1-3 substituents independently selected from:
(a) halogen,
(b) —CN,
(c) —O—CHF$_2$,
(d) —O—CF$_3$,
(e) —CHF$_2$, and
(f) —CF$_3$ and
R$^3$ is H.

In one embodiment of a compound of formula (I) described above, or a pharmaceutically acceptable salt thereof, n is 1; p is 1; and M is —O—.

In one embodiment of a compound of formula (I) described above, or a pharmaceutically acceptable salt thereof:
each A group is —CH═;
R$^1$ is selected from:
(1) phenyl and
(2) pyridinyl;
wherein each of the phenyl of (1) and pyridinyl of (2) is substituted with 1-3 substituents independently selected from:
(a) halogen,
(b) cyclopropyl optionally substituted with —OH,
(c) —O—CH$_3$,
(d) —O—CF$_3$,
(e) —O—CHF$_2$,
(f) —CHF$_2$,
(g) —CF$_3$,
(h) —CH$_2$CF$_3$,
(i) —CH$_2$OH,
(j) —CH(CH$_3$)OH,
(k) —CH$_2$CH$_2$OH,
(l) —CH(CHF$_2$)OH,
(m) —C(CH$_3$)$_2$OH and
(n) —C(CF$_3$)$_2$OH; and
R$^2$ is phenyl, optionally substituted with 1-3 substituents independently selected from:
(a) halogen,
(b) —CN,
(c) —O—CHF$_2$,
(d) —O—CF$_3$,
(e) —CHF$_2$ and
(f) —CF$_3$; and
R$^3$ is H.

In one embodiment of a compound of formula (I) described above, or a pharmaceutically acceptable salt thereof:
one A group is —N═ and three other A groups are each —CH═;
R$^1$ is selected from:
(1) phenyl and
(2) pyridinyl;

wherein each of the phenyl of (1) and pyridinyl of (2) is substituted with 1-3 substituents independently selected from:
(a) halogen,
(b) cyclopropyl optionally substituted with —OH,
(c) —O—CH₃,
(d) —O—CF₃,
(e) —O—CHF₂,
(f) —CHF₂,
(g) —CF₃,
(h) —CH₂CF₃,
(i) —CH₂OH,
(j) —CH(CH₃)OH,
(k) —CH₂CH₂OH,
(l) —CH(CHF₂)OH,
(m) —C(CH₃)₂OH and
(n) —C(CF₃)₂OH; and
R² is phenyl, optionally substituted with 1-3 substituents independently selected from:
(a) halogen,
(b) —CN,
(c) —O—CHF₂,
(d) —O—CF₃,
(e) —CHF₂, and
(f) —CF₃; and
R³ is H.

In one embodiment of a compound of formula (I), or a pharmaceutically acceptable salt thereof, the compound is of formula (Ia) or (Ib):

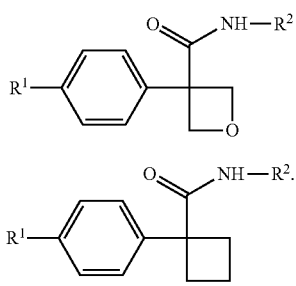

(Ia)

(Ib)

In one embodiment of a compound of formula (I), or a pharmaceutically acceptable salt thereof, the compound is of formula (Ic) or (Id):

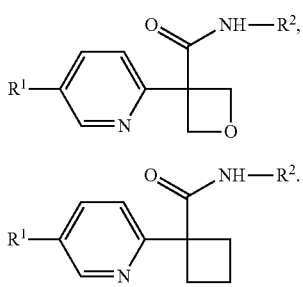

(Ic)

(Id)

In one embodiment of a compound of formula (I), or a pharmaceutically acceptable salt thereof, the compound is of formula (Ie) or (If):

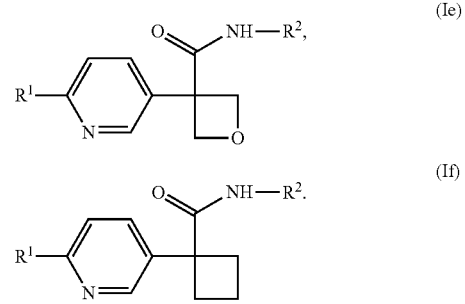

(Ie)

(If)

In one embodiment of a compound of formula (I), or a pharmaceutically acceptable salt thereof, the compound is of formula (Ig) or (Ih):

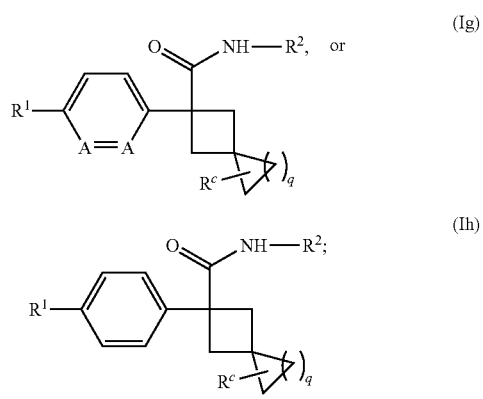

(Ig)

(Ih)

wherein q is 1 or 2; each A is independently —CH═ or —N═; and R^c is H, halogen or $C_{1-3}$ alkyl.

In one embodiment of a compound of formula (I), or a pharmaceutically acceptable salt thereof, the compound is of formula (Ii), (Ij) or (Ik):

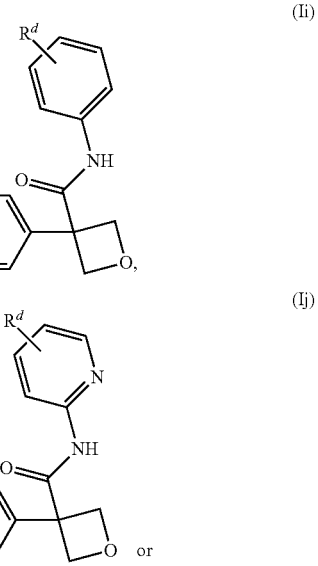

(Ii)

(Ij)

-continued (Ik)

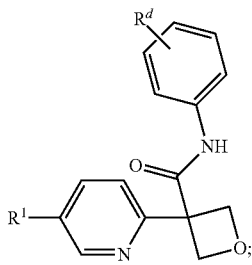

wherein:
R¹ is selected from:
(1) phenyl; and
(2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl;
(3) a 6-12 membered fused bicyclic heterocyclyl containing one to three heteroatoms independently selected from N, O and S in either of the rings;
wherein each of the phenyl of (1), mono-cyclic heterocyclyl of (2) and fused bicyclic heterocyclyl of (3) is substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl optionally substituted with 1-5 halogens,
(e) —O-cyclopropyl, and
(f) —$C_{1-4}$ alkyl optionally substituted with 1-4 substituents independently selected from halogen, —OH and —NH₂; and
$R^d$ is selected from:
(a) halogen,
(b) —CN,
(c) —O—$C_{1-3}$ alkyl optionally substituted with 1-3 halogens and
(d) $C_{1-3}$ alkyl optionally substituted with 1-3 halogens.

In one embodiment of a compound of formula (Ii), (Ij) or (Ik), or a pharmaceutically acceptable salt thereof:
R¹ is selected from:
(1) phenyl and
(2) pyridinyl;
wherein each of the phenyl of (1) and pyridinyl of (2) is substituted with 1-3 substituents independently selected from:
(a) halogen,
(b) cyclopropyl optionally substituted with —OH,
(c) —O—CH₃,
(d) —O—CF₃,
(e) —O—CHF₂,
(f) —CHF₂,
(g) —CF₃,
(h) —CH₂CF₃,
(i) —CH₂OH,
(j) —CH₂CH₃,
(k) —CH(CH₃)OH,
(l) —CH₂CH₂OH,
(m) —CH(CHF₂)OH,
(n) —C(CH₃)₂OH,
(o) —C(CF₃)₂OH, and
(p) —O-cyclopropyl; and
$R^d$ is selected from:
(a) halogen,
(b) —CN,
(c) —O—CHF₂,
(d) —O—CF₃,
(e) —CH₃,
(f) —CH₂F,
(g) —CHF₂ and
(h) —CF₃.

In one embodiment of a compound of formula (Ia), (Ib), (Ic), (Id), (Ie), (If), (Ig), (Ih), (Ii), (Ij) or (Ik), or a pharmaceutically acceptable salt thereof:
R¹ is selected from:
(1) phenyl;
(2) mono-cyclic heterocyclyl selected from a saturated, a partially unsaturated and an aromatic 4-7 membered ring containing one to four heteroatoms independently selected from N, O and S; and
(3) a 6-12 membered fused bicyclic heterocyclyl containing one to three heteroatoms independently selected from N, O and S in either of the rings;
wherein the phenyl of (1) is optionally substituted with 1-3 substituents independently selected from:
(a) halogen,
(b) —$C_{3-6}$ cycloalkyl,
(c) —CN,
(d) oxo,
(e) —O—$C_{1-6}$ alkyl optionally substituted with 1-3 halogens,
(f) —O—$C_{3-6}$ cycloalkyl,
(g) —$C_{1-6}$ alkyl optionally substituted with 1-4 substituents independently selected from halogen, —OH, —NH₂ and —S(O)₂—$C_{1-6}$ alkyl,
(h) —NH—S(O)₂—$R^c$, wherein $R^c$ is selected from —$C_{1-6}$ alkyl and —$C_{3-6}$ cycloalkyl,
(i) —C(O)—OH,
(j) phenyl optionally substituted with 1-3 halogens and
(k) an aromatic 4-7 membered monocyclic ring containing one to three heteroatoms independently selected from N, O, and S, optionally substituted with —$C_{1-6}$ alkyl;
wherein the mono-cyclic heterocyclyl of (2) and fused bicyclic heterocyclyl of (3) is substituted with 1-3 substituents independently selected from:
(a) halogen,
(b) —$C_{3-6}$ cycloalkyl,
(c) —CN,
(d) oxo,
(e) —O—$C_{1-6}$ alkyl substituted with 1-3 halogens,
(f) —O—$C_{3-6}$ cycloalkyl,
(g) —$C_{1-6}$ alkyl substituted with 1-4 substituents independently selected from halogen, —NH₂ and —S(O)₂—$C_{1-6}$ alkyl,
(h) —NH—S(O)₂—$R^c$, wherein $R^c$ is selected from —$C_{1-6}$ alkyl and —$C_{3-6}$ cycloalkyl,
(i) —C(O)—OH,
(j) phenyl optionally substituted with 1-3 halogens and
(k) an aromatic 4-7 membered monocyclic ring containing one to three heteroatoms independently selected from N, O, and S, optionally substituted with —$C_{1-6}$ alkyl; and
R², when present, is selected from:
(1) $C_{1-6}$ alkyl, optionally substituted with 1-3 halogens,
(2) $C_{3-6}$ cycloalkyl,
(3) $C_{4-6}$ bridged bicyclic saturated carbocyclyl,
(4) phenyl and (5) mono-cyclic heterocyclyl selected from a saturated, a partially unsaturated and an aromatic 4-7 membered ring containing one to four heteroatoms independently selected from N, O and S;
wherein each of the $C_{3-6}$ cycloalkyl of (2), $C_{4-6}$ bridged bicyclic saturated carbocyclyl of (3), phenyl of (4) and heterocyclyl of (5) is optionally substituted with 1-3 substituents independently selected from:
(a) halogen,
(b) —CN,
(c) —O—$C_{1-6}$ alkyl optionally substituted with 1-3 halogens and
(d) —$C_{1-6}$ alkyl optionally substituted with 1-3 halogens.

In one embodiment of a compound of formula (Ia), (Ib), (Ic), (Id), (Ie), (If), (Ig), (Ih), (Ii), (Ij) or (Ik), or a pharmaceutically acceptable salt thereof:
$R^1$ is selected from:
(1) phenyl; and
(2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl;
wherein the phenyl of (1) is optionally substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl optionally substituted with 1-5 halogens,
(e) —O-cyclopropyl, and
(f) —$C_{1-4}$ alkyl optionally substituted with 1-4 substituents independently selected from halogen, —OH and —$NH_2$;
wherein the mono-cyclic heterocyclyl of (2) is substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl substituted with 1-5 halogens,
(e) —O-cyclopropyl, and
(f) —$C_{1-4}$ alkyl substituted with 1-4 substituents independently selected from halogen and —$NH_2$; and
$R^2$, when present, is selected from:
(1) phenyl and
(2) pyridinyl;
wherein each of the phenyl of (1) and pyridinyl of (2) is optionally substituted with 1-3 substituents independently selected from:
(a) halogen,
(b) —CN,
(c) —O—$C_{1-3}$ alkyl optionally substituted with 1-3 halogens and
(d) $C_{1-3}$ alkyl optionally substituted with 1-3 halogens.

In one embodiment of a compound of formula (Ia), (Ib), (Ic), (Id), (Ie), (If), (Ig), (Ih), (Ii), (Ij) or (Ik), or a pharmaceutically acceptable salt thereof:
$R^1$ is selected from:
(1) phenyl and
(2) pyridinyl;
wherein each of the phenyl of (1) and pyridinyl of (2) is optionally substituted with 1-3 substituents independently selected from:
(a) halogen,
(b) cyclopropyl optionally substituted with —OH,
(c) —O—$CH_3$, (d) —O—$CF_3$,
(e) —O—$CHF_2$,
(f) —O—$CF_2CF_3$,
(g) —$CH_3$,
(h) —$CH_2F$,
(i) —$CHF_2$,
(j) —$CF_3$,
(k) —$CH_2CF_3$,
(l) —$CH_2OH$,
(m) —$CH(CH_3)OH$,
(n) —$CH_2CH_2OH$,
(o) —$CH(CHF_2)OH$,
(p) —$C(CH_3)_2OH$,
(q) —$C(CF_3)_2OH$, and
$R^2$, when present, is phenyl, optionally substituted with 1-3 substituents independently selected from:
(a) halogen,
(b) —CN,
(c) —O—$CHF_2$,
(d) —O—$CF_3$,
(e) —$CH_3$,
(f) —$CH_2F$,
(g) —$CHF_2$, and
(h) —$CF_3$.

In one embodiment, a compound disclosed herein is selected from the group consisting of the compounds exemplified in Examples 1 to 131; or a pharmaceutically acceptable salt, solvate or hydrate thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{4-7}$cycloalkyl or $C_{4-7}$cycloalkenyl ring. Aryl groups may be optionally substituted with one or more substituents as defined herein. Bonding can be through any of the carbon atoms of any ring. In one embodiment, the aryl is phenyl.

"Carbocyclyl" refers to a nonaromatic (i.e., saturated or partially unsaturated) monocyclic carbocyclic radical or a fused bicyclic, bridged bicyclic, or spirocyclic carbocyclic radical having the specified ring carbon atoms. For example, "$C_{3-8}$ carbocyclyl" refers to a nonaromatic 3 to 8-membered monocyclic carbocyclic radical or a nonaromatic 6 to 8-membered fused bicyclic, bridged bicyclic, or spirocyclic carbocyclic radical. The carbocycle may be attached by any atom of the cycle which results in the creation of a stable structure. Non-limiting examples of 3 to 8-membered monocyclic carbocycles include cyclopropyl, cyclobutyl, cyclopentyl, cyclopentenyl, cyclohexyl, cyclohexenyl, cycloheptanyl and cycloheptenyl. Non-limiting examples of 6 to 8-membered fused bicyclic carbocyclic radicals include, but are not limited to, bicyclo[3.3.0]octane. Non-limiting examples of 5 to 8-membered bridged bicyclic carbocyclic radicals include, but are not limited to, bicyclo[1.1.1]pentanyl, bicyclo[2.2.2]heptanyl, bicyclo[2.2.2]octanyl, and bicyclo[3.2.1]octanyl. Non-limiting examples of 6 to 8-membered spirocyclic carbocyclic radicals include, but are not limited to, spiro[3,3]heptanyl and spiro[3,4]octanyl.

"Cycloalkyl" refers to a monocyclic saturated carbocyclic ring having the specified number of ring carbon atoms. For example, $C_{3-8}$ cycloalkyl refers to a cycloalkyl group as defined herein having 3 to 8 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, the heterocyclyl is a 4-7 membered mono-cyclic heterocyclyl selected from a saturated, a partially unsaturated and an aromatic ring containing one to four heteroatoms independently selected from N, O and S.

In one embodiment, the heterocyclyl is a 6-12 membered fused bicyclic heterocyclyl containing one to three heteroatoms independently selected from N, O and S in either of the rings In one embodiment, the heterocyclyl is a mono-cyclic heterocyclyl selected from imidazolyl, oxazolyl, piperidinyl, pyrazolyl, pyridinyl, pyrimidinyl, thiazolyl, tetrazolyl, and 1,2,4-oxadiazolyl.

In one embodiment, the heterocyclyl is a mono-cyclic heterocyclyl selected from oxazolyl, pyridinyl, and thiazolyl.

In one embodiment, the heterocyclyl is pyridinyl.

In one embodiment, the heterocyclyl is a fused bicyclic heterocyclyl selected from 3a,4,5,6,7,7a-hexahydro-1H-benzo[d]imidazolyl, imidazol[4,5-b]pyridinyl, imidazol[4,5-c]pyridinyl, indolyl, isoindolinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s).

Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers-Diastereomers-Geometric Isomers-Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from a combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinyimethyj)amino]-3-pyfidinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL

The following synthetic schemes and examples are intended to be illustrative only and not limiting in any way. Abbreviations used are those conventional in the art or the following.

ACN acetonitrile
aq. aqueous
Boc tert-butyloxycarbonyl
Boc$_2$O di-tert-butyl dicarbonate
Calc'd calculated
Celite diatomaceous earth used as a filtration medium
Cu(I)I copper(I) iodide
CV column volume
° C. degree celsius
DAST (dimethylamino)sulfur trifluoride
DCM dichloromethane
DIEA N,N-diisopropylethylamine
DIPEA N,N-diisopropylethylamine
DMA dimethylamine
DMF N,N-dimethylformamide
DMSO dimethylsulfoxide
dppf or DPPF 1,1'-bis(diphenylphosphino)ferrocene
dtbpf 1,1'-bis(di-t-butylphosphino)ferrocene
EDC N-(3-dimethylaminopropyl)-N'-ethylcarbodiimide hydrochloride
EDCI 1-ethyl-3-(3-dimethylaminopropyl)carbodiimide
EI electron ionization
EMEM Eagle's minimal essential medium
Et ethyl
Et$_2$O diethyl ether
Et$_3$N triethylamine
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HCl hydrochloric acid
HPLC high pressure liquid chromatography
K$_3$PO$_4$ potassium phosphate tribasic
kg kilogram
KHMDS potassium bis(trimethylsilyl)amide
KO$^t$Bu potassium tert-butoxide
L liter
LC liquid chromatography
LCMS liquid chromatography and mass spectrometry
LDA lithium diisopropylamide
LiHMDS lithium bis(trimethylsilyl)amide
LiOH lithium hydroxide
M molar
Me methyl
MeOH methanol
MeMgBr methyl magnesium bromide
mg miligram
MgSO$_4$ magnesium sulfate
mmol milimole
MS mass spectrometry
MTBE methyl tert-butyl ether
min minutes
mL milliliter(s)
m/z mass to charge ratio
nm nanometer
nM nanomolar
N normal
N$_2$ nitrogen
Na$_2$SO$_4$ sodium sulfate
NaH sodium hydride
NaHCO$_3$ sodium bicarbonate
NaHMDS sodium bis(trimethylsilyl)amide
NaN$_3$ sodium azide
NaOH sodium Hydroxide
NH$_4$Cl ammonium chloride
OTBDPS tert-butyldiphenylsilyl
OTf trifluoromethanesulfonate
Pd$_2$(dba)$_3$ tris(dibenzylideneacetone)dipalladium(0)
PdCl$_2$(dppf) 1,1'-bis(diphenylphosphino)ferrocene]palladium(II) dichloride
Pd(dppf)$_2$Cl$_2$ 1,1'-bis(diphenylphosphino)ferrocene]dichloropalladium(II)
PdCl$_2$(dtbpf) 1,1'-bis(di-tert-butylphosphino)ferrocene]dichloropalladium(II)
PE petroleum ether
PG protecting group
PMP P-methoxyphenyl
POCl$_3$ phosphorus oxychloride
PS polystyrene
RPMI Roswell Park Memorial Institute
RT or rt room temperature
sat. saturated
T$_3$P propylphosphonic anhydride solution
TBAF tetrabutylammonium fluoride
TBAT tetrabutylammonium difluorotriphenylsilicate
TBS tert-butyldimethylsilyl ether
TBSCl tert-butyldimethylsilyl chloride
t-BuOH tert-butanol
t-BuONO tert-butyl nitrite
TEA triethyl amine
TEMPO (2,2,6,6-tetramethylpiperidin-1-yl)oxyl
TFA trifluoroacetic acid
THF tetrahydrofuran
TLC thin layer chromatography
TMPMgCl 2,2,6,6-tetramethylpiperidinylmagnesium chloride
TMSCF$_3$ trifluoromethyltrimethylsilane
TBSCl tert-butyldimethylsilyl chloride
TMSCHN$_2$ or TMSCH$_2$N$_2$ trimethylsilyldiazomethane
TMSCN trimethylsilyl cyanide
TosCl toluenesulfonyl chloride
uL microliter(s)
XPhos Pd G2 chloro(2-dicyclohexylphosphino-2',4',6'-triisopropyl-1,1'-biphenyl)[2-(2'-amino-1,1'-biphenyl)]palladium(II)
XPhos Pd G3 2-Dicyclohexylphosphino-2',4',6'-triisopropyl-1,1'-biphenyl)[2-(2'-amino-1,1'-biphenyl)]palladium(II) methanesulfonate

General Synthetic Schemes

The compounds of formula (I) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

Scheme 1

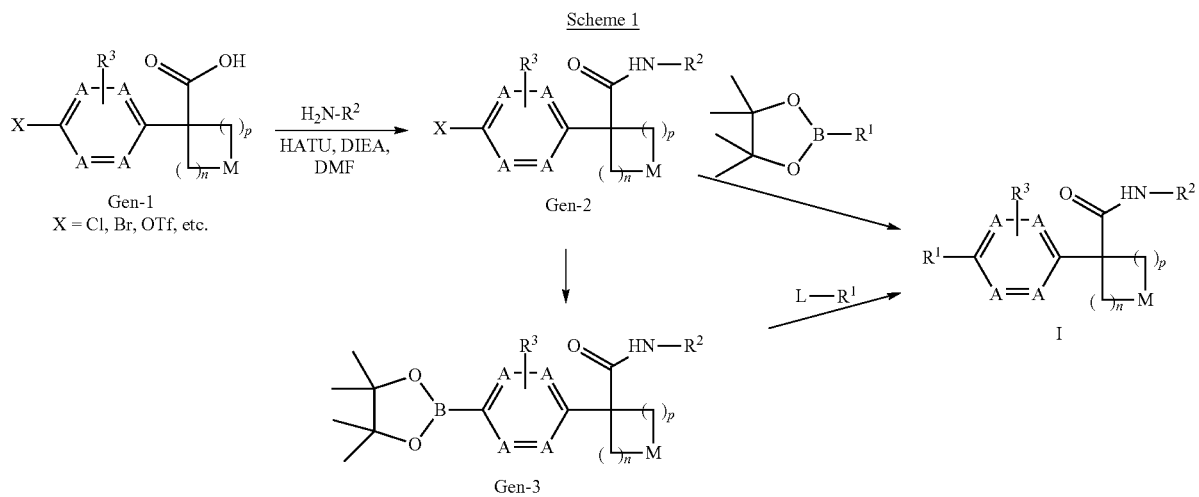

The compounds of formula I can be prepared by Scheme 1. An appropriate carboxylic acid of general structure Gen-1 is coupled with an appropriate amine R²—NH₂ under standard amide coupling conditions to give amide intermediate Gen-2. Gen-2 reacts with an appropriate boronic acid, boronic acid pinacol ester, silicon containing agent, zincate, stannane or appropriate metallic agents under the Suzuki, Negishi, Stille, or other coupling conditions to give compounds of formula I. Alternatively, Gen-2 is converted to the corresponding boronic acid pinacol ester Gen-3 by reacting with bis(pinacolato)diboron (B2pin2) under Pd-catalyzed cross-coupling conditions. Reaction of Gen-3 with an appropriate halide, triflate, etc. under Suzuki coupling conditions affords the compounds of formula I.

The compounds described herein may be made from commercially available starting materials or synthesized using known organic, inorganic, and/or enzymatic processes.

¹H NMR spectra were obtained on a Bruker Ultra Shield spectrometer at 600 MHz or a Varian 500 spectrometer at 499 MHz with tetramethylsilane used as an internal reference. LC/MS spectra were obtained on Agilent 6120 Quadrupole LC/MS spectrometers using electrospray ionization.

EXAMPLES

Example 1: 3-(4-(6-Cyclopropylpyridin-3-yl)phenyl)-N-(4-fluorophenyl)oxetane-3-carboxamide

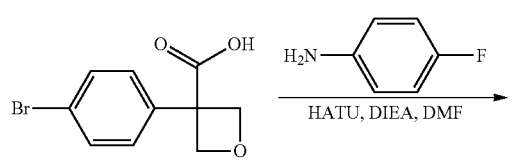

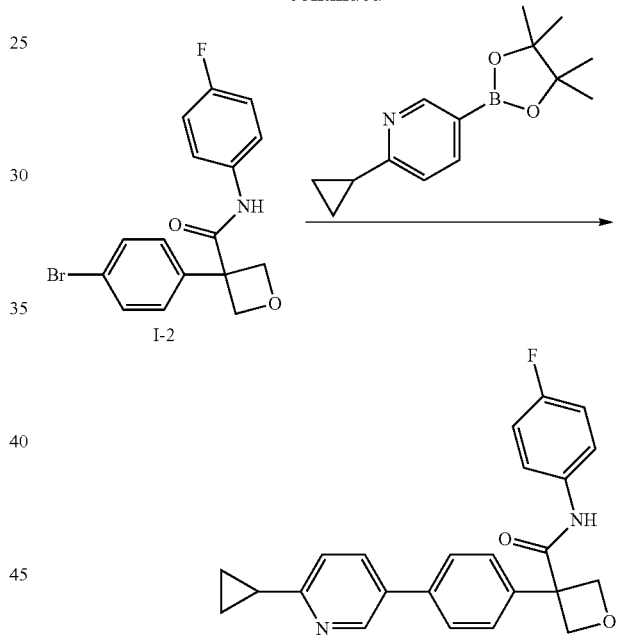

Step 1: 3-(4-bromophenyl)-N-(4-fluorophenyl)oxetane-3-carboxamide

To a stirring solution of commercially available 3-(4-bromophenyl)oxetane-3-carboxylic acid (4000.0 mg, 15.56 mmol) in DCM (20.0 ml) was added HATU (7099 mg, 18.67 mmol) and the suspension was stirred for 15 min at RT. Then 4-fluoroaniline (1729 mg, 15.56 mmol) and DIEA (8.15 ml, 46.7 mmol) were added sequentially, and the reaction mixture was stirred for 4 h at RT. The reaction was diluted with ethyl acetate and washed with 1 N aq. HCl (3×), water (2×), brine, and saturated aq. NaHCO₃. The organic phase was then dried over Na₂SO₄, filtered and concentrated. The residue was purified by flash silica gel chromatography (ISCO®; 120 g SepaFlash® Silica Flash Column, 10 to 100% ethyl acetate/DCM) to afford the title compound (I-2). MS (ESI) m/z 350 [M+H]⁺.

Hereinafter, the reaction conditions in step 1 are referred to as the standard amide coupling conditions.

Step 2: 3-(4-(6-Cyclopropylpyridin-3-yl)phenyl)-N-(4-fluorophenyl)oxetane-3-carboxamide To a stirred suspension of 2-cyclopropyl-5-(4,4,5,5-tetramethyl-1,3,2-dioxaborolan-2-yl)pyridine (47.6 mg, 0.194 mmol), 3-(4-bromophenyl)-N-(4-fluorophenyl)oxetane-3-carboxamide (68.0 mg, 0.194 mmol) and Palladium(II) dichloro[1,1'-bis(di-t-butylphosphino)ferrocene]palladium (II) (15.92 mg, 0.017 mmol) in 1,4-dioxane (1.5 ml) was added sodium carbonate (0.194 ml, 0.388 mmol). The reaction mixture was evacuated and refilled with nitrogen three times and heated to 80° C. for 4 h when LCMS showed complete conversion. The reaction mixture was cooled down to RT and filtered through a Celite pad. The filtrate was concentrated in vacuo. The residue was taken up in $CH_2Cl_2$, and washed with brine. The organic layer was dried over $MgSO_4$, filtered and the solvent was removed in vacuo. The crude material was purified by mass-directed reversed phase chromatography (ACN/water gradient with 0.1% TFA modifier) to afford the title compound. MS (ESI) [M+H]$^+$: m/z 389. $^1$H NMR (600 MHz, DMSO-d6) δ 10.00 (s, 1H), 8.82 (s, 1H), 8.21 (s, 1H), 7.79 (d, J=8.1 Hz, 2H), 7.70-7.58 (m, 4H), 7.50 (d, J=8.2 Hz, 1H), 7.15 (t, J=8.7 Hz, 2H), 5.23 (d, J=6.5 Hz, 2H), 4.91 (d, J=6.5 Hz, 2H), 2.29-2.16 (m, 1H), 1.14-1.09 (m, 2H), 1.05 (s, 2H).

Hereinafter, the reaction conditions in step 2 are referred to as the standard Suzuki cross-coupling conditions.

Example 2: 3-(4-(6-Cyclopropyl-4-fluoropyridin-3-yl)phenyl)-N-(4-fluorophenyl)oxetane-3-carboxamide

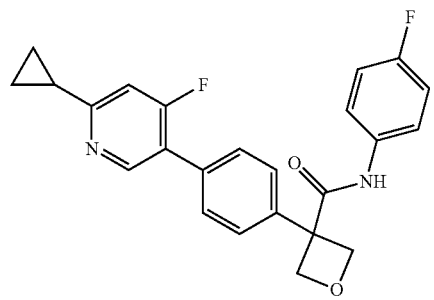 [SMILES: O=C(Nc1ccc(F)cc1)C1(c2ccc(-c3cnc(C4CC4)cc3F)cc2)COC1]

The title compound was prepared in a manner analogous to the synthesis of Example 1 except 2-cyclopropyl-4-fluoro-5-(4,4,5,5-tetramethyl-1,3,2-dioxaborolan-2-yl)pyridine was used. MS (ESI) [M+H]$^+$: m/z 407. $^1$H NMR (499 MHz, DMSO-d6) δ 10.03 (s, 1H), 8.58 (d, J=10.7 Hz, 1H), 7.72-7.51 (m, 4H), 7.39 (d, J=11.7 Hz, 1H), 7.15 (t, J=8.8 Hz, 2H), 5.22 (d, J=6.5 Hz, 2H), 4.91 (d, J=6.5 Hz, 2H), 2.26-2.12 (m, 1H), 1.05 (t, J=7.7 Hz, 2H), 1.01 (s, 2H).

Example 3: 3-(4-(6-Cyclopropyl-4-methylpyridin-3-yl)phenyl)-N-(4-fluorophenyl)oxetane-3-carboxamide

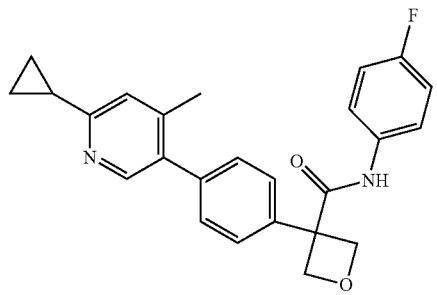 [SMILES: Cc1cc(C2CC2)ncc1-c1ccc(C2(C(=O)Nc3ccc(F)cc3)COC2)cc1]

The title compound was prepared in a manner analogous to the synthesis of Example 1 except 2-cyclopropyl-4-methyl-5-(4,4,5,5-tetramethyl-1,3,2-dioxaborolan-2-yl)pyridine was used. MS (ESI) [M+H]: m/z 403. $^1$H NMR (499 MHz, DMSO-d6) δ 10.11 (s, 1H), 8.48 (s, 1H), 7.70-7.60 (m, 4H), 7.58-7.49 (m, 3H), 7.15 (t, J=8.8 Hz, 2H), 5.25 (d, J=6.5 Hz, 2H), 4.92 (d, J=6.5 Hz, 2H), 2.38 (s, 3H), 2.28 (tt, J=8.5, 5.0 Hz, 1H), 1.32-1.22 (m, 2H), 1.20-1.07 (m, 2H).

Example 4: N-(4-fluorophenyl)-3-(4-(7-methylimidazo[1,2-a]pyridin-6-yl)phenyl)oxetane-3-carboxamide

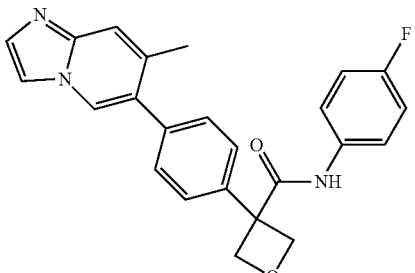

The title compound was prepared in a manner analogous to the synthesis of Example 1 except (7-methylimidazo[1,2-a]pyridin-6-yl)boronic acid was used. MS (ESI) [M+H]$^+$: m/z 402. $^1$H NMR (499 MHz, DMSO-d6) δ 10.09 (s, 1H), 8.83 (s, 1H), 8.19 (s, 1H), 8.15 (s, 1H), 7.92 (s, 1H), 7.66 (t, J=7.5 Hz, 4H), 7.56 (d, J=8.1 Hz, 2H), 7.17 (t, J=8.8 Hz, 2H), 5.26 (d, J=6.5 Hz, 2H), 4.93 (d, J=6.5 Hz, 2H), 2.42 (s, 3H).

Example 5: 3-(4-(4,6-Dimethylpyrimidin-5-yl)phenyl)-N-(4-fluorophenyl)oxetane-3-carboxamide

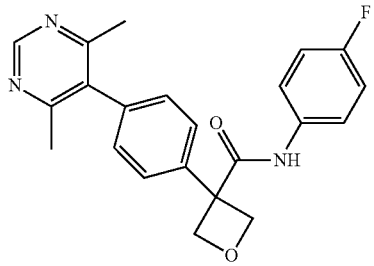 [SMILES: Cc1ncnc(C)c1-c1ccc(C2(C(=O)Nc3ccc(F)cc3)COC2)cc1]

The title compound was prepared in a manner analogous to the synthesis of Example 1 except (4,6-dimethylpyrimidin-5-yl)boronic acid was used. MS (ESI) [M+H]+: m/z 378. 1H NMR (499 MHz, DMSO-d6) δ 10.10 (s, 1H), 8.90 (s, 1H), 7.77-7.56 (m, 4H), 7.38 (d, J=8.1 Hz, 2H), 7.17 (t, J=8.8 Hz, 2H), 5.24 (d, J=6.5 Hz, 2H), 4.92 (d, J=6.5 Hz, 2H), 2.20 (s, 6H).

Example 6: N-(4-Fluorophenyl)-3-(4-(4-methyl-6-(trifluoromethyl)pyridin-3-yl)phenyl)oxetane-3-carboxamide

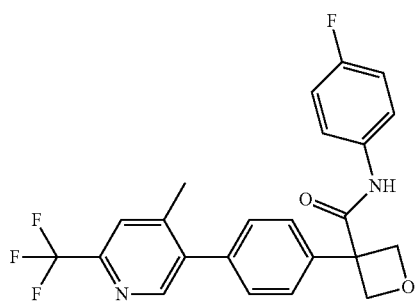 [SMILES: Cc1cc(C(F)(F)F)ncc1-c1ccc(C2(C(=O)Nc3ccc(F)cc3)COC2)cc1]

The title compound was prepared in a manner analogous to the synthesis of Example 1 except 4-methyl-5-(4,4,5,5-tetramethyl-1,3,2-dioxaborolan-2-yl)-2-(trifluoromethyl)pyridine was used as a coupling partner. MS (ESI) [M+H]+: m/z 431; found, 431. 1H NMR (499 MHz, DMSO-d6) δ 10.07 (s, 1H), 8.57 (s, 1H), 7.92 (s, 1H), 7.72-7.61 (m, 4H), 7.55 (d, J=8.0 Hz, 2H), 7.17 (t, J=8.7 Hz, 2H), 5.24 (d, J=6.5 Hz, 2H), 4.93 (d, J=6.5 Hz, 2H), 2.39 (s, 3H).

Example 7: N-(4-Fluorophenyl)-3-(4-(6-methoxy-2,4-dimethylpyridin-3-yl)phenyl)oxetane-3-carboxamide

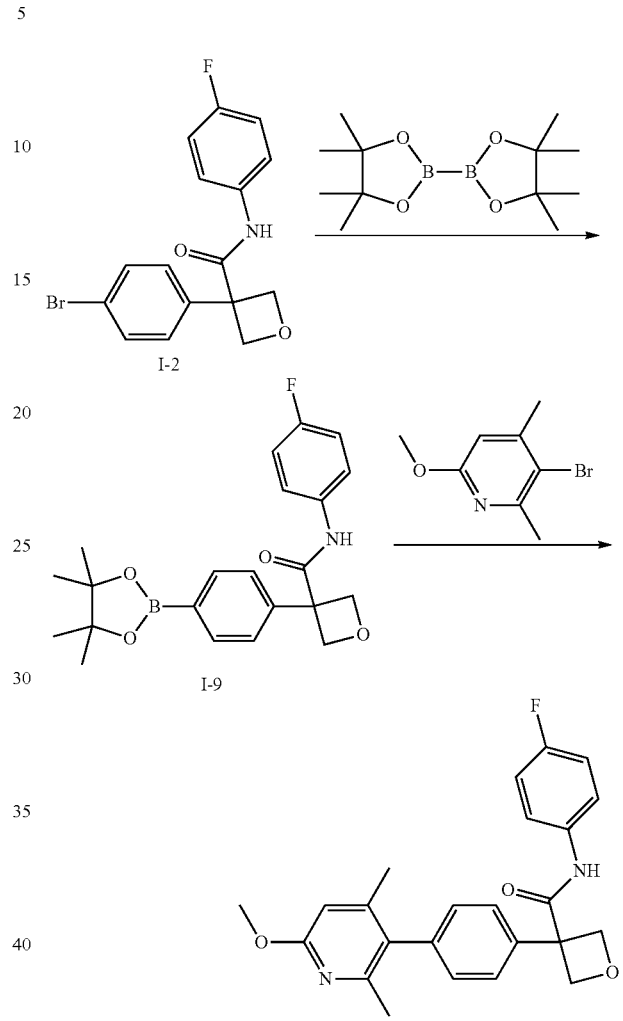

Step 1: N-(4-fluorophenyl)-3-(4-(4,4,5,5-tetramethyl-1,3,2-dioxaborolan-2-yl)phenyl)oxetane-3-carboxamide A dried round bottom flask was charged with 3-(4-bromophenyl)-N-(4-fluorophenyl)oxetane-3-carboxamide (I-2) (200.0 mg, 0.571 mmol), bis(pinacolato)diboron (377 mg, 1.485 mmol), potassium acetate (166 mg, 1.691 mmol) and PdCl2(dppf)-CH2Cl2 (46.6 mg, 0.057 mmol) in dioxane (5.0 ml). The resulting mixture was then evacuated and back filled with nitrogen (3 times). The mixture was heated to 80° C. for 4 h, then cooled to RT and filtered through a Celite pad. The filtrate was concentrated in vacuo to give a residue which was dissolved in dichloromethane. After washing with water (3×) and brine, the dichloromethane layer was dried over anhydrous Na2SO4 and concentrated in vacuo to give a crude product which was purified by column chromatography (silica gel, EtOAc/Hexane, 12 to 100%) to afford the title compound (I-9). MS (ESI) [M+H]+: m/z 398.

Step 2: N-(4-Fluorophenyl)-3-(4-(6-methoxy-2,4-dimethylpyridin-3-yl)phenyl)oxetane-3-carboxamide A solution of 3-bromo-6-methoxy-2,4-dimethylpyridine (16.32 mg, 0.076 mmol), N-(4-fluorophenyl)-3-(4-(4,4,5,5-tetramethyl-1,3,2-dioxaborolan-2-yl)phenyl)oxetane-3-carboxamide, (30.0 mg, 0.076 mmol), 1,1'-bis(di-tert-butylphosphino)ferrocene palladium dichloride (4.92 mg, 7.55 µmol) and sodium carbonate (0.076 ml, 0.151 mmol) in 1,4-dioxane (2.0 ml) was evacuated and refilled with nitrogen three times, and the mixture was heated under nitrogen at 80° C. for 4 h. Then the solvents were removed under vacuum and the resulting residue was suspended in EtOAc/DCM, filtered through a Celite pad which was washed with EtOAc/DCM. The combined filtrates were concentrated and the crude material was purified by mass-directed reversed phase chromatography (ACN/water gradient with 0.1% TFA modifier) to give the title compound. MS (ESI) [M+H]$^+$: m/z 407. $^1$H NMR (499 MHz, DMSO-d6) δ 10.09 (s, 1H), 7.66 (dd, J=8.7, 5.0 Hz, 2H), 7.59 (d, J=8.0 Hz, 2H), 7.26 (d, J=8.0 Hz, 2H), 7.17 (t, J=8.8 Hz, 2H), 6.68 (s, 1H), 5.23 (d, J=6.5 Hz, 2H), 4.90 (d, J=6.5 Hz, 2H), 3.86 (s, 3H), 2.11 (s, 3H), 1.97 (s, 3H).

Examples 8-33 in the table below were prepared in a similar manner as Example 7. Procedures for the syntheses of selected starting materials are described herein.

General Suzuki coupling conditions using X-Phos (X-phosG2 or G3) at temperatures ranging from 45-70° C. are exemplified in the preparations of Example 11 and compound I-14 below.

N-(4-fluorophenyl)-3-(4-(4,4,5,5-tetramethyl-1,3,2-dioxaborolan-2-yl)phenyl)oxetane-3-carboxamide (I-9) (70 mg, 0.141 mmol), (5-bromo-2-methoxypyridin-4-yl)methanol (30.7 mg, 0.141 mmol) and X-PhosPdG2 (11.09 mg, 0.014 mmol) were added to a 4 mL reaction tube which was evacuated and backfilled with nitrogen 3 times. THF (564 µl) and potassium phosphate tribasic (aq. solution 1M) (282 µl, 0.282 mmol) were added. The reaction mixture was warmed to 70° C. for 1 h and cooled to RT. The reaction was diluted with 4 mL DCM, poured through a phase separator, and the organic phase was collected and concentrated in vacuo. The residue was dissolved in 1 mL DMSO and submitted for reversed phase purifications (ACN/water gradient with 0.1% TFA modifier). The pure fractions were frozen and lyophilized to provide N-(4-fluorophenyl)-3-(4-(4-(hydroxymethyl)-6-methoxypyridin-3-yl)phenyl)oxetane-3-carboxamide (Example 11) as the TFA salt as a solid.

Preparation of 2-(3-chloro-5-(trifluoromethyl)pyridin-2-yl)ethan-1-ol (I-11): coupling partner for Example 15

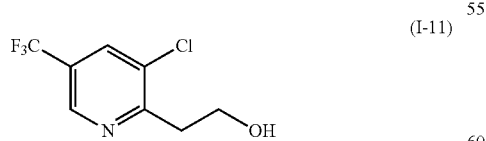

(I-11)

Methyl 2-(3-chloro-5-(trifluoromethyl)pyridin-2-yl)acetate (480 mg, 1.893 mmol) was dissolved in THF (9464 µl), and the mixture was cooled to −78° C. DIBAL-H (4732 µl, 4.73 mmol) was then added and the mixture was allowed to warm to RT over 1 h. The reaction was quenched with sat. aq. potassium sodium tartrate and allowed to stir overnight at RT. The organic layer was separated, and the aq. layer was extracted 1×50 mL EtOAc. The combined organics were washed with brine, dried over sodium sulfate, filtered and concentrated in vacuo to provide 2-(3-chloro-5-(trifluoromethyl)pyridin-2-yl)ethanol as an orange oil which was used for preparation of Example 15 without further purification. MS (ESI) [M+H]$^+$: m/z 226.

Preparation of 2-(5-bromo-2-(trifluoromethyl)pyridin-4-yl)propan-2-ol (I-12): coupling partner for Example 12

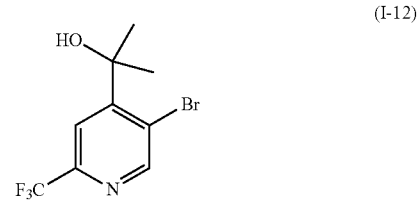

(I-12)

To a solution of methyl 5-bromo-2-(trifluoromethyl)isonicotinate (1.5 g, 5.28 mmol) in THF (21.12 ml) at −78° C. was added methyl magnesium bromide (3M in Et$_2$O) (3.52 ml, 10.56 mmol), and the mixture was allowed to warm to RT for 1 h. The reaction mixture was quenched with sat. aq. ammonium chloride and allowed to stir overnight at RT. The organics were separated, washed with brine, dried over sodium sulfate, and the solvents were removed in vacuo to provide 2-(5-bromo-2-(trifluoromethyl)pyridin-4-yl)propan-2-ol (I-12) as a solid which was used for the preparation of Examples 12 and 20 without further purification. MS (ESI) [M+H]$^+$: m/z 284/286.

Alternatively, I-12 can be prepared according to the following procedure: to a round-bottomed flask under nitrogen was charged with LDA (2 M, 33.2 mL). A solution of 5-bromo-2-(trifluoromethyl)pyridine (15 g, 66.4 mmol) in THF (15 mL) was added dropwise to the mixture at ≤−65° C. over 3 h and the mixture was stirred at ≤−65° C. for an additional 1 h. Acetone (3.8 g, 66.4 mmol) was added dropwise over 0.5 h at ≤−65° C., and the mixture was stirred at ≤−65° C. for 1 h. The mixture was then diluted with ethyl acetate (270 mL) and quenched with water (170 mL). The phases were separated and the aqueous phase was extracted with ethyl acetate (70 mL×2). The combined organic extracts were washed with brine, dried over anhydrous sodium sulfate, filtered, and concentrated to dryness under reduced pressure. The residue was purified by column chromatography to afford I-12. $^1$H NMR (400 MHz, DMSO-d6) δ 8.87 (s, 1H), 8.19 (s, 1H), 5.82 (s, 1H), 1.62 (s, 6H).

Preparation of 1-(5-bromo-2-(trifluoromethyl)pyridin-4-yl)ethan-1-ol (I-13): coupling partner for Examples 16-17

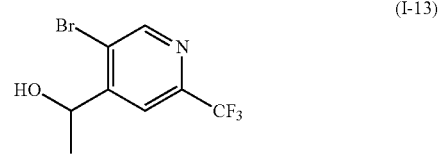

(I-13)

5-Bromo-2-(trifluoromethyl)isonicotinaldehyde (333 mg, 1.311 mmol) was dissolved in THF (6555 µl) in a 40 mL vial and the solution was degassed under nitrogen and cooled to −78° C. Methyl magnesium bromide (3M in Et$_2$O) (524 µl, 1.573 mmol) was added and the resultant mixture was slowly warmed to RT over 1 h. The reaction mixture was quenched with sat. aq. ammonium chloride and allowed to stir for 1 h. The organic layer was separated, and the aq. was extracted with 50 mL EtOAc and the combined organics were washed with brine, dried over sodium sulfate, filtered and concentrated in vacuo to provide 1-(5-bromo-2-(trifluoromethyl)pyridin-4-yl)ethanol which was used for the preparation of Examples 16-17 without further purification. MS (ESI) [M+H]$^+$: m/z 270/272.

The racemic mixture from the Suzuki coupling reaction was separated by SFC using a 21×250 mm Lux-2 column and 20% MeOH/0.25% DMEA as the modifier at a flow rate of 70 mL/min. The first eluting peak was collected and concentrated to give Compound 16. The second eluting peak was collected and concentrated to give Compound 17.

Preparation of 2-(5-bromo-2-(difluoromethoxy)pyridin-4-yl)propan-2-ol (I-14): coupling partner for Example 18

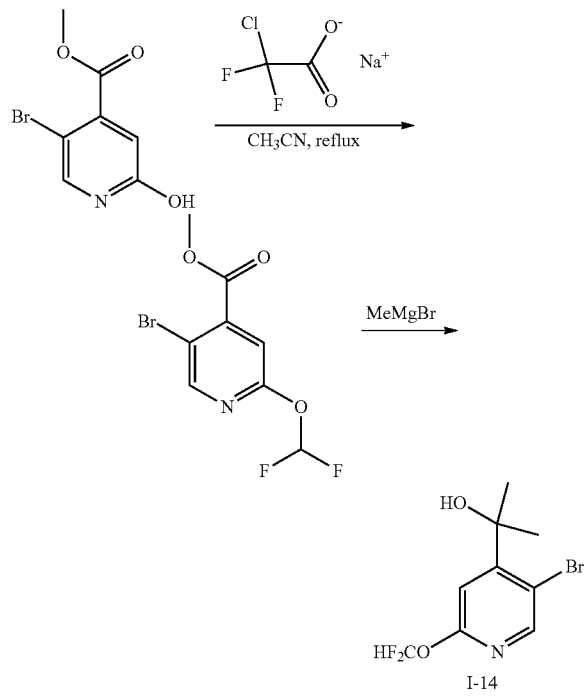

I-14

Step 1: Methyl 5-bromo-2-(difluoromethoxvy)isonicotinate

Methyl 5-bromo-2-hydroxyisonicotinate (1.13 g, 4.87 mmol) was charged with sodium chlorodifluoroacetate (0.891 g, 5.84 mmol) and ACN (30 ml) and the mixture was heated to reflux overnight. An additional portion of sodium chlorodifluoroacetate (0.891 g, 5.84 mmol) was added and the reaction was heated to reflux overnight. The reaction was quenched with sat. ammonium chloride, extracted 2× with 50 mL EtOAc, and the combined organics were washed with brine, and dried over sodium sulfate. The crude product was purified on silica gel 0-10% Et$_2$O/hexanes to provide methyl 5-bromo-2-(difluoromethoxy)isonicotinate as a solid. MS (ESI) [M+H]$^+$: m/z 282/284.

Step 2: 2-(5-Bromo-2-(difluoromethoxy)pyridin-4-yl)propan-2-ol (I-14)

This was prepared in a similar manner as illustrated above for Example 16. MS (ESI) [M+H]$^+$: m/z 282/284.

Preparation of 2-(5-bromo-2-(difluoromethoxy)pyridin-4-yl)propan-2-ol (I-15): coupling partner for Example 32

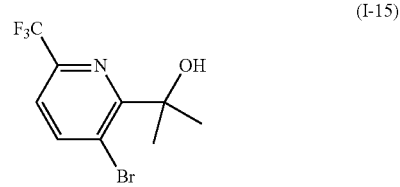

This was prepared from methyl 3-bromo-6-(trifluoromethyl) nicotinate in a similar manner as illustrated above for Example 16. MS (ESI) [M+H]$^+$: m/z 284/286.

Preparation of (5-bromo-2-(difluoromethoxy)pyridin-4-yl)methanol (I-16): coupling partner for Example 13

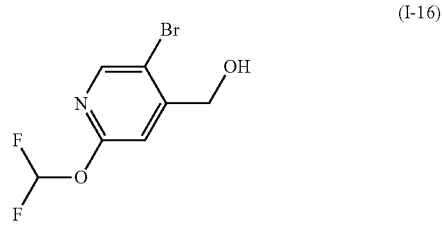 [SMILES: OCc1cc(OC(F)F)ncc1Br]

I-16 was prepared from methyl 5-bromo-2-(trifluoromethyl)isonicotinate and DIBAL-H in a similar fashion as the preparation of compound I-11. MS (ESI) [M+H]$^+$: m/z 254/256.

Synthesis of (3-bromo-6-cyclopropylpyridin-2-yl)methanol (I-17) is outlined in the following scheme:

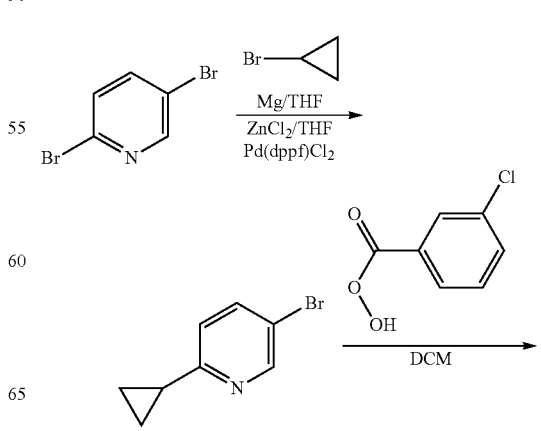

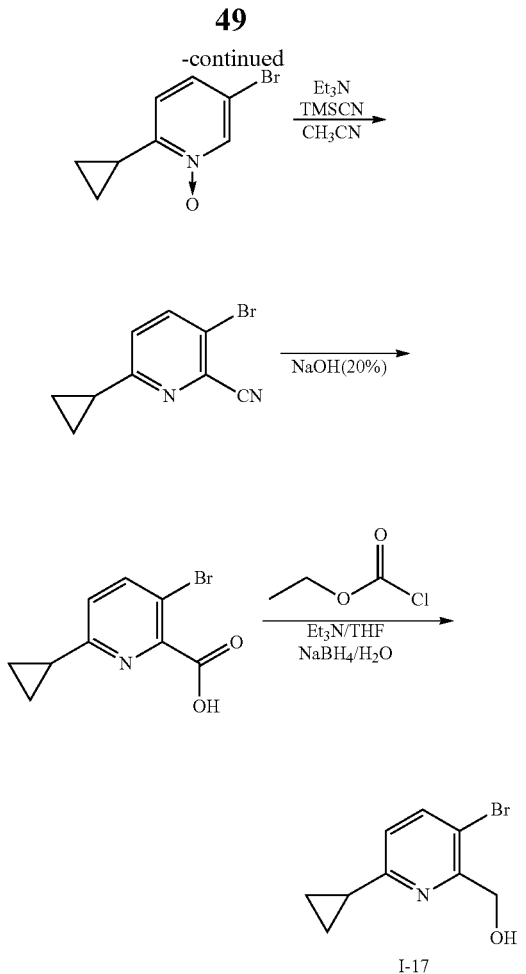

Step 1: Synthesis of 5-bromo-2-cyclopropylpyridine

To a 5-L, 4-necked round-bottom flask purged and maintained with an inert atmosphere of nitrogen was charged with a solution of Mg (200 g, 8.33 mol, 10.00 eq.) in tetrahydrofuran (1500 mL), I$_2$ (1 g) and bromocyclopropane (400 g, 3.33 mol, 4.00 eq.). The reaction mixture was stirred for 3 h at 65° C. and then was added to a solution of ZnCl$_2$ (560 g, 4.12 mol, 5.00 equiv.) in tetrahydrofuran (2000 mL) at 10° C. The resulting solution was stirred for 2 h at RT and then Pd(dppf)Cl$_2$ (20 g), 2,5-dibromopyridine (200 g, 843.88 mmol, 1.00 equiv) was added. The reaction mixture was allowed to stir overnight at RT and was quenched by the addition of 500 mL of water. The resulting mixture was concentrated under vacuum and then extracted with 3×5 L of ethyl acetate. The combined organic layer was dried over anhydrous sodium sulfate and concentrated under vacuum. The residue was purified by a silica gel column with EtOAc/petroleum ether (1/2) to give 5-bromo-2-cyclopropylpyridine as a solid.

Step 2: Synthesis of 5-bromo-2-cyclopropylpyridine 1-oxide

To a 3-L, 4-necked round-bottom flask was charged with a solution of 5-bromo-2-cyclopropylpyridine (184 g, 924.62 mmol, 1.00 equiv) in dichloromethane (1500 mL). To the solution was added 3-chlorobenzoperoxoic acid (209 g, 1.22 mol, 1.00 equiv) in portions at 0° C. in 5 min. The resulting solution was stirred overnight at RT. The pH of the solution was adjusted to 11 with sodium hydroxide (20%). The resulting solution was extracted with 4×400 mL of ethyl acetate and the combined organic layer was dried over anhydrous sodium sulfate and concentrated under vacuum. The residue was purified by a silica gel column with ethyl acetate to afford 5-bromo-2-cyclopropylpyridine 1-oxide as a solid.

Step 3: Synthesis of 3-bromo-6-cyclopropylpicolinonitrile

To a 3-L, 4-necked round-bottom flask was charged with a solution of 5-bromo-2 cyclopropylpyridine 1-oxide (100 g, 467.29 mmol, 1.00 equiv) in ACN (1200 mL), TMSCN (190 g, 1.92 mol, 4.00 equiv), and TEA (192 mL, 3.00 equiv). The resulting solution was stirred overnight at reflux and then diluted with water and extracted with 4×500 mL of ethyl acetate. The combined organic layer was dried over anhydrous sodium sulfate and concentrated under vacuum. The residue was purified by a silica gel column with ethyl acetate/petroleum ether (1/50) to give 3-bromo-6-cyclopropylpicolinonitrile as a solid.

Step 4: Synthesis of 3-bromo-6-cyclopropylpicolinic Acid

To a 3-L, 4-necked round-bottom flask was charged with 3-bromo-6-cyclopropylpicolinonitrile (74 g, 331.84 mmol, 1.00 equiv) and sodium hydroxide (20%, 1500 mL). The resulting solution was stirred overnight at reflux, cooled to RT and then extracted with 3×200 mL of ether. The pH of the combined aqueous layer was adjusted to 4 with hydrogen chloride (3N) and the resulting solution was extracted with 4×300 mL of ethyl acetate. The combined organic layer was dried over anhydrous sodium sulfate and concentrated under vacuum. The residue was purified by a silica gel column with ethyl acetate/petroleum ether (1/5) to give 3-bromo-6-cyclopropylpicolinic acid as a solid.

Step 5: Synthesis of (3-bromo-6-cyclopropylpyridin-2-yl)methanol (I-17)

To a 3-L, 4-necked round-bottom flask was charged with a solution of 3-bromo-6-cyclopropylpicolinic acid (80 g, 330.58 mmol, 1.00 equiv) in tetrahydrofuran (20 mL). To the reaction was added triethylamine (72 mL, 1.50 equiv) dropwise with stirring at −5-0° C. in 5 min and then was added ethyl carbonochloridate (41 g, 379.63 mmol, 1.30 equiv) dropwise with stirring at −20° C. The resulting solution was stirred for 60 min at −20° C. The solid was filtered out and to the filtrate was added a solution of NaBH$_4$ (28 g, 2.00 equiv) in water (84 g) dropwise with stirring at −10° C. The resulting solution was allowed to stir for an additional 20 min at −10° C. The reaction was then quenched by the addition of NH$_4$Cl (sat.). The resulting solution was extracted with 3×1000 mL of ethyl acetate and the combined organic layer was dried over anhydrous sodium sulfate and concentrated under vacuum. The residue was purified by a silica gel column with petroleum ether/ethyl acetate (50/1). This resulted in compound I-17 as a solid. MS (ESI) [M+H]$^+$: m/z 229. $^1$H NMR (300 MHz, DMSO-d6) δ 7.85 (1H, d, J=8.1 Hz), 7.16 (1H, t), 4.98 (1H, t, J=5.7 Hz), 4.52 (2H, d, J=5.7 Hz). This material was used for the preparation of Example 26.

| Ex. # | Structure | Chemical Name | Mass [M + H]+ |
|---|---|---|---|
| 8 | 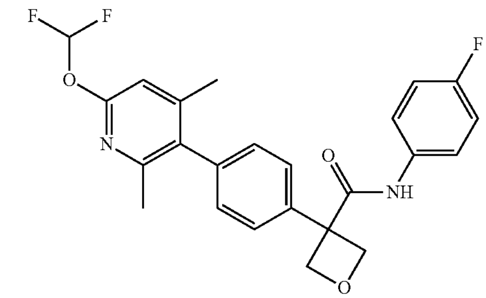 [SMILES: Cc1cc(OC(F)F)nc(C)c1-c1ccc(C2(C(=O)Nc3ccc(F)cc3)COC2)cc1] | 3-(4-(6-(difluoromethoxy)-2,4-dimethylpyridin-3-yl)phenyl)-N-(4-fluorophenyl)oxetane-3-carboxamide | 443 |
| 9 | 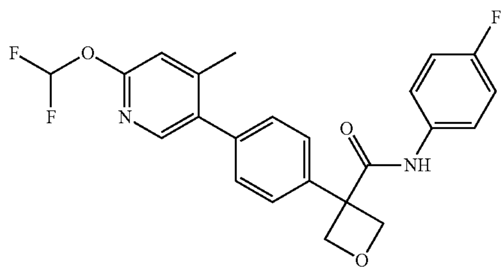 [SMILES: Cc1cc(OC(F)F)ncc1-c1ccc(C2(C(=O)Nc3ccc(F)cc3)COC2)cc1] | 3-(4-(6-(difluoromethoxy)-4-methylpyridin-3-yl)phenyl)-N-(4-fluorophenyl)oxetane-3-carboxamide | 429 |
| 10 | 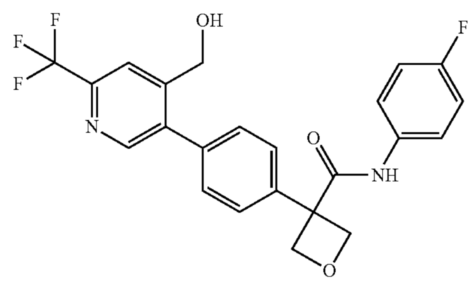 [SMILES: O=C(Nc1ccc(F)cc1)C1(c2ccc(-c3cnc(C(F)(F)F)cc3CO)cc2)COC1] | N-(4-fluorophenyl)-3-(4-(4-(hydroxymethyl)-6-(trifluoromethyl)pyridin-3-yl)phenyl)oxetane-3-carboxamide | 447 |
| 11 | 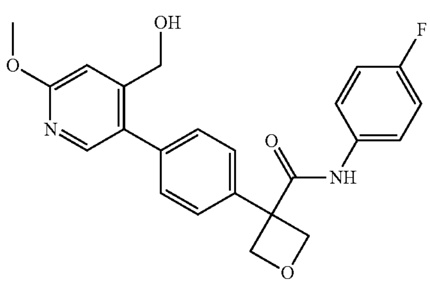 [SMILES: COc1cc(CO)c(-c2ccc(C3(C(=O)Nc4ccc(F)cc4)COC3)cc2)cn1] | N-(4-fluorophenyl)-3-[4-[4-(hydroxymethyl)-6-methoxy-pyridin-1-ium-3-yl]phenyl]oxetane-3-carboxamide | 431 [M + Na]+ |
| 12 | 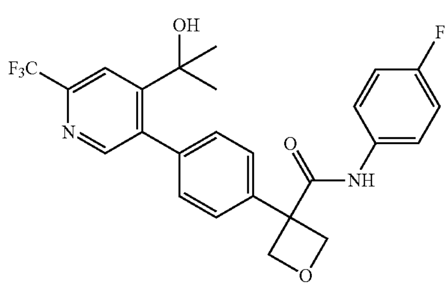 [SMILES: CC(C)(O)c1cc(C(F)(F)F)ncc1-c1ccc(C2(C(=O)Nc3ccc(F)cc3)COC2)cc1] | N-(4-fluorophenyl)-3-(4-(4-(2-hydroxypropan-2-yl)-6-(trifluoromethyl)pyridin-3-yl)phenyl)oxetane-3-carboxamide | 475 |

-continued

| Ex. # | Structure | Chemical Name | Mass [M + H]+ |
|---|---|---|---|
| 13 | 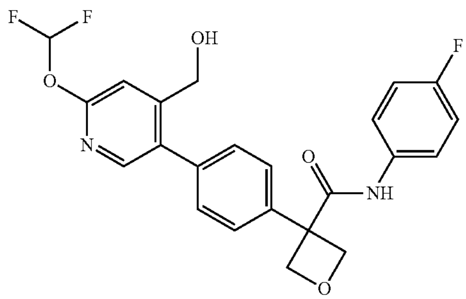 [SMILES: O=C(Nc1ccc(F)cc1)C1(c2ccc(-c3cnc(OC(F)F)cc3CO)cc2)COC1] | 3-[4-[6-(difluoromethoxy)-4-(hydroxymethyl)-3-pyridyl]phenyl]-N-(4-fluorophenyl)oxetane-3-carboxamide | 445 |
| 14 | 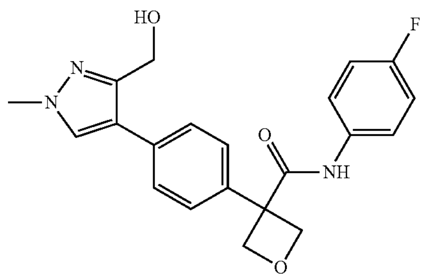 [SMILES: Cn1cc(-c2ccc(C3(C(=O)Nc4ccc(F)cc4)COC3)cc2)c(CO)n1] | N-(4-fluorophenyl)-3-[4-[3-(hydroxymethyl)-1-methyl-pyrazol-4-yl]phenyl]oxetane-3-carboxamide | 382 |
| 15 | 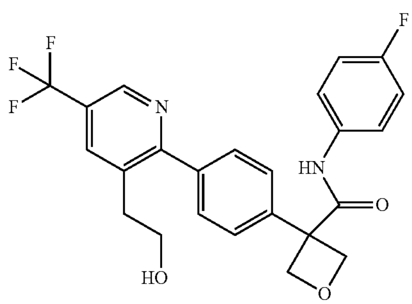 [SMILES: O=C(Nc1ccc(F)cc1)C1(c2ccc(-c3ncc(C(F)(F)F)cc3CCO)cc2)COC1] | N-(4-fluorophenyl)-3-[4-[3-(2-hydroxyethyl)-5-(trifluoromethyl)-2-pyridyl]phenyl]oxetane-3-carboxamide | 461 |
| 16 | 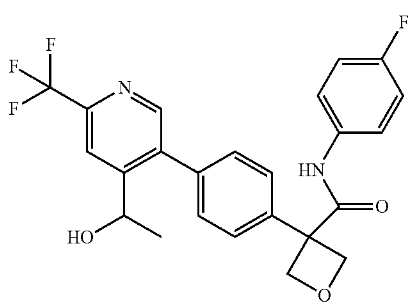 [SMILES: CC(O)c1cc(C(F)(F)F)ncc1-c1ccc(C2(C(=O)Nc3ccc(F)cc3)COC2)cc1] | (Isomer 1 from SFC (R or S)-N-(4-fluorophenyl)-3-(4-(4-(1-hydroxyethyl)-6-(trifluoromethyl)pyridin-3-yl)phenyl)oxetane-3-carboxamide | 461 |
| 17 | 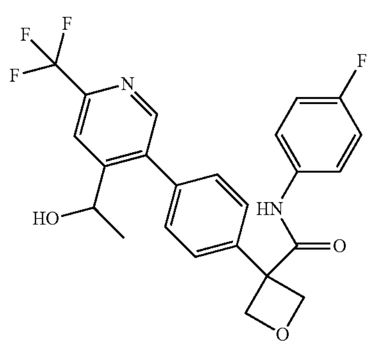 [SMILES: CC(O)c1cc(C(F)(F)F)ncc1-c1ccc(C2(C(=O)Nc3ccc(F)cc3)COC2)cc1] | (Isomer 2 from SFC) (S or R) N-(4-fluorophenyl)-3-(4-(4-(1-hydroxyethyl)-6-(trifluoromethyl)pyridin-3-yl)phenyl)oxetane-3-carboxamide | 461 |

| Ex. # | Structure | Chemical Name | Mass [M + H]+ |
|---|---|---|---|
| 18 | 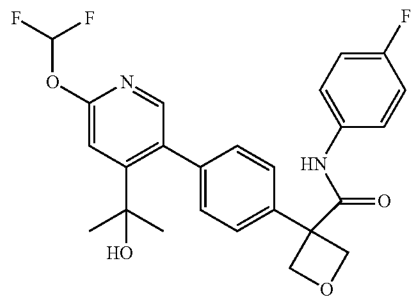 [SMILES: CC(C)(O)c1cc(OC(F)F)ncc1-c1ccc(C2(C(=O)Nc3ccc(F)cc3)COC2)cc1] | 3-[4-[6-(difluoromethoxy)-4-(1-hydroxy-1-methyl-ethyl)pyridin-1-ium-3-yl]phenyl]-N-(4-fluorophenyl)oxetane-3-carboxamide; 2,2,2-trifluoroacetate | 473 |
| 19 | 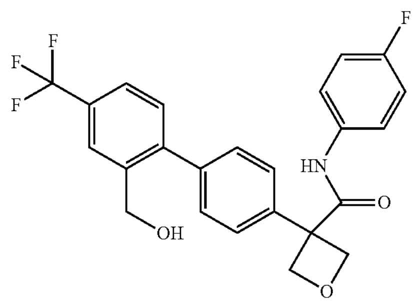 [SMILES: O=C(Nc1ccc(F)cc1)C1(c2ccc(-c3ccc(C(F)(F)F)cc3CO)cc2)COC1] | 3-[4-[6-(difluoromethoxy)-4-(1-hydroxy-1-methyl-ethyl)pyridin-1-ium-3-yl]phenyl]-N-(4-fluorophenyl)oxetane-3-carboxamide; 2,2,2-trifluoroacetate | 446 |
| 20 | 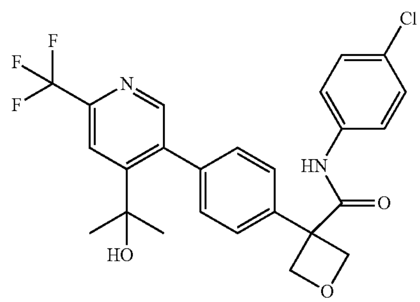 [SMILES: CC(C)(O)c1cc(C(F)(F)F)ncc1-c1ccc(C2(C(=O)Nc3ccc(Cl)cc3)COC2)cc1] | N-(4-chlorophenyl)-3-(4-(4-(2-hydroxypropan-2-yl)-6-(trifluoromethyl)pyridin-3-yl)phenyl)oxetane-3-carboxamide | 491 |
| 21 | 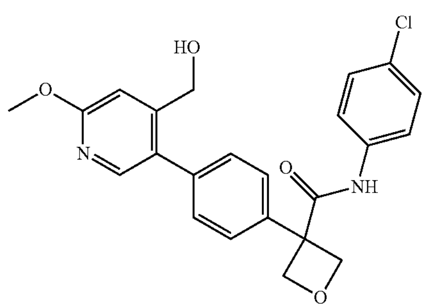 [SMILES: COc1cc(CO)c(-c2ccc(C3(C(=O)Nc4ccc(Cl)cc4)COC3)cc2)cn1] | N-(4-chlorophenyl)-3-[4-[4-(hydroxymethyl)-6-methoxy-pyridin-1-ium-3-yl]phenyl]oxetane-3-carboxamide; 2,2,2-trifluoroacetate | 425 |
| 22 | 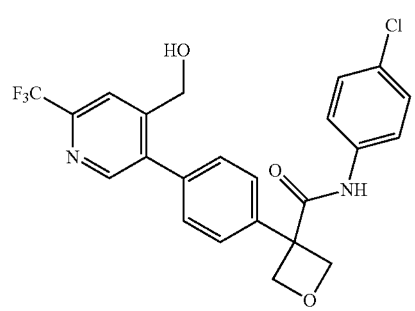 [SMILES: O=C(Nc1ccc(Cl)cc1)C1(c2ccc(-c3cnc(C(F)(F)F)cc3CO)cc2)COC1] | N-(4-chlorophenyl)-3-[4-[4-(hydroxymethyl)-6-(trifluoromethyl)-3-pyridyl]phenyl]oxetane-3-carboxamide | 463 |

-continued

| Ex. # | Structure | Chemical Name | Mass [M + H]+ |
|---|---|---|---|
| 23 | 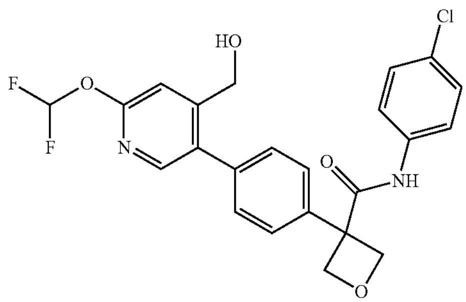 [SMILES: O=C(Nc1ccc(Cl)cc1)C1(c2ccc(-c3cnc(OC(F)F)cc3CO)cc2)COC1] | N-(4-chlorophenyl)-3-[4-[6-(difluoromethoxy)-4-(hydroxymethyl)-3-pyridyl]phenyl]oxetane-3-carboxamide | 461 |
| 24 | 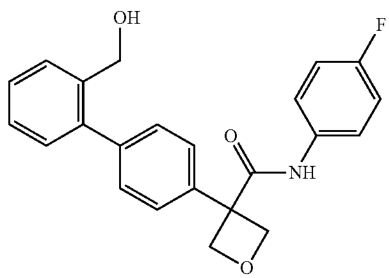 [SMILES: O=C(Nc1ccc(F)cc1)C1(c2ccc(-c3ccccc3CO)cc2)COC1] | N-(4-fluorophenyl)-3-[4-[2-(hydroxymethyl)phenyl]phenyl]oxetane-3-carboxamide | 378 |
| 25 | 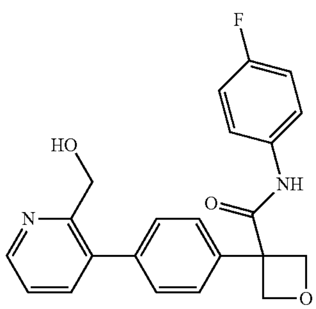 [SMILES: O=C(Nc1ccc(F)cc1)C1(c2ccc(-c3cccnc3CO)cc2)COC1] | N-(4-fluorophenyl)-3-[4-[2-(hydroxymethyl)pyridin-1-ium-3-yl]phenyl]oxetane-3-carboxamide; 2,2,2-trifluoroacetate | 379 |
| 26 | 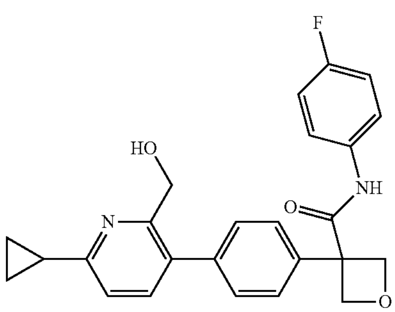 [SMILES: O=C(Nc1ccc(F)cc1)C1(c2ccc(-c3ccc(C4CC4)nc3CO)cc2)COC1] | 3-[4-[6-cyclopropyl-2-(hydroxmethyl)pyridin-1-ium-3-yl]phenyl]-N-(4-fluorophenyl)oxetane-3-carboxamide; 2,2,2-trifluoroacetate | 419 |
| 27 | 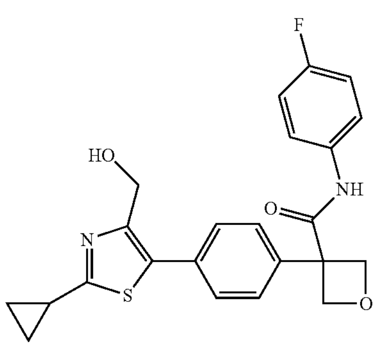 [SMILES: O=C(Nc1ccc(F)cc1)C1(c2ccc(-c3sc(C4CC4)nc3CO)cc2)COC1] | 3-[4-[2-cyclopropyl-4-(hydroxymethyl)thiazol-3-ium-5-yl]phenyl]-N-(4-fluorophenyl)oxetane-3-carboxamide; 2,2,2-trifluoroacetate | 425 |

-continued

| Ex. # | Structure | Chemical Name | Mass [M + H]+ |
|---|---|---|---|
| 28 | 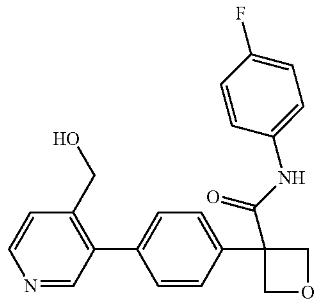 | N-(4-fluorophenyl)-3-[4-[4-(hydroxymethyl)pyridin-1-ium-3-yl]phenyl]oxetane-3-carboxamide; 2,2,2-trifluoroacetate | 379 |
| 29 | 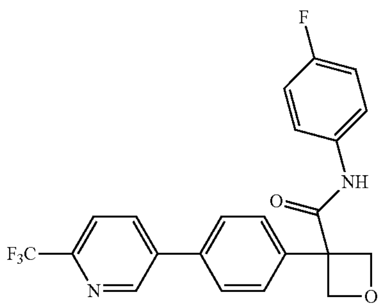 [SMILES: O=C(Nc1ccc(F)cc1)C1(c2ccc(-c3ccc(C(F)(F)F)nc3)cc2)COC1] | N-(4-fluorophenyl)-3-[4-[6-(trifluoromethyl)pyridin-1-ium-3-yl]phenyl]oxetane-3-carboxamide; 2,2,2-trifluoroacetate | 417 |
| 30 | 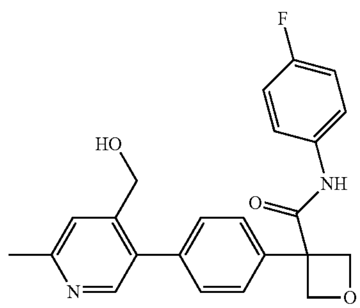 [SMILES: Cc1cc(CO)c(-c2ccc(C3(C(=O)Nc4ccc(F)cc4)COC3)cc2)cn1] | N-(4-fluorophenyl)-3-[4-[4-(hydroxymethyl)-6-methyl-pyridin-1-ium-3-yl]phenyl]oxetane-3-carboxamide; 2,2,2-trifluoroacetate | 393 |
| 31 | 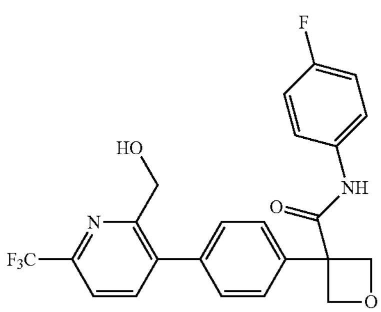 [SMILES: O=C(Nc1ccc(F)cc1)C1(c2ccc(-c3ccc(C(F)(F)F)nc3CO)cc2)COC1] | N-(4-fluorophenyl)-3-[4-[2-(hydroxymethyl)-6-(trifluoromethyl)-3-pyridyl]phenyl]oxetane-3-carboxamide | 447 |
| 32 | 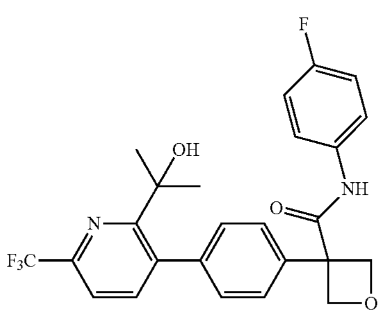 [SMILES: CC(C)(O)c1nc(C(F)(F)F)ccc1-c1ccc(C2(C(=O)Nc3ccc(F)cc3)COC2)cc1] | N-(4-fluorophenyl)-3-(4-(2-(2-hydroxypropan-2-yl)-6-(trifluoromethyl)pyridin-3-yl)phenyl)oxetane-3-carboxamide | 475 |

| Ex. # | Structure | Chemical Name | Mass [M + H]+ |
|---|---|---|---|
| 33 | 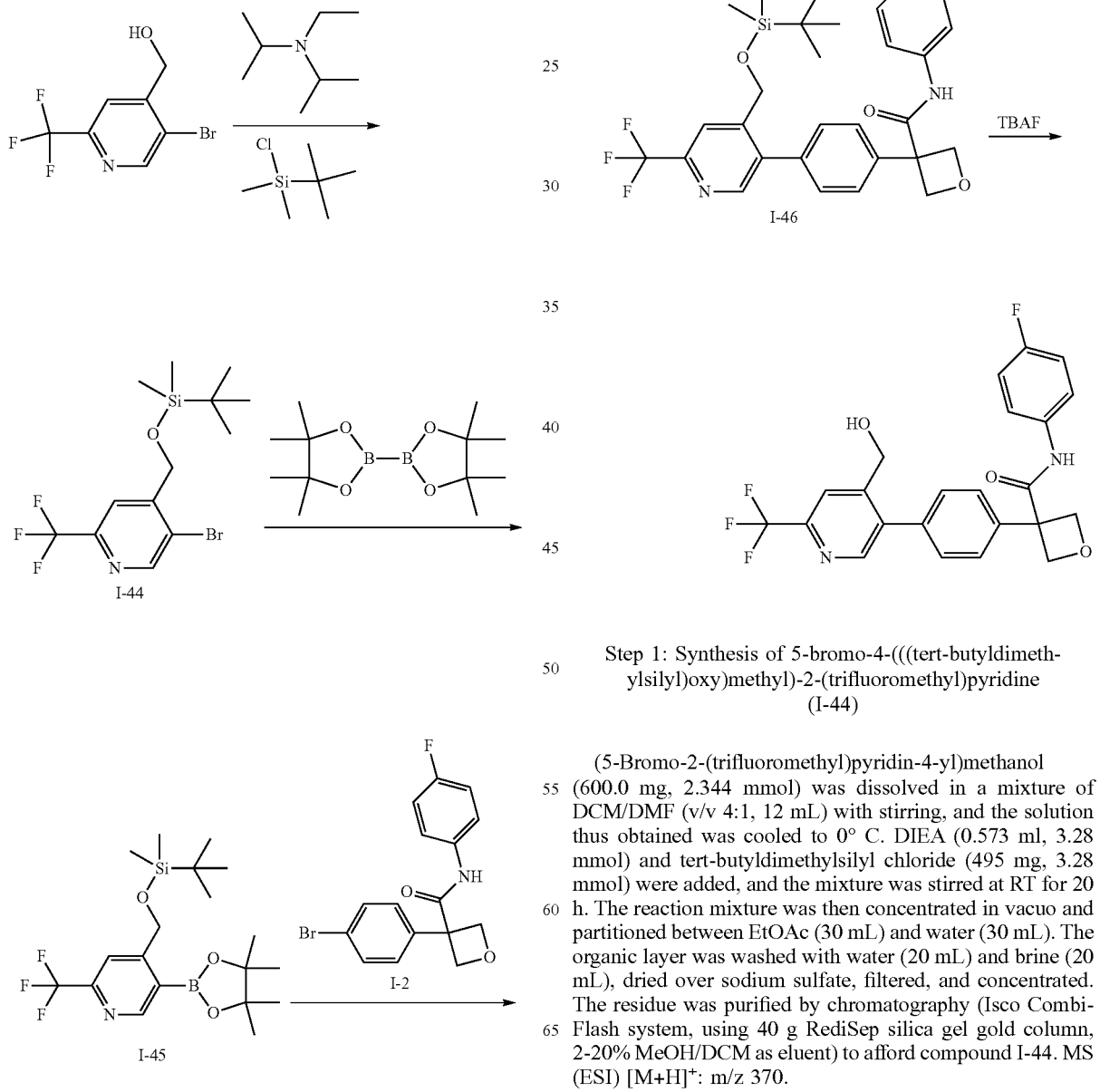 | N-(6-chloropyridin-3-yl)-3-(4-(4-(hydroxymethyl)-6-(trifluoromethyl)pyridin-3-yl)phenyl)oxetane-3-carboxamide | 464 |

Example 10 can also be prepared according to the following procedure:

Step 1: Synthesis of 5-bromo-4-(((tert-butyldimethylsilyl)oxy)methyl)-2-(trifluoromethyl)pyridine (I-44)

(5-Bromo-2-(trifluoromethyl)pyridin-4-yl)methanol (600.0 mg, 2.344 mmol) was dissolved in a mixture of DCM/DMF (v/v 4:1, 12 mL) with stirring, and the solution thus obtained was cooled to 0° C. DIEA (0.573 ml, 3.28 mmol) and tert-butyldimethylsilyl chloride (495 mg, 3.28 mmol) were added, and the mixture was stirred at RT for 20 h. The reaction mixture was then concentrated in vacuo and partitioned between EtOAc (30 mL) and water (30 mL). The organic layer was washed with water (20 mL) and brine (20 mL), dried over sodium sulfate, filtered, and concentrated. The residue was purified by chromatography (Isco Combi-Flash system, using 40 g RediSep silica gel gold column, 2-20% MeOH/DCM as eluent) to afford compound I-44. MS (ESI) [M+H]+: m/z 370.

Step 2: Synthesis of 4-(((tert-butyldimethylsilyl)oxy)methyl)-5-(4,4,5,5-tetramethyl-1,3,2-dioxaborolan-2-yl)-2-(trifluoromethyl)pyridine (I-45)

A mixture of compound I-44 (720.0 mg, 1.944 mmol), 4,4,4',4',5,5,5',5'-octamethyl-2,2'-bi(1,3,2-dioxaborolane) (593 mg, 2.333 mmol), 1,1'-bis(di-tert-butylphosphino)ferrocene palladium dichloride (127 mg, 0.194 mmol) and potassium acetate (573 mg, 5.83 mmol) in 1,4-dioxane (5.0 ml) was evacuated and back filled with nitrogen 3 times. The mixture was heated to 80° C. in a sealed tube for 2 h. After cooling to RT, the reaction mixture was filtered through a Celite pad. The filtrate was concentrated in vacuo to give a residue which was dissolved in dichloromethane. After washing with water (3×) and brine, the dichloromethane layer was dried over anhydrous $Na_2SO_4$ and concentrated in vacuo to give the crude product which was used directly in the next step without purification. MS (ESI) [M+H]$^+$: m/z 418.

Step 3: Synthesis of 3-(4-(4-(((tert-butyldimethylsilyl)oxy)methyl)-6-(trifluoromethyl)pyridin-3-yl)phenyl)-N-(4-fluorophenyl)oxetane-3-carboxamide (I-46)

A solution of (4-(((tert-butyldimethylsilyl)oxy)methyl)-6-(trifluoromethyl)pyridin-3-yl)boronic acid, (96 mg, 0.286 mmol), 3-(4-bromophenyl)-N-(4-fluorophenyl)oxetane-3-carboxamide (I-2), (100 mg, 0.286 mmol), 1,1'-bis(di-tert-butylphosphino)ferrocene palladium dichloride (18.61 mg, 0.029 mmol) and sodium carbonate (0.286 ml, 0.571 mmol) in 1,4-dioxane (2.0 ml) was subjected to the standard Suzuki cross-coupling conditions and the crude product was purified by silica gel column chromatography (ethyl acetate/DCM, 10-70%) to afford compound I-46. MS (ESI) [M+H]$^+$: m/z 561.

Step 4: N-(4-fluorophenyl)-3-(4-(4-(hydroxymethyl)-6-(trifluoromethyl)pyridin-3-yl)phenyl)oxetane-3-carboxamide To a solution of compound I-46, (143.0 mg, 0.255 mmol) in THF (5.0 ml) was added tetra-N-butylammonium chloride in 1 M THF (0.255 ml, 0.255 mmol) at 0° C., and the reaction mixture was stirred for 2 h at RT. The solvent was evaporated in vacuo and the residue was redissolved in dichloromethane. After washing successively with water, sat. aq. sodium bicarbonate and brine, the organic phase was dried over sodium sulphate, filtered, and the filtrate was evaporated in vacuo. The crude material was purified by mass-directed reversed phase chromatography (ACN/water gradient with 0.1% TFA modifier) to afford the title compound.

Example 12: N-(4-Fluorophenyl)-3-(4-(4-(2-hydroxypropan-2-yl)-6-(trifluoromethyl)pyridin-3-yl)phenyl)oxetane-3-carboxamide A 3-neck round-bottomed flask under nitrogen was charged with N-(4-fluorophenyl)-3-(4-(4,4,5,5-tetramethyl-1,3,2-dioxaborolan-2-yl)phenyl)oxetane-3-carboxamide (I-9) (5 g, 12.5 mmol), 2-(5-bromo-2-(trifluoromethyl)pyridin-4-yl)propan-2-ol (I-12) (4 g, 14 mmol), and $PdCl_2$(dtbpf) (0.53 g, 8.15 mmol) and the flask was subjected to vacuum/nitrogen cycle three times. Ethanol (100 mL) was then added followed by aq. potassium phosphate (40 mL, 1 M). The mixture was subjected to vacuum/nitrogen cycle three times again and then was heated to 60° C. under nitrogen for 4 h. The mixture was allowed to cool to RT, transferred to a separatory funnel and diluted with water (50 mL) and dichloromethane (100 mL). The organic phase was collected and the aq. phase was extracted once more with dichloromethane (100 mL). The combined organic extracts were washed with brine and was stirred with SiliaMetS Thiol (6.5 g). The resulting suspension was dried over anhydrous sodium sulfate, filtered, and the filtrate was concentrated to dryness under reduced pressure. The resulting crude was purified by silica gel chromatography using a gradient of ethyl acetate in hexane to afford a crude material. This crude material was resuspended in diethyl ether (25 mL) and stirred for 15 min. The solids were filtered, and washed with diethyl ether to afford the title compound. MS (ESI+) m/z [M+H]$^+$: 475. $^1$H NMR (600 MHz, DMSO-d6) δ 10.07 (s, 1H), 8.35 (s, 1H), 8.22 (s, 1H), 7.67-7.62 (m, 2H), 7.58 (d, 2H), 7.41 (d, 2H), 7.20-7.14 (m, 2H), 5.49 (s, 1H), 5.24 (d, 2H), 4.91 (d, 2H), 1.25 (s, 6H).

Example 34: 3-(4-(4-(Fluoromethyl)-6-(trifluoromethyl)pyridin-3-yl)phenyl)-N-(4-fluorophenyl)oxetane-3-carboxamide

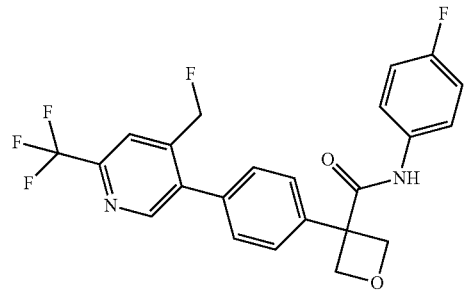 [SMILES: O=C(Nc1ccc(F)cc1)C1(c2ccc(-c3cnc(C(F)(F)F)cc3CF)cc2)COC1]

To a solution of N-(4-fluorophenyl)-3-(4-(4-(hydroxymethyl)-6-(trifluoromethyl)pyridin-3-yl)phenyl)oxetane-3-carboxamide (I-20) (70.0 mg, 0.157 mmol) in DCM (3 ml) at 0° C. was added 1,1,1-trifluoro-N,N-bis(2-methoxyethyl)-1,4-sulfanamine. After stirring at 0° C. for 1 h. The reaction was carefully quenched with aq. $NaHCO_3$ and extracted with ethyl acetate. The organic layer was concentrated and the crude material was purified by mass-directed reversed phase chromatography (ACN/water gradient with 0.1% TFA modifier) to afford the title compound. MS (ESI) [M+H]$^+$: m/z 449. $^1$H NMR (499 MHz, DMSO-d6) δ 10.07 (s, 1H), 8.76 (s, 1H), 8.03 (s, 1H), 7.65 (t, J=6.9 Hz, 4H), 7.57 (d, J=8.1 Hz, 2H), 7.17 (t, J=8.8 Hz, 2H), 5.60 (d, J=46.4 Hz, 2H), 5.25 (d, J=6.5 Hz, 2H), 4.93 (d, J=6.5 Hz, 2H).

Example 35: 3-(4-(4-(Hydroxymethyl)-6-(trifluoromethyl)pyridin-3-yl)phenyl)-N-(4-(trifluoromethoxy)phenyl)oxetane-3-carboxamide

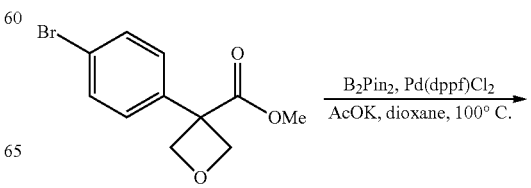

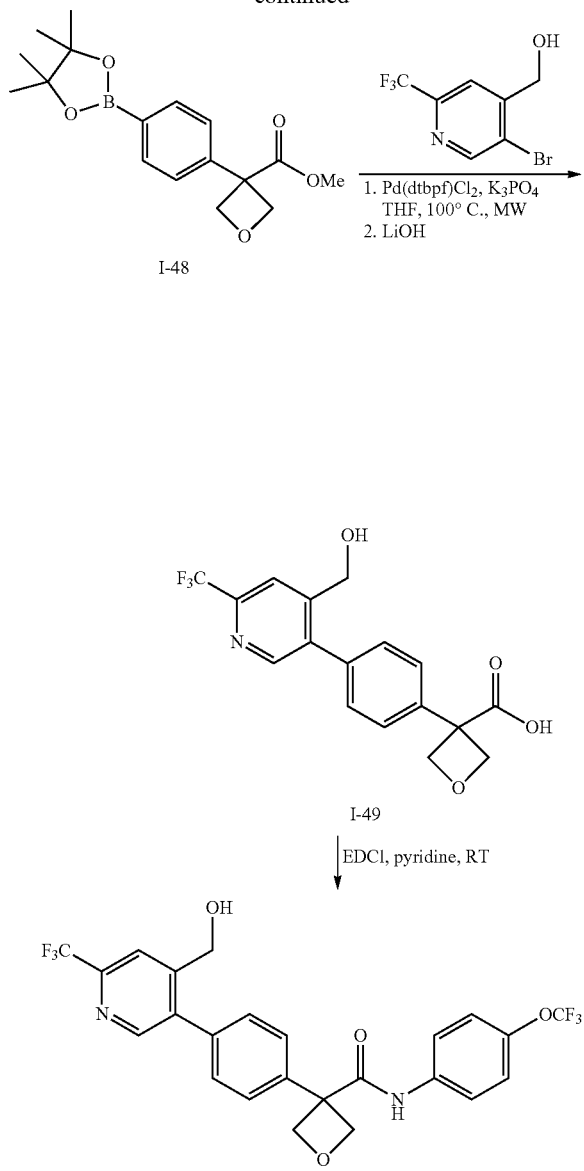

Step 1: methyl 3-(4-(4,4,5,5-tetramethyl-1,3,2-dioxaborolan-2-yl)phenyl)oxetane-3-carboxylate (I-48)

To a solution of methyl 3-(4-bromophenyl)oxetane-3-carboxylate (2.1 g, 7.75 mmol) and 4,4,4',4',5,5,5',5'-octamethyl-2,2'-bi(1,3,2-dioxaborolane) (2.065 g, 8.13 mmol) in dioxane (30 mL) were added AcOK (2.281 g, 23.24 mmol) and Pd(dppf)Cl$_2$ (0.567 g, 0.775 mmol) with stirring at RT under a nitrogen atmosphere. After the addition was complete, the reaction mixture was stirred at 80° C. for 14 h, cooled to RT and diluted with EtOAc (30 mL). The mixture was filtered and the filtrate was concentrated. The residue was purified by flash silica gel chromatography (ISCO®; Agela® Flash Column Silica-CS (12 g), Eluent of 0~7% ethyl acetate/petroleum ether gradient @ 30 mL/min) to afford compound I-48 as a solid. MS (ESI) m/z: 360 [M+ACN+H$^+$].

Step 2: Preparation of 3-(4-(4-(hydroxymethyl)-6-(trifluoromethyl)pyridin-3-yl)phenyl)oxetane-3-carboxylic acid (I-49)

To a solution of compound I-48 (500 mg, 1.571 mmol) and (5-bromo-2-(trifluoromethyl)pyridin-4-yl)methanol (402 mg, 1.571 mmol) in THF (6 mL) and water (1 mL) were added K$_3$PO$_4$ (1.001 g, 4.71 mmol) and Pd(dtbpf)Cl$_2$ (102 mg, 0.157 mmol). The reaction mixture was sealed and stirred at 100° C. under nitrogen, promoted with microwave. After stirring at 100° C. for 0.5 h, the reaction was cooled to RT and diluted with water (10 mL). The mixture was extracted with EtOAc (30 mL×3). The combined organic layers were washed with brine (20 mL) and dried over Na$_2$SO$_4$, filtered and concentrated. The residue was purified by flash silica gel chromatography (ISCO®; Agela® Flash Column Silica-CS (12 g), eluent of 0~27% ethyl acetate/petroleum ether gradient @ 30 mL/min) to afford methyl 3-(4-(4-(hydroxymethyl)-6-(trifluoromethyl)pyridin-3-yl)phenyl)oxetane-3-carboxylate as a solid. MS (ESI) m/z: 368.0 [M+H$^+$].

To a solution of methyl 3-(4-(4-(hydroxymethyl)-6-(trifluoromethyl)pyridin-3-yl)phenyl)oxetane-3-carboxylate from above (520 mg, 1.416 mmol) in THF (4 mL), MeOH (4 mL) and water (2 mL) was added LiOH (102 mg, 4.25 mmol) at RT with stirring, and the reaction mixture was stirred at RT for 14 h. 3N HCl was added to the mixture with stirring until pH ~4. Then the reaction was diluted with water (5 mL) and was extracted with EtOAc (10 mL×5). The combined organic layer was washed with brine (10 mL) and dried over Na$_2$SO$_4$, filtered and concentrated to afford compound I-49 as a solid, which was used for next step without further purification. MS (ESI) m/z: 354 [M+H$^+$].

Step 3: 3-(4-(4-(Hydroxymethyl)-6-(trifluoromethyl) pyridin-3-yl)phenyl)-N-(4-(trifluoromethoxy)phenyl) oxetane-3-carboxamide To a solution of compound I-49 (30 mg, 0.085 mmol) and 4-(trifluoromethoxy)aniline (30 mg, 0.169 mmol) in pyridine (1.0 mL) was added EDCI (50 mg, 0.261 mmol) with stirring at RT. After the addition was complete, the reaction mixture was stirred at RT for 1 h. The reaction mixture was concentrated and the residue was purified by reversed phase HPLC on a GILSON 281 instrument fitted with a YMC-Actus Pro C18 150*30 5 u column using water (0.1% TFA) and ACN as eluents. The desired fractions were concentrated and then lyophilized to afford the title compound as a solid. MS (ESI) m/z: 513.2 [M+H$^+$]. $^1$H NMR (400 MHz, CD$_3$OD) δ 8.54 (s, 1H), 8.07 (s, 1H), 7.61-7.74 (m, 4H), 7.50 (d, J=8.3 Hz, 2H), 7.24 (d, J=8.3 Hz, 2H), 5.37 (d, J=6.6 Hz, 2H), 5.04 (d, J=6.6 Hz, 2H), 4.65 (s, 2H).

Examples 36-42 in the following table were prepared in a similar fashion to Example 35.

| Ex. # | Structure | Chemical Name | Mass [M + H]+ |
|---|---|---|---|
| 36 | 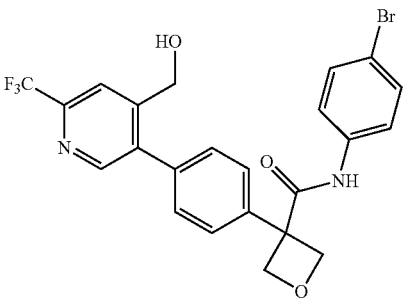 [SMILES: O=C(Nc1ccc(C(F)(F)F)cc1)C1(c2ccc(-c3cnc(C(F)(F)F)cc3CO)cc2)COC1] | N-(4-bromophenyl)-3-(4-(4-(hydroxymethyl)-6-(trifluoromethyl)pyridin-3-yl)phenyl)oxetane-3-carboxamide | 507 |
| 37 | 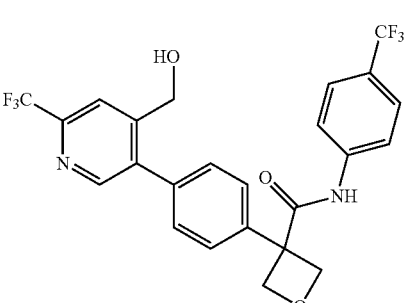 | 3-(4-(4-(hydroxymethyl)-6-(trifluoromethyl)pyridin-3-yl)phenyl)-N-(4-(trifluoromethyl)phenyl)oxetane-3-carboxamide | 497 |
| 38 | 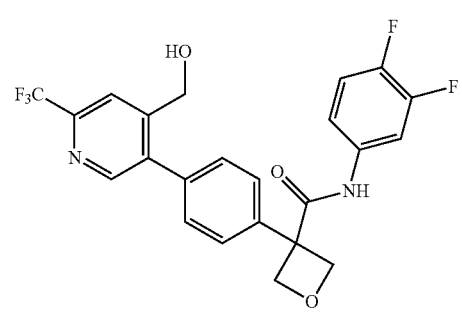 [SMILES: O=C(Nc1ccc(F)c(F)c1)C1(c2ccc(-c3cnc(C(F)(F)F)cc3CO)cc2)COC1] | N-(3,4-difluorophenyl)-3-(4-(4-(hydroxymethyl)-6-(trifluoromethyl)pyridin-3-yl)phenyl)oxetane-3-carboxamide | 465 |
| 39 | 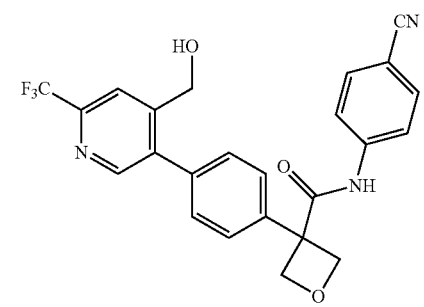 | N-(4-cyanophenyl)-3-(4-(4-(hydroxymethyl)-6-(trifluoromethyl)pyridin-3-yl)phenyl)oxetane-3-carboxamide | 454 |
| 40 | 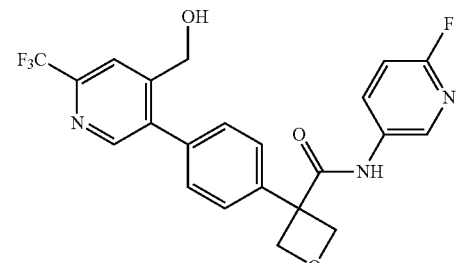 | N-(6-fluoropyridin-3-yl)-3-(4-(4-(hydroxymethyl)-6-(trifluoromethyl)pyridin-3-yl)phenyl)oxetane-3-carboxamide | 448 |

| Ex. # | Structure | Chemical Name | Mass [M + H]+ |
|---|---|---|---|
| 41 | 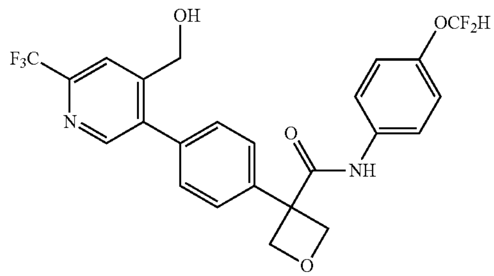 | N-(4-(difluoromethoxy)phenyl)-3-(4-(4-(hydroxymethyl)-6-(trifluoromethyl)pyridin-3-yl)phenyl)oxetane-3-carboxamide | 495 |
| 42 | 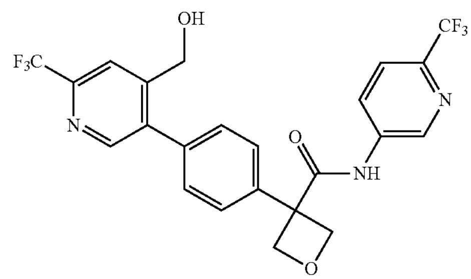 [SMILES: O=C(Nc1ccc(C(F)(F)F)nc1)C1(c2ccc(-c3cnc(C(F)(F)F)cc3CO)cc2)COC1] | 3-(4-(4-(hydroxymethyl)-6-(trifluoromethyl)pyridin-3-yl)phenyl)-N-(6-(trifluoromethyl)pyridin-3-yl)oxetane-3-carboxamide | 498 |

Example 43: 3-(4-(1H-Tetrazol-5-yl)phenyl)-N-(4-fluorophenyl)oxetane-3-carboxamide

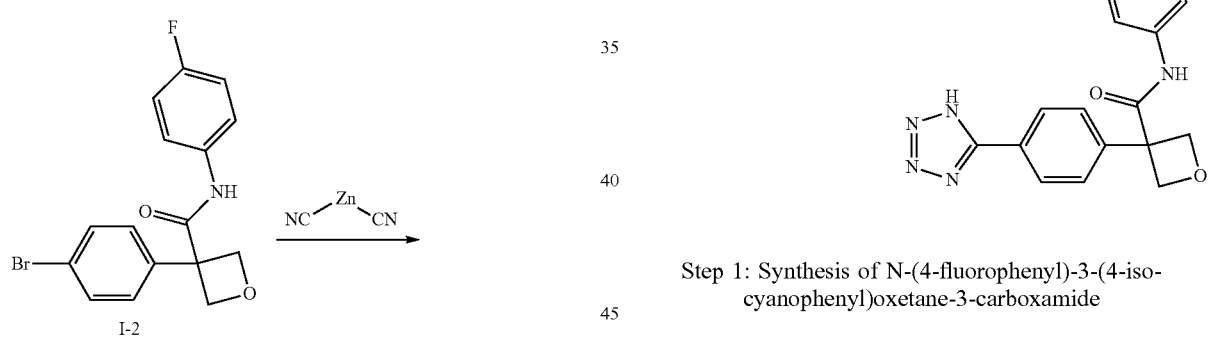

Step 1: Synthesis of N-(4-fluorophenyl)-3-(4-isocyanophenyl)oxetane-3-carboxamide A dried flask was charged with 3-(4-bromophenyl)-N-(4-fluorophenyl)oxetane-3-carboxamide (I-2) (1000.0 mg, 2.86 mmol) in anhydrous DMF (10.0 ml). To this was added zinc cyanide (671 mg, 5.71 mmol), $Pd_2(dba)_3$ (105 mg, 0.114 mmol), and dppf (79 mg, 0.143 mmol) followed by zinc dust (18.67 mg, 0.286 mmol). The reaction mixture was then purged with nitrogen for 5 min. The reaction mixture was heated at 120° C. for 4 h and cooled to RT, filtered through a Celite pad which was further washed with DCM. The filtrate was concentrated in vacuo and the crude was purified in a Biotage silica column (EtOAc/Hex 5 to 40) to afford N-(4-fluorophenyl)-3-(4-isocyanophenyl)oxetane-3-carboxamide. MS (ESI) [M+H]+: m/z 297.

Step 2: 3-(4-(1H-Tetrazol-5-yl)phenyl)-N-(4-fluorophenyl)oxetane-3-carboxamide (Compound 43)

N-(4-fluorophenyl)-3-(4-isocyanophenyl)oxetane-3-carboxamide, (41.0 mg, 0.138 mmol), sodium azide (17.99 mg, 0.277 mmol) and zinc bromide (31.2 mg, 0.138 mmol) were added to a mixture of water (923 μl) and 2-propanol (461 μl).

The resulting suspension was then heated to reflux and allowed to stir overnight. The mixture was cooled to RT, filtered through a Celite pad and concentrated. The crude material was purified by mass-directed reversed phase chromatography (ACN/water gradient with 0.1% TFA modifier) to afford the title compound. MS (ESI) [M+H]$^+$: m/z 340. $^1$H NMR (600 MHz, DMSO-d6) δ 10.03 (s, 1H), 8.09 (d, J=8.1 Hz, 2H), 7.71 (d, J=8.1 Hz, 2H), 7.61 (dd, J=8.6, 5.0 Hz, 2H), 7.15 (t, J=8.7 Hz, 2H), 5.23 (d, J=6.5 Hz, 2H), 4.92 (d, J=6.5 Hz, 2H).

Example 44: N-(4-Fluorophenyl)-3-(4-(5-(trifluoromethyl)-1,2,4-oxadiazol-3-yl)phenyl)oxetane-3-carboxamide

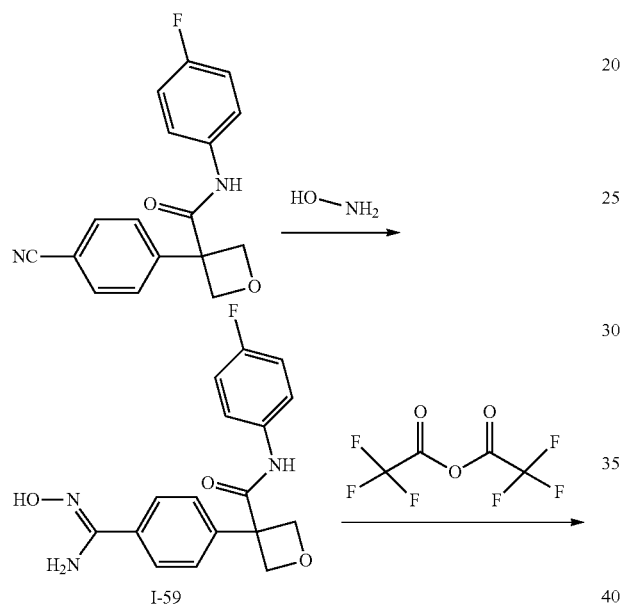

Step 1: Synthesis of (Z)—N-(4-fluorophenyl)-3-(4-(N'-hydroxycarbamimidoyl)phenyl)oxetane-3-carboxamide (I-59)

Nitrile N-(4-fluorophenyl)-3-(4-isocyanophenyl)oxetane-3-carboxamide (60.0 mg, 0.203 mmol) was dissolved in MeOH (1.0 mL), and then hydroxylamine (50 wt % in water) (0.137 mL, 2.228 mmol) was added. The mixture was heated to 60° C. for 2 h. The reaction mixture was diluted with brine and extracted with EtOAc (3×). The combined organic layers were dried over MgSO$_4$, filtered, and the filtrate concentrated under reduced pressure to afford compound I-59. MS (ESI) [M+H]$^+$: m/z 330. The crude was used directly in the next step without purification.

Step 2: N-(4-Fluorophenyl)-3-(4-(5-(trifluoromethyl)-1,2,4-oxadiazol-3-yl)phenyl)oxetane-3-carboxamide TFAA (0.064 ml, 0.455 mmol) was added to a mixture of compound I-59 (50.0 mg, 0.152 mmol) and pyridine (0.037 ml, 0.455 mmol) in toluene (2.0 ml) at 10° C. After the addition was completed, the mixture was stirred at 110° C. for 3 h. After cooling to RT, the mixture was concentrated under reduced pressure and the residue was partitioned between EtOAc and water. The aqueous layer was extracted with EtOAc (2×) and the collected organic layers were washed with brine, dried over anhydrous Na$_2$SO$_4$. The mixture was filtered and the filtrate was concentrated under reduced pressure. The crude material was purified by mass-directed reversed phase chromatography (ACN/water gradient with 0.1% TFA modifier) to afford the title compound. MS (ESI) [M+H]$^+$: m/z 408. $^1$H NMR (600 MHz, DMSO-d6) δ 10.07 (s, 1H), 8.13 (d, J=8.2 Hz, 2H), 7.74 (d, J=8.2 Hz, 2H), 7.61 (dd, J=8.5, 5.0 Hz, 2H), 7.16 (t, J=8.7 Hz, 2H), 5.24 (d, J=6.6 Hz, 2H), 4.91 (d, J=6.6 Hz, 2H).

Examples 45: 3-(4-(1H-Benzo[d]imidazol-2-yl)phenyl)-N-(4-fluorophenyl)oxetane-3-carboxamide

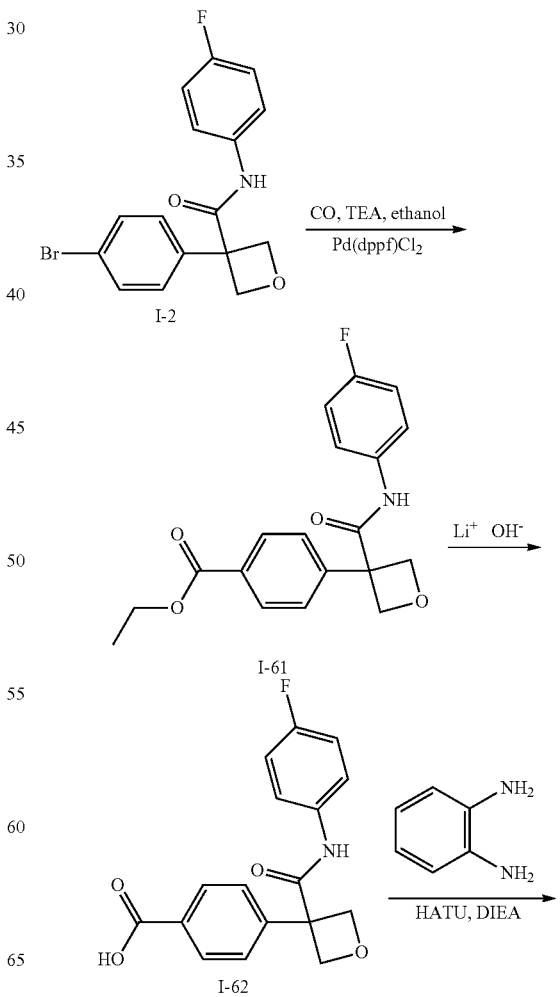

-continued

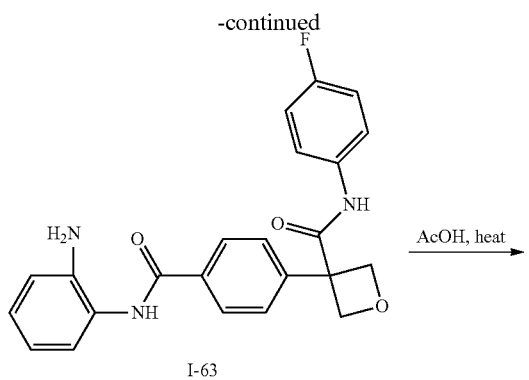

I-63

Step 1: Synthesis of ethyl 4-(3-((4-fluorophenyl)carbamoyl)oxetan-3-yl)benzoate (I-61)

1,1'-Bis(diphenylphosphino)ferrocene-palladium(II)dichloride dichloromethane complex (152 mg, 0.186 mmol) was added to a stirring solution containing compound I-2 (325.0 mg, 0.928 mmol), TEA (517 μl, 3.71 mmol) in EtOH (1084 μl, 18.56 mmol) and DMF (4640 μl). The mixture was stirred under carbon monoxide at 90° C. overnight. The reaction mixture was cooled down to RT and then filtered through a Celite pad. The filtrate was concentrated, diluted with ethyl acetate, washed with water (2×) and brine. The organic layer was dried over Na$_2$SO$_4$, filtered and concentrated. The crude was purified in a Biotage column (silica) using EtOAc/Hex (5 to 40%) as eluents to afford compound I-61. MS (ESI) [M+H]$^+$: m/z 344.

Step 2: Synthesis of 4-(3-((4-fluorophenyl)carbamoyl)oxetan-3-yl)benzoic acid (I-62)

1 M LiOH (3.0 ml, 3.00 mmol) was added to a solution of compound I-61 (300.0 mg, 0.874 mmol) in MeOH (5.0 ml). This mixture was stirred at RT for 4 h and evaporated under reduced pressure. The residue was diluted with water and acidified with an aqueous solution of hydrochloric acid (2N). This aqueous mixture was extracted with ethyl acetate (2×50 ml) and the combined organic extracts were washed with brine, dried over MgSO$_4$, filtered, and evaporated under reduced pressure to afford compound I-62. MS (ESI) [M+H]$^+$: m/z 316.

Step 3: 3-(4-(1H-Benzo[d]imidazol-2-yl)phenyl)-N-(4-fluorophenyl)oxetane-3-carboxamide To a 20-mL vial was charged with a magnetic spin bar, compound I-62 (50.0 mg, 0.159 mmol) and DMF (1.91 ml). HATU (60.3 mg, 0.159 mmol) was added with stirring, and the mixture was stirred for a few minutes. To the mixture was then added benzene-1,2-diamine (17.15 mg, 0.159 mmol), DIEA (83 μl, 0.476 mmol) and the reaction was stirred for 4 h at RT. The reaction was diluted with 50 mL of ethyl acetate which was washed with 1N aqueous HCl, water, brine and saturated aqueous NaHCO$_3$. The organic layer was dried over Na$_2$SO$_4$, filtered, and the filtrate was concentrated. The residue was dissolved into DCM and purified by silica gel chromatography (12 g flash column, EtOAc in hexane 0-50%, 15CV) to afford compound I-63. MS (ESI) [M+H]$^+$: m/z 406.

Compound I-63 was dissolved in MeOH (1910 μl) and acetic acid (200.0 μl, 3.49 mmol), and was then heated at 100° C. for 1 h. The mixture was diluted with MeOH, filtered and purified by mass guided reversed phase HPLC (ACN/water, TFA) to afford the title compound. MS (ESI) [M+H]$^+$: m/z 388. $^1$H NMR (600 MHz, DMSO-d6) δ 10.06 (s, 1H), 8.25 (s, 1H), 8.23 (s, 1H), 7.79 (s, 1H), 7.76 (dd, J=7.4, 4.6 Hz, 3H), 7.62 (dd, J=8.6, 5.0 Hz, 2H), 7.51-7.38 (m, 2H), 7.16 (t, J=8.8 Hz, 2H), 5.25 (d, J=6.6 Hz, 2H), 4.96 (d, J=6.6 Hz, 2H).

Examples 46-50 were prepared in a similar fashion as Example 45 using acid I-62 and 4-chlorophenylenediamine, pyridine-3,4-diamine, 4-fluorobenzene-1,2-diamine, 4,5-difluorobenzene-1,2-diamine, pyridine-2,3-diamine and 5-bromopyridine-2,3-diamine, respectively.

| Ex. # | Structure | Chemical Name | Mass [M + H]+ |
|---|---|---|---|
| 46 | <br> | 3-(4-(5-chloro-1H-benzo[d]imidazol-2-yl)phenyl)-N-(4-fluorophenyl)oxetane-3-carboxamide | 422 |

| Ex. # | Structure | Chemical Name | Mass [M + H]+ |
|---|---|---|---|
| 47 | 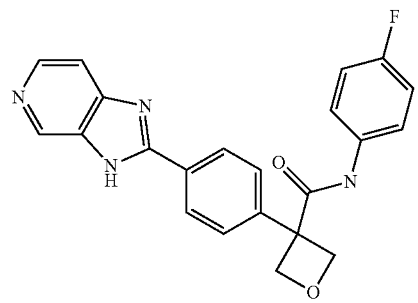 [SMILES: O=C(Nc1ccc(F)cc1)C1(c2ccc(-c3nc4ccncc4[nH]3)cc2)COC1] | 3-(4-(3H-imidazo[4,5-c]pyridin-2-yl)phenyl)-N-(4-fluorophenyl)-oxetane-3-carboxamide | 389 |
| 48 | 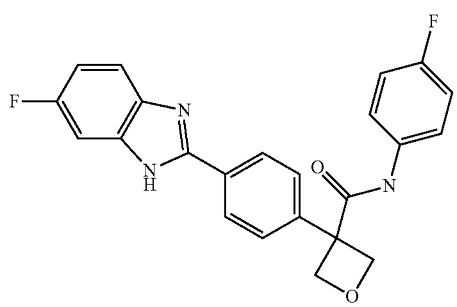 [SMILES: O=C(Nc1ccc(F)cc1)C1(c2ccc(-c3nc4ccc(F)cc4[nH]3)cc2)COC1] | 3-(4-(6-fluoro-1H-benzo[d]imidazol-2-yl)phenyl)-N-(4-fluorophenyl)oxetane-3-carboxamide | 389 |
| 49 | 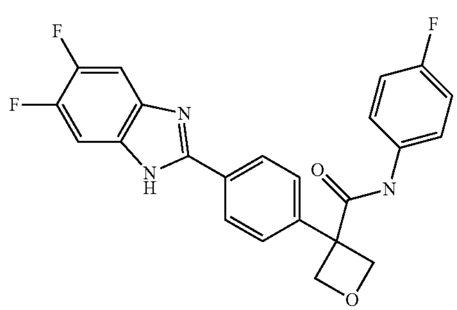 [SMILES: O=C(Nc1ccc(F)cc1)C1(c2ccc(-c3nc4cc(F)c(F)cc4[nH]3)cc2)COC1] | 3-(4-(5,6-difluoro-1H-benzo[d]imidazol-2-yl)phenyl)-N-(4-fluorophenyl)oxetane-3-carboxamide | 424 |
| 50 | 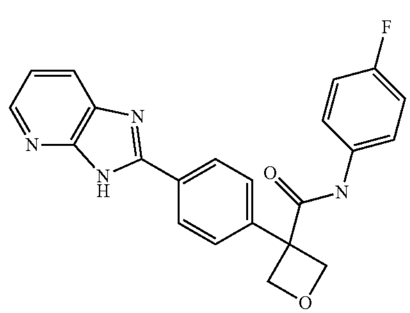 [SMILES: O=C(Nc1ccc(F)cc1)C1(c2ccc(-c3nc4cccnc4[nH]3)cc2)COC1] | 3-(4-(3H-imidazo[4,5-b]pyridin-2-yl)phenyl)-N-(4-fluorophenyl)oxetane-3-carboxamide | 389 |

Example 51: 3-(4-(6-Cyano-3H-imidazo[4,5-b]pyridin-2-yl)phenyl)-N-(4-fluorophenyl)oxetane-3-carboxamide

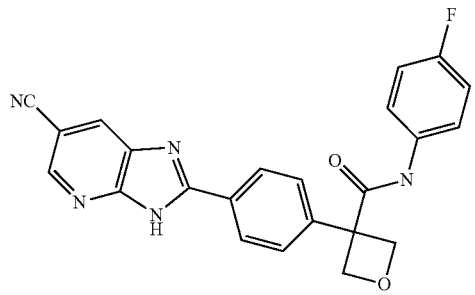 [SMILES: N#Cc1cnc2[nH]c(-c3ccc(C4(C(=O)Nc5ccc(F)cc5)COC4)cc3)nc2c1]

3-(4-(6-Bromo-3H-imidazo[4,5-b]pyridin-2-yl)phenyl)-N-(4-fluorophenyl)oxetane-3-carboxamide (prepared according to procedures described for Example 45) (70.0 mg, 0.150 mmol), zinc cyanide (42.2 mg, 0.360 mmol), zinc powder (7.05 mg, 0.108 mmol), $Pd_2(dba)_3$ (21.95 mg, 0.024 mmol) and DPPF (26.6 mg, 0.048 mmol) in N,N-dimethylacetamide (2.0 ml) was added to a microwave reaction vessel. The mixture was then irradiated at 130° C. for 60 min. The reaction mixture was cooled down then filtered through a Celite pad and concentrated. The crude material was purified by mass-directed reversed phase chromatography (ACN/water gradient with 0.1% TFA modifier) to afford the title compound. MS (ESI) [M+H]$^+$: m/z 414. $^1$H NMR (499 MHz, DMSO-d6) δ 10.05 (s, 1H), 8.77 (s, 1H), 8.61 (s, 1H), 8.32 (d, J=8.2 Hz, 2H), 7.71 (d, J=8.2 Hz, 2H), 7.63 (dd, J=8.7, 5.0 Hz, 2H), 7.16 (t, J=8.8 Hz, 2H), 5.24 (d, J=6.5 Hz, 2H), 4.94 (d, J=6.5 Hz, 2H).

Example 52: 3-(4-(6-Cyclopropylpyridin-3-ylphenyl)-N-(5-fluoropyridin-2-yl)oxetane-3-carboxamide

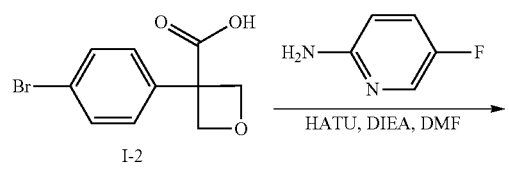

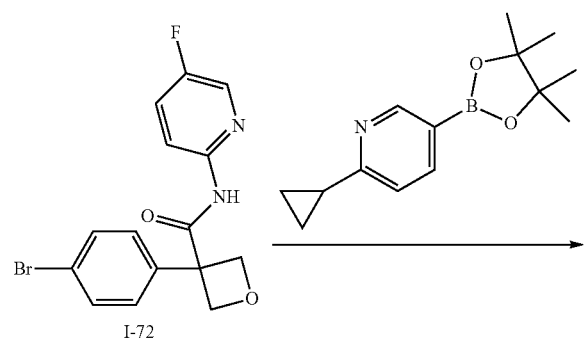

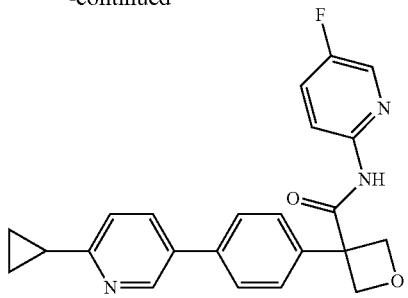

Step 1: 3-(4-bromophenyl)-N-(5-fluoropyridin-2-yl)oxetane-3-carboxamide

To a 100 mL vial was charged with a magnetic spin bar, 3-(4-bromophenyl)oxetane-3-carboxylic acid (1000.0 mg, 3.89 mmol) and DMF (10.0 ml). To this was added HATU (1775 mg, 4.67 mmol) at RT with stirring, and the reaction mixture was stirred for a few minutes. 5-Fluoropyridin-2-amine (436 mg, 3.89 mmol) and DIEA (2.038 ml, 11.67 mmol) were added, and the reaction mixture was stirred for 4 h at RT. The reaction mixture was diluted with ethyl acetate and washed with 1N aqueous HCl (3×), water, brine and sat. aq. NaHCO$_3$. The organic solution was then dried over Na$_2$SO$_4$, filtered, and the filtrate was concentrated. The crude product was purified in Biotage column DCM/EtOAc (10 to 100%) to afford compound I-72. MS (ESI) [M+H]$^+$: m/z 351.

Step 2: 3-(4-(6-Cyclopropylpyridin-3-yl)phenyl)-N-(5-fluoropyridin-2-yl)oxetane-3-carboxamide To a stirred suspension of compound I-72, (50.0 mg, 0.142 mmol) and 1,1'-bis(di-tert-butylphosphino)ferrocene palladium dichloride (11.68 mg, 0.013 mmol) in 1,4-dioxane (1.5 ml) was added sodium carbonate (0.142 ml, 0.285 mmol). The reaction mixture was evacuated and refilled with nitrogen three times and then heated to 80° C. for 4 h. The reaction mixture was cooled down to RT, filtered through a Celite pad and concentrated. The product was purified by mass-directed reverse phase chromatography (ACN/water gradient with 0.1% TFA modifier) to afford the title compound. MS (ESI) [M+H]$^+$: m/z 390. $^1$H NMR (499 MHz, DMSO-d6) δ 12.86 (s, 1H), 9.25 (s, 1H), 8.74 (s, 1H), 8.45 (t, J=7.3 Hz, 1H), 8.05 (d, J=7.6 Hz, 1H), 7.75 (d, J=8.3 Hz, 2H), 7.51 (d, J=8.3 Hz, 2H), 7.42 (dd, J=15.3, 6.3 Hz, 2H), 5.57 (d, J=15.0 Hz, 2H), 5.22 (d, J=15.0 Hz, 2H), 2.24-2.11 (m, 1H), 1.10-1.02 (m, 2H), 0.99 (s, 2H).

Example 53: 3-(4-(3-Cyclopropyl-1,2,4-oxadiazol-5-yl)phenyl)-N-(4-fluorophenyl)oxetane-3-carboxamide

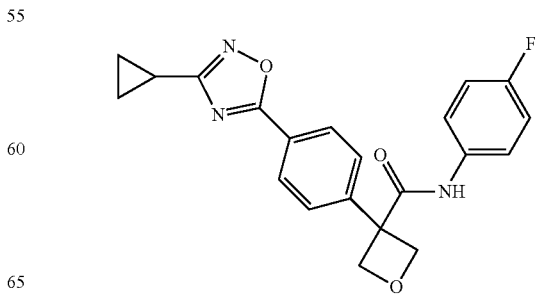

N, N'-carbonyldiimidazole (94 mg, 0.579 mmol)) was added to a stirred mixture of 4-(3-(4-fluorophenyl)carbamoyl)oxetan-3-yl)benzoic acid (I-62) (112.0 mg, 0.355 mmol) in DCM (2.0 ml), and the mixture was stirred at RT for 2 h. N'-hydroxycyclopropanecarboximidamide (89 mg, 0.888 mmol) was then added and the mixture was stirred at RT for another 2 h, concentrated, co-evaporated with toluene, redissolved in toluene (2 ml) and heated at 110° C. for 2 h. The mixture was cooled and quenched with water, and was extracted with ethyl acetate (3×). The combined organic fractions were washed with brine, dried over Na$_2$SO$_4$, filtered and the solvents were evaporated under reduced pressure. The crude material was purified by mass-directed reverse phase chromatography (ACN/water gradient with 0.1% TFA modifier) to afford the title compound. MS (ESI) [M+H]$^+$: m/z 380. $^1$H NMR (600 MHz, DMSO-d6) δ 10.06 (s, 1H), 8.10 (d, J=8.2 Hz, 2H), 7.71 (d, J=8.2 Hz, 2H), 7.60 (dd, J=8.6, 5.0 Hz, 2H), 7.15 (t, J=8.8 Hz, 2H), 5.23 (d, J=6.6 Hz, 2H), 4.90 (d, J=6.6 Hz, 2H), 2.19 (tt, J=8.4, 4.8 Hz, 1H), 1.20-1.06 (m, 2H), 1.06-0.91 (m, 2H).

Example 54: 3-(4-(4-Cyclopropyl-6-oxopyrimidin-1 (6H)-yl)phenyl)-N-(4-fluorophenyl)oxetane-3-carboxamide

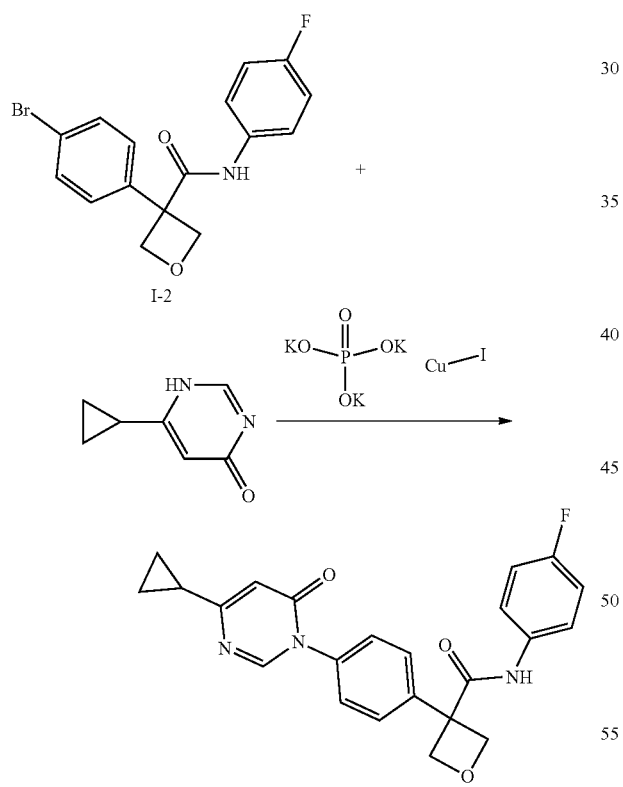

To a reaction vessel was charged with 6-cyclopropylpyrimidin-4(1H)-one (43.0 mg, 0.316 mmol), copper iodide (6.01 mg, 0.032 mmol), 3-(4-bromophenyl)-N-(4-fluorophenyl)oxetane-3-carboxamide (I-2) (111 mg, 0.316 mmol) and trans-N,N'-dimethylcyclohexane-1,2-diamine (8.98 mg, 0.063 mmol). This mixture was then evacuated and backfilled with nitrogen (3 times). Then dry, degassed 1,4-dioxane (1263 µl) was added and the mixture was then heated at 110° C. for 24 h. The crude material was purified by mass-directed reversed phase chromatography (ACN/water gradient with 0.1% TFA modifier) to afford the title compound. MS (ESI) [M+H]$^+$: m/z 406. $^1$H NMR (499 MHz, DMSO-d6) δ 10.05 (s, 1H), 8.33 (s, 1H), 7.63 (t, J=8.4 Hz, 4H), 7.49 (d, J=8.4 Hz, 2H), 7.15 (t, J=8.8 Hz, 2H), 6.44 (s, 1H), 5.23 (d, J=6.5 Hz, 2H), 4.91 (d, J=6.6 Hz, 2H), 3.36 (s, 2H), 1.95 (p, J=6.9 Hz, 1H), 1.05-0.71 (m, 2H).

Example 55: 3-(4-(4-Cyclopropyl-6-methyl-2-oxopyrimidin-1 (2H)-yl)phenyl)-N-(4-fluorophenyl)oxetane-3-carboxamide

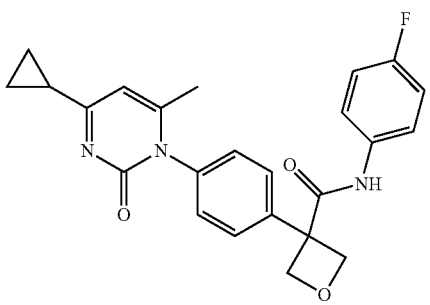 [SMILES: Cc1cc(C2CC2)nc(=O)n1-c1ccc(C2(C(=O)Nc3ccc(F)cc3)COC2)cc1]

Example 55 was prepared in an analogous manner to Example 54. MS (ESI) [M+H]$^+$: m/z 420. $^1$H NMR (499 MHz, DMSO-d6) δ 9.96 (s, 1H), 7.79 (d, J=8.3 Hz, 2H), 7.60 (dd, J=8.8, 5.0 Hz, 2H), 7.29 (d, J=8.3 Hz, 3H), 7.15 (t, J=8.8 Hz, 2H), 5.17 (d, J=6.5 Hz, 2H), 4.82 (d, J=6.5 Hz, 2H), 3.37 (s, 4H), 2.50 (s, 3H), 2.08 (s, 1H).

Example 56: N-(4-fluorophenyl)-1-(6-(2-phenyloxazol-4-yl)pyridin-3-yl)cyclobutane-1-carboxamide

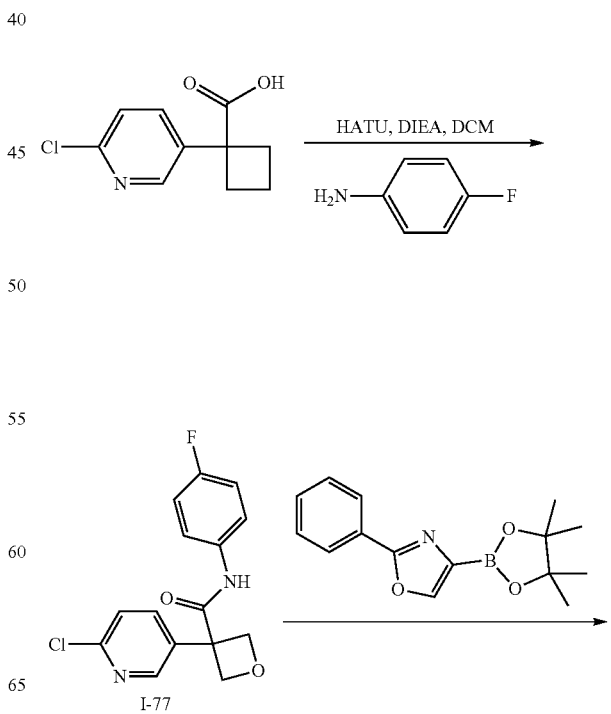

81

-continued

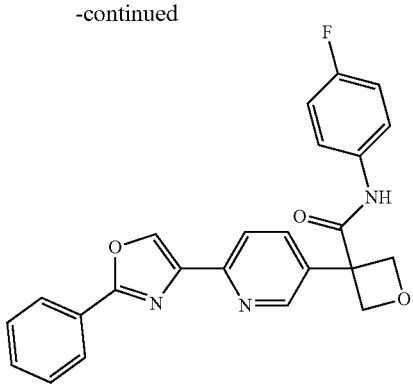

Step 1: Synthesis of 1-(6-chloropyridin-3-yl)-N-(4-fluorophenyl)cyclobutane-1-carboxamide (I-77)

To a 100 mL vial was charged with a magnetic spin bar, 1-(6-chloropyridin-3-yl)cyclobutanecarboxylic acid (715.0 mg, 3.38 mmol) in DCM (20.0 ml). HATU (1541 mg, 4.05 mmol) was added with stirring and the reaction mixture was stirred for a few minutes. 4-Fluoroaniline (375 mg, 3.38 mmol) and DIEA (1.770 ml, 10.13 mmol) were added, and the reaction mixture was stirred for 4 h at RT. The reaction was diluted with ethyl acetate and washed with 1N HCl (2×), water, brine and sat. aq. NaHCO$_3$. The organic layer was then dried over Na$_2$SO$_4$, filtered, and concentrated. The crude product was purified by Biotage silica column using DCM/EtOAc (10 to 100%) as eluents to afford compound I-77. MS (ESI) [M+H]$^+$: m/z 305.

Step 2: N-(4-Fluorophenyl)-1-(6-(2-phenyloxazol-4-yl)pyridin-3-yl)cyclobutane-1-carboxamide Compound I-77 (50 mg, 0.164 mmol), palladium(II) acetate/1,1'-bis(di-tert-butylphosphino)ferrocene/potassium phosphate admixture (13.46 mg, 0.015 mmol) were dissolved in 1,4-dioxane (1.5 ml) in a 20 mL round bottom flask. Sodium carbonate (0.164 ml, 0.328 mmol) was added and the reaction mixture was evacuated and refilled with nitrogen 3 times and heated at 80° C. for 12 h. The reaction mixture was cooled down then filtered through a Celite pad. The crude material was purified by mass-directed reversed phase chromatography (ACN/water gradient with 0.1% TFA modifier) to afford the title compound. MS (ESI) [M+H]$^+$: m/z 414.

Example 57-63 in the following table were prepared in a similar fashion to Example 56 using the respective boronates.

| Ex. # | Structure | Chemical Name | Mass [M + H]+ |
|---|---|---|---|
| 57 | 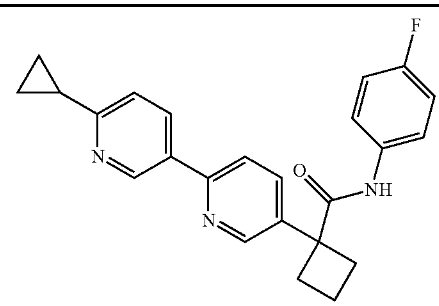 | 1-(6'-cyclopropyl-[2,3'-bipyridin]-5-yl)-N-(4-fluorophenyl)cyclobutane-1-carboxamide | 388 |
| 58 | 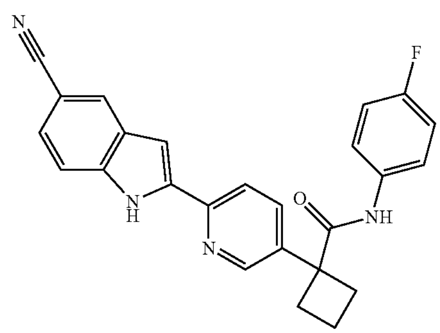 [SMILES: N#Cc1ccc2[nH]c(-c3ccc(C4(C(=O)Nc5ccc(F)cc5)CCC4)cn3)cc2c1] | 1-(6-(5-cyano-1H-indol-2-yl)pyridin-3-yl)-N-(4-fluorophenyl)cyclobutane-1-carboxamide | 411 |
| 59 | 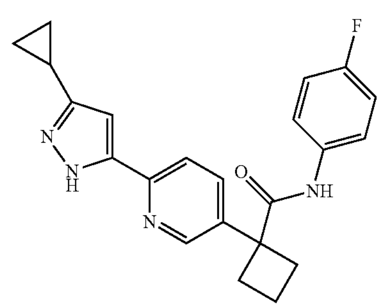 [SMILES: O=C(Nc1ccc(F)cc1)C1(c2ccc(-c3cc(C4CC4)n[nH]3)nc2)CCC1] | 1-(6-(3-cyclopropyl-1H-pyrazol-5-yl)pyridin-3-yl)-N-(4-fluorophenyl)cyclobutane-1-carboxamide | 377 |

| Ex. # | Structure | Chemical Name | Mass [M + H]+ |
|---|---|---|---|
| 60 | 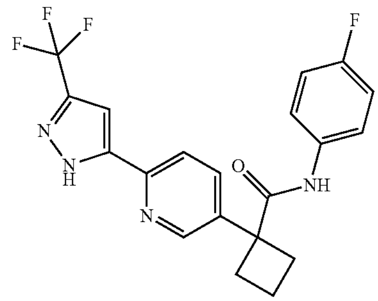 [SMILES: O=C(Nc1ccc(F)cc1)C1(c2ccc(-c3cc(C(F)(F)F)n[nH]3)nc2)CCC1] | N-(4-fluorophenyl)-1-(6-(3-(trifluoromethyl)-1H-pyrazol-5-yl)pyridin-3-yl)cyclobutane-1-carboxamide | 405 |
| 61 | 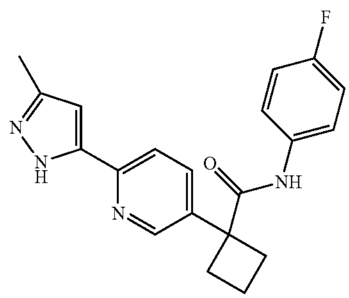 [SMILES: Cc1cc(-c2ccc(C3(C(=O)Nc4ccc(F)cc4)CCC3)cn2)[nH]n1] | N-(4-fluorophenyl)-1-(6-(3-methyl-1H-pyrazol-5-yl)pyridin-3-yl)cyclobutane-1-carboxamide | 351 |
| 62 | 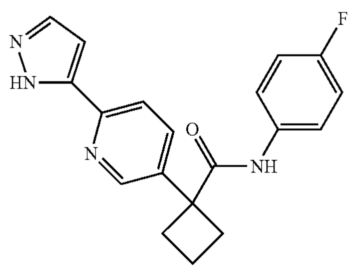 [SMILES: O=C(Nc1ccc(F)cc1)C1(c2ccc(-c3ccn[nH]3)nc2)CCC1] | 1-(6-(1H-pyrazol-5-yl)pyridin-3-yl)-N-(4-fluorophenyl)cyclobutane-1-carboxamide | 337 |
| 63 | 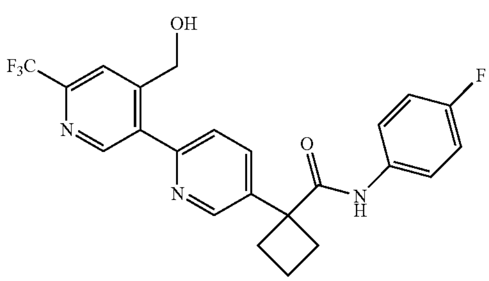 [SMILES: O=C(Nc1ccc(F)cc1)C1(c2ccc(-c3cnc(C(F)(F)F)cc3CO)nc2)CCC1] | N-(4-fluorophenyl)- 1-(4'-(hydroxymethyl)-6'-(trifluoromethyl)-[2,3'-bipyridin]-5-yl) cyclobutane-1-carboxamide | 446 |

Example 64: 1-(4-(4-Cyclopropyl-1H-pyrazol-1-yl)phenyl)-N-propylcyclobutane-1-carboxamide

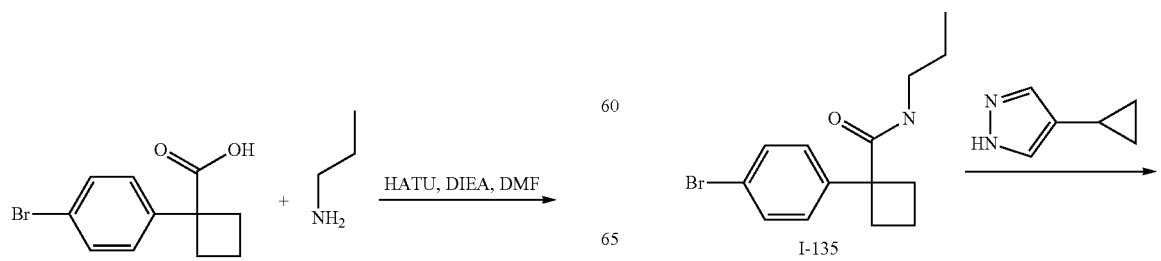

-continued

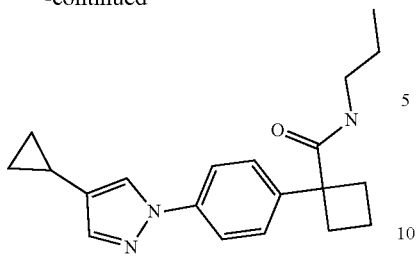

Step 1: Synthesis of 1-(4-bromophenyl)-N-propyl-cyclobutane-1-carboxamide (I-135)

To a 20 mL vial was charged with a magnetic stir bar, 1-(4-bromophenyl)cyclobutanecarboxylic acid (800.0 mg, 3.14 mmol) in DMF (4.0 ml) was added with stirring HATU (1431 mg, 3.76 mmol) and the reaction mixture was stirred for a few minutes. Propan-1-amine (185 mg, 3.14 mmol) and DIEA (1.643 ml, 9.41 mmol) were then added and the mixture was stirred for 4 h at RT. The reaction was diluted with ethyl acetate and washed with 1N aq. HCl (3×), water, brine and saturated aqueous $NaHCO_3$. The solution was then dried over $Na_2SO_4$, filtered, and concentrated. The residue was purified by chromatography (Isco CombiFlash system, using 48 g RediSep silica gel gold column, 10-100% EtOAc/Hex as eluent) to afford compound I-135. MS (ESI) [M+H]+: m/z 296.

Step 2: Synthesis of 1-(4-(4-cyclopropyl-1H-pyrazol-1-yl)phenyl)-N-propylcyclobutane-1-carboxamid To a 20 ml vial, compound I-135 (25.0 mg, 0.084 mmol) and copper iodide (1.607 mg, 8.44 µmol) were added followed by 4-cyclopropyl-1H-pyrazole (9.13 mg, 0.084 mmol) and trans-N,N'-dimethylcyclohexane-1,2-diamine (2.401 mg, 0.017 mmol). This mixture was then evacuated and backfilled with nitrogen (3 times). Then dry, degassed 1,2-dioxane (338 µl) was added. The mixture was heated at 110° C. for 24 h and cooled to RT. The crude material was purified by mass-directed reversed phase chromatography (ACN/water gradient with 0.1% TFA modifier) to afford the title compound. MS (ESI) [M+H]+: m/z 324. $^1$H NMR (600 MHz, DMSO-d6) δ 8.22 (s, 1H), 7.70 (d, J=8.4 Hz, 2H), 7.59 (q, J=6.1, 5.5 Hz, 1H), 7.51 (d, J=18.9 Hz, 1H), 7.39 (d, J=8.4 Hz, 2H), 2.96 (p, J=7.0 Hz, 2H), 2.77-2.62 (m, 2H), 2.33 (dq, J=19.2, 10.1, 9.3 Hz, 2H), 1.86-1.68 (m, 3H), 1.32 (p, J=7.1 Hz, 2H), 0.86 (t, J=6.2 Hz, 2H), 0.70 (t, J=7.3 Hz, 3H), 0.58 (d, J=4.0 Hz, 2H).

Example 65: 1-(4-(2-(4-Fluorophenyl)oxazol-4-yl)phenyl)-N-propylcyclobutane-1-carboxamide

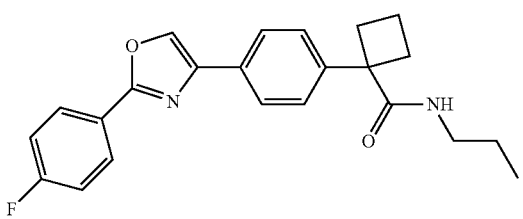 [SMILES: CCCNC(=O)C1(c2ccc(-c3coc(-c4ccc(F)cc4)n3)cc2)CCC1]

The title compound was prepared from bromo intermediate I-98 and (2-(4-fluorophenyl)oxazol-4-yl)boronic acid under the standard Suzuki coupling conditions. MS (ESI) [M+H]+: m/z 279.

Example 66: 1-(4-(6-Cyclopropylpyridin-3-yl)phenyl)-N-propylcyclobutane-1-carboxamide

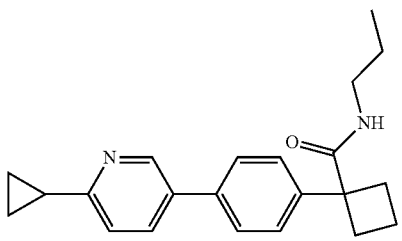 [SMILES: CCCNC(=O)C1(c2ccc(-c3ccc(C4CC4)nc3)cc2)CCC1]

This compound was prepared in a manner analogous to the synthesis of Example 64 except (6-cyclopropylpyridin-3-yl)boronic acid was used. MS (ESI) [M+H]+: m/z 335.

Example 67: 1-(4-(6-(4-Fluorophenyl)pyridin-3-yl)phenyl)-N-propylcyclobutane-1-carboxamide

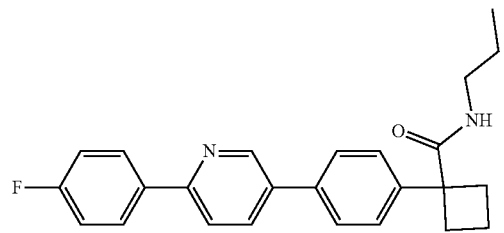 [SMILES: CCCNC(=O)C1(c2ccc(-c3ccc(-c4ccc(F)cc4)nc3)cc2)CCC1]

This compound was prepared in a manner analogous to synthesis of Example 64 except (6-(4-fluorophenyl)pyridin-3-yl)boronic acid was used. MS (ESI) [M+H]+: m/z 389.

Example 68: 1-(4-(6-Cyclopropylpyridin-3-yl)phenyl)-N-(5-fluoropyridin-2-yl)cyclobutane-1-carboxamide

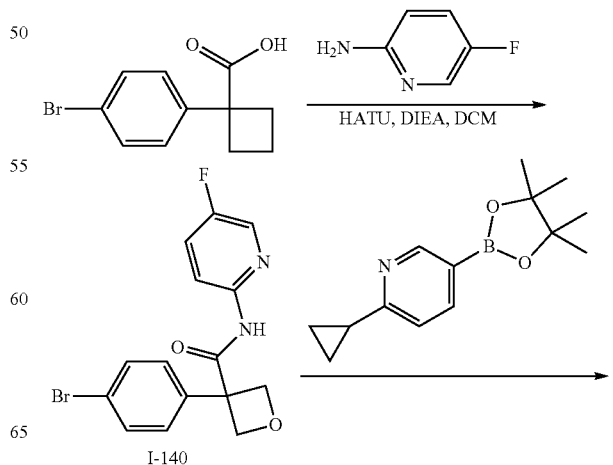

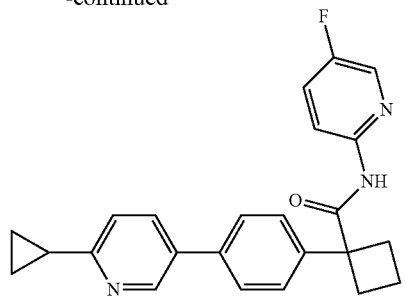

Step 1: 1-(4-bromophenyl)-N-(5-fluoropyridin-2-yl) cyclobutane-1-carboxamide (I-140)

To a 100 mL vial was charged with a magnetic spin bar, 1-(4-bromophenyl)cyclobutanecarboxylic acid (1000.0 mg, 3.92 mmol) in DMF (10.0 ml) was added with stirring HATU (1789 mg, 4.70 mmol), and the mixture was stirred for a few minutes. 5-Fluoropyridin-2-amine (439 mg, 3.92 mmol), DIEA (2.054 ml, 11.76 mmol) were added and the reaction mixture was stirred for 4 h at RT. The reaction was worked up as usual and the crude was purified by chromatography (Isco CombiFlash system, using 48 g RediSep silica gel gold column, 10-100% EtOAc/Hex as eluent) to afford compound I-140. MS (ESI) [M+H]$^+$: m/z 349.

Step 2: 1-(4-(6-cyclopropylpyridin-3-yl)phenyl)-N-(5-fluoropyridin-2-yl)cyclobutane-1-carboxamide A mixture of 2-cyclopropyl-5-(4,4,5,5-tetramethyl-1,3,2-dioxaborolan-2-yl)pyridine (42.1 mg, 0.172 mmol), compound I-140 (60.0 mg, 0.172 mmol) and 1,1'-bis(di-tert-butylphosphino)ferrocene palladium dichloride (14.09 mg, 0.015 mmol) and sodium carbonate (0.172 ml, 0.344 mmol) in 1,4-dioxane (1.5 ml) was subjected to the usual Suzuki coupling conditions. The crude material was purified by mass-directed reversed phase chromatography (ACN/water gradient with 0.1% TFA modifier) to afford the title compound. MS (ESI) [M+H]$^+$: m/z 388. $^1$H NMR (499 MHz, DMSO-d6) δ 10.19 (s, 1H), 8.82 (s, 2H), 8.29 (d, J=2.7 Hz, 1H), 8.08 (dd, J=9.2, 4.0 Hz, 1H), 7.74 (d, J=8.0 Hz, 2H), 7.64 (d, J=8.1 Hz, 2H), 7.52 (d, J=8.3 Hz, 2H), 2.89 (q, J=8.6 Hz, 2H), 2.25 (s, 2H), 1.83 (dt, J=22.2, 8.5 Hz, 3H), 1.24-1.10 (m, 2H), 1.07 (s, 2H).

Example 69: 1-(4-(6-Cyclopropyl-4-fluoropyridin-3-yl)phenyl)-N-(5-fluoropyridin-2-yl)cyclobutane-1-carboxamide

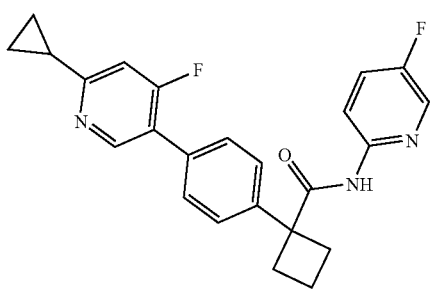 [SMILES: O=C(Nc1ccc(F)cn1)C1(c2ccc(-c3cnc(C4CC4)cc3F)cc2)CCC1]

This compound was prepared in a manner analogous to the synthesis of Example 68 except 2-cyclopropyl-4-fluoro-5-(4,4,5,5-tetramethyl-1,3,2-dioxaborolan-2-yl)pyridine was used. MS (ESI) [M+H]$^+$: m/z 406. $^1$H NMR (499 MHz, DMSO-d6) δ 10.20 (s, 1H), 8.59 (d, J=10.5 Hz, 1H), 8.29 (d, J=2.7 Hz, 1H), 8.09 (dd, J=9.2, 4.0 Hz, 1H), 7.76-7.68 (m, 1H), 7.63 (d, J=8.2 Hz, 2H), 7.57 (d, J=7.9 Hz, 2H), 7.40 (d, J=11.7 Hz, 1H), 2.88 (q, J=8.6 Hz, 2H), 2.20 (d, J=4.8 Hz, 2H), 1.84 (dt, J=16.3, 8.4 Hz, 3H), 1.05 (d, J=7.9 Hz, 2H), 1.02 (s, 2H).

Example 70: 1-(4-(6-Cyclopropyl-4-methylpyridin-3-yl)phenyl)-N-(5-fluoropyridin-2-yl)cyclobutane-1-carboxamide

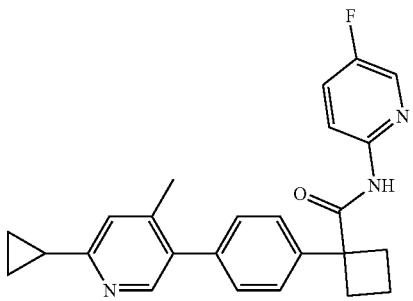 [SMILES: Cc1cc(C2CC2)ncc1-c1ccc(C2(C(=O)Nc3ccc(F)cn3)CCC2)cc1]

This compound was prepared in a manner analogous to the synthesis of Example 68 except 2-cyclopropyl-4-methyl-5-(4,4,5,5-tetramethyl-1,3,2-dioxaborolan-2-yl)pyridine was used. MS (ESI) [M+H]$^+$: m/z 402. $^1$H NMR (499 MHz, DMSO-d6) δ 10.25 (s, 1H), 8.45 (s, 1H), 8.30 (d, J=2.8 Hz, 1H), 8.10 (dd, J=9.2, 4.1 Hz, 1H), 7.73 (td, J=8.8, 2.9 Hz, 1H), 7.64 (d, J=8.1 Hz, 2H), 7.50 (s, 1H), 7.45 (d, J=8.0 Hz, 2H), 2.99-2.72 (m, 3H), 2.37 (s, 3H), 2.28-2.19 (m, 1H), 1.84 (dt, J=18.4, 8.5 Hz, 3H), 1.31-1.18 (m, 2H), 1.11 (s, 2H).

Example 71: 1-(4-(6,7-Difluoro-1H-benzo[d]imidazol-2-yl)phenyl)-N-(5-fluoropyridin-2-yl)cyclobutane-1-carboxamide

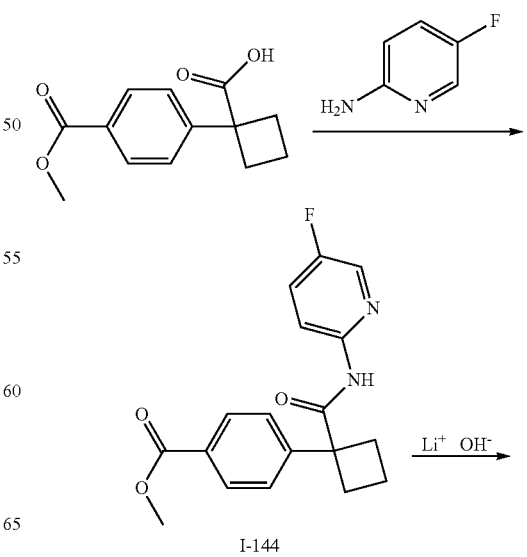

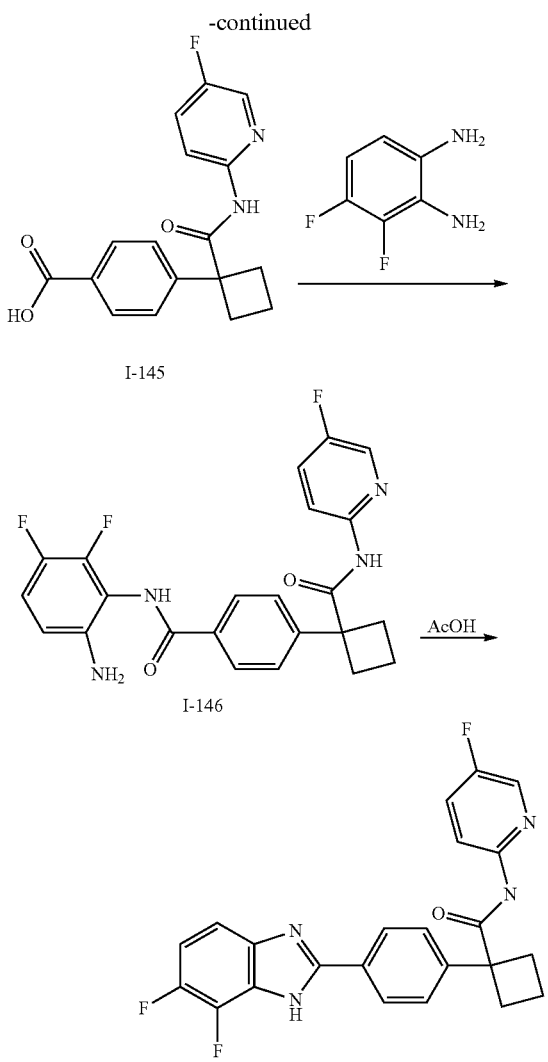

adding HCl (1N) then extracted with DCM 3 times. The organic phases were combined, washed with brine, dried and concentrated to afford compound I-145. MS (ESI) [M+H]⁺: m/z 315.

Step 3: Synthesis of N-(6-amino-2,3-difluorophenyl)-4-(1-((5-fluoropyridin-2-yl)carbamoyl)cyclobutyl)-benzamide (I-146)

To a 20 mL vial was charged with compound I-145 (30.0 mg, 0.095 mmol) in DMF (1.0 ml) then HATU (43.6 mg, 0.115 mmol) was added with stirring. After a few minutes 1,2-diamino-3,4-difluorobenzene (13.76 mg, 0.095 mmol) and DIEA (0.100 ml, 0.573 mmol) were added and the reaction mixture was stirred for 4 h at RT. The reaction was diluted with ethyl acetate and washed with 1 N (3×). The organic layer was concentrated and the residue was purified by chromatography (Isco CombiFlash system, using 12 g RediSep silica gel gold column, and 0-20% MeOH/DCM as eluent) to afford compound I-146. MS (ESI) [M+H]⁺: m/z 441.

Step 4: 1-(4-(6,7-Difluoro-1H-benzo[d]imidazol-2-yl)phenyl)-N-(5-fluoropyridin-2-yl)cyclobutane-1-carboxamide A solution of compound I-146 (17.0 mg, 0.039 mmol) in AcOH (1.5 ml) was heated at 150° C. in a microwave oven for 30 min. The mixture was evaporated under reduced pressure. The crude material was purified by mass-directed reversed phase chromatography (ACN/water gradient with 0.1% TFA modifier) to afford the title compound. MS (ESI) [M+H]⁺: m/z 423. ¹H NMR (499 MHz, DMSO-d6) δ 10.24 (s, 1H), 8.29 (d, J=2.7 Hz, 1H), 8.18 (d, J=8.2 Hz, 3H), 8.09 (dd, J=9.2, 4.0 Hz, 1H), 7.73 (dd, J=8.6, 2.6 Hz, 1H), 7.69 (d, J=8.3 Hz, 3H), 7.37 (dd, J=8.6, 3.1 Hz, 1H), 7.31-7.17 (m, 1H), 2.90 (dt, J=14.6, 8.6 Hz, 2H), 2.59-2.53 (m, 2H), 1.86 (dt, J=14.8, 7.4 Hz, 2H).

Example 72: 1-(4-(7-Fluoro-1H-benzo[d]imidazol-2-yl)phenyl)-N-(5-fluoropyridin-2-yl)cyclobutane-1-carboxamide Step 1: methyl 4-(1-((5-fluoropyridin-2-yl)carbamoyl)cyclobutyl)benzoate (I-144)

1-(4-(Methoxycarbonyl)phenyl)cyclobutanecarboxylic acid (2000.0 mg, 8.54 mmol) and oxalyl chloride (0.747 ml, 8.54 mmol) were stirred in DCM (10.0 ml), to it was added DMF (0.2 ml). The reaction mixture was stirred at RT for 4 h and was concentrated in vacuo and left overnight in lyophilizer. Then a mixture of 2-amino-5-fluoropyridine (957 mg, 8.54 mmol) in pyridine (10.0 ml) was added to the crude and the mixture was cooled to 0° C. The mixture was slowly warmed up to RT and stirred overnight, concentrated in vacuo and the crude was purified in biotage (SiO₂, CH₂Cl₂/MeOH; 0-10%) to afford compound I-144. MS (ESI) [M+H]⁺: m/z 329.

Step 2: 4-(1-((5-fluoropyridin-2-yl)carbamoyl)cyclobutyl)benzoic acid (I-145)

To a vial containing compound I-144 (1000.0 mg, 3.05 mmol) in tetrahydrofuran (4.0 ml) and MeOH (1.333 ml) was added LiOH in water (6.09 ml, 12.18 mmol) and the mixture was stirred at RT for 24 h. The organic solvents were evaporated and the aqueous layer was acidified to pH~3 by

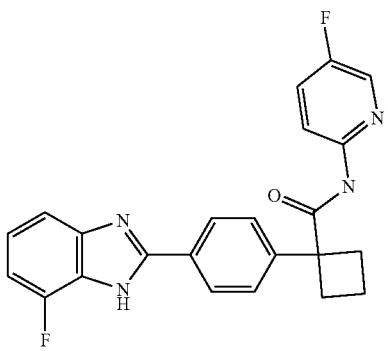 [SMILES: O=C(Nc1ccc(F)cn1)C1(c2ccc(-c3nc4cccc(F)c4[nH]3)cc2)CCC1]

The title compound was prepared in a manner analogous to the synthesis of Example 71 except 3-fluorobenzene-1,2-diamine was used. MS (ESI) [M+H]⁺: m/z 405. ¹H NMR (499 MHz, DMSO-d6) δ 10.26 (s, 1H), 8.29 (d, J=2.7 Hz, 1H), 8.16 (d, J=8.3 Hz, 2H), 8.09 (dd, J=9.2, 4.0 Hz, 1H), 7.78-7.66 (m, 4H), 7.54 (d, J=8.9 Hz, 1H), 7.23 (t, J=9.2 Hz, 1H), 2.92 (dt, J=14.6, 8.6 Hz, 2H), 2.60-2.53 (m, 2H), 1.98-1.78 (m, 2H).

Example 73: 1-(4-(5-Cyano-1H-benzo[d]imidazol-2-yl)phenyl)-N-(5-fluoropyridin-2-yl)cyclobutane-1-carboxamide

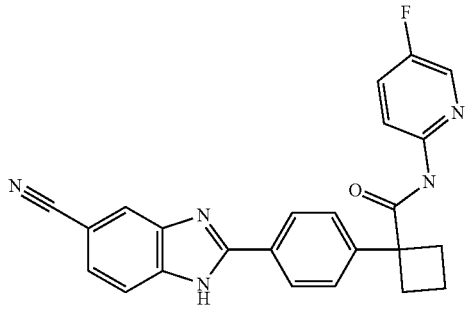 [SMILES: N#Cc1ccc2[nH]c(-c3ccc(C4(C(=O)Nc5ccc(F)cn5)CCC4)cc3)nc2c1]

The title compound was prepared in a manner analogous to the synthesis of Example 71 except 3,4-diaminobenzonitrile was used. MS (ESI) [M+H]+: m/z 412. $^1$H NMR (499 MHz, DMSO-d6) δ 10.25 (s, 1H), 8.29 (d, J=2.7 Hz, 1H), 8.20 (d, J=8.2 Hz, 2H), 8.16 (s, 1H), 8.09 (dd, J=9.2, 4.0 Hz, 1H), 7.76 (d, J=8.3 Hz, 1H), 7.71 (d, J=8.3 Hz, 3H), 7.62 (d, J=8.3 Hz, 1H), 2.91 (dt, J=14.6, 8.6 Hz, 2H), 2.59-2.52 (m, 2H), 1.86 (dt, J=17.4, 8.6 Hz, 2H).

Example 74: 1-(4-(4,7-Difluoro-1H-benzo[d]imidazol-2-yl)phenyl)-N-(5-fluoropyridin-2-yl)cyclobutane-1-carboxamide

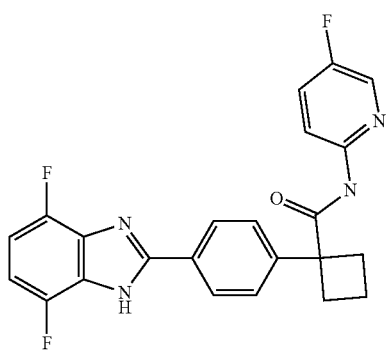 [SMILES: O=C(Nc1ccc(F)cn1)C1(c2ccc(-c3nc4c(F)ccc(F)c4[nH]3)cc2)CCC1]

The title compound was prepared in a manner analogous to the synthesis of Example 71 except 3,6-difluorobenzene-1,2-diamine was used. MS (ESI) [M+H]+: m/z 423. $^1$H NMR (499 MHz, DMSO-d6) δ 10.25 (s, 1H), 8.29 (d, J=2.7 Hz, 1H), 8.24 (d, J=8.2 Hz, 2H), 8.09 (dd, J=9.2, 4.0 Hz, 1H), 7.73 (dd, J=8.6, 2.7 Hz, 1H), 7.69 (d, J=8.3 Hz, 2H), 7.08-7.00 (m, 2H), 2.91 (dt, J=14.7, 8.6 Hz, 2H), 2.59-2.52 (m, 2H), 1.86 (dt, J=17.2, 8.6 Hz, 2H).

Example 75: 1-(4-(4,4-Difluoro-3a,4,5,6,7,7a-hexahydro-1H-benzo[d]imidazol-2-yl)phenyl)-N-(5-fluoropyridin-2-yl)cyclobutane-1-carboxamide

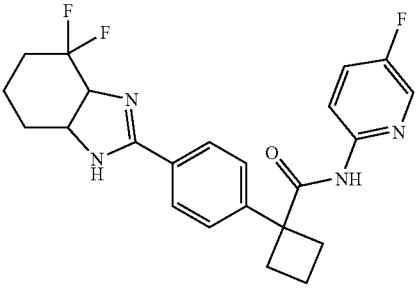 [SMILES: O=C(Nc1ccc(F)cn1)C1(c2ccc(C3=NC4C(CCCC4(F)F)N3)cc2)CCC1]

The title compound was prepared in a manner analogous to the synthesis of Example 71 except (1R,2R)-3,3-difluorocyclohexane-1,2-diamine was used. MS (ESI) [M+H]+: m/z 429. $^1$H NMR (499 MHz, DMSO-d6) δ 11.12 (s, 1H), 11.01 (s, 1H), 10.32 (s, 1H), 8.30 (d, J=2.8 Hz, 1H), 8.11-7.97 (m, 3H), 7.80 (d, J=8.3 Hz, 1H), 7.73 (td, J=8.8, 2.9 Hz, 1H), 4.71 (s, 2H), 3.19-2.72 (m, 2H), 2.55 (d, J=8.6 Hz, 2H), 2.24-2.07 (m, 1H), 1.97-1.85 (m, 3H), 1.85-1.58 (m, 4H).

Example 76: N-(4-Fluorophenyl)-3-(4'-(hydroxymethyl)-6'-(trifluoromethyl)-[3,3'-bipyridin]-6-yl)oxetane-3-carboxamide

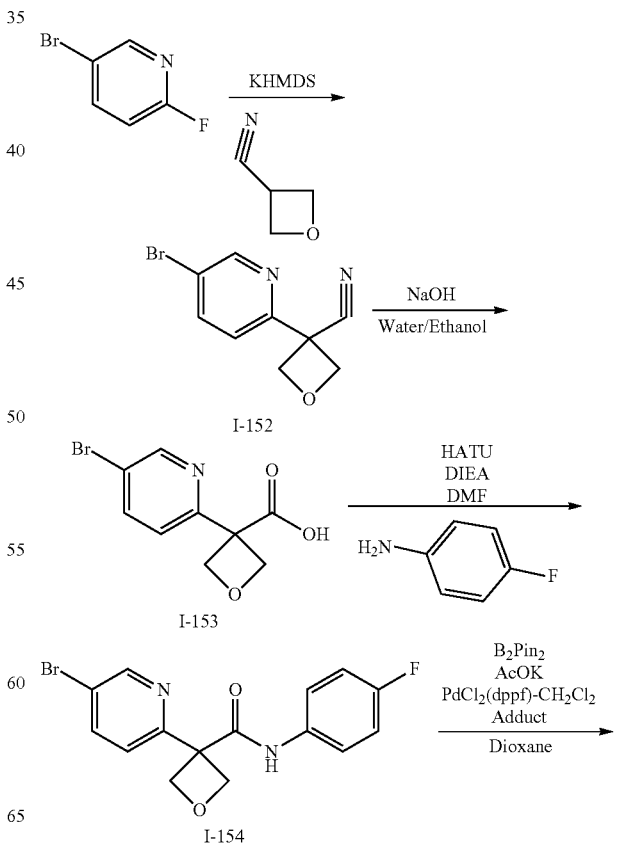

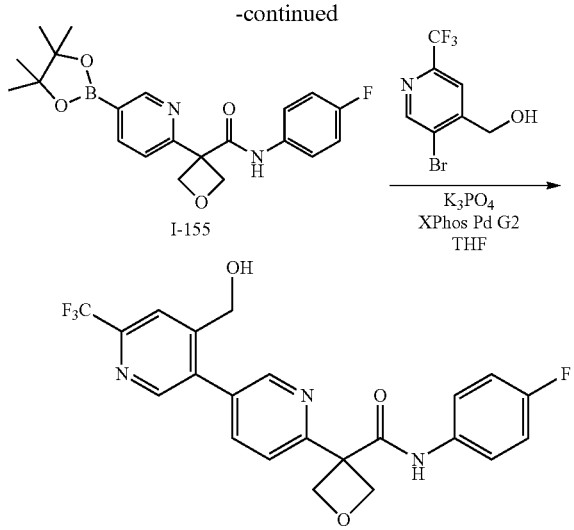

Step 1: 3-(5-bromopyridin-2-yl)oxetane-3-carbonitrile (I-152)

To a vial equipped with a stir bar was added 5-bromo-2-fluoropyridine (58.5 µl, 0.568 mmol), oxetane-3-carbonitrile (47.2 µl, 0.625 mmol) and toluene (2840 µl). The reaction mixture was cooled to 0° C. while stirring under nitrogen. KHMDS 1.0 M in THF (682 µl, 0.682 mmol) was slowly added to the stirring reaction mixture. After 5 min the reaction was quenched with MeOH (~5 ml). The crude reaction mixture was filtered over a Celite pad which was rinsed with ethyl acetate. The reaction mixture was concentrated under reduced pressure. The residue was purified by silica gel column chromatography (0-100% EtOAc/hexanes). Desired product was eluted and fractions were collected and concentrated under reduced pressure to afford compound I-152. MS (ESI) [M+H]$^+$: m/z 239.

Step 2: Preparation of 3-(5-bromopyridin-2-yl)oxetane-3-carboxylic acid (I-153)

To a vial equipped with a stir bar was added compound I-152 (190 mg, 0.795 mmol), NaOH (127 mg, 3.18 mmol), ethanol (2660 µl) and water (1310 µl). The vial was sealed and heated to 80° C. for 20 h. After 20 h the crude reaction mixture was concentrated under reduced pressure. The residue was dissolved in EtOAc, and the pH was adjusted to ~2 by adding 1N HCl dropwise. The mixture was washed with water. The combined organics were dried over MgSO$_4$, filtered, and concentrated under reduced pressure to afford compound I-153. MS (ESI) [M+H]$^+$: m/z 258.

Step 3: Preparation of 3-(5-bromopyridin-2-yl)-N-(4-fluorophenyl)oxetane-3-carboxamide (I-154)

To a vial equipped with a stir bar was added compound I-153 (127 mg, 0.493 mmol), HATU (281 mg, 0.739 mmol) and DMF (4930 µl). 4-Fluoroaniline (56.0 µl, 0.591 mmol) was added, followed by DIEA (258 µl, 1.48 mmol). The reaction mixture was stirred at RT for 21 h. After 21 h the crude reaction mixture was diluted with ethyl acetate and washed with sat. NaHCO$_3$, and the aqueous layer was extracted with ethyl acetate. The combined organics were dried over MgSO$_4$, filtered, and concentrated under reduced pressure. The residue was purified by silica gel column chromatography (0-100% EtOAc/hexanes) to afford compound I-154. MS (ESI) [M+H]$^+$: m/z 351.

Step 4: Preparation of N-(4-fluorophenyl)-3-(5-(4,4,5,5-tetramethyl-1,3,2-dioxaborolan-2-yl)pyridin-2-yl)oxetane-3-carboxamide (I-155)

To a vial equipped with a stir bar was added compound I-154 (113 mg, 0.320 mmol), bis(pinacolato)diboron (203 mg, 0.801 mmol), potassium acetate (94 mg, 0.961 mmol), and PdCl$_2$(dppf)-CH$_2$Cl$_2$ Adduct (26.2 mg, 0.032 mmol) in dioxane (1600 µl). The vial was purged with nitrogen for 5 min, and was then sealed and heated to 80° C. for 23 h. The crude reaction mixture was filtered over a Celite pad which was rinsed with ethyl acetate. The combined organics were concentrated under reduced pressure. The residue was diluted with ethyl acetate and water, and extracted with ethyl acetate. The combined organics were dried over MgSO$_4$, filtered, and concentrated under reduced pressure. The residue was dissolved in ACN/water, and dried on the lyophilizer overnight to afford compound I-155. MS (ESI) [M+H]$^+$: m/z calc'd: 399; found 317 (mass of boronic acid).

Step 5: N-(4-Fluorophenyl)-3-(4'-(hydroxymethyl)-6'-(trifluoromethyl)-[3,3'-bipyridin]-6-yl)oxetane-3-carboxamide To a vial equipped with a stir bar was added compound I-155 (17 mg, 0.043 mmol), (5-bromo-2-(trifluoromethyl)pyridin-4-yl)methanol (10.9 mg, 0.043 mmol), chloro(2-dicyclohexylphosphino-2',4',6'-tri-I-propyl-1,1'-biphenyl)(2'-amino-1,1'-biphenyl-2-yl) palladium(II) (3.36 mg, 4.27 µmol), potassium phosphate tribasic (aq. 1M solution) (85 µl, 0.085 mmol) and THF (427 µl). The vial was purged with nitrogen, sealed, and heated to 40° C. for 1 h. After 1 h the crude reaction mixture was filtered over a Celite pad which was rinsed with ethyl acetate. The reaction mixture was concentrated under reduced pressure and the residue was diluted with ethyl acetate, and washed with sat. NaCl. The organics were dried over MgSO$_4$, filtered, and concentrated under reduced pressure. The residue was purified by silica gel column chromatography (0-100% EtOAc/hexanes) to afford the title compound. MS (ESI) [M+H]$^+$: m/z 448. $^1$H NMR (600 MHz, DMSO-d6) δ 10.15 (s, 1H), 8.80 (s, 1H), 8.72 (s, 1H), 8.12-8.03 (m, 2H), 7.75-7.69 (m, 3H), 7.21 (t, J=8.6 Hz, 2H), 5.76 (t, J=5.2 Hz, 1H), 5.22 (d, J=6.3 Hz, 2H), 5.08 (d, J=6.2 Hz, 2H), 4.62 (d, J=5.2 Hz, 2H).

Example 77: 3-(6'-(Difluoromethoxy)-4'-(hydroxymethyl)-[3,3'-bipyridin]-6-yl)-N-(4-fluorophenyl)oxetane-3-carboxamide

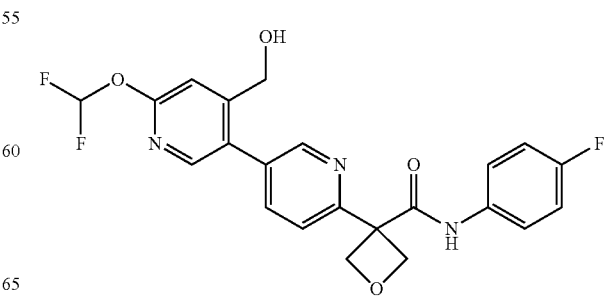

The title compound was prepared from intermediate I-155 and (5-bromo-2-(difluoromethoxy)pyridin-4-yl)methanol in a manner analogous to the synthesis of Example 76. MS (ESI)) [M+H]⁺: m/z 446. ¹H NMR (600 MHz, DMSO-d₆) δ 10.14 (s, 1H), 8.72 (s, 1H), 8.20 (s, 1H), 7.99 (d, J=7.9 Hz, 1H), 7.74-7.69 (m, 2H), 7.67 (d, J=8.4 Hz, 1H), 7.26 (s, 1H), 7.20 (t, J=8.6 Hz, 2H), 5.14 (dd, J=80.5, 6.2 Hz, 4H), 4.52 (s, 2H).

Example 78: 3-(6'-(Difluoromethoxy)-4'-(2-hydroxypropan-2-yl)-[3,3'-bipyridin]-6-yl)-N-(4-fluorophenyl)oxetane-3-carboxamide

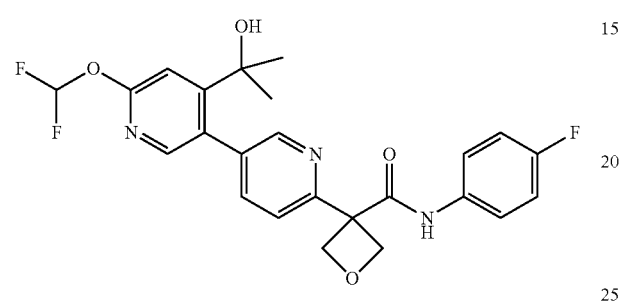

The title compound was prepared in a similar manner to Example 76. MS (ESI) [M+H]⁺: m/z 474. ¹H NMR (600 MHz, DMSO-d₆) δ 10.18 (s, 1H), 8.60 (s, 1H), 7.94 (s, 1H), 7.86 (d, J=8.0 Hz, 1H), 7.78 (t, J=72 Hz, 1H), 7.74-7.70 (m, 2H), 7.60 (d, J=8.1 Hz, 1H), 7.34 (s, 1H), 7.21 (t, J=8.7 Hz, 2H), 5.13 (dd, J=83.1, 6.2 Hz, 4H), 1.32 (s, 6H).

Example 79: N-(4-Fluorophenyl)-3-(4'-(2-hydroxypropan-2-yl)-6'-(trifluoromethyl)-[3,3'-bipyridin]-6-yl)oxetane-3-carboxamide

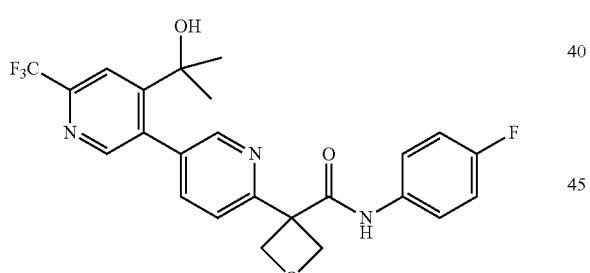

The title compound was prepared in a similar manner to Example 76. MS (ESI) [M+H]⁺: m/z 476.

Example 80: 3,3-Difluoro-N-(4-fluorophenyl)-1-(4-(4-(hydroxymethyl)-6-(trifluoro methyl) pyridin-3-yl)phenyl)cyclobutane-1-carboxamide

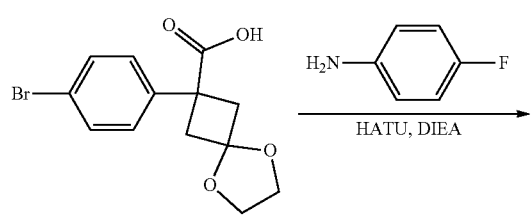

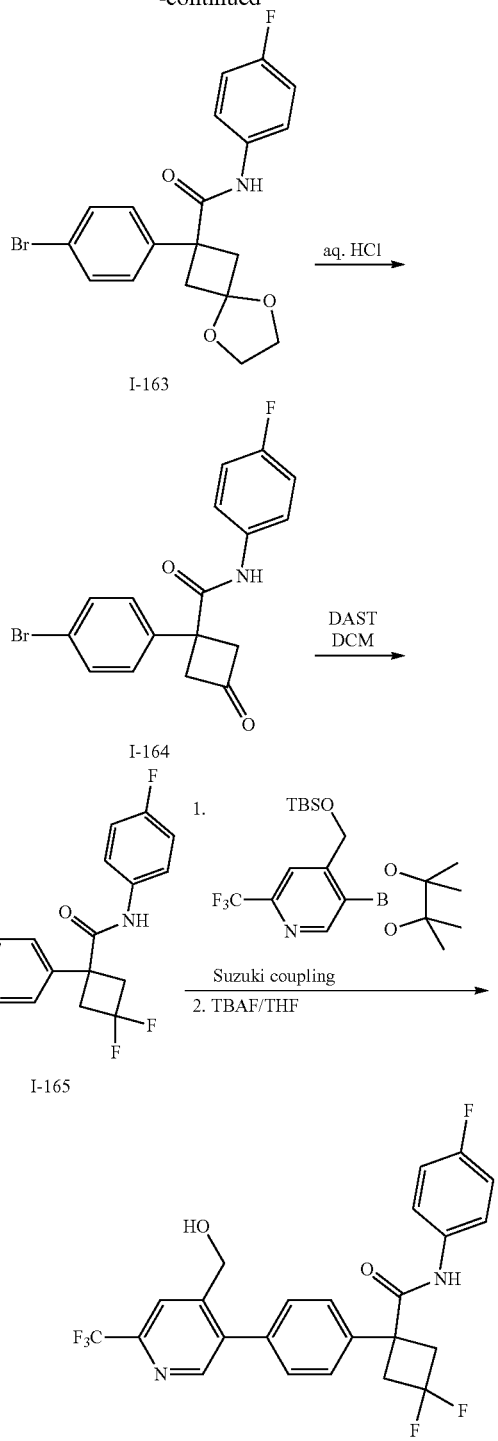

Step 1. 2-(4-bromophenyl)-N-(4-fluorophenyl)-5,8-dioxaspiro[3.4]octane-2-carboxamide (I-163)

To a solution of 2-(4-bromophenyl)-5,8-dioxaspiro[3.4]octane-2-carboxylic acid (1.0 g, 3.2 mmol) in DMF (6.4 ml) were added 4-fluoroaniline (0.30 ml, 3.2 mmol) and Hunig's base (1.12 ml, 6.4 mmol), followed by the addition of HATU (1.58 g, 4.2 mmol) portion wise. The mixture was stirred at RT for 14 h. The reaction mixture was diluted with aq. NaHCO₃, and extracted with EtOAc. The organic layer was separated, washed with water, brine, dried over MgSO$_4$, and concentrated. The residue was purified by flash chromatography (0-100% EtOAc/hexanes) to give compound I-163. MS (ESI) [M+H]$^+$: m/z 406.

Step 2: 1-(4-bromophenyl)-N-(4-fluorophenyl)-3-oxocyclobutane-1-carboxamide (I-164)

To a flask containing compound I-163 (380 mg, 0.94 mmol) was added HCl (4N in dioxane, 2 ml) and H$_2$O (2 ml). The mixture was heated at 80° C. for 2 h. The mixture was cooled down, neutralized with sat. NaHCO$_3$, and extracted with EtOAc. The organic layer was washed with brine, dried over MgSO$_4$, and concentrated to give compound I-164 as a solid. This material was used directly for next step. MS (ESI) [M+H]$^+$: m/z 362.

Step 3: 1-(4-bromophenyl)-3,3-difluoro-N-(4-fluorophenyl)cyclobutane-1-carboxamide (I-165)

To a solution of compound I-164 (127 mg, 0.35 mmol) in CH$_2$Cl$_2$ (2.3 ml) at −30° C. was added DAST (185 µl, 1.4 mmol). After the addition, the reaction mixture was slowly warmed up to RT and kept stirring for 3 h. The mixture was quenched at this point by adding aq. NaHCO$_3$, and extracted with EtOAc. The organic layer was separated, washed with brine, dried over MgSO$_4$, and concentrated. The residue was purified by flash chromatography (0-100% EtOAc/hexanes) to give compound I-165. MS (ESI) [M+H]$^+$: m/z 384.

Step 4: 3,3-Difluoro-N-(4-fluorophenyl)-1-(4-(4-(hydroxymethyl)-6-(trifluoro methyl) pyridin-3-yl) phenyl)cyclobutane-1-carboxamide A mixture of 4-(((tert-butyldimethylsilyl)oxy)methyl)-5-(4,4,5,5-tetramethyl-1,3,2-dioxaborolan-2-yl)-2-(trifluoromethyl)pyridine (98 mg, 0.23 mmol), compound I-165 (60 mg, 0.15 mmol), 1,1'-bis(di-tert-butylphosphino)ferrocene palladium dichloride (15 mg, 0.023 mmol), and sodium carbonate (195 µl, 0.39 mmol) in 1,4-dioxane (1.0 ml) was evacuated and refilled with nitrogen for 3 times and the mixture was heated under nitrogen at 90° C. for 2 h. The reaction mixture was cooled down, diluted with water, and extracted with EtOAc. The organic layer was separated, washed with brine, dried over MgSO$_4$, and concentrated. The residue was purified by flash chromatography (0-100% EtOAc/hexanes) to give 1-(4-(4-(((tert-butyldimethylsilyl)oxy)methyl)-6-(trifluoromethyl)pyridin-3-yl)phenyl)-3,3-difluoro-N-(4-fluorophenyl)cyclobutane-1-carboxamide as an oil. MS (ESI) [M+H]$^+$: m/z 595.

To a flask containing 1-(4-(4-(((tert-butyldimethylsilyl)oxy)methyl)-6-(trifluoromethyl)pyridin-3-yl)phenyl)-3,3-difluoro-N-(4-fluorophenyl)cyclobutanecarboxamide (83 mg, 0.14 mmol) at RT was added TBAF (1.0 M in THF, 42 µl, 0.42 mmol) and THF (0.3 ml). The mixture was kept stirring at RT for 1 h. The mixture was diluted with sat. NaHCO$_3$, and extracted with EtOAc. The organic layer was washed with brine, dried over MgSO$_4$, and concentrated. The residue was purified by flash chromatography (0-100% EtOAc/hexanes) to afford the title compound. MS (ESI) [M+H]$^+$: m/z 480. $^1$HNMR (500 MHz, DMSO-d$_6$): δ 9.92 (s, 1H), 8.61 (s, 1H), 8.02 (s, 1H), 7.75-7.59 (m, 4H), 7.53 (d, J=8.0 Hz, 2H), 7.14 (t, J=8.8 Hz, 2H), 5.66 (t, J=5.3 Hz, 1H), 4.55 (d, J=5.2 Hz, 2H), 3.55 (q, J=13.2 Hz, 2H), 3.21 (q, J=13.2 Hz, 2H).

Example 81: N-(4-Fluorophenyl)-1-(4-(4-(hydroxymethyl)-6-(trifluoromethyl)pyridin-3-yl) phenyl)cyclobutane-1-carboxamide

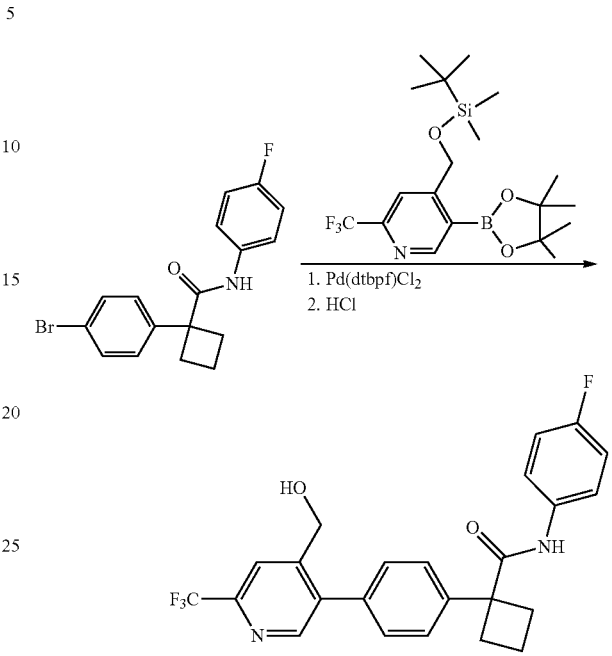

Step 1. 1-(4-(4-(((Tert-butyldimethylsilyl)oxy)methyl)-6-(trifluoromethyl)pyridin-3-yl)phenyl)-N-(4-fluorophenyl)cyclobutane-1-carboxamide A mixture of 4-(((tert-butyldimethylsilyl)oxy)methyl)-5-(4,4,5,5-tetramethyl-1,3,2-dioxaborolan-2-yl)-2-(trifluoromethyl)pyridine (180 mg, 0.43 mmol), 1-(4-bromophenyl)-N-(4-fluorophenyl) cyclobutanecarboxamide (100 mg, 0.29 mmol), 1,1'-bis(di-tert-butylphosphino)ferrocene palladium dichloride (28 mg, 0.043 mmol) and sodium carbonate (287 µl, 0.57 mmol) in 1,4-dioxane (1.9 ml) was evacuated and refilled with nitrogen for 3 times and the mixture was heated under nitrogen at 90° C. for 3 h. The reaction mixture was cooled down, diluted with water, and extracted with EtOAc. The organic layer was separated, washed with brine, dried over MgSO$_4$, and concentrated. The residue was purified by flash chromatography (0-100% EtOAc/hexanes) to give the title compound as a solid. MS (ESI) [M+H]$^+$: m/z 559.

Step 2. N-(4-fluorophenyl)-1-(4-(4-(hydroxymethyl)-6-(trifluoromethyl)pyridin-3-yl)phenyl) cyclobutane-1-carboxamide To a flask containing 1-(4-(4-(((tert-butyldimethylsilyl)oxy)methyl)-6-(trifluoromethyl) pyridin-3-yl)phenyl)-N-(4-fluorophenyl)cyclobutanecarboxamide (107 mg, 0.19 mmol) at RT was added TBAF (1.0M in THF, 575 µl, 0.575 mmol) and THF (0.3 ml). The mixture was kept stirring at RT for 1 h. The mixture was diluted with sat. NaHCO$_3$, and extracted with EtOAc. The organic layer was washed with brine, dried over MgSO$_4$, and concentrated. The residue was purified by flash chromatography (0-100% EtOAc/hexanes) to afford the title compound. MS (ESI) [M+H]$^+$: m/z 445. $^1$HNMR (500 MHz, DMSO-d$_6$: δ 9.62 (s, 1H), 8.62 (s, 1H), 8.03 (s, 1H), 7.75-7.55 (m, 4H), 7.50 (d, J=7.5 Hz, 2H), 7.14

(t, J=8.2 Hz, 2H), 5.68 (s, 1H), 4.57 (d, J=4.3 Hz, 2H), 2.95-2.75 (m, 2H), 2.40-2.60 (m, 2H), 1.98-1.77 (m, 2H).

Example 82: N-(4-Fluorophenyl)-5-(4-(4-(hydroxymethyl)-6-(trifluoromethyl)pyridin-3-yl)phenyl)spiro[2.3]hexane-5-carboxamide

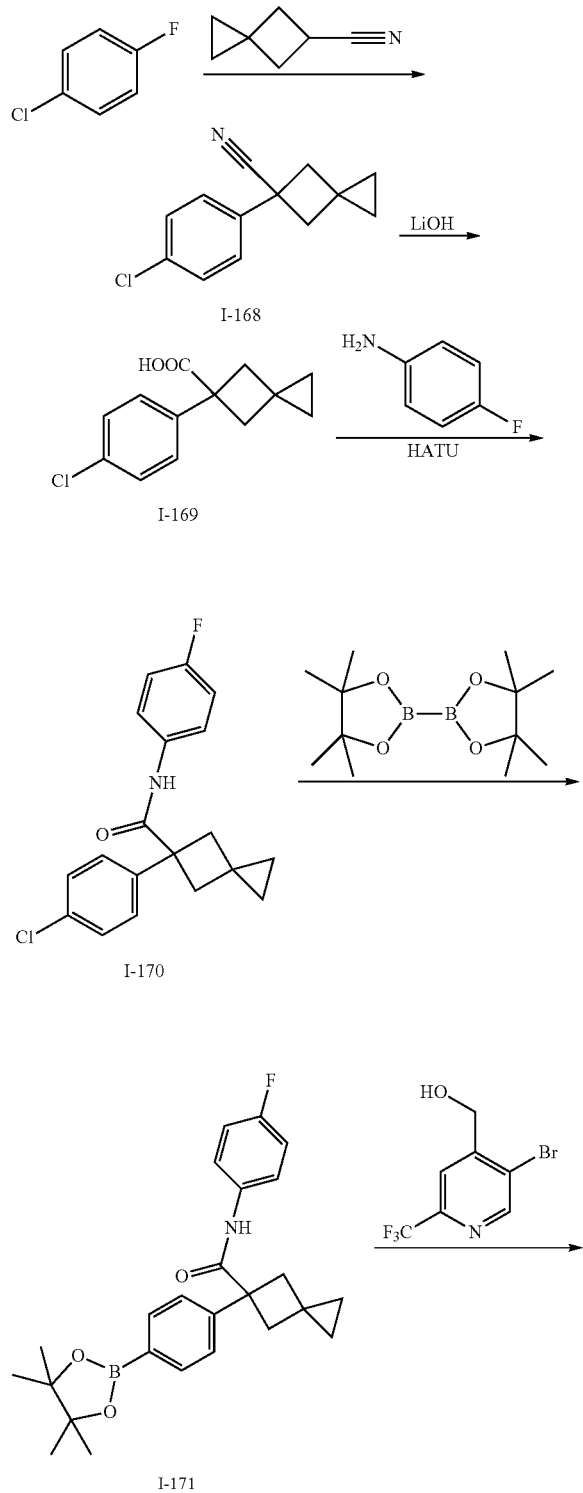

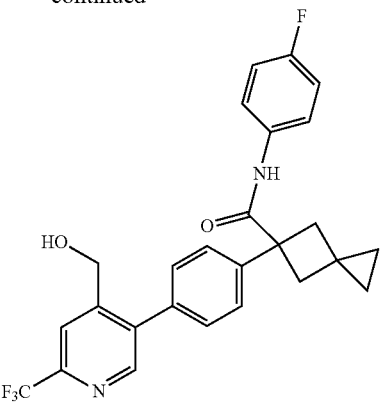

Step 1: 5-(4-chlorophenyl)spiro[2.3]hexane-5-carbonitrile (I-168)

1-Chloro-4-fluorobenzene (193 µl, 1.8 mmol) and spiro[2.3]hexane-5-carbonitrile (179 µl, 1.5 mmol) were added to a flask under nitrogen, and then 1.5 ml of THF was added. To this was added the KHMDS (1M in THF, 1.58 ml, 1.58 mmol) dropwise. It was allowed to stir for 15 h at RT, evaporated in vacuo, and then checked by NMR for conversion. The residue was purified by chromatography (Isco CombiFlash system, using hexanes and ethyl acetate as eluent) to give compound I-168. $^1$H NMR (600 MHz, CDCl$_3$) δ 7.46 (d, J=8.2 Hz, 2H), 7.37 (d, J=8.3 Hz, 2H), 2.96 (d, J=12.3 Hz, 2H), 2.68 (d, J=12.4 Hz, 2H), 0.77-0.69 (m, 2H), 0.60-0.53 (m, 2H).

Step 2: 5-(4-chlorophenyl)spiro[2.3]hexane-5-carboxylic acid (I-169)

Lithium hydroxide (99 mg, 4.1 mmol) was added to a flask containing compound I-168 (150 mg, 0.69 mmol). To this was added 1 ml of water and 1 ml of ethanol. This was then heated in a sealed flask under argon at 65° C. for 72 h. When done, it was made acidic with 1 M HCl (aq.) until pH-3. Then it was extracted with ethyl acetate, dried with MgSO$_4$, filtered through a Celite pad, and then evaporated in vacuo to afford compound I-169 which was used in the next step directly. MS (ESI) [M+H]$^+$: m/z 237.

Step 3: 5-(4-chlorophenyl)-N-(4-fluorophenyl)spiro[2.3]hexane-5-carboxamide (I-170)

5-(4-Chlorophenyl)spiro[2.3]hexane-5-carboxylic acid (125 mg, 0.53 mmol) and HATU (221 mg, 0.58 mmol) were added to a vial with 1.5 ml DMF. To this was added the 4-fluoroaniline (55 µl, 0.58 mmol) followed by the DIPEA (231 µl, 1.3 mmol). This mixture was allowed to stir for 2 h at which point it was evaporated in vacuo. The crude residue was purified by chromatography (Isco CombiFlash system, using hexanes and ethyl acetate as eluent) to give compound I-170. MS (ESI) [M+H]$^+$: m/z 330.

Step 4: N-(4-fluorophenyl)-5-(4-(4,4,5,5-tetramethyl-1,3,2-dioxaborolan-2-yl)phenyl)spiro[2.3]-hexane-5-carboxamide (I-171)

A dried round bottom flask was charged with compound I-170 (118 mg, 0.36 mmol), bis(pinacolato)diboron (236 mg, 0.93 mmol), potassium acetate (105 mg, 1.1 mmol), and XPhos G3 (5%, 15 mgs). Then dioxane (2.4 ml) was added and it was purged with argon and heated to 80° C. for 15 h. The reaction mixture was cooled to RT and filtered through a Celite pad. The filtrate was concentrated in vacuo to give a residue which was purified via chromatography (Isco CombiFlash system, using hexanes and ethyl acetate as eluent) to afford compound I-171. MS (ESI) [M+H]+: m/z 422.

Step 5: N-(4-Fluorophenyl)-5-(4-(4-(hydroxymethyl)-6-(trifluoromethyl)pyridin-3-yl)phenyl)spiro[2.3]hexane-5-carboxamide To a dried vial equipped with a stir bar was charged with Xphos G3 (8.46 mg, 10.00 μmol), (5-bromo-2-(trifluoromethyl)pyridin-4-yl)methanol (28.2 mg, 0.11 mmol), and compound I-171 (42.1 mg, 0.1 mmol) and it was placed under nitrogen. To this was added THF 0.50 ml and potassium phosphate tribasic (1 M in H$_2$O, 0.200 ml, 0.200 mmol). The reaction mixture was then purged with argon and heated at 70° C. overnight. It was allowed to cool to RT and then filtered through a pad of Celite. This crude material was purified by mass-directed reversed phase chromatography (ACN/water gradient with 0.1% TFA modifier) to afford the title compound. MS (ESI) [M+H]+: m/z 471. $^1$H NMR (600 MHz, DMSO-d$_6$) δ 9.71 (s, 1H), 8.61 (s, 1H), 8.02 (s, 1H), 7.71-7.66 (m, 2H), 7.63 (d, J=7.6 Hz, 2H), 7.49 (d, J=7.5 Hz, 2H), 7.13 (t, J=8.3 Hz, 2H), 4.57 (s, 2H), 3.04 (d, J=11.9 Hz, 2H), 2.63 (d, J=11.9 Hz, 2H), 0.49 (s, 4H).

Example 83: 1-(4-(4,7-Difluoro-1-oxoisoindolin-2-yl)phenyl)-N-(4-fluorophenyl)cyclobutane-1-carboxamide

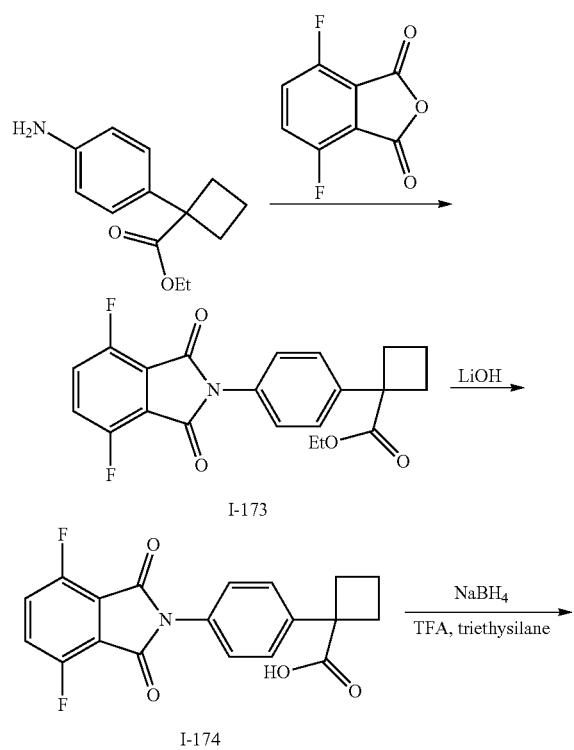

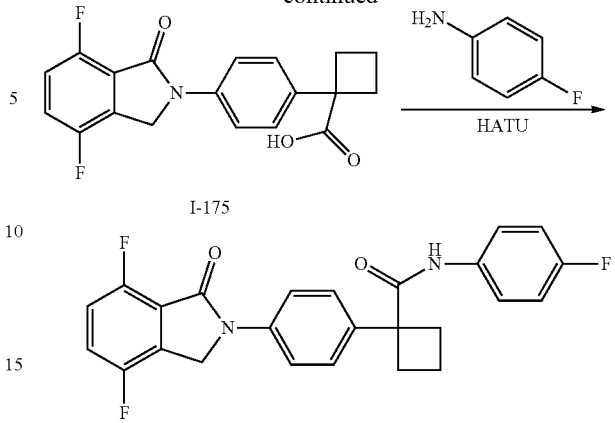

Step 1: ethyl 1-(4-(4,7-difluoro-1,3-dioxoisoindolin-2-yl)phenyl)cyclobutane-1-carboxylate (I-173)

To a vial was charged with 4,7-difluoroisobenzofuran-1,3-dione (184 mg, 1 mmol) and ethyl 1-(4-aminophenyl)cyclobutanecarboxylate (329 mg, 1.500 mmol). To this vial was added 4 ml of glacial acetic, and then the vial was purged with argon and heated at 80° C. for 15 h. The reaction mixture was then concentrated in vacuo. This crude material was dissolved in DCM (10 ml) and added to a separatory funnel. It was washed with sat. sodium bicarbonate and the organics were separated, dried over sodium sulfate, filtered, and concentrated. The residue was purified by chromatography (Isco CombiFlash system, using hexanes and ethyl acetate as eluent) to give compound I-173. MS (ESI) [M+H]+: m/z 386.

Step 2: 1-(4-(4,7-difluoro-1,3-dioxoisoindolin-2-yl)phenyl)cyclobutane-1-carboxylic acid (I-174)

To a vial was charged with compound I-173 (200 mg, 0.519 mmol) and to this was added 2 ml of dioxane. Then lithium hydroxide (37.3 mg, 1.557 mmol) was added followed by the addition of 2 ml of water. This was allowed to stir at RT for 2 h. The organics were then evaporated in vacuo and the water layer was made acidic with 1M HCl to pH ~2. This was then extracted 3× with DCM (5 ml), dried with magnesium sulfate, filtered, and evaporated in vacuo. The lactam ring opened under these conditions, so this crude material was then dissolved in 2 ml of acetic acid in a vial, the vial was purged with argon, and it was heated to 100° C. for 15 h. The reaction mixture was then concentrated in vacuo. This crude material was dissolved in DCM (10 ml) and added to a separatory funnel. It was washed with sat. sodium carbonate and the organics were separated, dried over sodium sulfate, filtered, and concentrated to afford compound I-174 which was used directly. MS (ESI) [M+H]+: m/z 358.

Step 3: 1-(4-(4,7-difluoro-1-oxoisoindolin-2-yl)phenyl)cyclobutane-1-carboxylic acid (I-175)

Compound I-174 (90 mg, 0.252 mmol) and NaBH$_4$ (10.48 mg, 0.277 mmol) were added to a vial under nitrogen and placed under nitrogen. To this was added 1 mL of THF and 1 ml of MeOH. This was allowed to stir for 5 mins at 0° C., and then it was stirred at RT for 2 h. When done, 2 drops of acetic acid was added and it was evaporated in vacuo. Then 5 ml of DCM and 5 ml of sat. sodium bicarbonate was added, and the organics were separated. It was extracted two more times with 5 ml of DCM and the organics were combined, dried with magnesium sulfate, filtered, and evaporated in vacuo. This crude material was then dissolved in TFA (1 ml) and triethylsilane (0.161 ml, 1.008 mmol) was added. This was stirred at RT for 30 min and was evaporated in vacuo. The crude residue was purified by chromatography (Isco CombiFlash system, using hexanes and ethyl acetate as eluent) to give compound I-175. MS (ESI) [M+H]+: m/z 344.

Step 4: 1-(4-(4,7-Difluoro-1-oxoisoindolin-2-yl)phenyl)-N-(4-fluorophenyl)cyclobutane-1-carboxamide Compound I-175 (17 mg, 0.050 mmol) and HATU (19.77 mg, 0.052 mmol) were added to a vial with 1.5 ml DMF. To this was added 4-fluoroaniline (5.17 µl, 0.054 mmol) followed by DIPEA (12.97 µl, 0.074 mmol). It was allowed to stir for 24 h. When done, it was evaporated in vacuo. The crude material was purified by mass-directed reversed phase chromatography (ACN/water gradient with 0.1% TFA modifier) to afford the title compound. MS (ESI) [M+H]+: m/z 437. $^1$H NMR (600 MHz, DMSO-$d_6$) δ 9.49 (s, 1H), 7.85 (d, J=8.1 Hz, 2H), 7.65-7.59 (m, 2H), 7.59-7.55 (m, 1H), 7.53 (d, J=8.1 Hz, 2H), 7.45-7.39 (m, 1H), 7.10 (t, J=8.3 Hz, 2H), 5.10 (s, 2H), 2.88-2.80 (m, 2H), 2.50-2.44 (m, 2H), 1.89-1.77 (m, 2H).

Example 84: N-(4-fluorophenyl)-3-(4'-(hydroxymethyl)-6'-(trifluoromethyl)-[2,3'-bipyridin]-5-yl)oxetane-3-carboxamide

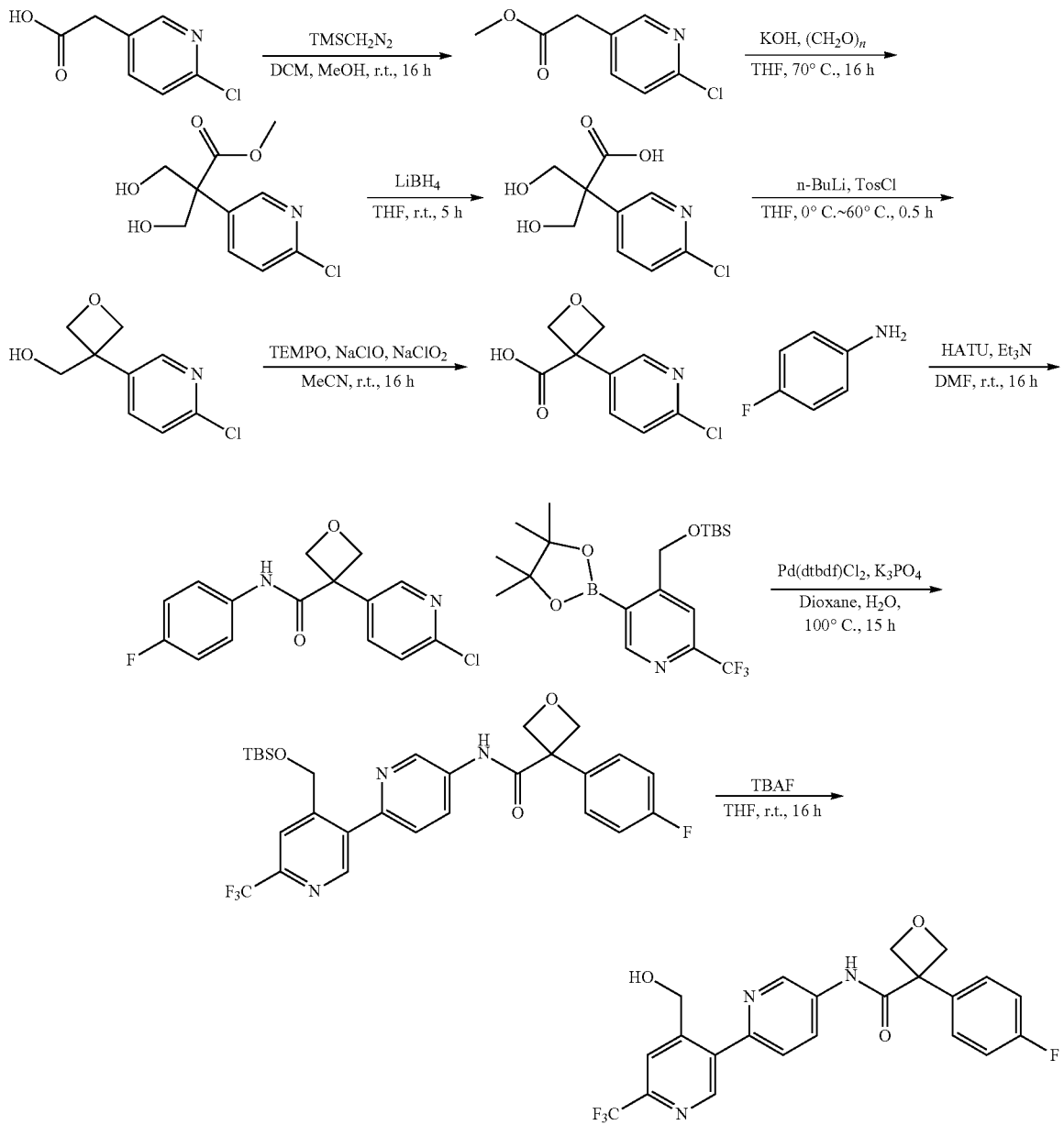

Step 1: methyl 2-(6-chloropyridin-3-yl)acetate

To a stirred solution of 2-(6-chloropyridin-3-yl)acetic acid (10 g, 58.3 mmol) in DCM (100 mL) and MeOH (50 mL) was added ((trimethylsilyl)methyl)diazene (8.3 mL, 175 mmol) at 0° C. The reaction was stirred at RT for 16 h and then the solvent was concentrated under reduced pressure. The residue was dilute with water (100 mL), extracted with EtOAc (100 mL×3), and the organic layers were collected, washed with brine (50 mL), dried over $Na_2SO_4$, filtered, and the filtrate was concentrated in vacuo. The residue was purified by flash silica gel chromatography to afford the title compound as an oil. MS (ESI) m/z: 185.8 [M+H$^+$].

Step 2: 4-methyl 2-(6-chloropyridin-3-yl)-3-hydroxy-2-(hydroxymethyl)propanoate To a stirred solution of methyl 2-(6-chloropyridin-3-yl) acetate (7.5 g, 40.4 mmol) in THF (50 mL) was added potassium hydroxide (0.227 g, 4.04 mmol), paraformaldehyde (4.85 g, 162 mmol) at RT, and the reaction was stirred at 60° C. for 16 h. The mixture was filtered and the filtrate concentrated under reduced pressure. The residue was purified by flash silica gel chromatography to give the title compound as an oil. MS (ESI) m/z: 245.9 [M+H$^+$].

Step 3: 2-(6-chloropyridin-3-yl)-2-(hydroxymethyl) propane-1,3-diol

To a stirred solution of methyl 2-(6-chloropyridin-3-yl)-3-hydroxy-2-(hydroxymethyl)propanoate (4.6 g, 18.73 mmol) in THF (50 mL) was added lithium tetrahydroborate (1.224 g, 56.2 mmol) at 0° C., and the reaction was stirred at 0° C. for 5 h. The mixture was quenched with MeOH (50 mL) and concentrated under reduced pressure. The residue was purified by flash silica gel chromatography to afford the title compound as a solid. MS (ESI) m/z: 217.8 [M+H$^+$].

Step 4: (3-(6-chloropyridin-3-yl)oxetan-3-yl)methanol

To a stirred solution of 2-(6-chloropyridin-3-yl)-2-(hydroxymethyl)propane-1,3-diol (1.7 g, 7.81 mmol) in THF (70 mL) was added n-BuLi (4 mL, 10.0 mmol) (2.5M) dropwise at 0° C., and the mixture was stirred at 0° C. for 30 min. Then a solution of TsCl (1.340 g, 7.03 mmol) in 5 mL of THF was added at 0° C. and stirring was continued at 0° C. for 1 h. n-BuLi (3.12 mL, 7.80 mmol) (2.5 M) was added to the above mixture at 0° C. and the mixture was stirred at 0° C. for an additional 0.5 h, and then was heated to 60° C. for 0.5 h. After cooling to RT, the reaction was quenched with aq. NH$_4$Cl (30 mL), extracted with EtOAc (30 mL×3), and the organic layers were collected, washed with brine (20 mL), dried over $Na_2SO_4$, filtered, the filtrate was concentrated in vacuo. The residue was purified by flash silica gel chromatography to afford title compound. MS (ESI) m/z: 199.9 [M+H$^+$].

Step 5: 3-(6-chloropyridin-3-yl)oxetane-3-carboxylic acid

To a stirred solution of (3-(6-chloropyridin-3-yl)oxetan-3-yl)methanol (270 mg, 1.352 mmol) in ACN (10 mL) was successively added TEMPO (42 mg, 0.269 mmol), sodium chlorite (489 mg, 5.41 mmol) in 1 mL of water and sodium hypochlorite (1007 mg, 1.352 mmol) (10% in water) at RT. The mixture was stirred at RT for 16 h. The reaction was treated with 2 M NaOH to pH 10, followed by the addition of 10% sodium thiosulfate (30 mL). The mixture was partitioned between ethyl acetate (30 mL) and water (15 mL), and the aqueous phase was acidified with HCl (2 M in water) to pH 4 and extracted with ethyl acetate (30 mL×3). The organic phase was dried over $Na_2SO_4$, filtered and concentrated in vacuo to afford the title compound as an oil, which was used in next step without further purification. MS (ESI) m/z: 214.0 [M+H$^+$].

Step 6: 3-(6-chloropyridin-3-yl)-N-(4-fluorophenyl) oxetane-3-carboxamide

To a stirred solution of 3-(6-chloropyridin-3-yl)oxetane-3-carboxylic acid (250 mg, 1.170 mmol) in DMF (10 mL) were added HATU (667 mg, 1.755 mmol), Et$_3$N (0.5 mL, 3.59 mmol) and 4-fluoroaniline (195 mg, 1.755 mmol) at RT and stirring continued for 16 h. The reaction mixture was worked up and the crude was purified by prep-TLC (petroleum ether/EtOAc=1:1) to afford the title compound as an oil. MS (ESI) m/z: 307.1 [M+H$^+$].

Step 7: 3-(4'-(((tert-butyldimethylsilyl)oxy)methyl)-6'-(trifluoromethyl)-[2,3'-bipyridin]-5-yl)-N-(4-fluorophenyl)oxetane-3-carboxamide To a stirred solution of 3-(6-chloropyridin-3-yl)-N-(4-fluorophenyl)oxetane-3-carboxamide (30 mg, 0.098 mmol) and 4-(((tert-butyldimethylsilyl)oxy)methyl)-5-(4,4,5,5-tetramethyl-1,3,2-dioxaborolan-2-yl)-2-(trifluoromethyl)pyridine (49 mg, 0.117 mmol) in dioxane (2 mL) and water (0.4 mL) were added K$_3$PO$_4$ (62 mg, 0.292 mmol) and Pd(dtbpf) Cl$_2$ (7 mg, 10.74 μmol) at RT. The mixture was heated to 100° C. with stirring for 15 h, and was cooled to RT. The reaction mixture was diluted with ethyl acetate (5 mL) and filtered. The filtrate was washed with water (2 mL) and brine, dried over $Na_2SO_4$, filtered and concentrated in vacuum. The residue was purified by prep-TLC (petroleum ether/EtOAc=1:1 as eluent) to afford the title compound as an oil. MS (ESI) m/z: 562.3[M+H$^+$].

Step 8: N-(4-fluorophenyl)-3-(4'-(hydroxymethyl)-6'-(trifluoromethyl)-[2,3'-bipyridin]-5-yl)oxetane-3-carboxamide To a stirred solution of 3-(4'-(((tert-butyldimethylsilyl) oxy)methyl)-6'-(trifluoromethyl)-[2,3'-bipyridin]-5-yl)-N-(4-fluorophenyl)oxetane-3-carboxamide (21 mg, 0.037 mmol) in THF (2 mL) was added TBAF (0.05 mL, 0.050 mmol) at RT and the mixture was stirred at RT for 16 h. The mixture was concentrated under reduced pressure and the residue was purified by reversed phase HPLC on a GILSON 281 instrument fitted with a Column Phenomenex Synergi (C18 150*30 mm*4 um) using water (0.225% FA) and ACN as eluent followed by freeze drying to afford the title compound as a solid. $^1$H NMR (400 MHz, CD$_3$OD) δ 8.85 (d, 1H), 8.79 (s, 1H), 8.12 (t, 2H), 7.82 (d, 1H), 7.60-7.56 (m, 2H), 7.07 (t, 2H), 5.38 (d, 2H), 5.06 (d, 2H), 4.82 (s, 2H); MS (ESI) m/z: 448.0 [M+H$^+$].

Example 85: N-(4-fluorophenyl)-3-(6-(2-(hydroxymethyl)-4-(trifluoromethyl)phenyl)pyridin-3-yl)oxetane-3-carboxamide

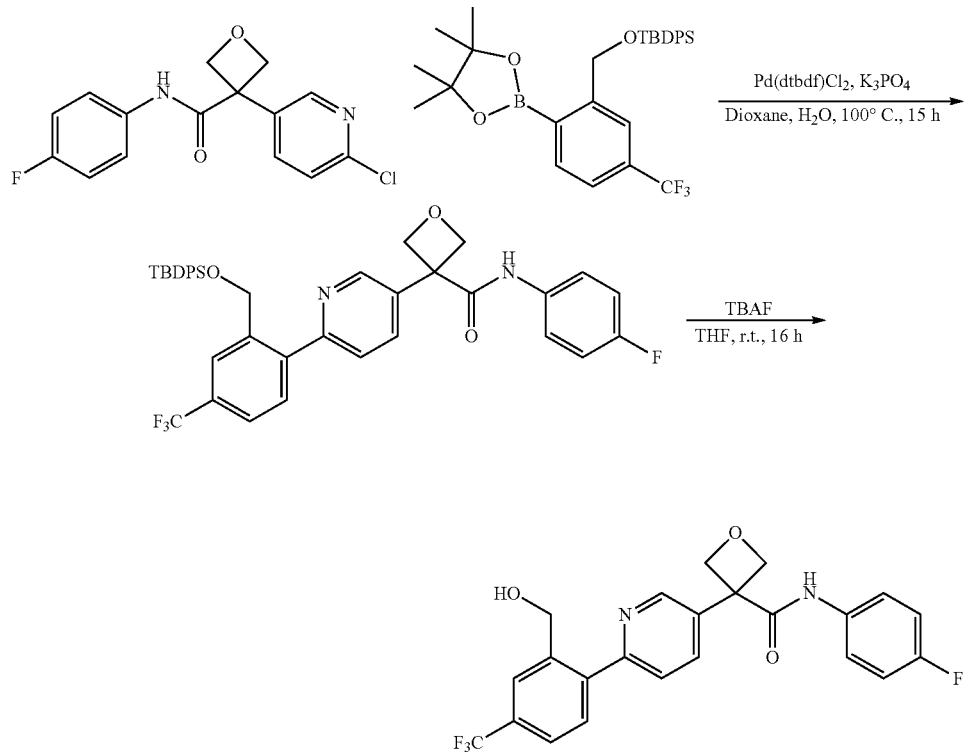

Step 1: 3-(6-(2-(((tert-butyldiphenylsilyl)oxy)methyl)-4-(trifluoromethyl)phenyl)pyridin-3-yl)-N-(4-fluorophenyl)oxetane-3-carboxamide To a stirred solution of 3-(6-chloropyridin-3-yl)-N-(4-fluorophenyl)oxetane-3-carboxamide (42 mg, 0.137 mmol) and tert-butyldiphenyl((2-(4,4,5,5-tetramethyl-1,3,2-dioxaborolan-2-yl)-5-(trifluoromethyl)benzyl)oxy)silane (89 mg, 0.164 mmol) in dioxane (1.0 mL) and water (0.2 mL) were added $K_3PO_4$ (87 mg, 0.411 mmol) and Pd(dtbpf)$Cl_2$ (9 mg, 0.014 mmol) at RT. The mixture was heated to 100° C. with stirring for 15 h. The reaction mixture was cooled to RT, diluted with EtOAc (5 mL) and filtered. The filtrate was washed with water (2 mL) and brine, dried over $Na_2SO_4$, filtered and concentrated in vacuo. The residue was purified by prep-TLC (petroleum ether/EtOAc=1:1 as eluent) to afford the title compound as an oil. MS (ESI) m/z: 685.4 [M+H$^+$].

Step 2: N-(4-fluorophenyl)-3-(6-(2-(hydroxymethyl)-4-(trifluoromethyl)phenyl)pyridin-3-yl)oxetane-3-carboxamide To a stirred solution of 3-(6-(2-(((tert-butyldiphenylsilyl)oxy)methyl)-4-(trifluoromethyl)phenyl)pyridin-3-yl)-N-(4-fluorophenyl)oxetane-3-carboxamide (40 mg, 0.058 mmol) in THF (2 mL) was added TBAF (0.1 mL, 0.100 mmol) at RT. The mixture was stirred at RT for 16 h. The mixture was concentrated under reduced pressure and the residue was purified by reversed phase HPLC to afford the title compound as a solid. $^1$H NMR (400 MHz, CD$_3$OD) δ 8.80 (d, 1H), 8.12 (dd, 8.3 Hz, 1H), 7.92 (s, 1H), 7.78 (d, 1H), 7.71 (s, 2H), 7.59 (dd, 9.2 Hz, 2H), 7.10-7.04 (m, 2H), 5.38 (d, 2H), 5.06 (d, 2H), 4.66 (s, 2H); MS (ESI) m/z: 447.0 [M+H$^+$].

Example 86: N-(4-fluorophenyl)-3-(6-(2-(2-hydroxypropan-2-yl)-4-(trifluoromethyl)phenyl)pyridin-3-yl)oxetane-3-carboxamide

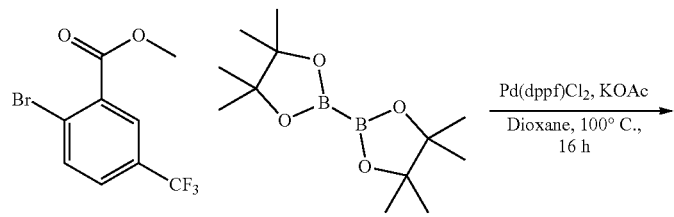

-continued

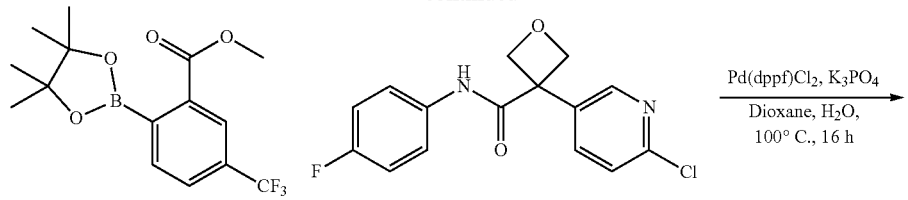

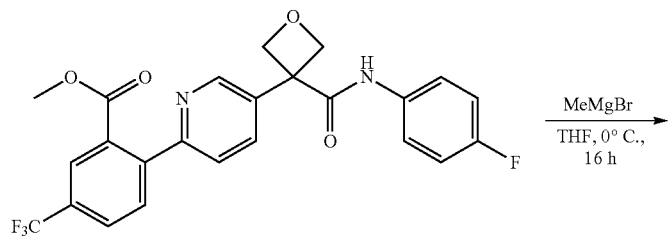

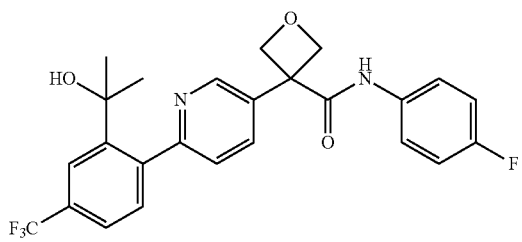

Step 1: methyl 2-(4,4,5,5-tetramethyl-1,3,2-dioxaborolan-2-yl)-5-(trifluoromethyl)benzoate To a stirred solution of methyl 2-bromo-5-(trifluoromethyl)benzoate (510 mg, 1.802 mmol), 4,4,4',4',5,5',5'-octamethyl-2,2'-bi(1,3,2-dioxaborolane) (686 mg, 2.70 mmol) in dioxane (2 mL) was added potassium acetate (531 mg, 5.41 mmol) and Pd(dppf)Cl$_2$ (132 mg, 0.180 mmol) at RT. The mixture was heated to 100° C. with stirring for 16 h and the solvent was concentrated under reduced pressure. To the residue was added sat. NaHCO$_3$ to adjust pH >8 and the mixture was extracted with EtOAc (20 mL×3). The organic layers were collected, washed with brine (10 mL), dried over Na$_2$SO$_4$, filtered, and the filtrate was concentrated in vacuo. The residue was purified by prep-TLC (petroleum ether/EtOAc=5:1) to afford the title compound as an oil. MS (ESI) m/z: 331.1 [M+H$^+$].

Step 2: methyl 2-(5-(3-((4-fluorophenyl)carbamoyl)oxetan-3-yl)pyridin-2-yl)-5-(trifluoromethyl)benzoate To a stirred solution of 3-(6-chloropyridin-3-yl)-N-(4-fluorophenyl)oxetane-3-carboxamide (30 mg, 0.098 mmol) and (2-(2-(methoxycarbonyl)-4-(trifluoromethyl)phenyl)-4,5,5-trimethyl-1,3,2-dioxaborolan-4-yl)methylium (62 mg, 0.188 mmol) in dioxane (2 mL) and water (0.4 mL) were added K$_3$PO$_4$ (62 mg, 0.292 mmol) and Pd(dtbpf)Cl$_2$(7 mg, 10.74 μmol) at RT. The mixture was heated to 100° C. for 15 h. The reaction mixture was diluted with EtOAc (5 mL) and filtered. The filtrate was washed with water (2 mL) and brine, dried over Na$_2$SO$_4$, filtered and concentrated in vacuo. The residue was purified by prep-TLC (SiO$_2$, petroleum ether/EtOAc=1:1 as eluent) to afford the title compound as an oil. MS (ESI) m/z: 475.2[M+H$^+$].

Step 3: N-(4-fluorophenyl)-3-(6-(2-(2-hydroxypropan-2-yl)-4-(trifluoromethyl)phenyl)-pyridin-3-yl)oxetane-3-carboxamide To a stirred solution of methyl 2-(5-(3-((4-fluorophenyl)carbamoyl)oxetan-3-yl)pyridin-2-yl)-5-(trifluoromethyl)benzoate (30 mg, 0.063 mmol) in THF (2 mL) was added 3 M MeMgBr (0.1 mL, 0.300 mmol) at 0° C. The reaction was stirred at RT under nitrogen for 15 h. The reaction mixture was quenched with sat. NH$_4$Cl (10 mL, aq.) slowly and extracted with EtOAc (20 mL×3). The combined organic layer was washed with brine (5 mL), dried over anhydrous Na$_2$SO$_4$, and concentrated in vacuo. The crude product was purified by reversed phase HPLC on a GILSON 281 instrument fitted with a Phenomenex Synergi C 18 150×30 mm×4 um column to afford the title compound as a solid. $^1$H NMR (400 MHz, CD$_3$OD) δ 8.74 (d, 1H), 8.16 (dd, 8.2 Hz, 1H), 7.96 (s, 1H), 7.70 (d, 1H), 7.66 (br d, 1H), 7.57 (tdd, 6.9 Hz, 2H), 7.47 (d, 1H), 7.07 (t, 2H), 5.38 (d, 2H), 5.05 (d, 2H), 1.43 (s, 6H); MS (ESI) m/z: 475.2 [M+H$^+$].

Example 87: N-(4-fluorophenyl)-3-(4'-(2-hydroxypropan-2-yl)-6'-(trifluoromethyl)-[2,3'-bipyridin]-5-yl)oxetane-3-carboxamide

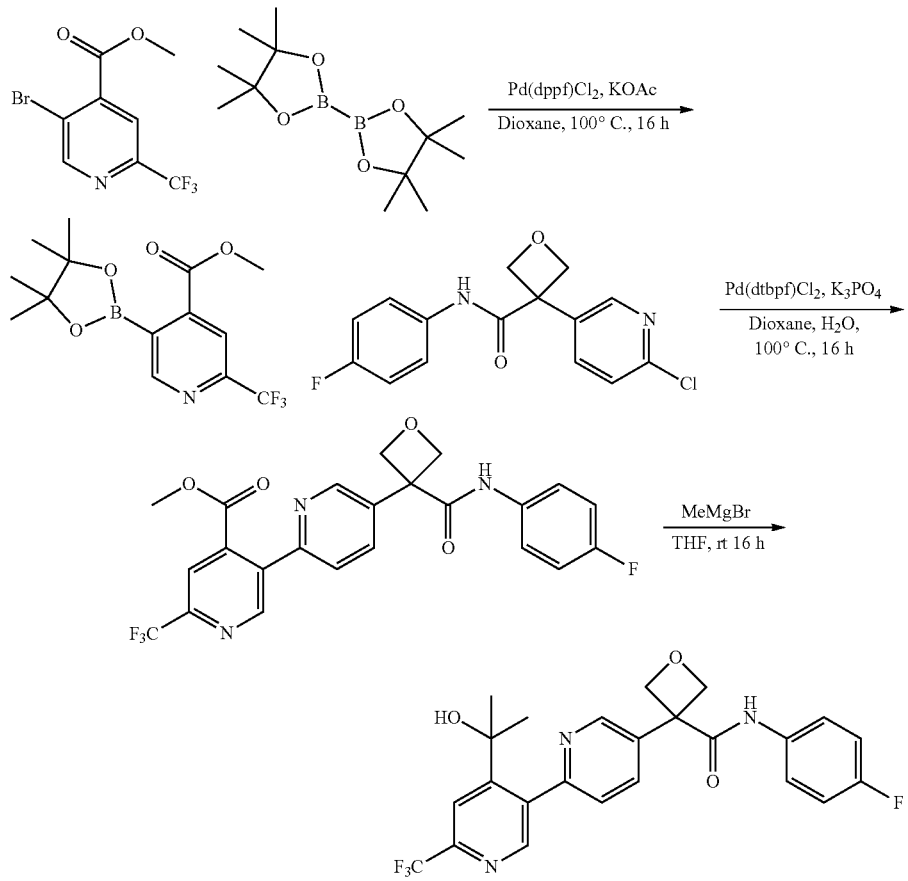

Step 1: methyl 5-(4,4,5,5-tetramethyl-1,3,2-dioxaborolan-2-yl)-2-(trifluoromethyl)isonicotinate To a stirred solution of methyl 5-bromo-2-(trifluoromethyl)isonicotinate (520 mg, 1.831 mmol), 4,4,4',4',5,5,5',5'-octamethyl-2,2'-bi(1,3,2-dioxaborolane) (697 mg, 2.75 mmol) in dioxane (2 mL) were added potassium acetate (539 mg, 5.49 mmol) and Pd(dppf)Cl₂ (134 mg, 0.183 mmol) at RT. The mixture was heated to 100° C. with stirring for 16 h. The mixture was concentrated under reduced pressure and sat. NaHCO₃ solution was added to adjust pH to >8. It was then extracted with EtOAc (20 mL×3) and the organic layers were collected, washed with brine (10 mL), dried over Na₂SO₄, filtered, and the filtrate was concentrated in vacuo. The residue was purified by prep-TLC (petroleum ether/EtOAc=5:1) to afford the title compound as an oil. $^1$H NMR (500 MHz, CD$_3$OD) δ 8.86 (s, 1H), 8.44 (s, 1H), 3.86 (s, 3H), 1.37-1.32 (m, 8H), 1.30 (s, 1H).

Step 2: methyl 5-(3-((4-fluorophenyl)carbamoyl)oxetan-3-yl)-6'-(trifluoromethyl)-[2,3'-bipyridine]-4'-carboxylate To a stirred solution of 3-(6-chloropyridin-3-yl)-N-(4-fluorophenyl)oxetane-3-carboxamide (30 mg, 0.098 mmol) and methyl 5-(4,4,5,5-tetramethyl-1,3,2-dioxaborolan-2-yl)-2-(trifluoromethyl)isonicotinate (48 mg, 0.145 mmol) in dioxane (2 mL) and water (0.4 mL) were added K$_3$PO$_4$ (62 mg, 0.292 mmol) and Pd(dtbpf)Cl$_2$ (15 mg, 0.023 mmol) at RT. The reaction mixture was subjected to the same condition as in Step 1 and the crude product was purified by reversed phase HPLC on a GILSON 281 instrument fitted with a Phenomenex Synergi C 18 150×30 mm×4 um column to afford the title compound as an oil. MS (ESI) m/z: 475.9 [M+H⁺].

Step 3: N-(4-fluorophenyl)-3-(4'-(2-hydroxypropan-2-yl)-6'-(trifluoromethyl)-[2,3'-bipyridin]-5-yl)oxetane-3-carboxamide To a stirred solution of methyl 5-(3-((4-fluorophenyl)carbamoyl)oxetan-3-yl)-6'-(trifluoromethyl)-[2,3'-bipyridine]-4'-carboxylate (10 mg, 0.021 mmol) in THF (2 mL) was added methylmagnesium bromide (0.1 mL, 0.300 mmol) (3 M in ether) dropwise at RT. The reaction was stirred at RT for 16 h. The reaction mixture was diluted with water (5 mL) and then filtered under reduced pressure to give a residue, which was purified by reversed phase HPLC on a GILSON 281 instrument fitted with a Phenomenex Synergi C 18 150×30 mm×4 um column to afford the title compound as a solid. $^1$H NMR (500 MHz, CD$_3$OD) δ 8.83 (d, 1H), 8.57 (s, 1H), 8.19-8.16 (m, 1H), 8.14 (s, 1H), 7.73 (d, 1H), 7.63-7.60 (m, 2H), 7.60-7.59 (m, 1H), 7.10 (t, 2H), 5.42 (d, 2H), 5.09 (d, 2H), 2.71 (brs, 1H), 2.55 (brs, 1H), 2.07-2.03 (m, 1H), 1.47 (s, 6H). MS (ESI) m/z: 476.2[M+H⁺]

Example 88: 3-(6'-cyclopropoxy-4'-(hydroxymethyl)-[2,3'-bipyridin]-5-yl)-N-(4-fluorophenyl)oxetane-3-carboxamide

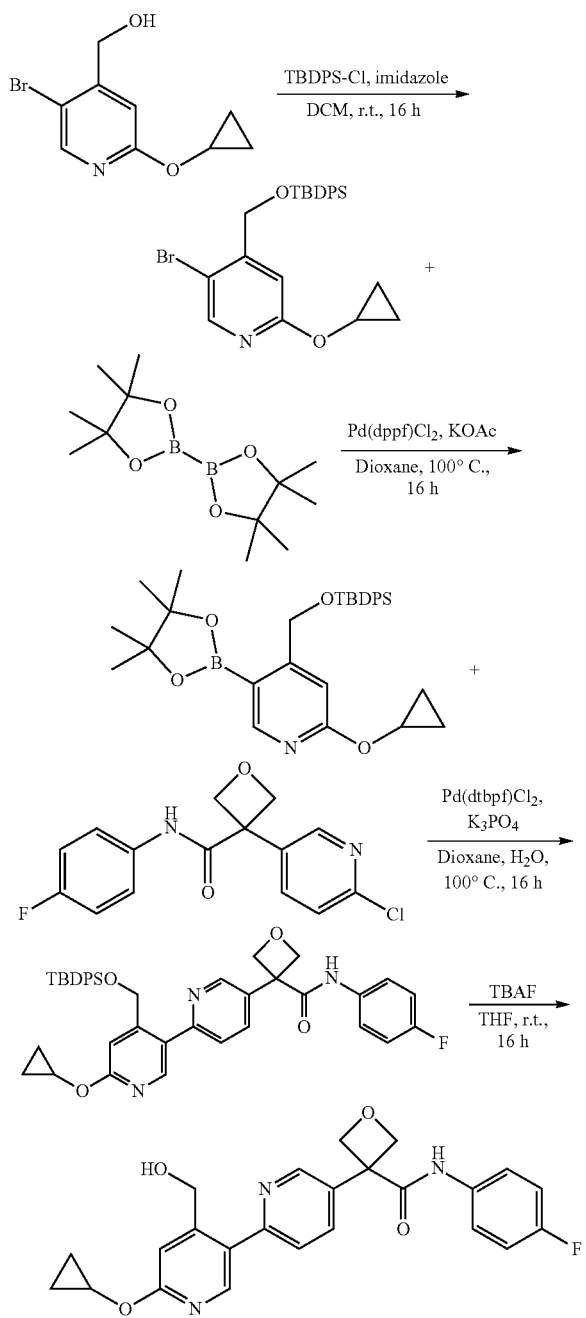

Step 1: 5-bromo-4-(((tert-butyldiphenylsilyl)oxy)methyl)-2-cyclopropoxypyridine To a stirred solution of (5-bromo-2-cyclopropoxypyridin-4-yl)methanol (500 mg, 2.048 mmol) in DCM (10 mL) was added tert-butylchlorodiphenylsilane (619 mg, 2.253 mmol) and 1H-imidazole (307 mg, 4.51 mmol) at RT. The reaction was stirred at RT for 16 h. The mixture was diluted with water (50 mL), extracted with EtOAc (50 mL×3), and the organic layers were collected, washed with brine (20 mL), and dried over Na$_2$SO$_4$. After filtration, the filtrate was concentrated in vacuo and the residue was purified by flash silica gel chromatography to afford title compound. $^1$H NMR (400 MHz, CD$_3$OD) δ 8.12 (s, 1H), 7.70-7.63 (m, 4H), 7.48-7.36 (m, 6H), 7.29 (s, 1H), 4.71 (s, 2H), 4.09 (tt, 1H), 1.11 (s, 9H), 0.82-0.72 (m, 4H)

Step 2: 4-(((tert-butyldiphenylsilyl)oxy)methyl)-2-cyclopropoxy-5-(4,4,5,5-tetramethyl-1,3,2-dioxaborolan-2-yl)pyridine To a stirred solution of 5-bromo-4-(((tert-butyldiphenylsilyl)oxy)methyl)-2-cyclopropoxypyridine (940 mg, 1.948 mmol), 4,4,4',4',5,5,5',5'-octamethyl-2,2'-bi(1,3,2-dioxaborolane) (742 mg, 2.92 mmol) in dioxane (20 mL) was added potassium acetate (574 mg, 5.84 mmol) and Pd(dppf)Cl$_2$ (143 mg, 0.195 mmol) at RT. The reaction was stirred at 100° C. for 16 h. After cooled to RT, the mixture was extracted with EtOAc (50 mL×3), the organic layers were collected, washed with brine (30 mL), dried over Na$_2$SO$_4$, filtered, and the filtrate was concentrated in vacuo. The residue was purified by flash silica gel chromatography to afford the title compound as a solid. MS (ESI) m/z: 530.2 [M+H$^+$].

Step 3: 3-(4'-(((tert-butyldiphenylsilyl)oxy)methyl)-6'-cyclopropoxy-[2,3'-bipyridin]-5-yl)-N-(4-fluorophenyl)oxetane-3-carboxamide To a stirred solution of 3-(6-chloropyridin-3-yl)-N-(4-fluorophenyl)oxetane-3-carboxamide (30 mg, 0.098 mmol) and 4-(((tert-butyldiphenylsilyl)oxy)methyl)-2-cyclopropoxy-5-(4,4,5,5-tetramethyl-1,3,2-dioxaborolan-2-yl)pyridine (62 mg, 0.117 mmol in dioxane (2 mL) and water (0.4 mL) were added K$_3$PO$_4$ (62 mg, 0.292 mmol) and Pd(dtbpf)Cl$_2$ (7 mg, 10.74 μmol) at RT. The mixture was subjected to the usual Suzuki coupling conditions as stated above. The crude product was purified by prep-TLC (SiO$_2$, petroleum ether/EtOAc=1:1 as eluent) to afford title compound as an oil. MS (ESI) m/z: 674.2[M+H$^+$].

Step 4: 3-(6'-cyclopropoxy-4'-(hydroxymethyl)-[2,3'-bipyridin]-5-yl)-N-(4-fluorophenyl)oxetane-3-carboxamide To a stirred solution of 3-(4'-(((tert-butyldiphenylsilyl)oxy)methyl)-6'-cyclopropoxy-[2,3'-bipyridin]-5-yl)-N-(4-fluorophenyl)oxetane-3-carboxamide (25 mg, 0.037 mmol) in THF (2 mL) was added tetrabutylammonium fluoride (0.1 mL, 0.100 mmol) at RT. The mixture was stirred at RT for 16 h. The solvent was concentrated under reduced pressure and the residue was purified by reversed phase HPLC on a GILSON 281 instrument fitted with a Phenomenex Synergi C18 column (150×30 mm×4 um) to afford the title compound as a solid. $^1$H NMR (400 MHz, CD$_3$OD) δ 8.77 (d, 1H), 8.27 (s, 1H), 8.08 (dd, 1H), 7.73 (d, 1H), 7.58 (dd, 2H), 7.22 (s, 1H), 7.07 (t, 2H), 5.37 (d, 2H), 5.04 (d, 2H), 4.68 (s, 2H), 4.23-4.17 (m, 1H), 0.88-0.83 (m, 2H), 0.77 (br s, 2H). MS (ESI) m/z: 436.1 [M+H$^+$].

Example 89: N-(5-fluorothiazol-2-yl)-3-(4-(4-(hydroxymethyl)-6-(trifluoromethyl)pyridin-3-yl)phenyl)oxetane-3-carboxamide

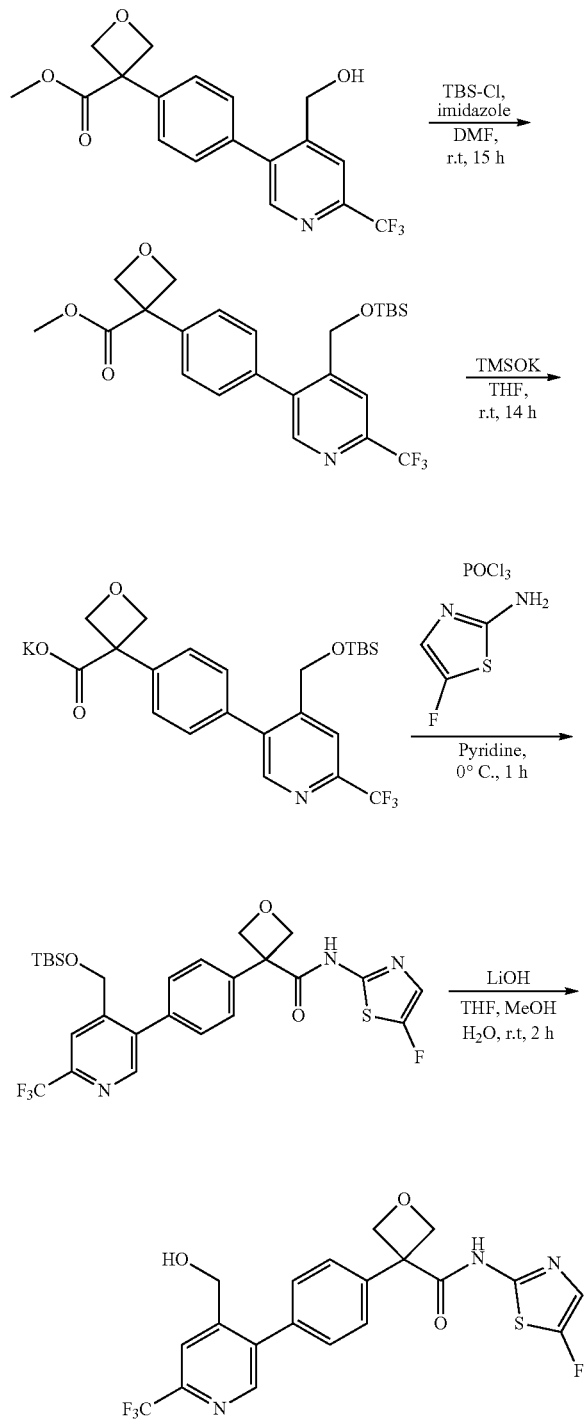

Step 1: methyl 3-(4-(4-(((tert-butyldimethylsilyl)oxy)methyl)-6-(trifluoromethyl)pyridin-3-yl)phenyl)oxetane-3-carboxylate To a solution of methyl 3-(4-(4-(hydroxymethyl)-6-(trifluoromethyl)pyridin-3-yl)phenyl)oxetane-3-carboxylate (220 mg, 0.599 mmol) and imidazole (82 mg, 1.198 mmol) in DMF (2.0 mL) was added TBS-Cl (108 mg, 0.719 mmol) with stirring at RT. The reaction mixture was stirred at RT for 14 h. The reaction was diluted with water (15 mL) and extracted with EtOAc (15 mL×3). The combined organic layer was washed with brine (20 mL), dried over $Na_2SO_4$, filtered and concentrated. The residue was purified by flash silica gel chromatography to afford the title compound as a solid. MS (ESI) m/z: 482.3 [M+H$^+$].

Step 2: potassium 3-(4-(4-(((tert-butyldimethylsilyl)oxy)methyl)-6-(trifluoromethyl)pyridin-3-yl)phenyl)oxetane-3-carboxylate To a solution of methyl 3-(4-(4-(((tert-butyldimethylsilyl)oxy)methyl)-6-(trifluoromethyl)pyridin-3-yl)phenyl)oxetane-3-carboxylate (168 mg, 0.349 mmol) in THF (5.0 mL) was added TMSOK (50 mg, 0.390 mmol) with stirring at RT under nitrogen. The reaction mixture was stirred at RT for 14 h. The solvent was concentrated to afford the title compound as a solid, which was used in next step without further purification. MS (ESI) m/z: 468.3 [M+H$^+$].

Step 3: 3-(4-(4-(((tert-butyldimethylsilyl)oxy)methyl)-6-(trifluoromethyl)pyridin-3-yl)phenyl)-N-(5-fluorothiazol-2-yl)oxetane-3-carboxamide To a solution of potassium 3-(4-(4-(((tert-butyldimethylsilyl)oxy)methyl)-6-(trifluoromethyl)pyridin-3-yl)phenyl)oxetane-3-carboxylate (15 mg, 0.030 mmol) and 5-fluorothiazol-2-amine (8 mg, 0.068 mmol) in pyridine (0.5 mL) was added POCl$_3$ (0.03 mL, 0.326 mmol) with stirring at 0° C. and the resulting mixture was stirred at 0° C. for 1 h. The reaction was quenched by the addition of sat. $Na_2CO_3$ (1.0 mL) and was then diluted with water (5 mL), and extracted with EtOAc (5 mL×3). The combined organic layer was washed with brine (5 mL), dried over $Na_2SO_4$, filtered and concentrated to afford a crude product, which was used in next step without further purification. MS (ESI) m/z: 568.1 [M+H$^+$].

Step 4: N-(5-fluorothiazol-2-yl)-3-(4-(4-(hydroxymethyl)-6-(trifluoromethyl)pyridin-3-yl)phenyl)oxetane-3-carboxamide To a solution of 3-(4-(4-(((tert-butyldimethylsilyl)oxy)methyl)-6-(trifluoromethyl)pyridin-3-yl)phenyl)-N-(5-fluorothiazol-2-yl)oxetane-3-carboxamide (16 mg, 0.028 mmol) in THF (2.0 mL), water (1.0 mL) and MeOH (2.0 mL) was added LiOH (5 mg, 0.209 mmol) with stirring at RT. The mixture was stirred at RT for 1 h. The reaction was quenched by the addition of 1N HCl until pH-7, and concentrated. The residue was purified by reversed phase HPLC on a GILSON 281 instrument fitted with a Xtimate C18 column (150×25 mm×5 um) using water and ACN as eluents, followed by lyophilization to afford the title compound as a solid. $^1$H NMR (400 MHz, CD$_3$OD) δ 8.53 (s, 1H), 8.07 (s, 1H), 7.56-7.65 (m, 2H), 7.50 (d, 2H), 7.09 (d, 1H), 5.34 (d, 2H), 5.06 (d, 2H), 4.64 (s, 2H). MS (ESI) m/z: 453.9 [M+H$^+$].

Examples 90-93 in the following table were prepared in a similar fashion as Example 89.

| Ex. # | Structure | Chemical Name | Mass [M + H]+ |
|---|---|---|---|
| 90 | 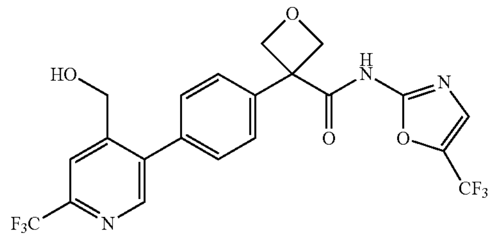 [SMILES: O=C(Nc1ncc(C(F)(F)F)o1)C1(c2ccc(-c3cnc(C(F)(F)F)cc3CO)cc2)COC1] | 3-(4-(4-(hydroxymethyl)-6-(trifluoromethyl)pyridin-3-yl)phenyl)-N-(5-(trifluoromethyl)oxazol-2-yl)oxetane-3-carboxamide | 488.1 |
| 91 | 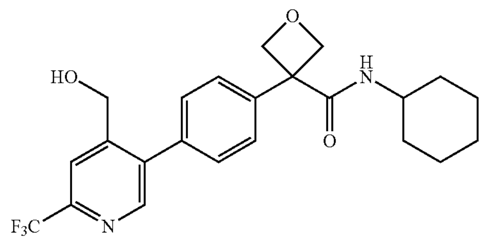 [SMILES: O=C(NC1CCCCC1)C1(c2ccc(-c3cnc(C(F)(F)F)cc3CO)cc2)COC1] | N-cyclohexyl-3-(4-(4-(hydroxymethyl)-6-(trifluoromethyl)pyridin-3-yl)phenyl)oxetane-3-carboxamide | 435.2 |
| 92 | 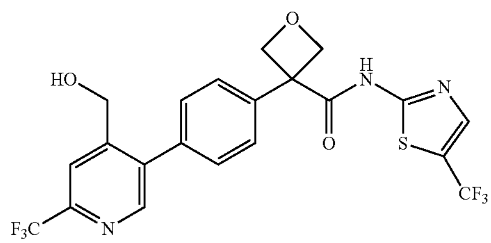 [SMILES: O=C(Nc1ncc(C(F)(F)F)s1)C1(c2ccc(-c3cnc(C(F)(F)F)cc3CO)cc2)COC1] | 3-(4-(4-(hydroxymethyl)-6-(trifluoromethyl)pyridin-3-yl)phenyl)-N-(5-(trifluoromethyl)thiazol-2-yl)oxetane-3-carboxamide | 503.9 |
| 93 | 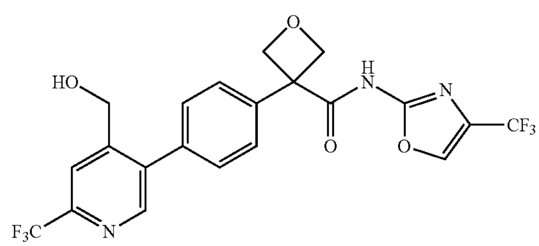 [SMILES: O=C(Nc1nc(C(F)(F)F)co1)C1(c2ccc(-c3cnc(C(F)(F)F)cc3CO)cc2)COC1] | 3-(4-(4-(hydroxymethyl)-6-(trifluoromethyl)pyridin-3-yl)phenyl)-N-(4-(trifluoromethyl)oxazol-2-yl)oxetane-3-carboxamide | 488.0 |

Example 94: N-(4-fluorophenyl)-1-(4'-(hydroxymethyl)-6'-(trifluoromethyl)-[3,3'-bipyridin]-6-yl)cyclobutanecarboxamide

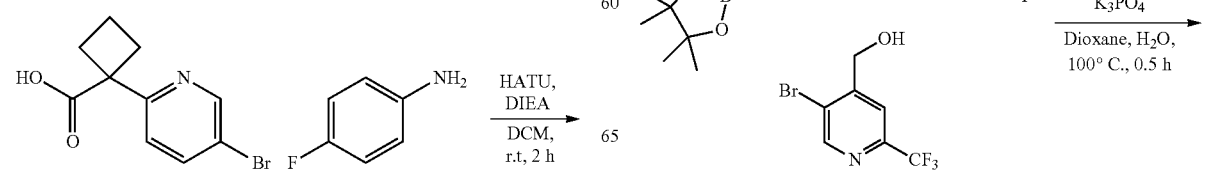

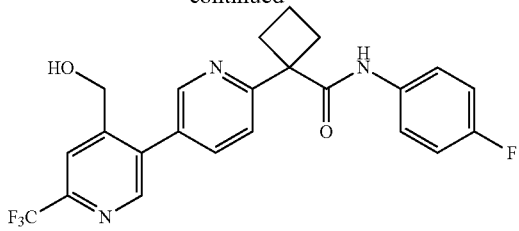

Step 1: 1-(5-bromopyridin-2-yl)cyclobutanecarboxylic Acid

To a solution of 1-(5-bromopyridin-2-yl)cyclobutanecarbonitrile (2.0 g, 8.44 mmol) in water (2 mL) and EtOH (15 mL) was added NaOH (1.687 g, 42.2 mmol) with stirring at RT under nitrogen and the reaction mixture was stirred at 85° C. for 18 h. The reaction was cooled to RT and concentrated. The residue was diluted with DCM (20 mL) and filtered. The filtered cake was suspended in EtOAc (20 mL) and water (20 mL) with stirring, then 3N HCl was added until pH-3 and all solid was dissolved. The mixture was extracted with EtOAc (20 mL×2), the organic layers were combined, washed with brine (60 mL), dried over Na$_2$SO$_4$, filtered and concentrated to afford the title compound as an oil, which was used directly in the next step without further purification. MS (ESI) m/z: 257.9 [M+H$^+$].

Step 2: 1-(5-bromopyridin-2-yl)-N-(4-fluorophenyl)cyclobutanecarboxamide

To a stirred solution of 1-(5-bromopyridin-2-yl)cyclobutanecarboxylic acid (2.16 g, 8.43 mmol) and DIEA (4.72 mL, 27.0 mmol) in DCM (20 mL) were added HATU (4.11 g, 10.80 mmol) and 4-fluoroaniline (1.0 g, 9.00 mmol) at RT. The reaction was stirred at RT for 2 h. The reaction mixture was poured into water (100 mL) and extracted with EtOAc (15 mL×3). The combined organic layer was washed with brine (20 mL) and concentrated in vacuo. The residue was purified by silica gel flash column chromatography to afford the title compound as a solid. MS (ESI) m/z: 350.8 [M+H$^+$].

Step 3: N-(4-fluorophenyl)-1-(5-(4,4,5,5-tetramethyl-1,3,2-dioxaborolan-2-yl)pyridin-2-yl)cyclobutanecarboxamide To a solution of 1-(5-bromopyridin-2-yl)-N-(4-fluorophenyl)cyclobutanecarboxamide (500 mg, 1.432 mmol) and 4,4,4',4',5,5,5',5'-octamethyl-2,2'-bi(1,3,2-dioxaborolane) (545 mg, 2.148 mmol) in dioxane (20 mL) were added KOAc (281 mg, 2.86 mmol) and Pd(dtbpf)Cl$_2$ (47 mg, 0.072 mmol) with stirring at RT under nitrogen. The reaction mixture was stirred at 90° C. for 14 h. After cooled to RT and diluted with water (30 mL), the mixture was extracted with EtOAc (30 mL×3). The combined organic layer was washed with brine (20 mL) and dried over Na$_2$SO$_4$, filtered and concentrated. The residue was purified by flash silica gel chromatography to afford the title compound as a solid. MS (ESI) m/z: 315.0 (the mass of the corresponding boronic acid).

Step 4: N-(4-fluorophenyl)-1-(4'-(hydroxymethyl)-6'-(trifluoromethyl)-[3,3'-bipyridin]-6-yl)cyclobutanecarboxamide To a solution of N-(4-fluorophenyl)-1-(5-(4,4,5,5-tetramethyl-1,3,2-dioxaborolan-2-yl)pyridin-2-yl)cyclobutanecarboxamide (50 mg, 0.126 mmol) in 1,4-dioxane (1 mL) and water (0.2 mL) were added Pd(dtbpf)Cl$_2$ (8 mg, 0.012 mmol), (5-bromo-2-(trifluoromethyl)pyridin-4-yl)methanol (33 mg, 0.129 mmol) and potassium phosphate (80 mg, 0.379 mmol) at RT. The reaction was stirred at 100° C. in a microwave for 0.5 h. The solvent was removed, and the residue was diluted with water (5 mL), and extracted with EtOAc (5 mL×3). The organic layers were collected, washed with brine (10 mL), dried over Na$_2$SO$_4$, filtered, and the filtrate was concentrated in vacuo. The reaction mixture was purified by reversed phase HPLC on a GILSON 281 instrument fitted with a Waters XSELECT C18 column (150×30 mm×5 um) using water (0.1% TFA)-ACN as eluents, followed by lyophilization to afford the title compound as a solid. $^1$H NMR (400 MHz, CD$_3$OD) δ 8.71 (d, 1H), 8.61 (s, 1H), 8.09 (s, 1H), 8.02 (br d, 1H), 7.74 (d, 1H), 7.51-7.58 (m, 2H), 7.03 (t, 2H), 4.66 (s, 2H), 2.91-3.09 (m, 2H), 2.71-2.88 (m, 2H), 1.93-2.16 (m, 2H). MS (ESI) m/z: 446.0 [M+H$^+$].

Example 95: N-(4-fluorophenyl)-1-(4'-(1-hydroxycyclobutyl)-6'-(trifluoromethyl)-[3,3'-bipyridin]-6-yl)cyclobutanecarboxamide

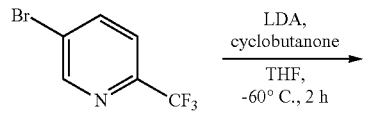

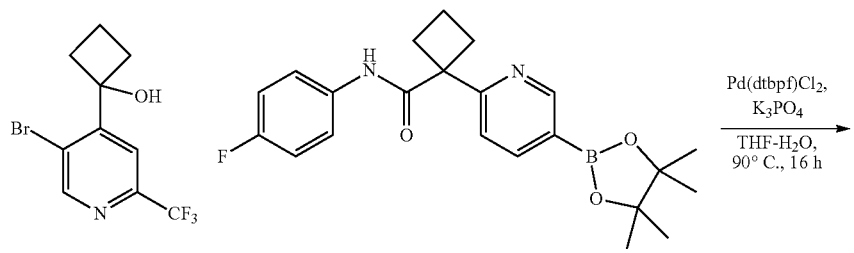

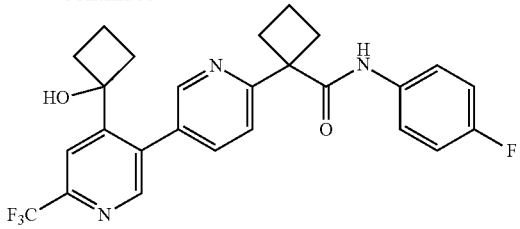

Step 1: 1-(5-bromo-2-(trifluoromethyl)pyridin-4-yl) cyclobutanol

To a solution of 5-bromo-2-(trifluoromethyl)pyridine (1 g, 4.42 mmol) in THF (20 mL) was added LDA (2.4 mL, 4.87 mmol) dropwise at −60° C. under nitrogen. After 3 h, cyclobutanone (0.372 g, 5.31 mmol) was added dropwise at −60° C., the mixture was stirred at this temperature for 1 h, and allowed to warm up to RT. The reaction was quenched with sat. aq. NH₄Cl (10 mL) and extracted with EtOAc (15 mL×2). The organic layer was dried over Na₂SO₄, filtered and concentrated. The residue was purified by flash silica gel chromatography to afford the title compound as a solid. MS (ESI) m/z: 295.9, 297.9 [M+H⁺].

Step 2: N-(4-fluorophenyl)-1-(4'-(1-hydroxycyclobutyl)-6'-(trifluoromethyl)-[3,3'-bipyridin]-6-yl) cyclobutanecarboxamide To a solution of N-(4-fluorophenyl)-1-(5-(4,4,5,5-tetramethyl-1,3,2-dioxaborolan-2-yl)pyridin-2-yl)cyclobutanecarboxamide (50 mg, 0.126 mmol) and 1-(5-bromo-2-(trifluoromethyl)pyridin-4-yl)cyclobutanol (45 mg, 0.152 mmol) in THF (2.0 mL) and water (0.2 mL) were added K₃PO₄ (80 mg, 0.379 mmol) and Pd(dtbpf)Cl₂ (8 mg, 0.012 mmol) with stirring at RT under nitrogen. The reaction mixture was stirred at 90° C. for 14 h. The reaction was cooled to RT, diluted with water (5 mL), and the mixture was extracted with EtOAc (5 mL×3). The combined organic layer was washed with brine (10 mL), dried over Na₂SO₄, filtered and concentrated. The residue was purified by reversed phase HPLC on a GILSON 281 instrument fitted with a YMC-Actus Pro C18 column (150×30×5 um) using water (0.1% TFA) and ACN as eluents, followed by lyophilization to afford the title compound as a solid. ¹H NMR (400 MHz, CD₃OD) δ 8.79 (s, 1H), 8.59 (s, 1H), 8.14 (dd, 1H), 7.80 (s, 1H), 7.73 (d, 1H), 7.53 (dd, 2H), 7.03 (t, J=8.8 Hz, 2H), 2.93-3.04 (m, 2H), 2.74-2.84 (m, 2H), 2.27-2.39 (m, 2H), 1.91-2.13 (m, 5H), 1.62 (br d, 1H). MS (ESI) m/z: 486.3 [M+H⁺].

Examples 96-97 in the following table were prepared in a similar fashion as Example 95.

| Ex. # | Structure | Chemical Name | Mass [M + H]+ |
|---|---|---|---|
| 96 | 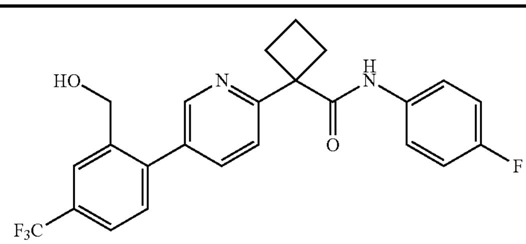 | N-(4-fluorophenyl)-1-(5-(2-(hydroxymethyl)-4-(trifluoromethyl)phenyl)pyridin-2-yl)cyclobutanecarboxamide | 444.9 |
| 97 | 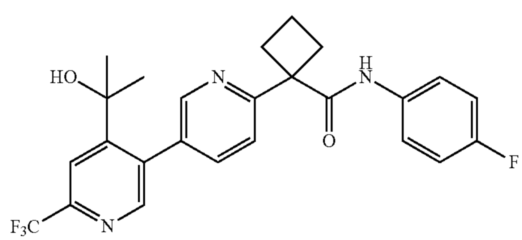 [SMILES: CC(C)(O)c1cc(C(F)(F)F)ncc1-c1ccc(C2(C(=O)Nc3ccc(F)cc3)CCC2)nc1] | N-(4-fluorophenyl)-1-(4'-(2-hydroxypropan-2-yl)-6'-(trifluoromethyl)-[3,3'-bipyridin]-6-yl)cyclobutanecarboxamide | 474.0 |

Example 98: N-(4-fluorophenyl)-3-(4-(3-(hydroxymethyl)-5-(trifluoromethyl)pyridin-2-yl)phenyl)oxetane-3-carboxamide

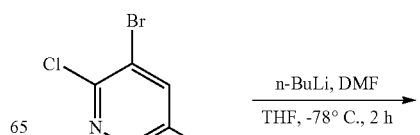

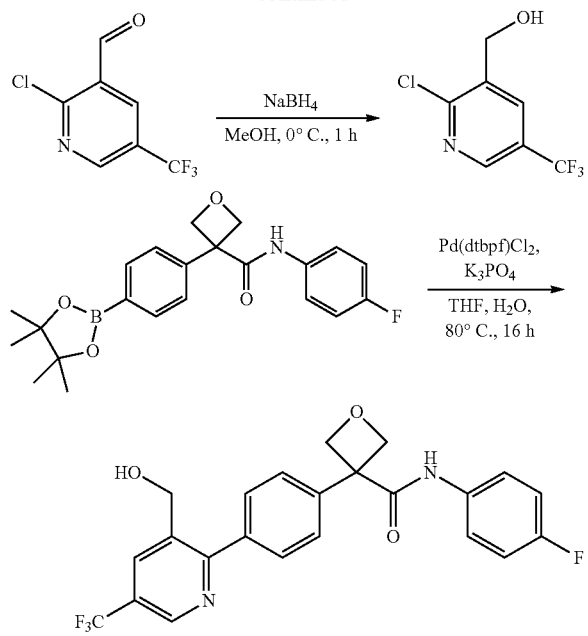

Step 1: 2-chloro-5-(trifluoromethyl)nicotinaldehyde

To a stirred solution of 3-bromo-2-chloro-5-(trifluoromethyl)pyridine (3 g, 11.52 mmol) in toluene (60 mL) was added n-BuLi (6 mL, 15.00 mmol) (2.5 M hexane) at −78° C., and the reaction was stirred at −78° C. for 1.5 h. Then DMF (1.2 mL, 15.5 mmol) was added at −78° C., and the resulting mixture was stirred at −78° C. for 0.5 h. The reaction was quenched with HCl (1 M) (60 mL), then extracted with EtOAc (50 mL×2). The organic layers were collected, washed with brine, dried over Na$_2$SO$_4$, filtered, and the filtrate was concentrated in vacuo. The residue was purified by flash silica gel chromatography to afford the title compound as an oil. $^1$H NMR (500 MHz, CDCl$_3$) δ 10.44-10.51 (m, 1H) 8.87 (d, 1H) 8.47 (d, 1H)

Step 2: (2-chloro-5-(trifluoromethyl)pyridin-3-yl)methanol

To a stirred solution of 2-chloro-5-(trifluoromethyl)nicotinaldehyde (780 mg, 3.72 mmol) in MeOH (5 mL) was added NaBH$_4$ (141 mg, 3.72 mmol) at 0° C. and the reaction was stirred at 0° C. for 1 h. The reaction mixture was quenched with sat. NH$_4$Cl (5 mL), then extracted with EtOAc (5 mL×2). The organic layers were collected, washed with brine, dried over Na$_2$SO$_4$, filtered, and the filtrate was concentrated in vacuo. The residue was purified by flash silica gel chromatography to give the title compound as an oil. MS (ESI) m/z: 212.0 [M+H$^+$].

Step 3: N-(4-fluorophenyl)-3-(4-(3-(hydroxymethyl)-5-(trifluoromethyl)pyridin-2-yl)phenyl)oxetane-3-carboxamide To a stirred solution of (2-chloro-5-(trifluoromethyl)pyridin-3-yl)methanol (40 mg, 0.189 mmol) and N-(4-fluorophenyl)-3-(4-(4,4,5,5-tetramethyl-1,3,2-dioxaborolan-2-yl)phenyl-)oxetane-3-carboxamide (75 mg, 0.189 mmol) in THF (2 mL) and Water (0.4 mL) was added K$_3$PO$_4$ (120 mg, 0.567 mmol) and Pd(dtbpf)Cl$_2$ (13 mg, 0.020 mmol) at RT. The reaction was stirred at 80° C. for 16 h. After cooled to RT, the reaction mixture was diluted with water (2 mL), and extracted with EtOAc (2 mL×2). The organic layers were collected, washed with brine, dried over Na$_2$SO$_4$, filtered, and the filtrate was concentrated in vacuo. The residue was purified by reversed phase HPLC on a GILSON 281 instrument fitted with a Boston Green ODS column (150×30×5 um) using water (0.1% TFA)-CH$_3$CN as eluents, followed by concentration (below 50° C.) to afford the title compound as an oil. $^1$H NMR (500 MHz, CD$_3$OD) δ 8.85 (br s, 1H) 8.38 (s, 1H) 7.63-7.70 (m, 4H) 7.52-7.61 (m, 2H) 7.00-7.10 (m, 2H) 5.36 (d, 2H) 5.04 (d, 2H) 4.67 (s, 2H). MS (ESI) m/z: 447.0 [M+H$^+$].

Example 99: N-(4-fluorophenyl)-3-(4-(4-(1-hydroxycyclobutyl)-6-(trifluoromethyl)pyridin-3-yl)phenyl)oxetane-3-carboxamide

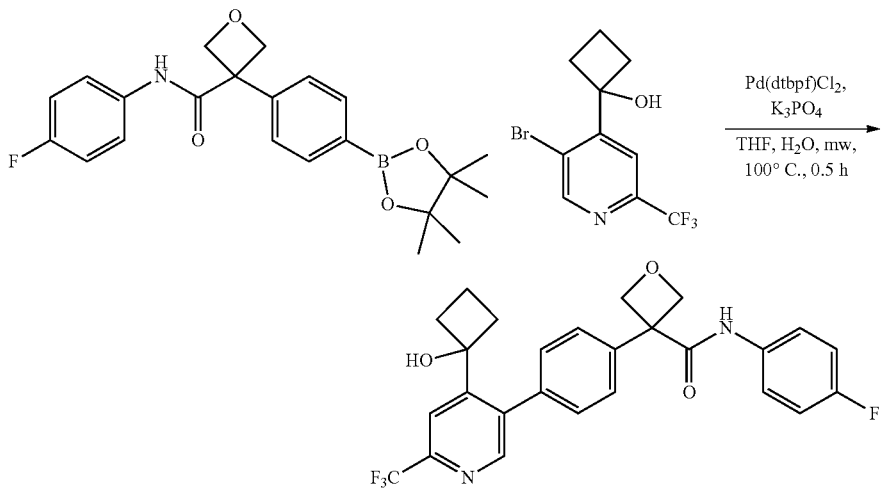

To a solution of N-(4-fluorophenyl)-3-(4-(4,4,5,5-tetramethyl-1,3,2-dioxaborolan-2-yl)phenyl)oxetane-3-carboxamide (35 mg, 0.088 mmol) and 1-(5-bromo-2-(trifluoromethyl)pyridin-4-yl)cyclobutanol (30 mg, 0.101 mmol) in THF (2.0 mL) and water (0.2 mL) were added K$_3$PO$_4$ (56 mg, 0.264 mmol) and Pd(dtbpf)Cl$_2$ (6 mg, 9.21 μmol). The reaction mixture was sealed and stirred at 100° C. in a microwave for 0.5 h. The reaction was cooled to RT and diluted with water (5 mL). The mixture was extracted with EtOAc (5 mL×3), the combined organic layer was washed with brine (5 mL), dried over Na$_2$SO$_4$, filtered and concentrated. The residue was purified by reversed phase HPLC on a GILSON 281 instrument fitted with a YMC-Actus Pro C18 column (150×30×5 um) using water (0.1% TFA) and ACN as eluents, followed by lyophilization to afford the title compound as a solid. $^1$H NMR (400 MHz, CD$_3$OD) δ 8.52 (s, 1H), 7.75 (s, 1H), 7.52-7.64 (m, 6H), 6.98-7.13 (m, 2H), 5.36 (d, 2H), 5.03 (d, 2H), 2.22-2.32 (m, 2H), 2.02-2.12 (m, 1H), 1.93-2.01 (m, 2H), 1.52-1.62 (m, 1H). MS (ESI) m/z: 487.0[M+H$^+$].

Example 100: N-(4-fluorophenyl)-3-(4-(4-(1-hydroxycyclopropyl)-6-(trifluoromethyl)pyridin-3-yl)phenyl)oxetane-3-carboxamide (12.12 mL, 12.12 mmol) dropwise at 0° C. under nitrogen. The mixture was stirred at RT for 0.5 h. Concurrently, to a separated flask containing a solution of 1-ethoxycyclopropanol (1.238 g, 12.12 mmol) in THF (12.0 mL) was added methylmagnesium bromide (4.04 mL, 12.12 mmol) dropwise at 0° C., and the resultant white suspension was stirred at 0° C. for 10 min. The above organolithium solution was then added into this suspension and the resultant reaction mixture was stirred at ambient temperature for 30 min, followed by stirring at 40° C. for 14 h. The reaction was cooled to 0° C. and quenched by slow addition of sat. NH$_4$Cl (25 mL). The mixture was diluted with EtOAc (20 mL), and filtered. The filtrate was extracted with EtOAc (15 mL×3). The combined organic layer was washed with brine (15 mL), dried over Na$_2$SO$_4$, filtered and concentrated. The residue was purified by silica gel column chromatography using petroleum ether/EtOAc (20:1-10:1) as eluent to give the crude product which was further purified by Prep-TLC (petroleum ether/ethyl acetate 4:1 as eluent) to afford 1-(5-

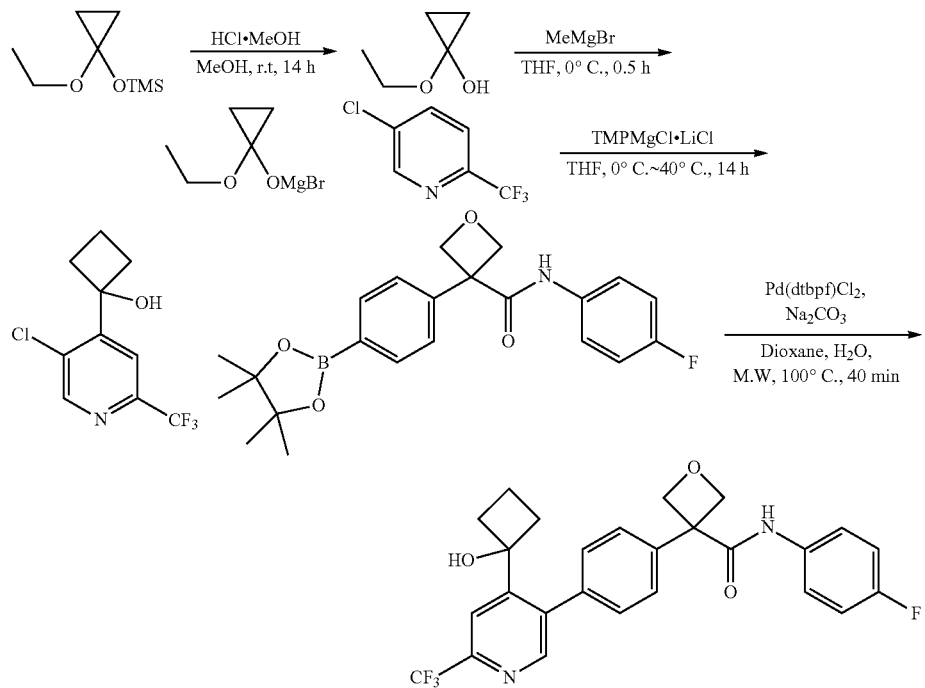

chloro-2-(trifluoromethyl)pyridin-4-yl)cyclopropanol as an oil. MS (ESI) m/z: 238 [M+H$^+$], Step 3: N-(4-fluorophenyl)-3-(4-(4-(1-hydroxycyclopropyl)-6-(trifluoromethyl)pyridin-3-yl)phenyl)oxetane-3-carboxamide To a solution of 1-(5-chloro-2-(trifluoromethyl)pyridin-4-yl)cyclopropanol (10 mg, 0.042 mmol) and N-(4-fluorophenyl)-3-(4-(4,4,5,5-tetramethyl-1,3,2-dioxaborolan-2-yl)phenyl)oxetane-3-carboxamide (17 mg, 0.043 mmol) in dioxane (1.0 mL) and water (0.1 mL) were added sodium carbonate (18 mg, 0.170 mmol) and Pd(dtbpf)Cl$_2$ (3 mg, 4.60 μmol) with stirring at RT under nitrogen. The mixture was sealed and heated to 100° C. promoted by microwave for 40 min and then cooled to RT. The cooled mixture was Step 1: 1-ethoxycyclopropanol To a solution of (1-ethoxycyclopropoxy)trimethylsilane (5.0 g, 28.7 mmol) in MeOH (35 mL) was added 4.0 M HCl (0.07 mL, 0.274 mmol, in MeOH) with stirring at RT. The reaction mixture was stirred at RT for 14 h. The solvent was removed and the residue was purified by distillation under reduced pressure (65° C., 10-12 mbar) to afford the title compound as an oil. $^1$H NMR (400 MHz, CDCl$_3$) δ 3.76 (q, 2H), 3.14 (br s, 1H), 1.22 (t, 3H), 0.91-0.99 (m, 4H).

Step 2: 1-(5-chloro-2-(trifluoromethyl)pyridin-4-yl)cyclopropan-1-ol

To a solution of 5-chloro-2-(trifluoromethyl)pyridine (2.0 g, 11.02 mmol) in THF (8 mL) was added TMPMgCl.LiCl diluted with water (2 mL) and extracted with EtOAc (5 mL×3). The combined organic layer was concentrated and the residue was purified by reversed phase HPLC on a GILSON 281 instrument fitted with a Xtimate C18 (150*25 mm*5 um) column using water (10 mM NH₄HCO₃) and ACN as eluents, followed by lyophilization to afford the title compound as a solid. ¹H NMR (500 MHz, CDCl₃) δ 8.62-8.74 (m, 1H), 7.78 (s, 1H), 7.67-7.72 (m, 1H), 7.71 (d, J=8.2 Hz, 1H), 7.49 (d, J=8.2 Hz, 2H), 7.41 (t, J=6.4 Hz, 2H), 6.97-7.07 (m, 3H), 5.43 (d, J=6.0 Hz, 2H), 5.12 (d, J=6.0 Hz, 2H), 2.48 (s, 1H), 1.05-1.16 (m, 2H), 0.79-0.89 (m, 2H). MS (ESI) m/z: 473.1[M+H⁺].

Examples 101-102 in the following table were prepared in a similar fashion as Example 100.

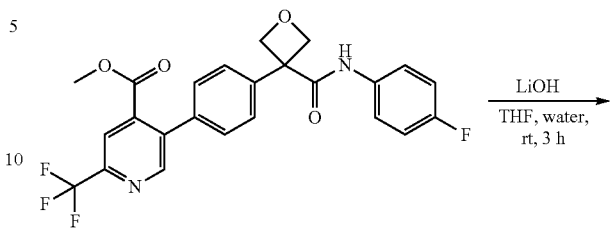

| Ex. # | Structure | Chemical Name | Mass [M + H]+ |
|---|---|---|---|
| 101 | 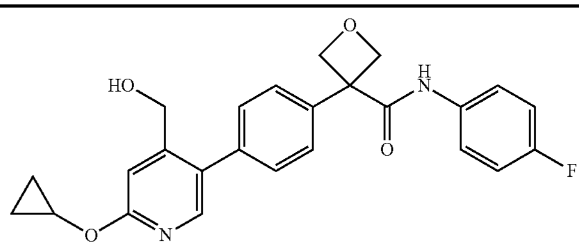 | 3-(4-(6-cyclopropoxy-4-(hydroxymethyl)pyridin-3-yl)phenyl)-N-(4-fluorophenyl)oxetane-3-carboxamide | 435.2 |
| 102 | 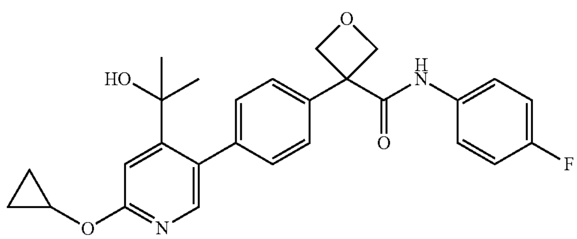 [SMILES: CC(C)(O)c1cc(OC2CC2)ncc1-c1ccc(C2(C(=O)Nc3ccc(F)cc3)COC2)cc1] | 3-(4-(6-cyclopropoxy-4-(2-hydroxypropan-2-yl)pyridin-3-yl)phenyl)-N-(4-fluorophenyl)oxetane-3-carboxamide | 463.2 |

Example 103: 5-(4-(3-((4-fluorophenyl)carbamoyl)oxetan-3-yl)phenyl)-N-methyl-2-(trifluoromethyl)isonicotinamide

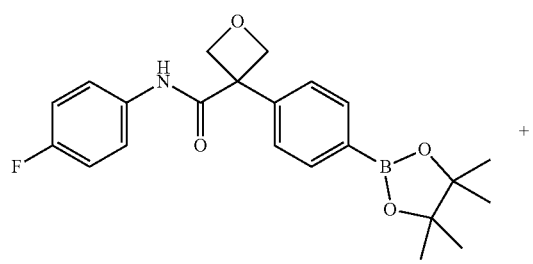

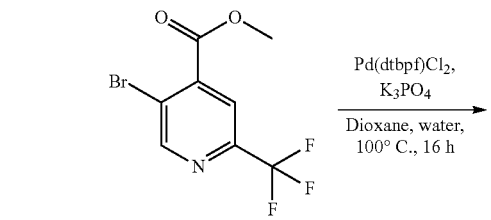

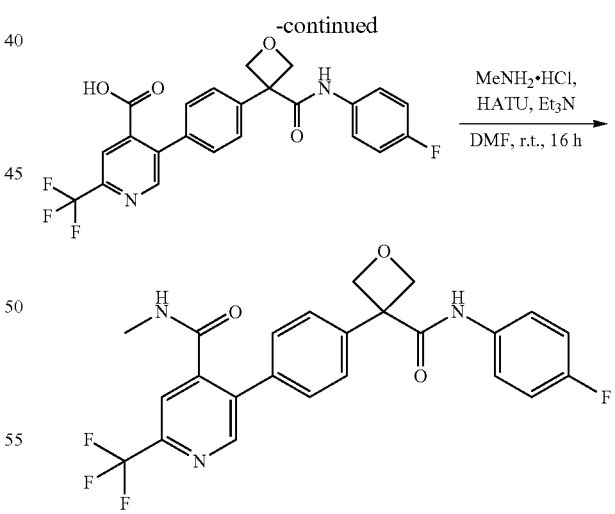

Step 1: methyl 5-(4-(3-((4-fluorophenyl)carbamoyl)oxetan-3-yl)phenyl)-2-(trifluoromethyl)isonicotinate To a solution of N-(4-fluorophenyl)-3-(4-(4,4,5,5-tetramethyl-1,3,2-dioxaborolan-2-yl)phenyl)oxetane-3-carboxamide (200 mg, 0.503 mmol) in dioxane (2.5 mL) and water (0.5 mL) were added Pd(dtbpf)Cl₂ (32.8 mg, 0.050 mmol), methyl 5-bromo-2-(trifluoromethyl)isonicotinate (143 mg, 0.503 mmol) and potassium phosphate (321 mg, 1.510 mmol) at RT. The mixture was subjected to the typical Suzuki coupling conditions and work up procedures to afford a crude product which was purified by flash silica gel chromatography to afford the title compound as an oil. MS (ESI) m/z: 475.2 [M+H⁺].

Step 2: 5-(4-(3-((4-fluorophenyl)carbamoyl)oxetan-3-yl)phenyl)-2-(trifluoromethyl)isonicotinic acid To a solution of methyl 5-(4-(3-((4-fluorophenyl)carbamoyl)oxetan-3-yl)phenyl)-2-(trifluoromethyl)isonicotinate (150 mg, 0.316 mmol) in THF (5 mL) and water (2.5 mL) was added LiOH (15 mg, 0.626 mmol) at RT. The reaction was stirred at RT for 3 h. The solvent was removed and the residue was acidified to pH=3 with 6 M HCl. The aqueous mixture was extracted with EtOAc (20 mL×3) with the addition of brine to the aqueous layer during extraction. The combined organics were washed with brine, dried over Na₂SO₄ and concentrated in vacuo to afford the title compound as an oil. MS (ESI) m/z: 461.2[M+H⁺].

Step 3: 5-(4-(3-((4-fluorophenyl)carbamoyl)oxetan-3-yl)phenyl)-N-methyl-2-(trifluoromethyl)isonicotinamide To a solution of 5-(4-(3-((4-fluorophenyl)carbamoyl)oxetan-3-yl)phenyl)-2-(trifluoromethyl)isonicotinic acid (120 mg, 0.261 mmol) in DMF (5 mL) were added TEA (0.2 mL, 1.435 mmol), HATU (99 mg, 0.261 mmol) and methylamine hydrochloride (18 mg, 0.267 mmol) at RT. The reaction was stirred for 16 h at RT. The reaction was diluted with water (40 mL), and extracted with EtOAc (30 mL×3). The combined organic layer was washed with brine (20 mL) and dried over Na₂SO₄, filtered and concentrated. The residue was purified by reversed phase HPLC using a Phenomenex Synergi C18 150×30 mm×4 um and eluting with water (0.1% TFA)-ACN to afford the title compound as a solid. $^1$H NMR (400 MHz, CD₃OD) δ 8.80 (s, 1H) 7.86 (s, 1H) 7.60-7.64 (m, 2H) 7.52-7.58 (m, 4H) 7.04 (t, 2H) 5.34 (d, 2H) 5.01 (d, 2H) 2.70-2.74 (m, 3H). MS (ESI) m/z: 474.2 [M+H⁺].

Example 104 in the following table was prepared in a similar fashion as Ex. 103.

| Ex. # | Structure | Chemical Name | Mass [M + H]+ |
|---|---|---|---|
| 104 | 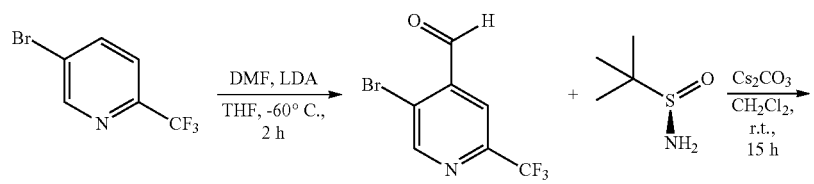 | 5-(4-(3-((4-fluorophenyl)carbamoyl)oxetan-3-yl)phenyl)-2-(trifluoromethyl)isonicotinamide | 460.1 |

Example 105: (R)-3-(4-(4-(1-amino-2,2,2-trifluoroethyl)-6-(trifluoromethyl)pyridin-3-yl)phenyl)-N-(4-fluorophenyl)oxetane-3-carboxamide

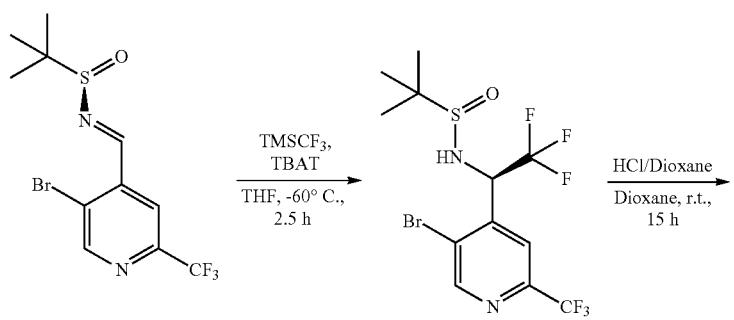

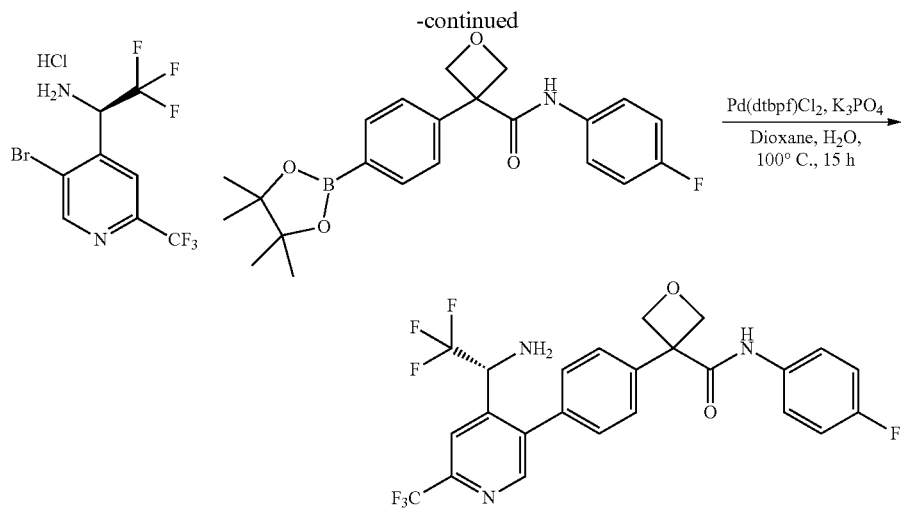

Step 1: 5-bromo-2-(trifluoromethyl)isonicotinaldehyde

To a solution of diisopropylamine (1.343 g, 13.27 mmol) in THF (20 mL) was added butyl lithium (4.60 mL, 11.50 mmol) dropwise at −60° C. under nitrogen. After 1 h, 5-bromo-2-(trifluoromethyl)pyridine (2.0 g, 8.85 mmol) in THF (5 mL) was added dropwise at −60° C. and the mixture was stirred at this temperature for 1 h. DMF (3.43 mL, 44.2 mmol) was added to the above mixture and the solution was stirred at −60° C. for another 1 h. The reaction was quenched with sat. aq. NH$_4$Cl (100 mL) and extracted with EtOAc (20 mL×2). The organic layer was dried over Na$_2$SO$_4$, filtered and concentrated. The residue was purified by flash silica gel chromatography to afford the title compound as an oil. $^1$H NMR (400 MHz, CDCl$_3$) δ 10.4 (s, 1H), 9.0 (s, 1H), 8.1 (s, 1H).

Step 2: (R,E)-N-((5-bromo-2-(trifluoromethyl)pyridin-4-yl)methylene)-2-methylpropane-2-sulfinamide To a stirred solution of 5-bromo-2-(trifluoromethyl)isonicotinaldehyde (721 mg, 2.84 mmol) in CH$_2$Cl$_2$ (20 mL) were added (R)-2-methylpropane-2-sulfinamide (344 mg, 2.84 mmol) and Cs$_2$CO$_3$ (1110 mg, 3.41 mmol) at RT. The reaction mixture was stirred at RT for 15 h. The reaction was concentrated to remove CH$_2$Cl$_2$ and then diluted with water (30 mL) and extracted with EtOAc (30 mL×2). The organic layers were collected, washed with brine (20 mL), dried over Na$_2$SO$_4$, and after filtration, the filtrate was concentrated in vacuo. The residue was purified by flash silica gel chromatography to afford the title compound as a solid. $^1$H NMR (400 MHz, CDCl$_3$) δ 8.9-9.0 (m, 2H), 8.2 (s, 1H), 1.3 (s, 9H).

Step 3: (R)—N-(1-(5-bromo-2-(trifluoromethyl)pyridin-4-yl)-2,2,2-trifluoroethyl)-2-methylpropane-2-sulfinamide To a stirred solution of (R,Z)—N-((5-bromo-2-(trifluoromethyl)pyridin-4-yl)methylene)-2-methylpropane-2-sulfinamide (659 mg, 1.845 mmol) in THF (10 mL) was added TBAT (1195 mg, 2.214 mmol) at RT. The reaction was stirred at RT for 0.5 h. Then the mixture was cooled to −60° C. and to it was added trimethyl(trifluoromethyl)silane (1312 mg, 9.22 mmol), and stirring continued at −60° C. for 2 h. The mixture was quenched with aq. NH$_4$Cl (15 mL), extracted with EtOAc (30 mL×2), and the organic layers were collected, washed with brine (30 mL), dried over Na$_2$SO$_4$, filtered, and the filtrate was concentrated in vacuo. The residue was purified by silica gel chromatography to afford the title compound as a solid. MS (ESI) m/z: 467.8 [M+ACN+H$^+$].

Step 4: (R)-1-(5-bromo-2-(trifluoromethyl)pyridin-4-yl)-2,2,2-trifluoroethanamine hydrochloride To a stirred solution of (R)—N-(1-(5-bromo-2-(trifluoromethyl)pyridin-4-yl)-2,2,2-trifluoroethyl)-2-methylpropane-2-sulfinamide (90 mg, 0.211 mmol) in 1,4-dioxane (5 mL) was added 4 M HCl (5 mL, 20.00 mmol, in dioxane) at RT. The reaction was stirred at RT for 15 h. The solvent was concentrated in vacuo to afford the title compound as a solid which was used in the next step without further purification. MS (ESI) m/z: 363.8 [M+ACN+H$^+$].

Step 5: (R)-3-(4-(4-(1-amino-2,2,2-trifluoroethyl)-6-(trifluoromethyl)pyridin-3-yl)phenyl)-N-(4-fluorophenyl)oxetane-3-carboxamide To a stirred solution of (R)-1-(5-bromo-2-(trifluoromethyl)pyridin-4-yl)-2,2,2-trifluoroethanamine hydrochloride (76 mg, 0.211 mmol) in 1,4-dioxane (2.5 mL) and water (0.5 mL) were added N-(4-fluorophenyl)-3-(4-(4,4,5,5-tetramethyl-1,3,2-dioxaborolan-2-yl)phenyl)oxetane-3-carboxamide (101 mg, 0.254 mmol), K$_3$PO$_4$ (135 mg, 0.634 mmol) and Pd(dtbpf)Cl$_2$ (16 mg, 0.025 mmol) at RT. The mixture was subjected to the usual Suzuki coupling and workup conditions to give a crude title compound which was purified by HPLC on a GILSON 281 instrument fitted with a Waters XSELECT C18 150×30 mm×5 um column using water (0.1% TFA)-CH$_3$CN as mobile phases to afford the title compound as a solid. $^1$H NMR (500 MHz, CDCl$_3$) δ 8.7 (s, 1H), 8.0 (s, 1H), 7.4-7.5 (m, 6H), 7.1 (br s, 1H), 7.0 (t, 2H), 5.4 (t, 2H), 5.1 (dd, 2H), 4.6 (q, 1H). MS (ESI) m/z: 514.2 [M+H$^+$].

Example 106: (S)-3-(4-(4-(4-(1-amino-2,2,2-trifluoroethyl)-6-(trifluoromethyl)pyridin-3-yl)phenyl)-N-(4-fluorophenyl)oxetane-3-carboxamide

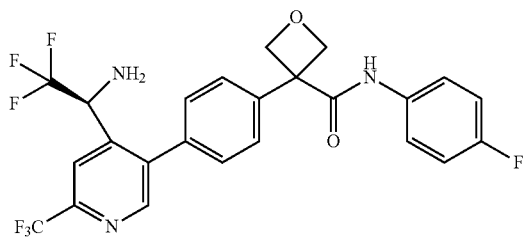 [SMILES: N[C@@H](c1cc(C(F)(F)F)ncc1-c1ccc(C2(C(=O)Nc3ccc(F)cc3)COC2)cc1)C(F)(F)F]

Step 1: (S,E)-N-((5-bromo-2-(trifluoromethyl)pyridin-4-yl)methylene)-2-methylpropane-2-sulfinamide This compound was prepared in a similar fashion as Example 105 except (S)-2-methylpropane-2-sulfinamide was used. MS (ESI) m/z: 400.1 [M+ACN+H⁺].

Step 2: N—((S)-1-(5-bromo-2-(trifluoromethyl)pyridin-4-yl)-2,2,2-trifluoroethyl)-2-methylpropane-2-sulfinamide This compound was prepared in a similar fashion as Example 105. MS (ESI) m/z: 470.1[M+ACN+H⁺].

Step 3: (S)-1-(5-bromo-2-(trifluoromethyl)pyridin-4-yl)-2,2,2-trifluoroethanamine hydrochloride The hydrolysis was preformed similarly to step 3 of Example 105. MS (ESI) m/z: 364.0 [M+ACN+H⁺].

Step 5: (S)-3-(4-(4-(1-amino-2,2,2-trifluoroethyl)-6-(trifluoromethyl)pyridin-3-yl)phenyl)-N-(4-fluorophenyl)oxetane-3-carboxamide The title compound was prepared in a similar fashion as Example 105. $^1$H NMR (400 MHz, CDCl$_3$) δ 8.7 (s, 1H), 8.0 (s, 1H), 7.4-7.5 (m, 6H), 7.1 (br s, 1H), 7.0 (br t, 2H), 5.4 (t, 2H), 5.1-5.2 (m, 2H), 4.6 (q, 1H). MS (ESI) m/z: 514.1 [M+H⁺].

Example 107: N-(4-fluorophenyl)-3-(4-(3-(2-hydroxypropan-2-yl)-5-(trifluoromethyl)pyridin-2-yl)phenyl)oxetane-3-carboxamide

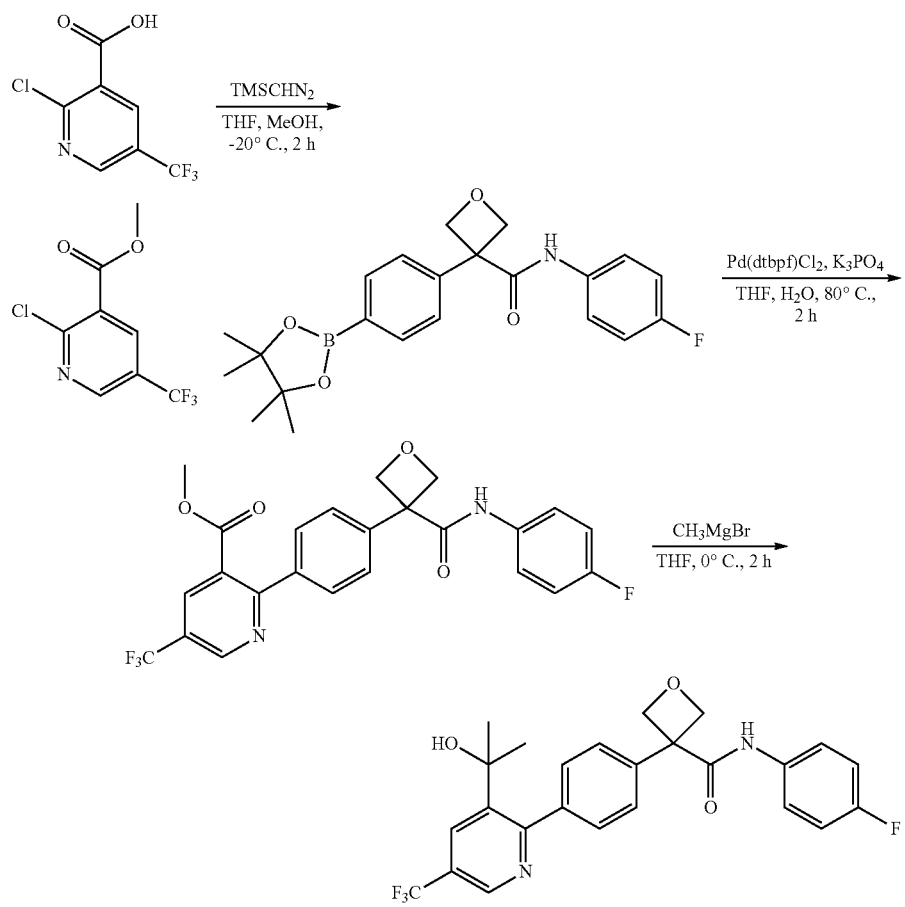

Step 1: methyl 2-chloro-5-(trifluoromethyl)nicotinate

To a stirred solution of 2-chloro-5-(trifluoromethyl)pyridine-3-carboxylic acid (2 g, 8.87 mmol) in THF (5 mL) and MeOH (5 mL) was added (trimethylsilyl)diazomethane (8.87 mL, 17.73 mmol) (2 M in hexane) dropwise at −20° C. and the reaction was stirred at −20° C. for 2 h. The solvent was concentrated under reduced pressure and the residue was purified by flash silica gel chromatography to afford the title compound as an oil. MS (ESI) m/z: 242.2 [M+H$^+$]

Step 2: methyl 2-(4-(3-((4-fluorophenyl)carbamoyl)oxetan-3-yl)phenyl)-5-(trifluoromethyl) nicotinate To a stirred solution of methyl 2-chloro-5-(trifluoromethyl)nicotinate (100 mg, 0.417 mmol) and N-(4-fluorophenyl)-3-(4-(4,4,5,5-tetramethyl-1,3,2-dioxaborolan-2-yl)phenyl)oxetane-3-carboxamide (166 mg, 0.417 mmol) in THF (2 mL) were added Pd(dtbpf)Cl$_2$ (28 mg, 0.043 mmol) and potassium phosphate (266 mg, 1.252 mmol) at RT. The mixture was stirred at 80° C. for 2 h. After cooled to RT, the reaction mixture was diluted with water (2 mL), extracted with EtOAc (1 mL×2), and the organic layers were collected, washed with brine, dried over Na$_2$SO$_4$. After filtration, the filtrate was concentrated in vacuo. The residue was purified by silica gel chromatography to afford the title compound as an oil. MS (ESI) m/z: 474.9 [M+H$^+$].

Step 3: N-(4-fluorophenyl)-3-(4-(3-(2-hydroxypropan-2-yl)-5-(trifluoromethyl)pyridin-2-yl)phenyl)oxetane-3-carboxamide To a stirred solution of methylmagnesium bromide (0.1 mL, 0.300 mmol) (3 M in hexane) in THF (0.5 mL) was added methyl 2-(4-(3-((4-fluorophenyl)carbamoyl)oxetan-3-yl)phenyl)-5-(trifluoromethyl)nicotinate (50 mg, 0.105 mmol) in THF (0.5 mL) at 0° C. The mixture was stirred at 0° C. for 2 h. The reaction was quenched with NH$_4$Cl (3 mL), diluted with water (2 mL), and extracted with EtOAc (5 mL×2). The organic layers were collected, washed with brine, dried over Na$_2$SO$_4$, and after filtration, the filtrate was concentrated in vacuo. The residue was purified by reversed phase HPLC on a GILSON 281 instrument fitted with a YMC-Actus Pro C18 150×30×5 u column using water (0.1% TFA)-CH$_3$CN as eluents to afford the title compound as a solid after lyophilization. $^1$H NMR (500 MHz, CD$_3$OD) δ 8.75-8.80 (m, 1H) 8.68 (d, 1H) 7.60-7.65 (m, 2H) 7.52-7.58 (m, 2H) 7.45-7.51 (m, 2H) 7.01-7.12 (m, 2H) 5.37 (d, 2H) 5.05 (d, 2H) 1.33-1.43 (m, 6H). MS (ESI) m/z: 475.2 [M+H$^+$]

Example 108: 3-(4-(5-cyclopropoxy-3-(hydroxymethyl)pyridin-2-yl)phenyl)-N-(4-fluorophenyl)oxetane-3-carboxamide

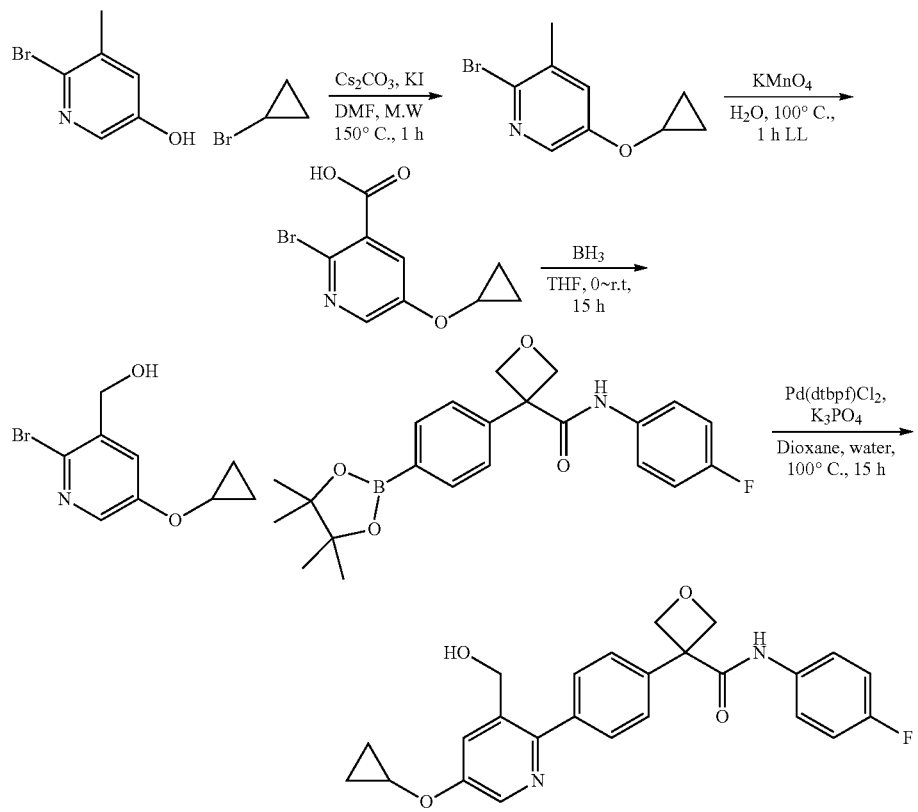

Step 1: 2-bromo-5-cyclopropoxy-3-methylpyridine

To a solution of 6-bromo-5-methylpyridin-3-ol (500 mg, 2.66 mmol), bromocyclopropane (1287 mg, 10.64 mmol) and potassium iodide (50 mg, 0.301 mmol) in DMF (4.0 mL) was added cesium carbonate (1300 mg, 3.99 mmol) at RT. The reaction vessel was sealed and heated in a microwave at 150° C. under nitrogen for 1 h. The reaction mixture was cooled to RT and poured into water (20.0 mL) and extracted with ethyl acetate (10.0 mL×3). The combined organic layer was washed with brine, dried over $Na_2SO_4$, and concentrated in vacuo. The residue was purified by flash silica gel chromatography to afford the title compound as an oil. MS (ESI) m/z: 229.9[M+H$^+$].

Step 2: 2-bromo-5-cyclopropoxynicotinic Acid

To a stirred mixture of 2-bromo-5-cyclopropoxy-3-methylpyridine (160 mg, 0.701 mmol) in water (10.0 mL) was added KMnO4 (443 mg, 2.81 mmol) in portions at RT. The reaction mixture was stirred at 100° C. for 3 h. The resulting mixture was then filtered hot through a pad of Celite, the filtrate was cooled and washed with EtOAc (5 mL×3). The aqueous layer was acidified with 6 N HCl to pH=4, concentrated to a small volume (5 mL) and extracted with EtOAc (10 mL×3). The combined organic layer was washed with brine, dried over $Na_2SO_4$, and concentrated in vacuo to afford crude title compound as a solid. MS (ESI) m/z: 259.9 [M+H$^+$].

Step 3: (2-bromo-5-cyclopropoxypyridin-3-yl)methanol

To a stirred solution of 2-bromo-5-cyclopropoxynicotinic acid (30 mg, 0.116 mmol) in THF (2.0 mL) was added BH$_3$.THF (0.50 mL, 0.500 mmol) dropwise at 0° C. and the reaction mixture was stirred at RT for 15 h. The mixture was carefully quenched with MeOH (5 mL), then concentrated in vacuo. The residue was purified by prep-TLC to afford the title compound as an oil. MS (ESI) m/z: 243.9 [M+H$^+$].

Step 4: 3-(4-(5-cyclopropoxy-3-(hydroxymethyl) pyridin-2-yl)phenyl)-N-(4-fluorophenyl)oxetane-3-carboxamide To a stirred solution of N-(4-fluorophenyl)-3-(4-(4,4,5,5-tetramethyl-1,3,2-dioxaborolan-2-yl)phenyl)oxetane-3-carboxamide (41 mg, 0.103 mmol) in dioxane (2.0 mL) and water (0.4 mL) were added K$_3$PO$_4$ (65 mg, 0.306 mmol) and Pd(dtbpf)Cl$_2$ (7 mg, 10.74 µmol) at RT. The reaction was subjected to the typical Suzuki coupling and workup procedures to give the crude product which was purified by reversed phase HPLC on a GILSON 281 instrument fitted with a Phenomenex Synergi C18 column (250×21.2 mm×4 m) using water (0.2% Formic acid) and ACN as eluents followed by freeze-drying to afford the title compound as a solid. $^1$H NMR (400 MHz, CD$_3$OD) δ 8.34 (d, 1H), 8.01 (d, 1H), 7.52-7.68 (m, 6H), 7.06 (t, 2H), 5.36 (d, 2H), 5.04 (d, 2H), 4.59 (s, 2H), 4.02 (dt, 1H), 0.79-0.96 (m, 4H). MS (ESI) m/z: 435.1 [M+H$^+$].

Example 109: 3-(4-(5-cyclopropoxy-3-(2-hydroxypropan-2-yl)pyridin-2-yl)phenyl)-N-(4-fluorophenyl) oxetane-3-carboxamide

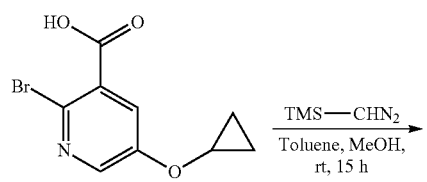

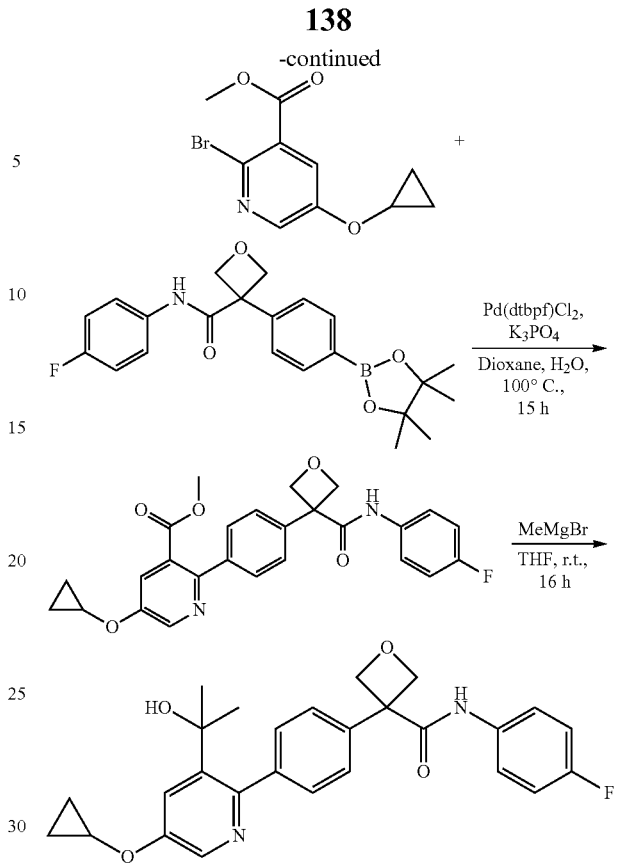

Step 1: methyl 2-bromo-5-cyclopropoxynicotinate

To a stirred solution of 2-bromo-5-cyclopropoxynicotinic acid (0.11 g, 0.426 mmol) in DCM (5 mL) and MeOH (2.5 mL) was added ((trimethylsilyl)methyl)diazene (0.64 mL, 1.280 mmol) at 0° C. and the mixture was stirred at RT for 15 h. The solvent was concentrated under reduced pressure and the residue was purified by Pre-TLC (petroleum ether/EtOAc=2:1) to afford the title compound as an oil. MS (ESI) m/z: 271.8&273.8 [M+H$^+$].

Step 2: methyl 5-cyclopropoxy-2-(4-(3-((4-fluorophenyl)carbamoyl)oxetan-3-yl)phenyl)nicotinate To a stirred solution of N-(4-fluorophenyl)-3-(4-(4,4,5,5-tetramethyl-1,3,2-dioxaborolan-2-yl)phenyl)oxetane-3-carboxamide (52 mg, 0.131 mmol) and methyl 2-bromo-5-cyclopropoxynicotinate (30 mg, 0.110 mmol in dioxane (2 mL) and water (0.4 mL) were added K$_3$PO$_4$ (70 mg, 0.330 mmol) and Pd(dtbpf)Cl$_2$ (7 mg, 10.74 µmol) at RT. The mixture was heated to 100° C. with stirring for 16 h. After cooled to RT, the mixture was extracted with EtOAc (30 mL×2), the organic layers were collected, washed with brine, dried over Na$_2$SO$_4$, filtered, and the filtrate was concentrated in vacuo. The residue was purified by prep-TLC (petroleum ether/EtOAc=1:1) to afford the title compound as an oil. MS (ESI) m/z: 463.0 [M+H$^+$].

Step 3: 3-(4-(5-cyclopropoxy-3-(2-hydroxypropan-2-yl)pyridin-2-yl)phenyl)-N-(4-fluorophenyl)oxetane-3-carboxamide To a stirred solution of methyl 5-cyclopropoxy-2-(4-(3-((4-fluorophenyl)carbamoyl)oxetan-3-yl)phenyl)nicotinate (13 mg, 0.028 mmol) in THF (1 mL) was added 3 M MeMgBr (0.08 mL, 0.240 mmol) at RT. The mixture was stirred at RT for 15 h. The mixture was diluted with water (20 mL), extracted with EtOAc (20 mL×3), the organic layers were collected, washed with brine (10 mL), dried over Na$_2$SO$_4$, and after filtration, the filtrate was concentrated in vacuo. The residue was purified by reversed phase HPLC on a GILSON 281 instrument fitted with a Phenomenex Synergi C18 column (150×30 mm×4 um) eluting with water (0.225% FA)-ACN to afford the title compound as a solid after lyophilization of the desired fractions. $^1$H NMR (400 MHz, CD$_3$OD) δ 8.41 (d, 1H), 8.36 (d, 1H), 7.65 (d, 2H), 7.57-7.52 (m, 4H), 7.06 (t, 2H), 5.37 (d, 2H), 5.04 (d, 2H), 4.08 (br s, 1H), 1.38 (s, 6H), 0.94 (br d, 2H), 0.85 (br s, 2H). MS (ESI) m/z: 463.2 M+H$^+$].

Example 110: 3-(4'-cyclopropoxy-2'-(2-hydroxypropan-2-yl)-[1,1'-biphenyl]-4-yl)-N-(4-fluorophenyl)oxetane-3-carboxamide by flash silica gel chromatography to afford the title compound as an oil. $^1$H NMR (400 MHz, CD$_3$OD) δ 8.07 (d, 1H) 7.32 (dd, 2.8 Hz, 1H) 7.26-7.30 (m, 1H) 3.96 (tt, 3.0 Hz, 1H) 3.89 (s, 3H) 0.85-0.91 (m, 2H) 0.76-0.80 (m, 2H).

Step 2: methyl 2-amino-5-cyclopropoxybenzoate

To a solution of methyl 5-cyclopropoxy-2-nitrobenzoate (300 mg, 1.265 mmol) in EtOH (10 mL) and water (2 mL) were added iron (353 mg, 6.32 mmol) and ammonium chloride (338 mg, 6.32 mmol) at RT. The mixture was stirred at 80° C. for 3 h. The reaction was filtered and concentrated under reduced pressure. The residue was diluted with water (30 mL), extracted with EtOAc (15 mL×2), and the combined organic layer was washed with brine (10 mL), dried over Na$_2$SO$_4$, filtered and concentrated under reduced pressure to afford the title compound as an oil, which was used in the next step without further purification. MS (ESI) m/z: 208.1[M+H$^+$].

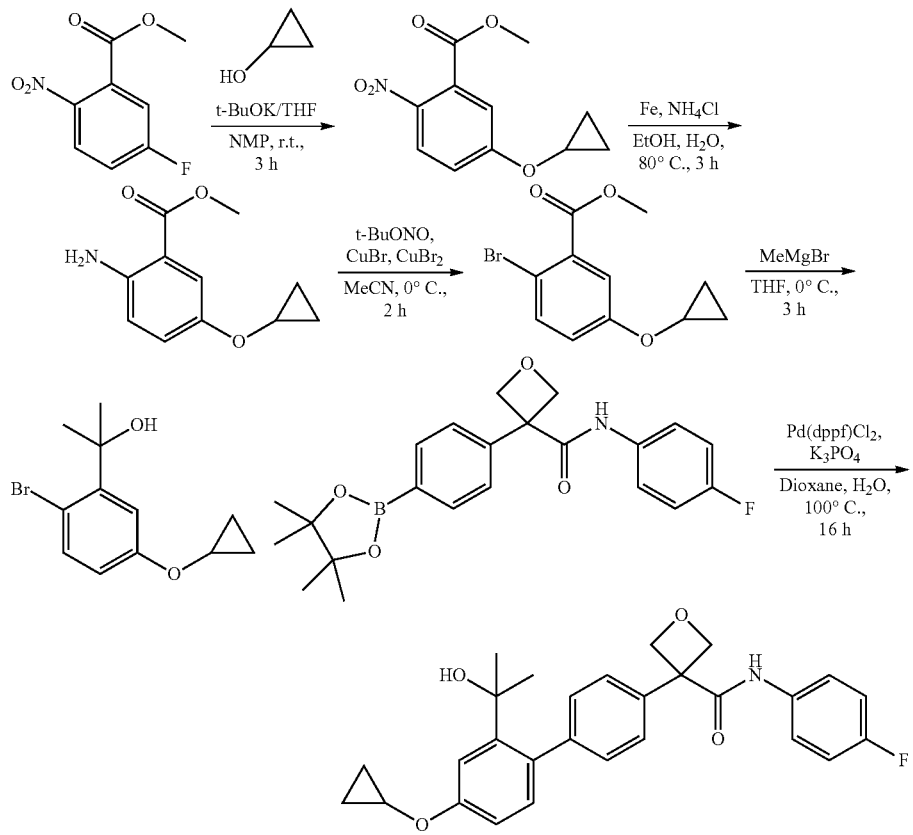

Step 1: methyl 5-cyclopropoxy-2-nitrobenzoate

To a stirred solution of methyl 5-fluoro-2-nitrobenzoate (1 g, 5.02 mmol) and cyclopropanol (0.3 g, 5.17 mmol) in NMP (20 mL) was added dropwise potassium 2-methylpropan-2-olate (7.5 mL, 7.50 mmol) (1 M in THF) at 0° C. The reaction was stirred at 0° C. for 30 min. The mixture was warmed to RT and stirred at RT for 3 h. The reaction mixture was partitioned between EtOAc/petroleum ether (100 mL, 1/1 v/v) and water (80 mL). The organic layer was separated, washed with brine (50 mL), dried over anhydrous sodium sulfate, filtered and concentrated. The residue was purified Step 3: methyl 2-bromo-5-cyclopropoxybenzoate To a solution of methyl 2-amino-5-cyclopropoxybenzoate (50 mg, 0.241 mmol) in CH$_3$CN (5 mL) were added copper (I) bromide (70 mg, 0.483 mmol) and tert-butyl nitrite (50 mg, 0.483 mmol) at 0° C. After stirring at RT for 16 h, the reaction was diluted with water (30 mL) and extracted with DCM (30 mL×3). The combined organic layer was washed with brine (20 mL) and dried over Na$_2$SO$_4$, filtered and concentrated. The residue was purified by pre-TLC (petroleum ether/EtOAc=2:1) to afford the title compound as an oil. ¹H NMR (400 MHz, CDCl3) δ 7.52 (d, 1H) 7.46 (d, 1H) 7.00 (dd, 1H) 3.92 (s, 3H) 3.71-3.76 (m, 1H) 0.75-0.81 (m, 4H).

Step 4: 2-(2-bromo-5-cyclopropoxyphenyl)propan-2-ol

To a solution of methyl 2-bromo-5-cyclopropoxybenzoate (70 mg, 0.258 mmol) in THF (5 mL) were added methylmagnesium bromide (0.3 mL, 0.900 mmol) (3 M in ethoxyethane) at 0° C. After the addition was finished, the reaction was stirred at RT for 16 h, quenched with saturated NH4Cl (20 mL, aq.) slowly, and extracted with EtOAc (10 mL×3). The combined organic layer was washed with brine, dried over anhydrous Na2SO4, filtered and concentrated under reduced pressure to afford the title compound as an oil, which was used in the next step without further purification. ¹H NMR (400 MHz, CD3OD) δ 7.51 (d, J1H), 7.44 (d, 1H), 6.83 (dd, 1H), 3.75 (td, 1H), 1.68 (s, 6H), 0.78 (br d, 2H), 0.67 (br s, 2H).

Step 5: 3-(4'-cyclopropoxy-2'-(2-hydroxypropan-2-yl)-[1,1'-biphenyl]-4-yl)-N-(4-fluorophenyl)oxetane-3-carboxamide To a solution of 2-(2-bromo-5-cyclopropoxyphenyl)propan-2-ol (80 mg, 0.295 mmol) in dioxane (5 mL) and water (1 mL) were added N-(4-fluorophenyl)-3-(4-(4,4,5,5-tetramethyl-1,3,2-dioxaborolan-2-yl)phenyl)oxetane-3-carboxamide (117 mg, 0.295 mmol), Pd(dtbpf)Cl2 (19.23 mg, 0.030 mmol) and K3PO4 (188 mg, 0.885 mmol) at RT. The mixture was subjected to the typical Suzuki coupling and workup conditions to afford the crude product which was purified by reversed phase HPLC on a GILSON 281 instrument fitted with a Xtimate C18 150×25 mm×5 um column and the desired fractions were collected and concentrated to afford the title compound as a solid. ¹H NMR (400 MHz, CD3OD) δ 7.56 (t, 2H) 7.43-7.48 (m, 3H) 7.32 (d, 2H) 7.06 (t, 2H) 6.89-6.94 (m, 2H) 5.34 (d, 2H) 5.02 (d, 2H) 3.80 (tt, 1H) 1.32 (s, 6H) 0.76-0.83 (m, 2H) 0.67-0.73 (m, 2H). MS (ESI) m/z: 484.3 [M+Na⁺].

Example 111: 3-(4'-cyclopropoxy-2'-(hydroxymethyl)-[1,1'-biphenyl]-4-yl)-N-(4-fluorophenyl)oxetane-3-carboxamide

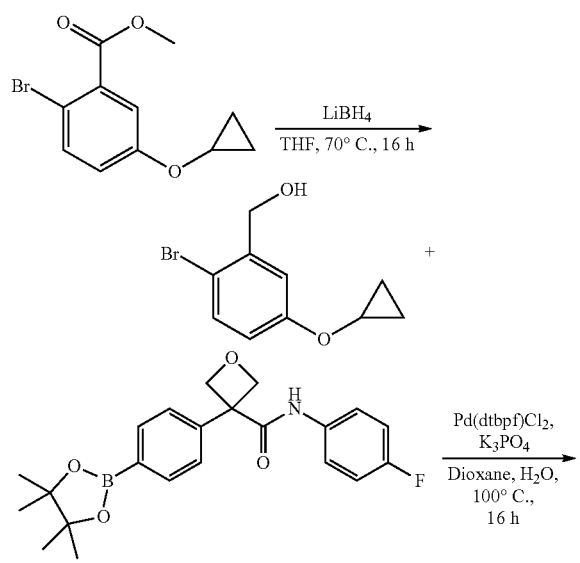

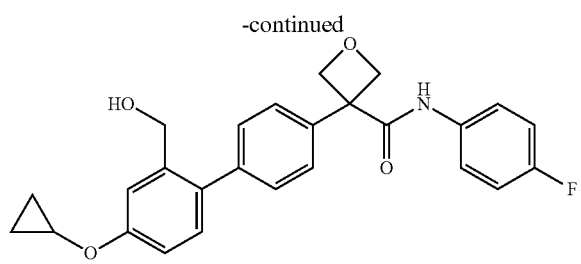

Step 1: (2-bromo-5-cyclopropoxyphenyl)methanol

To a stirred solution of methyl 2-bromo-5-cyclopropoxybenzoate (70 mg, 0.258 mmol) in THF (5 mL) was added lithium tetrahydroborate (16.87 mg, 0.775 mmol) at 0° C. and the mixture was heated to 70° C. for 16 h. The reaction was cooled, filtered and the filtrate was concentrated under reduced pressure. The residue was diluted with water (30 mL), extracted with EtOAc (15 mL×2), and the combined organic layer was washed with brine (10 mL) and dried over Na2SO4, filtered and concentrated under reduced pressure to afford the title compound as an oil, which was used in the next step without further purification.

Step 2: 3-(4'-cyclopropoxy-2'-(hydroxymethyl)-[1,1'-biphenyl]-4-yl)-N-(4-fluorophenyl)oxetane-3-carboxamide To a solution of (2-bromo-5-cyclopropoxyphenyl)methanol (50 mg, 0.206 mmol) in water (1 mL) and 1,4-Dioxane (5 mL) were added N-(4-fluorophenyl)-3-(4-(4,4,5,5-tetramethyl-1,3,2-dioxaborolan-2-yl)phenyl)oxetane-3-carboxamide (82 mg, 0.206 mmol), Pd(dppf)Cl2 (15.05 mg, 0.021 mmol) and potassium phosphate (131 mg, 0.617 mmol) at RT. The mixture was subjected to the typical Suzuki coupling and workup conditions to give a crude product which was purified by reversed phase HPLC on a GILSON 281 instrument fitted with a Phenomenex Synergi C18 column (150×30 mm×4 um) to afford the title compound as a solid. ¹H NMR (400 MHz, CD3OD) δ 7.46-7.61 (m, 4H) 7.40 (d, 2H) 7.26 (d, 1H) 7.16 (d, 1H) 6.96-7.11 (m, 3H) 5.33 (d, 2H) 5.01 (d, 2H) 4.48 (s, 2H) 3.81 (dt, 1H) 0.75-0.84 (m, 2H) 0.66-0.75 (m, 2H). MS (ESI) m/z: 456.1 [M+Na⁺].

Example 112: N-(4-fluorophenyl)-3-(4-(4-(hydroxymethyl)-6-isopropoxypyridin-3-yl)phenyl)oxetane-3-carboxamide

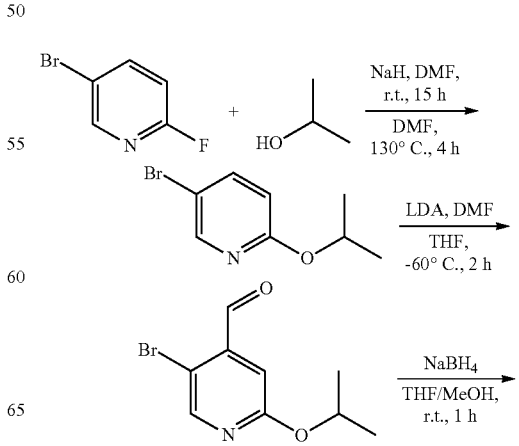

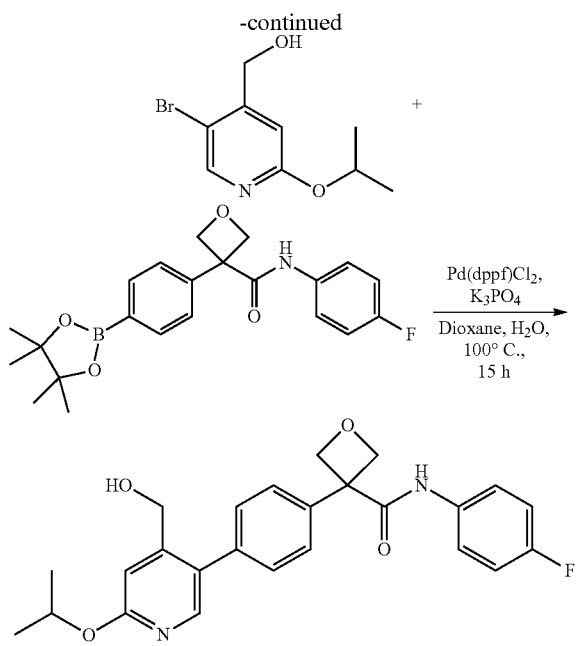

Step 1: 5-bromo-2-isopropoxypyridine

To a stirred solution of propan-2-ol (2.77 g, 46.0 mmol) in DMF (30 mL) was added sodium hydride (0.920 g, 23.01 mmol, 60% in oil) under nitrogen at 0° C. and the reaction mixture was stirred at RT for 15 h. Then 5-bromo-2-fluoropyridine (2.7 g, 15.34 mmol) in DMF (5 mL) was added and the reaction was heated to 130° C. for 4 h. After cooled to RT, the solvent was concentrated, and the residue was quenched with water (20 mL) and extracted with EtOAc (30×2 mL). The organic layers were combined, washed with brine (20 mL), dried over $Na_2SO_4$, filtered, and the filtrate was concentrated in vacuo. The residue was purified by flash silica gel chromatography to afford the title compound as an oil. MS (ESI) m/z: 215.9[M+H$^+$].

Step 2: 5-bromo-2-isopropoxyisonicotinaldehyde

To a solution of 5-bromo-2-isopropoxypyridine (1.8 g, 8.33 mmol) in THF (20 mL) was added LDA (5.00 mL, 10.00 mmol) at −60° C. and the mixture was stirred at the temperature for 1 h. Then N,N-dimethylformamide (0.913 g, 12.50 mmol) was added and the mixture was stirred at RT for 1 h. The solvent was concentrated, and the residue was quenched with water (20 mL) and extracted with EtOAc (30 mL×2). The organic layers were collected, washed with brine (20 mL), dried over $Na_2SO_4$, and after filtration, the filtrate was concentrated in vacuo. The residue was purified by silica gel chromatography to afford the title compound as an oil. MS (ESI) m/z: 243.9 [M+H$^+$].

Step 3: (5-bromo-2-isopropoxypyridin-4-yl)methanol

To a stirred solution of 5-bromo-2-isopropoxyisonicotinaldehyde (1.286 g, 5.27 mmol) in THF (20 mL) and MeOH (20 mL) was added $NaBH_4$ (0.299 g, 7.90 mmol) at 0° C. and the reaction was stirred at RT for 1 h. The reaction was quenched with $NH_4Cl$ (20 mL) and extracted with EtOAc (30 mL×2). The organic layers were collected, washed with brine (20 mL), dried over $Na_2SO_4$, filtered, and the filtrate was concentrated in vacuo. The residue was purified by silica gel chromatography to afford the title compound as an oil. $^1$H NMR (400 MHz, $CDCl_3$) δ 8.14 (s, 1H), 6.89 (s, 1H), 5.23 (spt, 1H), 4.67 (d, 2H), 4.12 (q, 1H), 1.34 (d, 6H).

Step 4: N-(4-fluorophenyl)-3-(4-(4-(hydroxymethyl)-6-isopropoxypyridin-3-yl)phenyl)oxetane-3-carboxamide To a stirred solution of N-(4-fluorophenyl)-3-(4-(4,4,5,5-tetramethyl-1,3,2-dioxaborolan-2-yl)phenyl)oxetane-3-carboxamide (300 mg, 0.755 mmol) in 1,4-dioxane (2.5 mL) and water (0.5 mL) were added $PdCl_2$(dppf) (45 mg, 0.062 mmol) and $K_3PO_4$ (388 mg, 1.829 mmol) at RT. The mixture was subjected to the typical Suzuki coupling and workup conditions to give a crude title compound which was purified by HPLC on a GILSON 281 instrument fitted with a Waters Xbridge Prep OBD C18 column (100×19 mm×5 um) eluting with water (0.225% formic acid)/$CH_3CN$ to afford the title compound as a solid after concentration of the desired fractions. $^1$H NMR (400 MHz, $CDCl_3$) δ 7.36-7.48 (m, 6H), 6.94-7.06 (m, 4H), 5.41 (d, 1H), 5.29-5.38 (m, 1H), 5.09 (d, 2H), 4.63 (s, 2H), 1.40 (d, 6H). MS (ESI) m/z: 437.2 [M+H$^+$].

Example 113: N-(4-fluorophenyl)-3-(4-(4-(2-hydroxypropan-2-yl)-6-(trifluoromethyl)pyridazin-3-yl)phenyl)oxetane-3-carboxamide

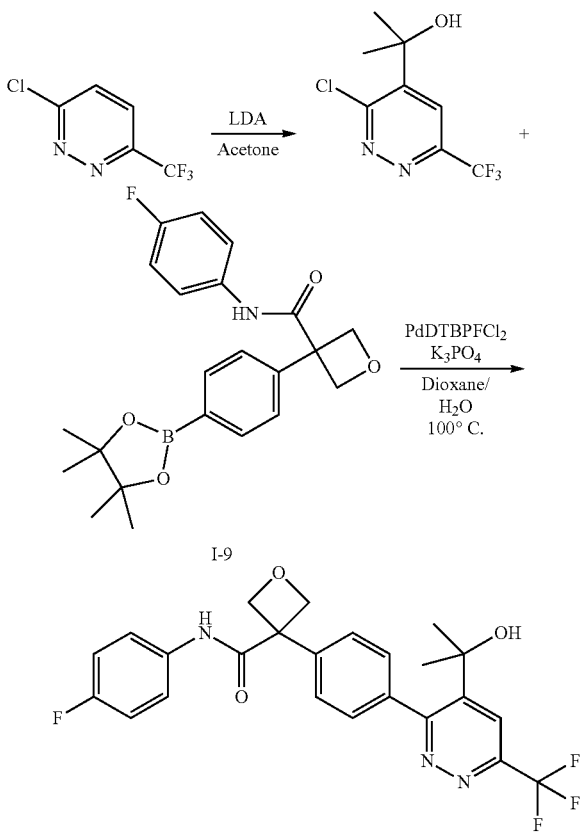

Step 1: 2-(3-chloro-6-(trifluoromethyl)pyridazin-4-yl)propan-2-ol

To a solution of 2.5 M BuLi in hexanes (1.3 ml, 3.3 mmol) was added THF (5 mL) dropwise with stirring –78° C. under nitrogen. 2,2,6,6-Tetramethylpiperidine (503 mg, 3.56 mmol) was added at 0° C. After stirred at 0° C. for 0.5 h, the mixture was cooled to –70° C. 3-Chloro-6-(trifluoromethyl)pyridazine (500 mg, 2.74 mmol) was added to the mixture dropwise. The reaction mixture was stirred at –70° C. for 1.5 h. Acetone (3 mL, 40.9 mmol) was added to the mixture dropwise. The reaction mixture was stirred at –70° C. for 1 h, quenched with aq. sat. ammonium chloride (5 mL) and extracted with EtOAc (20 mL×2). The combined organic layers were washed with brine, dried over MgSO$_4$, concentrated in vacuo, and the residue was purified by flash silica gel chromatography and then by Pre-TLC (SiO$_2$, petroleum ether/EtOAc=3/1) to afford the title compound as a solid. MS (ESI) m/z: 240.9 [M+H$^+$].

Step 2: N-(4-fluorophenyl)-3-(4-(4-(2-hydroxypropan-2-yl)-6-(trifluoromethyl)pyridazin-3-yl)phenyl)oxetane-3-carboxamide To a solution of 2-(3-chloro-6-(trifluoromethyl)pyridazin-4-yl)propan-2-ol (30 mg, 0.125 mmol) in dioxane (1 mL) and water (0.2 mL) were added N-(4-fluorophenyl)-3-(4-(4,4,5,5-tetramethyl-1,3,2-dioxaborolan-2-yl)phenyl)oxetane-3-carboxamide (I-9) (59 mg, 0.149 mmol), potassium phosphate tribasic (79 mg, 0.374 mmol) and 1,1'-Bis(di-tert-butylphosphino)ferrocene]dichloropalladium(II) (8 mg, 0.012 mmol). The reaction was stirred at 100° C. for 16 h under nitrogen. The mixture was concentrated under reduced pressure to afford a residue which was purified by Prep-HPLC (Column Phenomenex Synergi C 18 (150×30 mm×4 um) using water (0.1% TFA)-ACN as the mobile phases to afford the title compound as a solid. $^1$H NMR (400 MHz, MeOD) δ 8.47 (s, 1H), 7.68-7.66 (m, 2H), 7.58-7.55 (m, 4H), 5.38-5.37 (m, 2H), 5.06-5.05 (m, 2H), 3.3 (m, 4H), 1.38 (m, 6H). MS (ESI) m/z: 476 [M+H$^+$].

Example 114: N-(4-chlorophenyl)-1-(5-(2-(hydroxymethyl)-4-(trifluoromethyl)phenyl) pyrazin-2-yl)cyclobutane-1-carboxamide

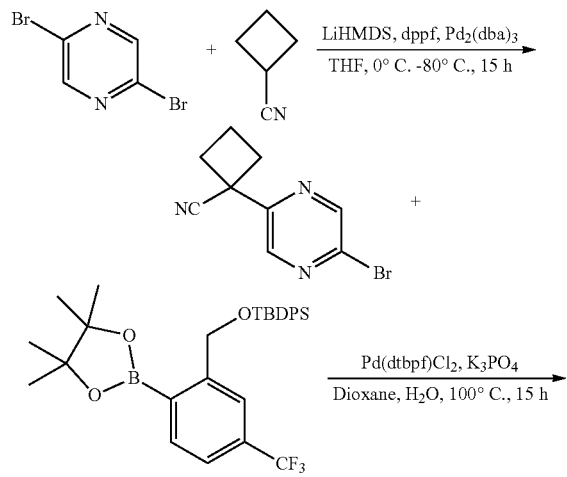

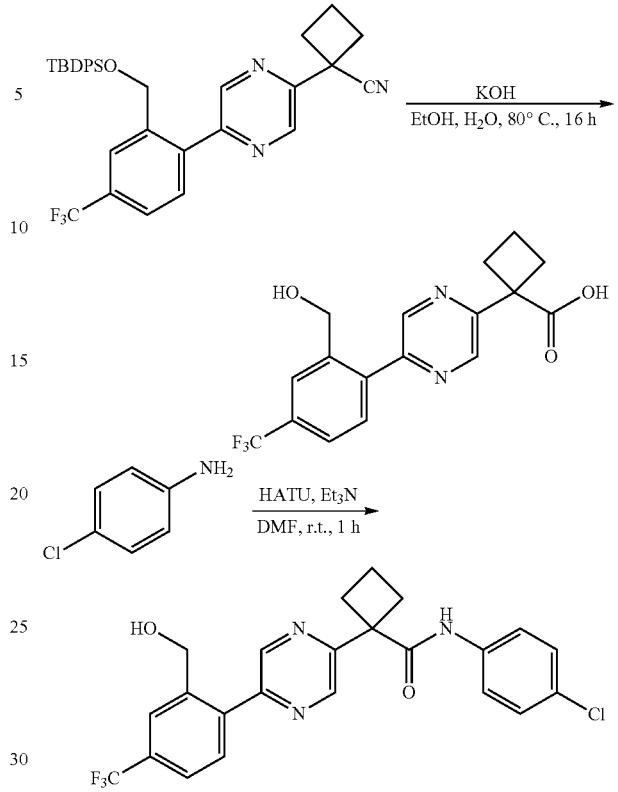

Step 1: 1-(5-bromopyrazin-2-yl)cyclobutane-1-carbonitrile

To a solution of 2,5-dibromopyrazine (200 mg, 0.841 mmol) in THF (10.0 mL) were added Nixantphos (46 mg, 0.083 mmol), Pd$_2$(dba)$_3$ (40 mg, 0.044 mmol) and cyclobutane carbonitrile (75 mg, 0.925 mmol), followed by the addition of LiHMDS (1.6 mL, 1.600 mmol) (1 M in THF) at 0° C. The resulting mixture was heated to 80° C. for 15 h and cooled to RT, quenched with NH$_4$Cl (10.0 mL) and extracted with EtOAc (20 mL×2). The combined organic layer was washed with brine and concentrated in vacuum. The residue was purified by reverse phase HPLC on a GILSON 281 instrument fitted with a Phenomenex Synergi C18 column (250×21.2 mm×4 m) using water (0.2% formic acid) and ACN as eluents. The desired fractions were collected and concentrated by freeze-drying to afford the title compound as a solid. MS (ESI) m/z: 237.9 [M+H$^+$].

Step 2: 1-(5-(2-(((tert-butyldiphenylsilyl)oxy)methyl)-4-(trifluoromethyl)phenyl)pyrazin-2-yl)cyclobutane-1-carbonitrile To a stirred solution of 1-(5-bromopyrazin-2-yl)cyclobutanecarbonitrile (50 mg, 0.210 mmol) and tert-butyldiphenyl((2-(4,4,5,5-tetramethyl-1,3,2-dioxaborolan-2-yl)-5-(trifluoromethyl)-benzyl)oxy)silane (125 mg, 0.231 mmol) in dioxane (1.0 mL) and water (0.2 mL) were added K$_3$PO$_4$ (134 mg, 0.630 mmol) and Pd(dtbpf)Cl$_2$ (10 mg, 0.015 mmol) at RT. The reaction was subjected to the typical Suzuki coupling and workup procedures to afford a crude title compound which was purified by prep-TLC (petroleum ether/ethyl acetate=5:1 as eluent) to afford the title compound as an oil. MS (ESI) m/z: 572.2[M+H$^+$].

Step 3: 1-(5-(2-(hydroxymethyl)-4-(trifluoromethyl)phenyl)pyrazin-2-yl)cyclobutane-1-carboxylic acid To a stirred solution of 1-(5-(3-(((tert-butyldiphenylsilyl)oxy)methyl)-4-(trifluoromethyl) phenyl)pyrazin-2-yl)cyclobutanecarbonitrile (45 mg, 0.079 mmol) in ethanol (6.0 mL) and water (2.0 mL) was added KOH (45 mg, 0.802 mmol) at RT and the reaction mixture was heated to 80° C. for 16 h. The solvent was removed by concentration in vacuo and the residue was diluted with water (2.0 mL) and extracted with EtOAc (3.0 mL). The aqueous layer was acidified with 3 N HCl to pH=5 and extracted with EtOAc (3 mL×3). The combined organic layer was washed with brine, dried over $Na_2SO_4$, and concentrated in vacuo to afford the title compound as an oil, which was used directly in the next step without further purification. MS (ESI) m/z: 353.0 [M+H$^+$].

Step 4: N-(4-chlorophenyl)-1-(5-(2-(hydroxymethyl)-4-(trifluoromethyl)phenyl)pyrazin-2-yl)cyclobutane-1-carboxamide To a stirred solution of 4-chloroaniline (20 mg, 0.16 mmol), TEA (40 mg, 0.395 mmol) and 1-(5-(3-(hydroxymethyl)-4-(trifluoromethyl)phenyl)pyrazin-2-yl)cyclobutane carboxylic acid (27 mg, 0.077 mmol) in DMF (1.0 mL) was added HATU (50 mg, 0.131 mmol) at RT and the reaction mixture was stirred at RT for 1 h. The residue was purified by reversed phase HPLC on a GILSON 281 instrument fitted with a Phenomenex Synergi C18 column (250×21.2 mm×4 µm) using water (0.2% formic acid) and ACN as eluents. The title compound was obtained as a solid after freeze-drying the desired fractions. $^1$H NMR (400 MHz, CDCl$_3$) δ 8.95 (d, 1H), 8.78 (d, 1H), 8.17 (s, 1H), 7.84 (s, 1H), 7.71-7.78 (m, 2H), 7.49 (d, 2H), 7.29 (s, 2H), 4.57 (s, 2H), 3.08 (ddd, 2H), 2.73-2.83 (m, 2H), 2.13-2.29 (m, 1H), 1.94-2.11 (m, 1H). MS (ESI) m/z: 461.9 [M+H$^+$].

Example 115: N-(6-fluoropyridin-3-yl)-3-(4-(4-(2-hydroxypropan-2-yl)-6-(trifluoromethyl)pyridin-3-yl)phenyl)oxetane-3-carboxamide

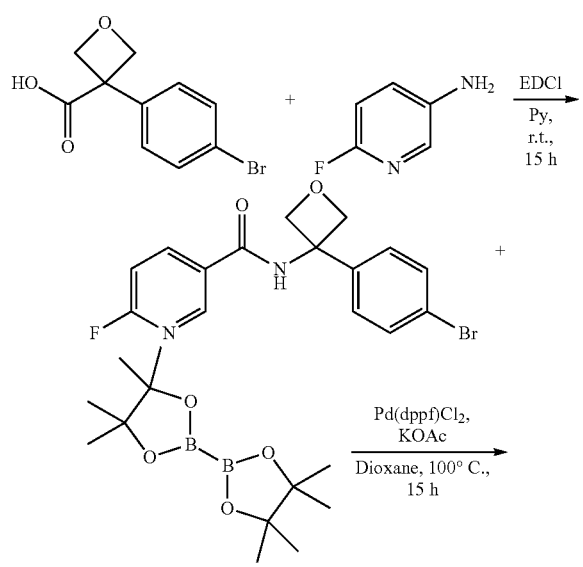

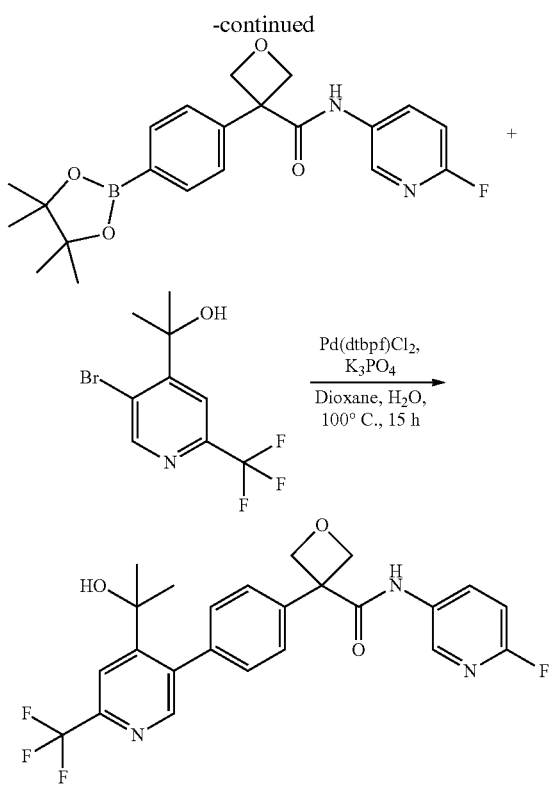

Step 1: 3-(4-bromophenyl)-N-(6-fluoropyridin-3-yl)oxetane-3-carboxamide

To a stirred solution of 3-(4-bromophenyl)oxetane-3-carboxylic acid (1 g, 3.89 mmol) in pyridine (20 mL) were added 6-fluoropyridin-3-amine (0.654 g, 5.83 mmol) and EDC (2.237 g, 11.67 mmol) at RT. The reaction mixture was stirred at RT for 15 h. The solvent was concentrated and the residue was diluted with water (20 mL) and extracted with ethyl acetate (30 mL×2). The organic layers were collected, washed with brine (20 mL), dried over $Na_2SO_4$, and after filtration, the filtrate was concentrated in vacuo. The residue was purified by flash silica gel chromatography to afford the title compound as a solid. MS (ESI) m/z: 351.0[M+H$^+$].

Step 2: N-(6-fluoropyridin-3-yl)-3-(4-(4,4,5,5-tetramethyl-1,3,2-dioxaborolan-2-yl)phenyl)oxetane-3-carboxamide To a stirred solution of 3-(4-bromophenyl)-N-(6-fluoropyridin-3-yl)oxetane-3-carboxamide (1.3 g, 3.70 mmol) in 1,4-dioxane (10 mL) were added 4,4,4',4',5,5,5',5'-octamethyl-2,2'-bi(1,3,2-dioxaborolane) (1.128 g, 4.44 mmol), potassium acetate (1.090 g, 11.11 mmol) and Pd(dppf)Cl$_2$ (0.271 g, 0.370 mmol) at RT. The reaction mixture was heated to 100° C. with stirring for 15 h. After cooled to RT, the reaction was quenched with water (30 mL) and extracted with EtOAc (30 mL×2). The organic layers were collected, washed with brine (30 mL), dried over $Na_2SO_4$, filtered, and the filtrate was concentrated in vacuo. The residue was purified by flash silica gel chromatography to afford the title compound as a solid. MS (ESI) m/z: 399.1 [M+H$^+$].

Step 3: N-(6-fluoropyridin-3-yl)-3-(4-(4-(2-hydroxpropan-2-yl)-6-(trifluoromethyl)pyridin-3-yl)phenyl) oxetane-3-carboxamide To a stirred solution of N-(6-fluoropyridin-3-yl)-3-(4-(4,4,5,5-tetramethyl-1,3,2-dioxaborolan-2-yl)phenyl)oxetane-3-carboxamide (220 mg, 0.552 mmol) in 1,4-dioxane (2.5 mL) and water (0.5 mL) were added 2-(5-bromo-2-(trifluoromethyl)pyridin-4-yl)propan-2-ol (189 mg, 0.665 mmol), K₃PO₄ (352 mg, 1.657 mmol) and Pd(dtbpf)Cl₂ (36 mg, 0.055 mmol) at RT. The mixture was subjected to the typical Suzuki coupling and workup conditions to give a crude title compound which was purified by reversed phase HPLC on a GILSON 281 instrument fitted with a Waters Xbridge Prep OBD C18 column (100×19 mm×5 um) using water (0.225% formic acid) and CH₃CN eluents to afford the title compound as a solid. ¹H NMR (500 MHz, CD₃OD) δ 8.4 (br s, 1H), 8.3 (s, 1H), 8.2-8.3 (m, 2H), 7.6 (br d, 2H), 7.4 (br d, 2H), 7.1 (dd, 1H), 5.4 (br d, 2H), 5.1 (br d, 2H), 1.4 (s, 6H). MS (ESI) m/z: 476.1 [M+H⁺].

Examples 116 and 117 in the following table were prepared in a similar fashion as Ex. 115.

| Ex. # | Structure | Chemical Name | Mass [M + H]+ |
|---|---|---|---|
| 116 | 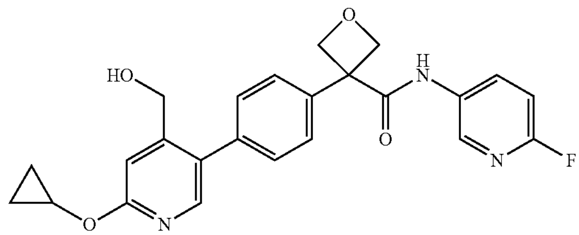 [SMILES: O=C(Nc1ccc(F)nc1)C1(c2ccc(-c3cnc(OC4CC4)cc3CO)cc2)COC1] | 3-(4-(6-cyclopropoxy-4-(hydroxymethyl)pyridin-3-yl)phenyl)-N-(6-fluoropyridin-3-yl)oxetane-3-carboxamide | 436.2 |
| 117 | 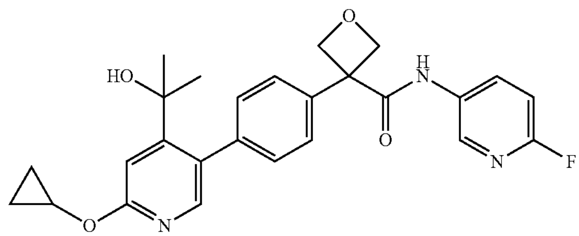 [SMILES: CC(C)(O)c1cc(OC2CC2)ncc1-c1ccc(C2(C(=O)Nc3ccc(F)nc3)COC2)cc1] | 3-(4-(6-cyclopropoxy-4-(2-hydroxypropan-2-yl)pyridin-3-yl)phenyl)-N-(6-fluoropyridin-3-yl)oxetane-3-carboxamide | 464.2 |

Example 118: 3-fluoro-N-(4-fluorophenyl)-1-(4'-(hydroxymethyl)-6'-(trifluoromethyl)-[3,3'-bipyridin]-6-yl)cyclobutanecarboxamide

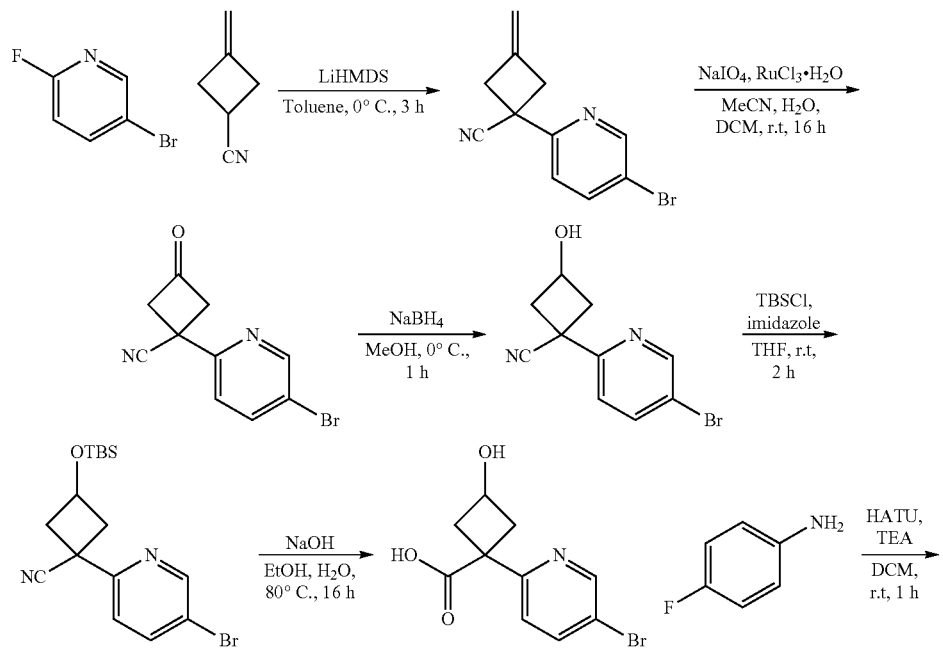

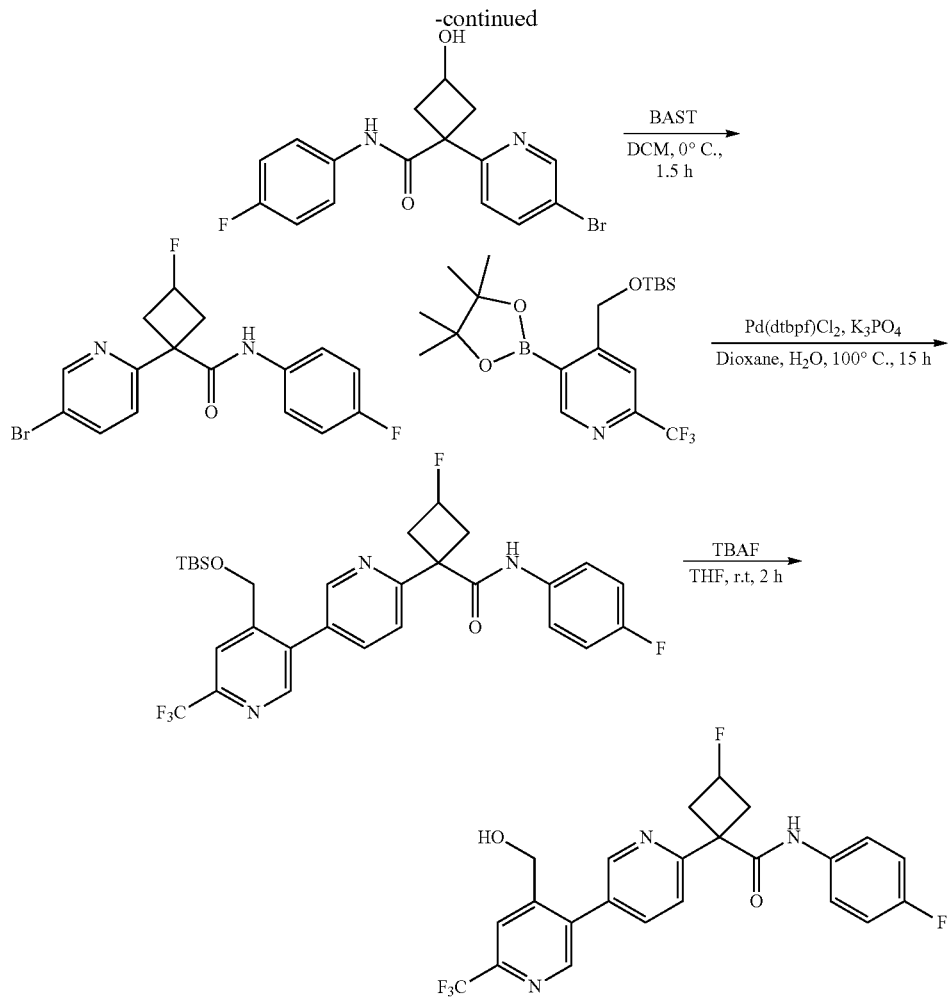

Step 1: 1-(5-bromopyridin-2-yl)-3-methylenecyclobutanecarbonitrile

To a solution of 5-bromo-2-fluoropyridine (10 g, 56.8 mmol) and 3-methylenecyclobutanecarbonitrile (5.29 g, 56.8 mmol) in toluene (50 mL) was added LiHMDS (31.3 mL, 62.5 mmol) at 0° C., and the mixture was stirred at 0° C. for 3 h. The reaction was diluted with aq. NH$_4$Cl (200 mL), extracted with EtOAc (100 mL×2), the organic was collected and washed with brine, dried over anhydrous Na$_2$SO$_4$, and then concentrated under reduced pressure. The residue was purified by flash silica gel chromatography to afford the title compound as an oil.

Step 2: 1-(5-bromopyridin-2-yl)-3-oxocyclobutanecarbonitrile

To a stirred solution of 1-(5-bromopyridin-2-yl)-3-methylenecyclobutanecarbonitrile (500 mg, 2.007 mmol) in ACN (4 mL), DCM (4 mL) and water (6 mL) were added ruthenium(III) chloride hydrate (46 mg, 0.204 mmol) and NaIO$_4$ (2147 mg, 10.04 mmol) in portions at RT. The reaction was stirred at RT for 16 h. The reaction was then quenched by the addition of sat. Na$_2$S$_2$O$_3$ solution (50 mL) and the resultant mixture was extracted with EtOAc (100 mL×2). The organic layers were collected, washed with brine (30 mL), dried over Na$_2$SO$_4$, filtered, and the filtrate was concentrated in vacuo. The residue was purified by flash silica gel chromatography to afford the title compound as a solid. MS (ESI) m/z: 292.0; 294.0 [M+ACN+H$^+$].

Step 3: 1-(5-bromopyridin-2-yl)-3-hydroxycyclobutanecarbonitrile

To a solution of 1-(5-bromopyridin-2-yl)-3-oxocyclobutanecarbonitrile (430 mg, 1.713 mmol) in MeOH (10 mL) was added NaBH$_4$ (130 mg, 3.43 mmol) at 0° C. and the mixture was stirred at 0° C. for 1 h. The reaction was carefully diluted with water (50 mL), and extracted with EtOAc (20 mL×2). The organic was collected and washed with brine, dried over anhydrous Na$_2$SO$_4$, filtered and the filtrate was concentrated under reduced pressure. The residue was purified by flash silica gel chromatography to afford the corresponding alcohol as a solid.

Step 4: 1-(5-bromopyridin-2-yl)-3-((tert-butyldimethylsilyl)oxy)cyclobutanecarbonitrile To a solution of 1-(5-bromopyridin-2-yl)-3-hydroxycyclobutanecarbonitrile (300 mg, 1.185 mmol) in THF (10 mL) were added imidazole (161 mg, 2.371 mmol) and tert-butylchlorodimethylsilane (214 mg, 1.422 mmol) at RT. The mixture was stirred at RT for 2 h. The reaction was diluted with water (100 mL) and extracted with EtOAc (50 mL×2). The organic was collected and washed with brine (10 mL), dried over anhydrous Na$_2$SO$_4$, filtered and the filtrate was concentrated under reduced pressure. The residue was purified by prep-TLC to afford the title compound as an oil.

Step 5: 1-(5-bromopyridin-2-yl)-3-hydroxycyclobutanecarboxylic acid

To a stirred solution of 1-(5-bromopyridin-2-yl)-3-(((tert-butyldimethylsilyl)oxy)cyclobutanecarbonitrile (200 mg, 0.544 mmol) in EtOH (5 mL) and water (2.5 mL) was added NaOH (87 mg, 2.178 mmol) at RT. The reaction mixture was heated to 80° C. with stirring for 16 h. The solvent was removed by concentration in vacuo and the residue was dissolved in EtOAc. 3N aq. HCl was added dropwise to adjust the pH ~2 and the mixture was extracted with EtOAc (20 mL×3). The organic layers were collected, washed with brine, dried over Na$_2$SO$_4$, and after filtration, the filtrate was concentrated to afford the title compound as a solid. MS (ESI) m/z: 272.0, 274.0 [M+H$^+$].

Step 6: 1-(5-bromopyridin-2-yl)-N-(4-fluorophenyl)-3-hydroxycyclobutanecarboxamide To a stirred solution of 1-(5-bromopyridin-2-yl)-3-hydroxycyclobutanecarboxylic acid (70 mg, 0.257 mmol) and HATU (293 mg, 0.772 mmol) in DCM (2 ml) were added TEA (0.2 mL, 1.435 mmol) and 4-fluoroaniline (35 mg, 0.315 mmol) at RT. The reaction was stirred at RT for 1 h. The reaction mixture was diluted with water (50 mL), extracted with EtOAc (20 mL×3), and the organic layers were collected, washed with brine (10 mL), dried over Na$_2$SO$_4$, filtered and the filtrate was concentrated in vacuo. The residue was purified by prep-TLC to afford the title compound as an oil. MS (ESI) m/z: 365.1, 367.1[M+H$^+$].

Step 7: 1-(5-bromopyridin-2-yl)-3-fluoro-N-(4-fluorophenyl)cyclobutanecarboxamide To a stirred solution of 1-(5-bromopyridin-2-yl)-N-(4-fluorophenyl)-3-hydroxycyclobutanecarboxamide (800 mg, 2.191 mmol) in DCM (20 mL) was added DAST (0.29 mL, 2.195 mmol) at 0° C. and the reaction was stirred at RT for 1.5 h. The reaction was quenched by the addition of sat. NaHCO$_3$ solution (20 mL) and extracted with DCM (10 mL×2). The organic layers were collected, washed with brine (10 mL), dried over Na$_2$SO$_4$, filtered, and the filtrate was concentrated in vacuo. The residue was purified by silica gel chromatography to afford the title compound as a solid. MS (ESI) m/z: 366.9[M+H$^+$].

Step 8: 1-(4'-(((tert-butyldimethylsilyl)oxy)methyl)-6'-(trifluoromethyl)-[3,3'-bipyridin]-6-yl)-3-fluoro-N-(4-fluorophenyl)cyclobutanecarboxamide To a stirred solution of 4-(((tert-butyldimethylsilyl)oxy)methyl)-5-(4,4,5,5-tetramethyl-1,3,2-dioxaborolan-2-yl)-2-(trifluoromethyl)pyridine (273 mg, 0.654 mmol) in 1,4-dioxane (5 mL) and water (1 mL) were added K$_3$PO$_4$ (347 mg, 1.634 mmol), Pd(dtbpf)Cl$_2$ (36 mg, 0.055 mmol) and 1-(5-bromopyridin-2-yl)-3-fluoro-N-(4-fluorophenyl)cyclobutanecarboxamide (200 mg, 0.545 mmol) at RT. The mixture was subjected to the typical Suzuki coupling and workup conditions to afford the title compound as an oil, which was used in the next step without further purification. MS (ESI) m/z: 578.2[M+H$^+$].

Step 9: 3-fluoro-N-(4-fluorophenyl)-1-(4'-(hydroxymethyl)-6'-(trifluoromethyl)-[3,3'-bipyridin]-6-yl)cyclobutanecarboxamide To a solution of 1-(4'-(((tert-butyldimethylsilyl)oxy)methyl)-6'-(trifluoromethyl)-[3,3'-bipyridin]-6-yl)-3-fluoro-N-(4-fluorophenyl)cyclobutanecarboxamide (50 mg, 0.087 mmol) in THF (2 mL) was added TBAF (0.17 mL, 0.170 mmol) (1M in THF) at RT. The mixture was stirred at RT for 2 h. The solvent was removed and the residue was purified by reversed phase HPLC on a GILSON 281 instrument fitted with Phenomenex Synergi C18 column (150×30 mm×4 um) using water (0.1% TFA)/ACN as eluents. The title compound was obtained as a solid after lyophilization of the desired fractions. $^1$H NMR (500 MHz, CD$_3$OD) δ 8.71 (d, 1H), 8.63 (s, 1H), 8.11 (s, 1H), 7.97 (dd, 1H), 7.62 (d, 1H), 7.53-7.58 (m, 2H), 7.04-7.09 (m, 2H), 5.09-5.30 (m, 1H), 4.68 (s, 2H), 3.36-3.43 (m, 2H), 2.89-3.01 (m, 2H). MS (ESI) m/z: 464.1 [M+H$^+$]

Example 119: 4-fluoro-N-(1-(7-hydroxy-5-(2-methylpyrimidin-4-yl)-5,6,7,8-tetrahydro-1,5-naphthyridin-2-yl)cyclopropyl)benzamide

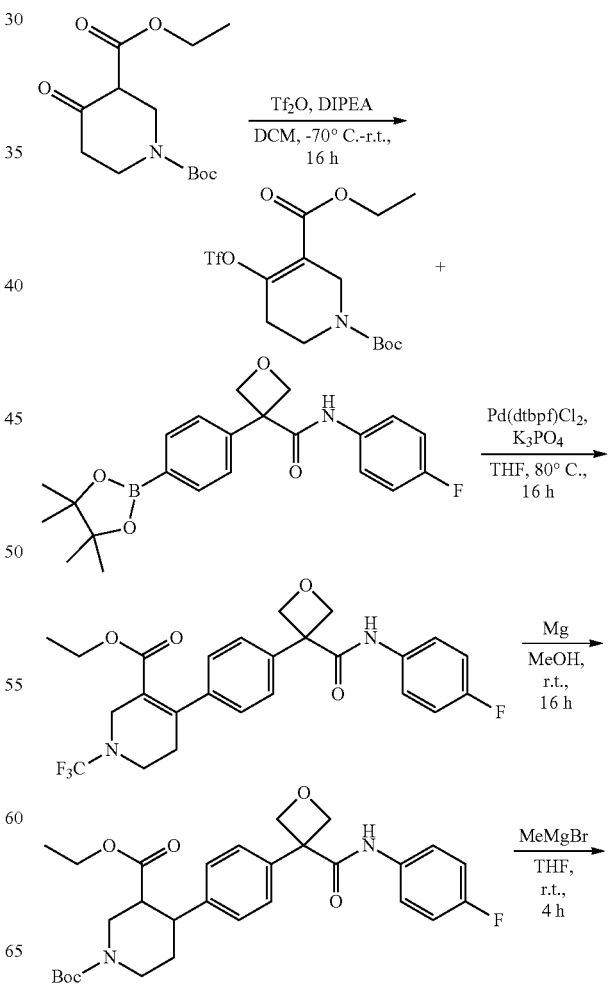

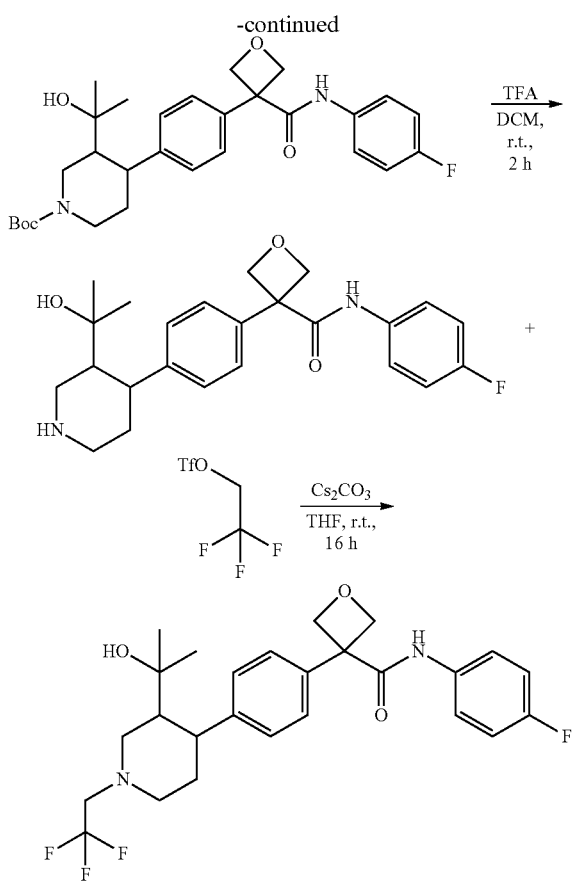

Step 1: 1-tert-butyl 3-ethyl 4-(((trifluoromethyl)sulfonyl)oxy)-5,6-dihydropyridine-1,3(2H)-dicarboxylate To a stirred solution of 1-tert-butyl 3-ethyl 4-oxopiperidine-1,3-dicarboxylate (4.0 g, 14.74 mmol) and DIPEA (4.76 g, 36.9 mmol) in DCM (60 mL) was added Tf$_2$O (3.2 mL, 18.94 mmol) dropwise at −70° C. and the reaction was stirred at −70° C. under nitrogen for 3 h. The mixture was diluted with water (40 mL) and extracted by DCM (20 mL×3). The organic layers were collected, washed with brine, dried over Na$_2$SO$_4$, filtered and the filtrate was concentrated in vacuo. The residue was purified by flash silica gel chromatography to afford the title compound as an oil.

Step 2: 1-tert-butyl 3-ethyl 4-(4-(3-((4-fluorophenyl)carbamoyl)oxetan-3-yl)phenyl)-5,6-dihydropyridine-1,3(2H)-dicarboxylate To a stirred solution of 1-tert-butyl 3-ethyl 4-(((trifluoromethyl)sulfonyl)oxy)-5,6-dihydropyridine-1,3(2H)-dicarboxylate (1.218 g, 3.02 mmol) and N-(4-fluorophenyl)-3-(4-(4,4,5,5-tetramethyl-1,3,2-dioxaborolan-2-yl)phenyl)oxetane-3-carboxamide (1.0 g, 2.52 mmol) in THF (18 mL) were added potassium phosphate (1.603 g, 7.55 mmol) and Pd(dtbpf)Cl$_2$ (9 mg, 0.014 mmol) at RT. The reaction mixture was stirred at 80° C. under nitrogen for 16 h. After cooled to RT, the reaction mixture was diluted with water (80 mL) and extracted with EtOAc (100 mL×2). The organic layers were collected, washed with brine, dried over Na$_2$SO$_4$, and after filtration, the filtrate was concentrated in vacuo. The residue was purified by flash silica gel chromatography to afford the title compound as a solid.

Step 3: 1-tert-butyl 3-ethyl 4-(4-(3-((4-fluorophenyl)carbamoyl)oxetan-3-yl)phenyl)piperidine-1,3-dicarboxylate To a stirred solution of 1-tert-butyl 3-ethyl 4-(4-(3-((4-fluorophenyl)carbamoyl)oxetan-3-yl)phenyl)-5,6-dihydropyridine-1,3(2H)-dicarboxylate (1.1 g, 2.097 mmol) in MeOH (20 ml) was added magnesium (0.153 g, 6.29 mmol) at RT. The mixture was stirred at RT for 16 h. The reaction mixture was filtered and the cake was washed with MeOH (10 mL×2). The filtrates were combined and concentrated in vacuo. The residue was diluted with EtOAc (30 mL), washed with HCl (20 mL, 2M) and brine, dried over Na$_2$SO$_4$, filtered, and the filtrate was concentrated in vacuo to afford the title compound as an oil, which was used in the next step without further purification. MS (ESI) m/z: 549.0 [M+Na$^+$].

Step 4: tert-butyl 4-(4-(3-((4-fluorophenyl)carbamoyl)oxetan-3-yl)phenyl)-3-(2-hydroxypropan-2-yl)piperidine-1-carboxylate To a stirred solution of methylmagnesium bromide (2.215 ml, 6.65 mmol, 3 M in Et$_2$O) in THF (5 mL) was added 1-tert-butyl 3-ethyl 4-(4-(3-((4-fluorophenyl)carbamoyl)oxetan-3-yl)phenyl)piperidine-1,3-dicarboxylate (1.0 g, 1.899 mmol) in THF (20 mL) dropwise at RT. The reaction mixture was stirred at RT for 4 h. The reaction mixture was diluted with water (20 mL) and extracted with EtOAc (10 mL×2). The organic layers were collected, washed with brine, dried over Na$_2$SO$_4$, filtered, and the filtrate was concentrated in vacuo. The residue was purified by silica gel chromatography to afford the title compound as an oil. MS (ESI) m/z: 513.1 [M+H$^+$].

Step 5: N-(4-fluorophenyl)-3-(4-(3-(2-hydroxypropan-2-yl)piperidin-4-yl)phenyl)oxetane-3-carboxamide To a stirred solution of tert-butyl 4-(4-(3-((4-fluorophenyl)carbamoyl)oxetan-3-yl)phenyl)-3-(2-hydroxypropan-2-yl)piperidine-1-carboxylate (310 mg, 0.605 mmol) in DCM (5 mL) was added TFA (3 mL, 38.9 mmol) at RT. The reaction was stirred at RT for 2 h. The reaction mixture was diluted with sat. NaHCO$_3$ (40 mL) and extracted with DCM (15 mL×2). The organic layers were collected, washed with brine, dried over Na$_2$SO$_4$, filtered, and the filtrate was concentrated in vacuo to afford the title compound as an oil, which was used in the next step without further purification. MS (ESI) m/z: 413.1 [M+H$^+$].

Step 6: N-(4-fluorophenyl)-3-(4-(3-(2-hydroxypropan-2-yl)-1-(2,2,2-trifluoroethyl)piperidin-4-yl)phenyl)oxetane-3-carboxamide To a stirred solution of N-(4-fluorophenyl)-3-(4-(3-(2-hydroxypropan-2-yl)piperidin-4-yl)phenyl)oxetane-3-carboxamide (210 mg, 0.509 mmol) in CH$_3$CN (10 mL) were added 2,2,2-trifluoroethyl trifluoromethanesulfonate (236 mg, 1.018 mmol) and Cs$_2$CO$_3$ (332 mg, 1.018 mmol) at RT. The reaction was stirred at RT for 2 h. After filtration, the reaction was purified by reversed phase HPLC on a GILSON 281 instrument fitted with a Column Phenomenex Synergi C18 column (150×30 mm×4 um) eluting with water (0.1% TFA) and CH$_3$CN to give peak 1, isomer 1 as a solid. Further elution gave peak 2, isomer 2 as a solid. MS (ESI) m/z: 495.0 [M+H$^+$].

Isomer 1 was further resolved by SFC separation using a Phenomenex-Amylose-1 (250 mm×30 mm×5 um) column to give Example 119a (enantiomer 1, peak 1) and Example 119b (Enantiomer 2, peak 2).

Example 119a: $^1$H NMR (400 MHz, CD$_3$OD) δ 7.50 (dd, 2H), 7.44 (d, 2H), 7.34 (d, 2H), 7.03 (t, 2H), 5.29 (d, 2H), 4.94 (d, 2H), 3.75 (br s, 3H), 3.61-3.62 (m, 1H), 3.34-3.40 (m, 1H), 2.62-2.96 (m, 3H), 2.23-2.34 (m, 1H), 1.81-2.04 (m, 2H), 1.06 (s, 3H), 0.70 (s, 3H). MS (ESI) m/z: 495.1 [M+H$^+$].

Example 119b: $^1$H NMR (400 MHz, CD$_3$OD) δ 7.50 (dd, Hz, 2H), 7.44 (d, 2H), 7.34 (d, 2H), 7.03 (t, 2H), 5.29 (d, 2H), 4.94 (d, 2H), 3.75 (br s, 3H), 3.61-3.62 (m, 1H), 3.34-3.40 (m, 1H), 2.62-2.96 (m, 3H), 2.23-2.34 (m, 1H), 1.81-2.04 (m, 2H), 1.06 (s, 3H), 0.70 (s, 3H). MS (ESI) m/z: 495.1 [M+H$^+$].

Isomer 2 was similarly resolved by SFC separation using a Phenomenex-Amylose-1 (250 mm×30 mm×5 um) column to give enantiomer 2-1 and Enantiomer 2-2.

Example 119c: $^1$H NMR (400 MHz, CD$_3$OD) δ 7.42-7.56 (m, 6H), 7.04 (t, 2H), 5.30 (dd, 2H), 4.94 (br t, 2H), 3.71-4.04 (m, 3H), 3.41-3.61 (m, 2H), 3.35 (br s, 1H), 3.17-3.25 (m, 1H), 2.16-2.58 (m, 3H), 1.21 (s, 3H), 0.71 (s, 3H). MS (ESI) m/z: 495.1 [M+H$^+$].

Example 119d: 1H NMR (400 MHz, CD$_3$OD) δ 7.42-7.58 (m, 6H), 7.04 (t, 2H), 5.30 (dd, 2H), 4.94 (t, 2H), 3.75-4.10 (m, 3H), 3.53 (br s, 2H), 3.34 (br s, 1H), 3.20-3.28 (m, 1H), 2.17-2.58 (m, 3H), 1.22 (s, 3H), 0.71 (s, 3H). MS (ESI) m/z: 495.1 [M+H$^+$].

Example 120: N-(4-fluorophenyl)-3-(4-(hydroxymethyl)-6'-(trifluoromethyl)-[3,3'-bipyridin]-6-yl)oxetane-3-carboxamide

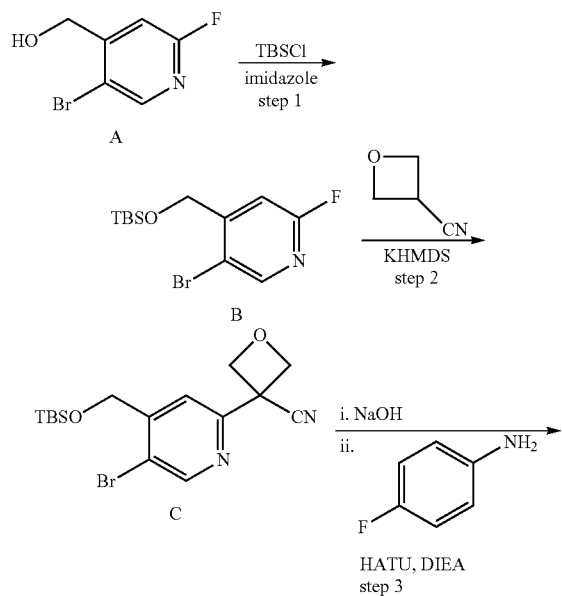

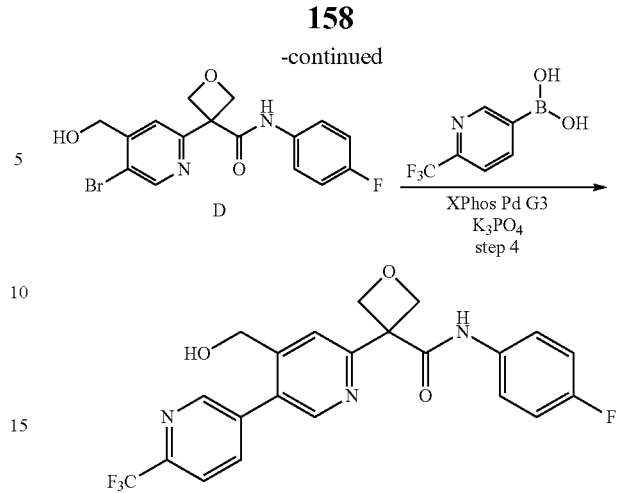

Step 1: 5-bromo-4-(((tert-butyldimethylsilyl)oxy)methyl)-2-fluoropyridine (B)

To a vial equipped with a stir bar was added (5-bromo-2-fluoropyridin-4-yl)methanol (A) (500 mg, 2.43 mmol), DMF (4.9 ml), imidazole (363 mg, 5.34 mmol) and tert-butyldimethylsilyl chloride (402 mg, 2.67 mmol). The mixture was stirred at RT for 63 h. The reaction mixture was then diluted with sat. NaHCO$_3$ and extracted with EtOAc. The organic layer was then separated, washed with brine, dried over MgSO$_4$, and concentrated under reduced pressure. The residue was purified via flash chromatography to afford the title compound. MS (ESI) m/z: 320, 322 [M+H]$^+$.

Step 2: 3-(5-bromo-4-(((tert-butyldimethylsilyl)oxy)methyl)pyridin-2-yl)oxetane-3-carbonitrile (C)

To a 50 ml round-bottomed flask with a stir bar under nitrogen was added 5-bromo-4-(((tert-butyldimethylsilyl)oxy)methyl)-2-fluoropyridine (B) (712 mg, 2.22 mmol), oxetane-3-carbonitrile (185 µl, 2.45 mmol), and toluene (18 mL). The flask was cooled to 0° C. and KHMDS (2668 µl, 2.67 mmol, 1.0 M in THF) was added dropwise with stirring. The solution was stirred for 10 min at 0° C., after which the reaction was quenched with the slow addition of MeOH with stirring. The resulting mixture was diluted with EtOAc and water, and the aqueous layer was extracted with EtOAc, and the combined organics were washed with brine, dried over MgSO$_4$, and concentrated under reduced pressure. The residue was then purified via flash chromatography to afford the title compound. MS (ESI): 383, 385 [M+H]$^+$.

Step 3: 3-(5-bromo-4-(hydroxymethyl)pyridin-2-yl)-N-(4-fluorophenyl)oxetane-3-carboxamide (D)

To a vial equipped with a stir bar was added 3-(5-bromo-4-(((tert-butyldimethylsilyl)oxy)methyl)pyridin-2-yl)oxetane-3-carbonitrile (D) (410 mg, 1.07 mmol), NaOH (1.07 ml, 1.07 mmol, 1N in water), and ethanol (2.7 ml). The vial was sealed and heated to 75° C. for 16 h. The reaction was then cooled and EtOAc was added (4 mL), followed by the addition of HCl (1N in water) dropwise to adjust the pH to ~2. The reaction mixture was then further diluted with water and extracted with EtOAc. The combined organics were washed with brine, dried over magnesium sulfate, filtered, and concentrated under reduced pressure to afford 3-(5- bromo-4-(hydroxymethyl)pyridin-2-yl)oxetane-3-carboxylic acid (loss of TBS group was observed under the reaction conditions).

To a vial equipped with a stir bar was added 3-(5-bromo-4-(hydroxymethyl)pyridin-2-yl)oxetane-3-carboxylic acid (308 mg, 1.069 mmol, crude material from the previous step), HATU (610 mg, 1.604 mmol), and DMF (5345 µl). 4-Fluoroaniline (304 µl, 3.21 mmol) was then added followed by DIEA (560 µl, 3.21 mmol). The reaction was allowed to stir at RT for 48 h. Water and EtOAc were then added and the mixture was extracted with EtOAc. The combined organics were washed with brine, dried over magnesium sulfate, filtered, and concentrated under reduced pressure. The residue was then purified via flash chromatography (silica gel, eluting with a gradient of 0-100% EtOAc in hexanes) to afford 3-(5-bromo-4-(hydroxymethyl)pyridin-2-yl)-N-(4-fluorophenyl)oxetane-3-carboxamide. MS (ESI): 381, 383 [M+H]+.

Step 4: N-(4-fluorophenyl)-3-(4-(hydroxymethyl)-6'-(trifluoromethyl)-[3,3'-bipyridin]-6-yl)oxetane-3-carboxamide To a vial equipped with a stir bar was charged with 3-(5-bromo-4-(hydroxymethyl)pyridin-2-yl)-N-(4-fluorophenyl)oxetane-3-carboxamide (65 mg, 0.17 mmol), (6-(trifluoromethyl)pyridin-3-yl)boronic acid (48.8 mg, 0.256 mmol), and Xphos Pd G3 (14.4 mg, 0.017 mmol). The vial was then sealed and was evacuated and backfilled with argon (×3). THF (3.4 ml) and potassium phosphate tribasic (512 µl, 0.512 mmol, 1M aqueous solution) were then added, and the reaction was warmed to 50° C. for 1 h, followed by 80° C. for 1 h. The reaction was then cooled to RT and was diluted with EtOAc and water. The reaction mixture was extracted with EtOAc and the combined organics were washed with brine, dried over magnesium sulfate, filtered, and concentrated under reduced pressure. The residue was dissolved in DMSO and purified by reverse-phase preparative HPLC (5:95 to 95:5 acetonitrile:water: 0.1% v/v TFA modifier) to afford the title compound as the TFA salt. 1H NMR (600 MHz, DMSO-d6) δ 10.11 (s, 1H), 8.87 (d, J=1.9 Hz, 1H), 8.58 (s, 1H), 8.22 (dd, J=8.1, 2.0 Hz, 1H), 8.04 (d, J=8.0 Hz, 1H), 7.81 (s, 1H), 7.67-7.71 (m, 2H), 7.24-7.08 (m, 2H), 5.20 (d, J=6.4 Hz, 2H), 5.05 (d, J=6.4 Hz, 2H), 4.51 (s, 2H). MS (ESI): 448 [M+H]+.

Example 121: 3-(4-(6-(2,2-difluoroethoxy)-4-(hydroxymethyl)pyridin-3-yl)phenyl)-N-(4-fluorophenyl)oxetane-3-carboxamide

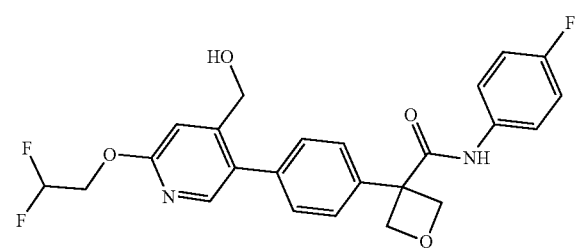 [SMILES: O=C(Nc1ccc(F)cc1)C1(c2ccc(-c3cnc(OCC(F)F)cc3CO)cc2)COC1]

To a vial were added N-(4-fluorophenyl)-3-(4-(4,4,5,5-tetramethyl-1,3,2-dioxaborolan-2-yl)phenyl)oxetane-3-carboxamide (50 mg, 0.12 mmol), (5-bromo-2-(2,2-difluoroethoxy)pyridin-4-yl)methanol (38.5 mg, 0.143 mmol), XPhos Pd G3 (10 mg, 0.012 mmol), THF (600 µL) and K3PO4 (1M) (250 µl, 0.250 mmol). The mixture was evacuated and back filled with nitrogen for 4 times and heated at 45° C. for 2 h. The mixture was filtered through Celite. The filtrate was diluted with water and EtOAc, transferred to a separatory funnel. The organic layer was washed with brine, dried over Na2SO4, filtered and concentrated in vacuo to afford a residue, which was purified by column chromatography on silica gel to afford the title compound. 1H NMR (600 MHz, DMSO-d6) δ 10.05 (s, 1H), 8.00 (s, 1H), 7.72-7.61 (m, 2H), 7.57 (d, 2H), 7.43 (d, 2H), 7.16 (t, 2H), 7.06 (s, 1H), 6.41 (t, 1H), 5.23 (d, 2H), 4.91 (d, 2H), 4.70-4.50 (m, 2H), 4.44 (s, 2H). MS (EI) m/z 459 [M+H]+.

Examples 122-124 in the following table were prepared in a similar fashion as Ex. 121.

| Ex. # | Structure | Chemical Name | Mass [M + H]+ |
|---|---|---|---|
| 122 | 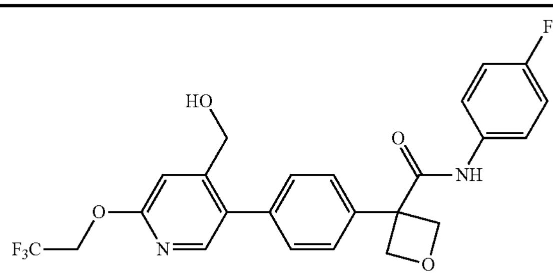 | N-(4-fluorophenyl)-3-(4-(4-(hydroxymethyl)-6-(2,2,2-trifluoroethoxy)pyridin-3-yl)phenyl)oxetane-3-carboxamide | 477 |
| 123 | 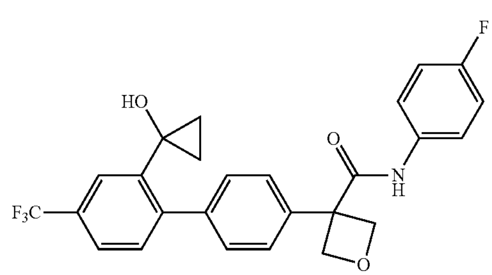 [SMILES: O=C(Nc1ccc(F)cc1)C1(c2ccc(-c3ccc(C(F)(F)F)cc3C3(O)CC3)cc2)COC1] | N-(4-fluorophenyl)-3-(2'-(1-hydroxycyclopropyl)-4'-(trifluoromethyl)-[1,1'-biphenyl]-4-yl)oxetane-3-carboxamide | 472 |

| Ex. # | Structure | Chemical Name | Mass [M + H]+ |
|---|---|---|---|
| 124 | 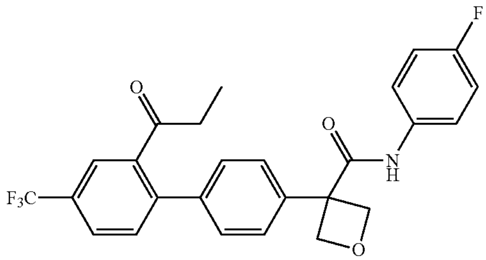 [SMILES: CCC(=O)c1cc(C(F)(F)F)ccc1-c1ccc(C2(C(=O)Nc3ccc(F)cc3)COC2)cc1] | N-(4-fluorophenyl)-1-(2'-propionyl-4'-(trifluoromethyl)-[1,1'-biphenyl]-4-yl)cyclobutane-1-carboxamide | 472 |

Example 125: N-(4-fluorophenyl)-3-(2'-(hydroxymethyl)-4'-(trifluoromethoxy)-[1,1'-biphenyl]-4-yl)oxetane-3-carboxamide

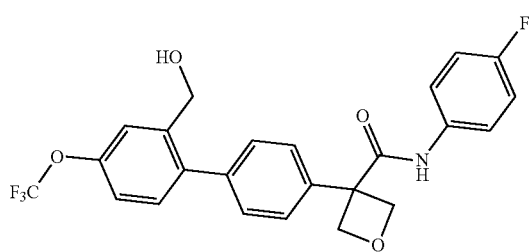 [SMILES: O=C(Nc1ccc(F)cc1)C1(c2ccc(-c3ccc(OC(F)(F)F)cc3CO)cc2)COC1]

Step 1: (2-bromo-5-(trifluoromethoxy)phenyl)methanol

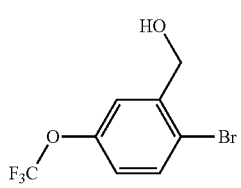

To a stirred solution of methyl 2-bromo-5-(trifluoromethoxy)benzoate (2.0 g, 6.7 mmol) in THF (21 ml) and MeOH (7 ml) was added NaBH4 (1.26 g, 33.4 mmol) at 0° C. The mixture was stirred at RT for 1 h, then quenched with NH$_4$Cl (sat.), diluted with EtOAc and water. The organic phase was separated from aqueous phase and the aqueous phase was extracted again with EtOAc. The combined organic layers were washed with brine, dried over MgSO$_4$, filtered and concentrated in vacuo to afford the title compound, which was used in next step directly. $^1$H NMR (600 MHz, DMSO-d$_6$) δ 7.72 (d, 1H), 7.46 (s, 1H), 7.30-7.16 (m, 1H), 5.68 (t, 1H), 4.52 (d, 2H).

Step 2: N-(4-fluorophenyl)-3-(2'-(hydroxymethyl)-4'-(trifluoromethoxy)-[1,1'-biphenyl]-4-yl)oxetane-3-carboxamide The title compound was prepared in an analogous manner to Example 121. $^1$H NMR (600 MHz, DMSO-d$_6$) δ 10.04 (s, 1H), 7.66 (ddt, 2H), 7.57 (d, 2H), 7.52 (s, 1H), 7.44 (d, 2H), 7.36 (d, 1H), 7.34-7.29 (m, 1H), 7.21-7.13 (m, 2H), 5.23 (d, 2H), 4.91 (d, 2H), 4.43 (s, 2H). MS (EI) m/z 462 [M+H]$^+$.

Example 126: 3-(3-fluoro-4-(4-(hydroxymethyl)-6-(trifluoromethyl)pyridin-3-yl)phenyl)-N-(4-fluorophenyl)oxetane-3-carboxamide

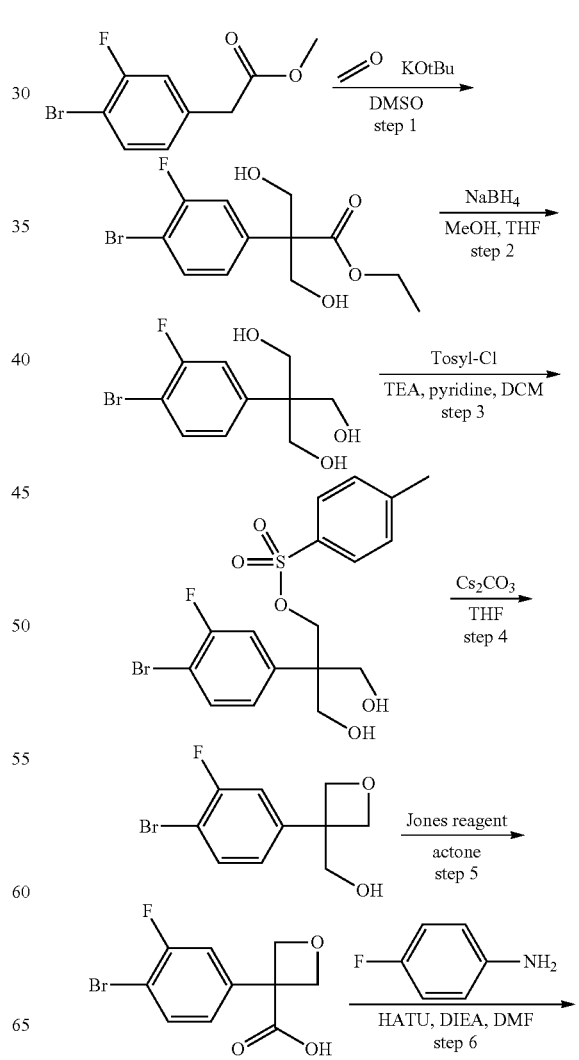

-continued

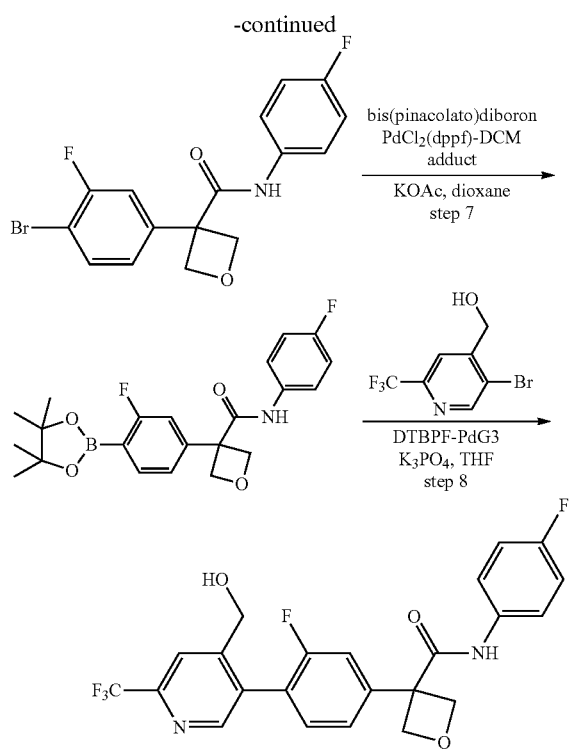

Step 1: ethyl 2-(4-bromo-3-fluorophenyl)-3-hydroxy-2-(hydroxymethyl)propanoate

To a flask were charged with ethyl 2-(4-bromo-3-fluorophenyl)acetate (4.01 g, 15.4 mmol), DMSO (40 ml) and formaldehyde (1.84 g, 61.4 mmol). To this slurry was added KOtBu (0.34 g, 3.07 mmol) in one portion. The mixture was stirred at RT for 30 min, quenched with 1 M HCl (aq.) and diluted with water. The mixture was transferred to separatory funnel and extracted with EtOAc. The combined organic layer was washed with brine, dried over MgSO$_4$, filtered and concentrated in vacuo to afford a crude product, which was purified by column chromatography on silica gel to afford the title compound. MS (EI) m/z 321 [M+H]$^+$.

Step 2: 2-(4-bromo-3-fluorophenyl)-2-(hydroxymethyl)propane-1,3-diol

To a flask were added ethyl 2-(4-bromo-3-fluorophenyl)-3-hydroxy-2-(hydroxymethyl)-propanoate (456.6 mg, 1.422 mmol). MeOH (2000 µl) and THF (6000 µl) To this mixture was added NaBH$_4$ (300 mg, 7.93 mmol) in one portion at 0° C. The mixture was heated at 60° C. for 2 h and another portion of NaBH$_4$ (172 mg, 4.55 mmol) was added and heating continued at 60° C. for another 1 h. The reaction was quenched with 5 mL of NH$_4$Cl (sat.) and 5 mL of HCl (1M) to adjust pH~2, then extracted with EtOAc. The combined organic phases were washed with brine, dried over MgSO$_4$, filtered, concentrated in vacuo to afford a crude product which was dissolve into 2 mL of DMSO and 1 mL of water. The mixture was stirred at RT overnight, then concentrated in vacuo and the residue was dissolved into DCM and washed with NaHCO$_3$, brine, dried over MgSO$_4$, filtered and concentrated to afford the title compound. $^1$H NMR (600 MHz, DMSO-d$_6$) δ 7.58 (t, 1H), 7.40 (dd, 1H), 7.22 (d, 1H), 4.51 (t, 3H), 3.67 (d, 6H).

Step 3: 2-(4-bromo-3-fluorophenyl)-3-hydroxy-2-(hydroxymethyl)propyl 4-methylbenzenesulfonate To a vial containing 2-(4-bromo-3-fluorophenyl)-2-(hydroxymethyl)propane-1,3-diol (118 mg, 0.423 mmol) were added DCM (3500 µL) and TEA (200 µL, 1.43 mmol). To this solution was added a solution of Tosyl-Cl (81 mg, 0.42 mmol) in DCM (1000 µl) at 0° C. Then the mixture was stirred at RT for 24 h. LCMS showed low conversion. To this mixture were added pyridine (150 µl, 1.86 mmol) and another batch of Tosyl-Cl (20 mg, 0.11 mmol). The mixture was stirred at RT for another 4 h and was diluted with DCM, washed with NaHCO$_3$ (sat.), brine, dried over MgSO$_4$, filtered, concentrated in vacuo to afford the title compound, which was used in next step directly. MS (EI) m/z 455 [M+Na]$^+$.

Step 4: (3-(4-bromo-3-fluorophenyl)oxetan-3-yl)methanol

To a vial were added 2-(4-bromo-3-fluorophenyl)-3-hydroxy-2-(hydroxymethyl)propyl 4-methylbenzenesulfonate (47.8 mg, 0.110 mmol), THF (1000 µl) and Cs$_2$CO$_3$ (108 mg, 0.331 mmol). The mixture was heated at 65° C. for 18 h, then at 70° C. for 3 h. The mixture was diluted with water and EtOAc. The aqueous layer was extracted with EtOAc 3 times. The combined organic layers were washed with brine, dried over Na$_2$SO$_4$, filtered and concentrated in vacuo to afford the title compound, which was used in next step directly. MS (EI) m/z 261 [M+H]$^+$.

Step 5: 3-(4-bromo-3-fluorophenyl)oxetane-3-carboxylic acid

To a vial containing (3-(4-bromo-3-fluorophenyl)oxetan-3-yl)methanol (26.2 mg, 0.100 mmol) were added acetone (500 µl) and Jones reagent (110 µl, 0.72 mmol). The mixture was stirred at RT for 5 h, then diluted with EtOAc and water. The organic phase was washed with water, brine, dried over MgSO$_4$, filtered and concentrated in vacuo to afford the title compound, which was used in next step directly. MS (EI) m/z 275 [M+H]$^+$.

Step 6: 3-(4-bromo-3-fluorophenyl)-N-(4-fluorophenyl)oxetane-3-carboxamide

To a vial were added 3-(4-bromo-3-fluorophenyl)oxetane-3-carboxylic acid (19.6 mg, 0.0710 mmol), HATU (54.2 mg, 0.143 mmol), DMF (800 µl), 4-fluoroaniline (30 mg, 0.27 mmol) and DIEA (100 µl, 0.573 mmol). The mixture was stirred at RT for 18 h, diluted with EtOAc and washed with 1M HCl, NaHCO$_3$ (sat.), brine, dried over Na$_2$SO$_4$, filtered and concentrated in vacuo to afford the title compound, which was used in next step directly. MS (EI) m/z 368 [M+H]$^+$.

Step 7: 3-(3-fluoro-4-(4,4,5,5-tetramethyl-1,3,2-dioxaborolan-2-yl)phenyl)-N-(4-fluorophenyl)oxetane-3-carboxamide To a vial were added 3-(4-bromo-3-fluorophenyl)-N-(4-fluorophenyl)oxetane-3-carboxamide (26.2 mg, 0.0710 mmol), bis(pinacolato)diboron (45.2 mg, 0.178 mmol), potassium acetate (20.9 mg, 0.213 mmol), PdCl$_2$(dppf)-CH$_2$Cl$_2$ adduct (5.81 mg, 7.12 µmol) and dioxane (700 µl). The mixture was then evacuated and back filled with N$_2$ for 3 times. The mixture was heated to 80° C. for 20 h cooled to rt and filtered through a celite pad. The filtrate was concentrated in vacuo to give a residue, which was dissolved in DCM, washed with water, brine, dried over Na$_2$SO$_4$, filtered and concentrated in vacuo to afford the title compound, which was used in next step directly. MS (EI) m/z 416 [M+H]$^+$.

Step 8: 3-(3-fluoro-4-(4-(hydroxymethyl)-6-(trifluoromethyl)pyridin-3-yl)phenyl)-N-(4-fluorophenyl) oxetane-3-carboxamide To a vial were added 3-(3-fluoro-4-(4,4,5,5-tetramethyl-1,3,2-dioxaborolan-2-yl)phenyl)-N-(4-fluorophenyl)oxetane-3-carboxamide (29.5 mg, 0.0710 mmol), (5-bromo-2-(trifluoromethyl)pyridin-4-yl)methanol (35 mg, 0.14 mmol), DTBPF-Pd G3 (8.8 mg, 10 µmol), THF (700 µl) and K$_3$PO$_4$ (1 M, 200 µl, 0.200 mmol). The mixture was evacuated and back filled with nitrogen for 4 times and heated at 50° C. for 1.5 h. The mixture was filtered through Celite, diluted with water and EtOAc, and was transferred to a separatory funnel. The organic layer was washed with water, brine, dried over Na$_2$SO$_4$, filtered and concentrated in vacuo to afford a residue, which was purified by column chromatography on silica gel to afford the title compound. $^1$H NMR (600 MHz, DMSO-d$_6$) δ 10.08 (s, 1H), 9.97 (s, 1H), 8.63 (s, 1H), 8.05 (s, 1H), 7.65 (dd, 1H), 7.61-7.51 (m, 2H), 7.43 (d, 1H), 7.26-7.04 (m, 2H), 5.68 (t, 1H), 5.24 (d, 2H), 4.95 (d, 2H), 4.46 (d, 2H). MS (EI) m/z 465 [M+H]$^+$.

Example 127: N-(6-chloropyridin-3-yl)-3-(4'-(hydroxymethyl)-6'-(trifluoromethyl)-[3,3'-bipyridin]-6-yl)oxetane-3-carboxamide

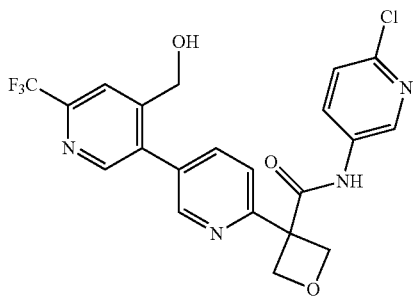 [SMILES: O=C(Nc1ccc(Cl)nc1)C1(c2ccc(-c3cnc(C(F)(F)F)cc3CO)cn2)COC1]

Step 1: 3-(5-bromopyridin-2-yl)-N-(6-chloropyridin-3-yl)oxetane-3-carboxamide

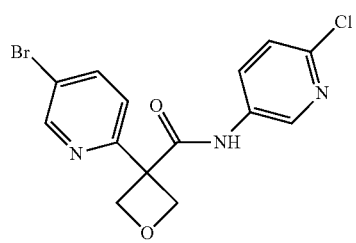 [SMILES: O=C(Nc1ccc(Cl)nc1)C1(c2ccc(Br)cn2)COC1]

To a vial equipped with a stir bar were added 3-(5-bromopyridin-2-yl)oxetane-3-carboxylic acid (1023 mg, 3.96 mmol), HATU (2261 mg, 5.95 mmol), and DMF (9910 µl). To it was added 6-chloropyridin-3-amine (612 mg, 4.76 mmol) followed by DIEA (2077 µl, 11.89 mmol). The mixture was stirred at 45° C. for 2 h and was diluted with EtOAc, and washed with sat. NaHCO$_3$. The organic layer was dried over MgSO$_4$, filtered, and concentrated under reduced pressure. The crude product was purified by flash silica gel chromatography to afford the title compound. MS (ESI) [M+H]$^+$ m/z: 368.

Step 2: Preparation of N-(6-chloropyridin-3-yl)-3-(5-(4,4,5,5-tetramethyl-1,3,2-dioxaborolan-2-yl) pyridin-2-yl)oxetane-3-carboxamide

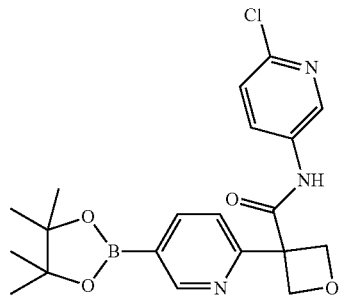 [SMILES: CC1(C)OB(c2ccc(C3(C(=O)Nc4ccc(Cl)nc4)COC3)nc2)OC1(C)C]

To a vial equipped with a stir bar were added 3-(5-bromopyridin-2-yl)-N-(6-chloropyridin-3-yl)oxetane-3-carboxamide (952 mg, 2.58 mmol), bis(pinacolato)diboron (1640 mg, 6.46 mmol), potassium acetate (761 mg, 7.75 mmol), and PdCl$_2$(dppf)-CH$_2$Cl$_2$ Adduct (211 mg, 0.26 mmol) in dioxane (8612 µl). The vial was purged with nitrogen for 5 min and was sealed and heated to 80° C. for 23 h. After cooled to RT, the mixture was diluted with EtOAc and washed with sat. NaHCO$_3$. The organics were dried over MgSO$_4$, filtered, and dry loaded onto a silica gel, which was loaded onto an 80 g silica gel column. The column was eluted with 100% DCM to 100% EtOAc. The desired product was eluted and fractions were collected and concentrated under reduced pressure to afford the title compound. MS (ESI) calc'd for C$_{20}$H$_{23}$BClN$_3$O$_4$[M+H]$^+$, 334; found, 334 (observe the mass of the boronic acid).

Step 3: Preparation of N-(6-chloropyridin-3-yl)-3-(4'-(hydroxymethyl)-6'-(trifluoromethyl)-[3,3'-bipyridin]-6-yl)oxetane-3-carboxamide To a vial equipped with a stir bar was added N-(6-chloropyridin-3-yl)-3-(5-(4,4,5,5-tetramethyl-1,3,2-dioxaborolan-2-yl)pyridin-2-yl)oxetane-3-carboxamide (212 mg, 0.51 mmol), (5-bromo-2-(trifluoromethyl)pyridin-4-yl) methanol (131 mg, 0.51 mmol), potassium phosphate tribasic (Aq. Solution 1M) (1020 µl, 1.02 mmol), (2-dicyclohexylphosphino-2',4',6'-triisopropyl-1,1'-biphenyl)[2-(2'-amino-1,1'-biphenyl)]palladium(II) methanesulfonate (43.2 mg, 0.05 mmol), and THF (2550 µl). The vial was purged with nitrogen, sealed, and heated to 40° C. for 1 h. After 1 h the crude was filtered over Celite and rinsed with methanol. The combined organics were concentrated under reduced pressure. The material was dissolved in EtOAc, and dry loaded onto silica gel. Material was loaded onto a 40 g gold column; was run from 100% DCM to 100% EtOAc. The desired product eluted; fractions were collected and concentrated under reduced pressure. Preparative resolution of the resulting material was performed using supercritical fluid chromatography on a Sepiatec Prep 100. An ES Industries GreenSep Ethyl Pyridine column (5 m, 20 mm×250 mm, ES Industries, West Berlin, N.J.) was used as the stationary phase. The compound mixture was dissolved in a 1:1:1 mixture of N,N-dimethylformamide, methanol, and ACN. Injection and collection were carried out using the following isocratic SFC conditions: 80% carbon dioxide and 20% methanol with 0.25% dimethylethyl amine as the mobile phase, 245 nm UV wavelength, 100 bar outlet pressure, 40° C. column compartment temperature, 70 mL/min total flow rate. Retention time for peak collection was 2.7 min. MS (ESI) calc'd for $C_{21}H_{16}ClF_3N_4O_3$ [M+H]$^+$, 465; found, 465. $^1$H NMR (600 MHz, DMSO-d6) δ 10.45 (s, 1H), 8.79 (d, J=1.7 Hz, 1H), 8.71 (s, 1H), 8.70 (d, J=2.7 Hz, 1H), 8.19 (dd, J=8.7, 2.8 Hz, 1H), 8.09 (s, 1H), 8.08 (d, J=2.4 Hz, 1H), 7.79-7.73 (m, 1H), 7.53 (d, J=8.7 Hz, 1H), 5.75 (t, J=5.5 Hz, 1H), 5.16 (dd, J=91.1, 6.4 Hz, 4H), 4.61 (d, J=5.4 Hz, 2H).

Example 128: N-(4-fluorophenyl)-3-(5-(2-(hydroxymethyl)-4-(trifluoromethyl)phenyl)pyridin-2-yl)oxetane-3-carboxamide

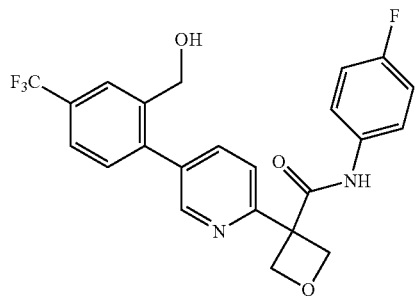 [SMILES: O=C(Nc1ccc(F)cc1)C1(c2ccc(-c3ccc(C(F)(F)F)cc3CO)cn2)COC1]

To a vial equipped with a stir bar were added N-(4-fluorophenyl)-3-(5-(4,4,5,5-tetramethyl-1,3,2-dioxaborolan-2-yl)pyridin-2-yl)oxetane-3-carboxamide (I-155; see Ex. 76 for preparation) (500 mg, 1.26 mmol), (2-bromo-5-(trifluoromethyl)phenyl)methanol (320 mg, 1.26 mmol), potassium phosphate tribasic (aq. solution 1M) (2511 µl, 2.51 mmol), (2-dicyclohexylphosphino-2',4',6'-triisopropyl-1,1'-biphenyl)[2-(2'-amino-1,1'-biphenyl)]palladium(II) methanesulfonate, and THF (1.26E+04 µl). The vial was purged with nitrogen, sealed, and heated to 40° C. for 1.5 h. After 1.5 h, the crude was washed with EtOAc and sat. NaHCO$_3$. Combined organics were dried over MgSO$_4$, filtered, and concentrated under reduced pressure. The material was dry loaded onto a 120 g column, and the column was run from 100% DCM to 100% EtOAc. The desired product was eluted and fractions were collected and concentrated under reduced pressure. The material was added to a vial, and ACN was slowly added dropwise. Almost immediately, a solid crashed out and there was a resulting liquid. More ACN was added dropwise, swirled, and the solid did not go into solution. The mixture was heated with a heat gun to obtain a uniform solution. The mixture was undisturbed for 3.5 h. After 3.5 h, the sample was moved to the refrigerator for 12 h. After 12 h, the mixture was rinsed with cold (chilled with ice bath) ACN, and the title compound was obtained as a solid. MS (ESI) calc'd for $C_{23}H_{18}F_4N_2O_3$[M+H]$^+$, 447; found, 447. $^1$H NMR (600 MHz, DMSO-d6) δ 10.14 (s, 1H), 8.75 (d, J=1.7 Hz, 1H), 8.01 (dd, J=8.2, 2.4 Hz, 1H), 7.97 (s, 1H), 7.78 (d, J=6.9 Hz, 1H), 7.75-7.70 (m, 2H), 7.63 (dd, J=60.7, 8.0 Hz, 2H), 7.25-7.17 (m, 2H), 5.51 (t, J=5.4 Hz, 1H), 5.15 (dd, J=76.2, 6.4 Hz, 4H), 4.52 (d, J=5.4 Hz, 2H).

Example 129: N-(6-chloropyridin-3-yl)-3-(4'-(2-hydroxypropan-2-yl)-6'-(trifluoromethyl)-[3,3'-bipyridin]-6-yl)oxetane-3-carboxamide

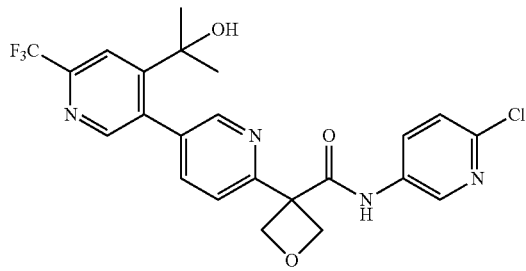 [SMILES: CC(C)(O)c1cc(C(F)(F)F)ncc1-c1ccc(C2(C(=O)Nc3ccc(Cl)nc3)COC2)nc1]

Step 1: 3-(5-(4,4,5,5-tetramethyl-1,3,2-dioxaborolan-2-yl)pyridin-2-yl)oxetane-3-carbonitrile

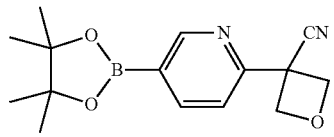 [SMILES: CC1(C)OB(c2ccc(C3(C#N)COC3)nc2)OC1(C)C]

To a flask equipped with a stir bar was added 3-(5-bromopyridin-2-yl)oxetane-3-carbonitrile (2 g, 8.37 mmol), bis(pinacolato)diboron (4.25 g, 16.73 mmol), potassium acetate (2.46 g, 25.10 mmol), and PdCl$_2$(dppf)-CH$_2$Cl$_2$Adduct (0.68 g, 0.84 mmol). The mixture was purged with nitrogen for 5 min. Dioxane (41.8 ml) was added and the mixture stirred. The resulting mixture was heated to 80° C. while stirring under nitrogen for 24 h. After 24 h, the crude reaction mixture was filtered over Celite, and rinsed with EtOAc. Combined organics were concentrated under reduced pressure. The residue was washed with EtOAc and water. Combined organics were dried over MgSO$_4$, filtered, and concentrated under reduced pressure. The residual was dissolved in DCM and loaded onto a 120 g gold column. The column was run from 100% DCM to 100% EtOAc. Desired product was eluted and fractions were collected and concentrated under reduced pressure to afford the title compound. MS (ESI) calc'd for $C_{15}H_{19}BN_2O_3$[M+H]$^+$, 205; found, 205 (detect the mass of the boronic acid).

Step 2: Preparation of 3-(4'-(2-hydroxypropan-2-yl)-6'-(trifluoromethyl)-[3,3'-bipyridin]-6-yl)oxetane-3-carbonitrile

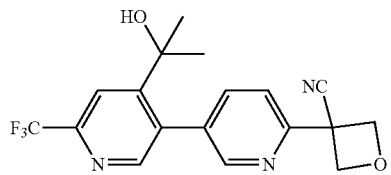 [SMILES: CC(C)(O)c1cc(C(F)(F)F)ncc1-c1ccc(C2(C#N)COC2)nc1]

To a round bottom flask equipped with a stir bar (under nitrogen) was added 3-(5-(4,4,5,5-tetramethyl-1,3,2-dioxaborolan-2-yl)pyridin-2-yl)oxetane-3-carbonitrile (1.72 g, 6.01 mmol), 2-(5-bromo-2-(trifluoromethyl)pyridin-4-yl)propan-2-ol (1.88 g, 6.61 mmol), potassium phosphate tribasic (Aq. Solution 1M) (12.02 ml, 12.02 mmol), 1,1'-bis(di-tert-butylphosphino)ferrocene-palladium dichloride (0.39 g, 0.60 mmol), and dioxane (10.02 ml). The vial was sealed with a septum and purged with nitrogen while heating to 65° C. for 4 h. After 4 h, the reaction was cooled to RT. The reaction mixture was filtered over Celite, and rinsed with EtOAc. Combined organics were concentrated under reduced pressure and washed with EtOAc and water; combined organics were dried over MgSO$_4$, filtered, and concentrated under reduced pressure. The resulting mixture was dry loaded onto an 80 g gold column; the column was run from 100% DCM to 100% EtOAc. Desired product was eluted and fractions were collected and concentrated under reduced pressure to afford the title compound. MS (ESI) calc'd for $C_{18}H_{16}F_3N_3O_2[M+H]^+$, 364; found, 364.

Step 3: Preparation of 3-(4'-(2-hydroxypropan-2-yl)-6'-(trifluoromethyl)-[3,3'-bipyridin]-6-yl)oxetane-3-carboxylic Acid

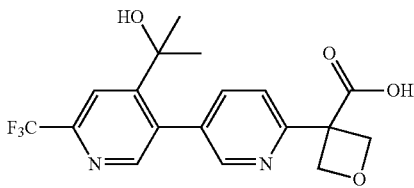 [SMILES: CC(C)(O)c1cc(C(F)(F)F)ncc1-c1ccc(C2(C(=O)O)COC2)nc1]

To a round bottom flask equipped with a stir bar were added 3-(4'-(2-hydroxypropan-2-yl)-6'-(trifluoromethyl)-[3,3'-bipyridin]-6-yl)oxetane-3-carbonitrile (932 mg, 2.57 mmol), NaOH (410 mg, 10.26 mmol), Ethanol (8550 µl), and water (4275 µl). The flask was sealed and heated to 65° C. for 2 h. After 2 h, the reaction mixture was cooled to RT and concentrated under reduced pressure. The reaction mixture was dissolved in EtOAc, and added 1 N HCl dropwise to adjust the pH ~2. The mixture was washed with water and EtOAc. Combined organics were dried over MgSO$_4$, filtered, and concentrated under reduced pressure to afford the title compound. MS (ESI) calc'd for $C_{18}H_{17}F_3N_2O_4[M+H]^+$, 383; found, 383.

Step 4: Preparation of N-(6-chloropyridin-3-yl)-3-(4'-(2-hydroxypropan-2-yl)-6'-(trifluoromethyl)-[3,3'-bipyridin]-6-yl)oxetane-3-carboxamide To a vial equipped with a stir bar was added 3-(4'-(2-hydroxypropan-2-yl)-6'-(trifluoromethyl)-[3,3'-bipyridin]-6-yl)oxetane-3-carboxylic acid (34.5 mg, 0.09 mmol), HATU (51.5 mg, 0.14 mmol), and DMF (902 µl). The mixture was stirred for 5 min. 6-Chloropyridin-3-amine (58.0 mg, 0.45 mmol) was added followed by DIEA (47.3 µl, 0.27 mmol). The mixture was stirred at 45° C. for 48 h. After 48 h, it was dry loaded onto a 24 g gold column; the column was run from 100% DCM to 100% EtOAc. The desired product was eluted and fractions were collected and concentrated under reduced pressure. The mixture was dissolved in ACN/water, then frozen and dried overnight. The resulting mixture was dissolved in 1.5 ml DMSO, and submitted directly for HPLC purification (purified by HPLC, eluting ACN/water gradient with TFA modifier, linear gradient) to afford the title compound. MS (ESI) calc'd for $C_{23}H_{20}ClF_3N_4O_3$ [M+H]$^+$, 493; found, 493. $^1$H NMR (600 MHz, DMSO-d6) δ 10.51 (s, 1H), 8.71 (d, J=2.7 Hz, 1H), 8.66 (d, J=1.8 Hz, 1H), 8.46 (s, 1H), 8.21 (d, J=2.8 Hz, 1H), 8.20 (d, J=2.7 Hz, 2H), 7.94 (dd, J=8.1, 2.3 Hz, 1H), 7.70 (d, J=8.0 Hz, 1H), 7.55 (d, J=8.7 Hz, 1H), 5.16 (dd, J=94.6, 6.4 Hz, 4H) 1.35 (s, 6H).

Example 130-131 in the following table were prepared in a similar fashion as Ex. 129.

| Ex. # | Structure | Chemical Name | Mass [M + H]+ |
|---|---|---|---|
| 130 | 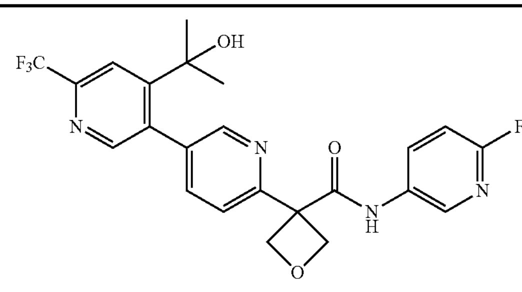 | N-(6-fluoropyridin-3-yl)-3-(4'-(2-hydroxypropan-2-yl)-6'-(trifluoromethyl)-[3,3'-bipyridin]-6-yl)oxetane-3-carboxamide | 477 |
| 131 | 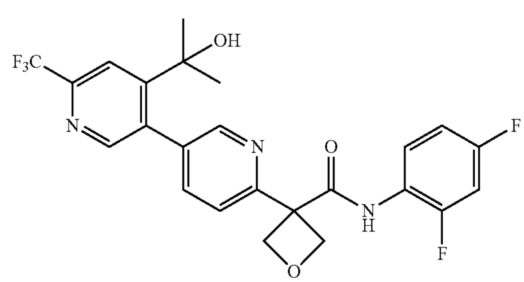 [SMILES: CC(C)(O)c1cc(C(F)(F)F)ncc1-c1ccc(C2(C(=O)Nc3ccc(F)cc3F)COC2)nc1] | N-(2,4-difluorophenyl)-3-(4'-(2-hydroxypropan-2-yl)-6'-(trifluoromethyl)-[3,3'-bipyridin]-6-yl)oxetane-3-carboxamide | 494 |

Example 132: N-(4-chlorophenyl)-3-(4'-(2-hydroxypropan-2-yl)-6'-(trifluoromethyl)-[3,3'-bipyridin]-6-yl)oxetane-3-carboxamide

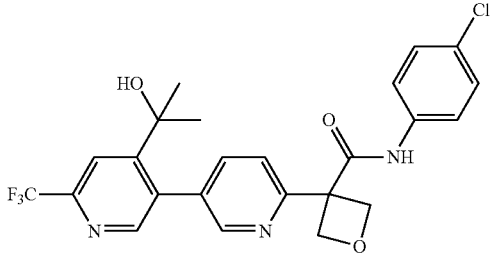 [SMILES: CC(C)(O)c1cc(C(F)(F)F)ncc1-c1ccc(C2(C(=O)Nc3ccc(Cl)cc3)COC2)nc1]

Step 1: 3-(5-bromopyridin-2-yl)-N-(4-chlorophenyl)oxetane-3-carboxamide

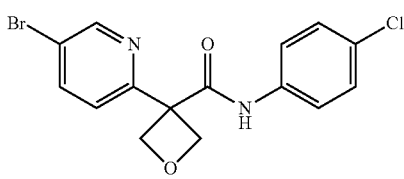 [SMILES: O=C(Nc1ccc(Cl)cc1)C1(c2ccc(Br)cn2)COC1]

To a vial equipped with a stir bar were added 3-(5-bromopyridin-2-yl)oxetane-3-carboxylic acid (500 mg, 1.94 mmol), HATU (1105 mg, 2.91 mmol), and DMF (4844 µl). 4-Chloroaniline (297 mg, 2.33 mmol) was added followed by DIEA (1015 µl, 5.81 mmol). The mixture was stirred at 45° C. for 4 h. After 4 h, the crude was washed with EtOAc and sat. NaHCO$_3$. Combined organics were dried over MgSO$_4$, filtered, and concentrated under reduced pressure. The material was dry loaded onto a 120 g gold column, and the column was run from 100% hexanes to 100% EtOAc. The desired product was eluted and fractions were collected and concentrated under reduced pressure to afford the title compound. MS (ESI) calc'd for $C_{15}H_{12}BrClN_2O_2[M+H]^+$, 367; found, 367.

Step 2: N-(4-chlorophenyl)-3-(5-(4,4,5,5-tetramethyl-1,3,2-dioxaborolan-2-yl)pyridin-2-yl)oxetane-3-carboxamide

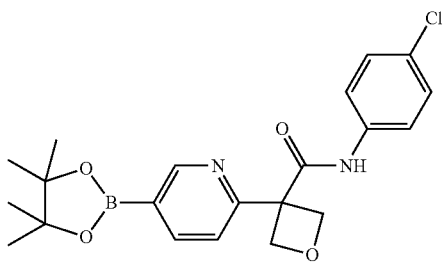 [SMILES: CC1(C)OB(c2ccc(C3(C(=O)Nc4ccc(Cl)cc4)COC3)nc2)OC1(C)C]

To a flask equipped with a stir bar were added 3-(5-bromopyridin-2-yl)-N-(4-chlorophenyl)oxetane-3-carboxamide (200 mg, 0.54 mmol), bis(pinacolato)diboron (207 mg, 0.82 mmol), potassium acetate (160 mg, 1.63 mmol), and PdCl$_2$(dppf)-CH$_2$Cl$_2$Adduct (44.4 mg, 0.054 mmol). The mixture was purged with nitrogen for 5 min. Dioxane (2720 µl) was added and the mixture stirred. The vial was heated to 80° C. for 12 h. After 12 h, the crude was washed with EtOAc and sat. NaHCO$_3$. The combined organics were dried over MgSO$_4$, filtered, and concentrated under reduced pressure. The material was dry loaded onto a 40 g gold column, and the column was run from 100% DCM to 100% EtOAc. Desired product was eluted and fractions were collected and concentrated under reduced pressure to afford the title compound. MS (ESI) calc'd for $C_{21}H_{24}BClN_2O_4$ [M+H]$^+$, 333; found, 333 (observe the mass of the boronic acid).

Step 3: N-(4-chlorophenyl)-3-(4'-(2-hydroxypropan-2-yl)-6'-(trifluoromethyl)-[3,3'-bipyridin]-6-yl)oxetane-3-carboxamide To a vial equipped with a stir bar were added N-(4-chlorophenyl)-3-(5-(4,4,5,5-tetramethyl-1,3,2-dioxaborolan-2-yl)pyridin-2-yl)oxetane-3-carboxamide (93.7 mg, 0.23 mmol), 2-(5-bromo-2-(trifluoromethyl)pyridin-4-yl)propan-2-ol (70.6 mg, 0.25 mmol), potassium phosphate tribasic (aq. solution 1M) (452 µl, 0.45 mmol), PdCl$_2$(dtbpf) (29.5 mg, 0.045 mmol), and dioxane (1130 µl). The vial was purged with nitrogen, sealed, and heated to 65° C. for 22 h. After 22 h, 1 small scoop of MgSO$_4$ was added, followed by EtOAc, and solid was filtered off. Organics were concentrated under reduced pressure and dissolved in 1.5 ml DMSO and submitted directly for HPLC purification (purified by HPLC, eluting ACN/water gradient with TFA modifier, linear gradient). Fractions were returned and frozen and dried on the lyophilizer overnight to afford the title compound. MS (ESI) calc'd for $C_{24}H_{21}ClF_3N_3O_3$ [M+H]$^+$, 492; found, 492. $^1$H NMR (600 MHz, DMSO-d6) δ 10.27 (s, 1H), 8.67 (d, J=1.7 Hz, 1H), 8.46 (s, 1H), 8.20 (s, 1H), 7.93 (dd, J=8.1, 2.3 Hz, 1H), 7.79-7.70 (m, 2H), 7.66 (d, J=8.0 Hz, 1H), 7.47-7.36 (m, 2H), 5.15 (dd, J=86.8, 6.4 Hz, 4H), 1.35 (s, 6H).

Examples 133-139 in the following table were prepared in a similar fashion as Ex. 112 using intermediate I-9 (see Ex. 7 for preparation) and corresponding alcohols.

| Ex. # | Structure | Chemical Name | Mass [M + H]+ |
|---|---|---|---|
| 133 | 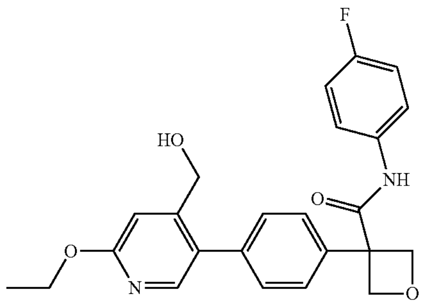 [SMILES: CCOc1cc(CO)c(-c2ccc(C3(C(=O)Nc4ccc(F)cc4)COC3)cc2)cn1] | 3-(4-(6-ethoxy-4-(hydroxymethyl)pyridin-3-yl)phenyl)-N-(4-fluorophenyl)oxetane-3-carboxamide | 423 |
| 134 | 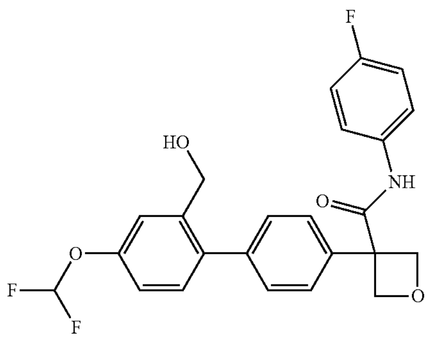 [SMILES: O=C(Nc1ccc(F)cc1)C1(c2ccc(-c3ccc(OC(F)F)cc3CO)cc2)COC1] | 3-(4'-(difluoromethoxy)-2'-(hydroxymethyl)-[1,1'-biphenyl]-4-yl)-N-(4-fluorophenyl)oxetane-3-carboxamide | 444 |
| 135 | 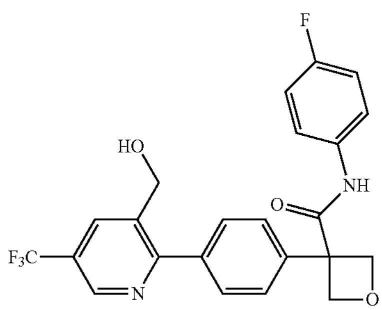 [SMILES: O=C(Nc1ccc(F)cc1)C1(c2ccc(-c3ncc(C(F)(F)F)cc3CO)cc2)COC1] | N-(4-fluorophenyl)-3-(4-(3-(hydroxymethyl)-5-(trifluoromethyl)pyridin-2-yl)phenyl)oxetane-3-carboxamide | 447 |
| 136 | 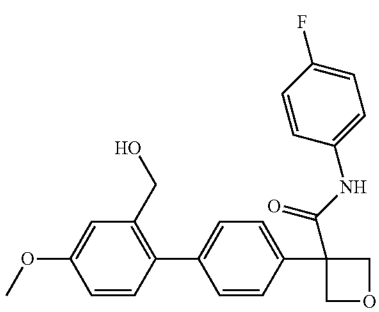 [SMILES: COc1ccc(-c2ccc(C3(C(=O)Nc4ccc(F)cc4)COC3)cc2)c(CO)c1] | N-(4-fluorophenyl)-3-(2'-(hydroxymethyl)-4'-methoxy-[1,1'-biphenyl]-4-yl)oxetane-3-carboxamide | 408 |
| 137 | 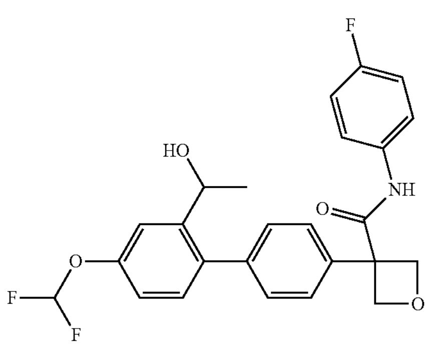 [SMILES: CC(O)c1cc(OC(F)F)ccc1-c1ccc(C2(C(=O)Nc3ccc(F)cc3)COC2)cc1] | 3-(4'-(difluoromethoxy)-2'-(1-hydroxyethyl)-[1,1'-biphenyl]-4-yl)-N-(4-fluorophenyl)oxetane-3-carboxamide | 458 |

| Ex. # | Structure | Chemical Name | Mass [M + H]+ |
|---|---|---|---|
| 138 | 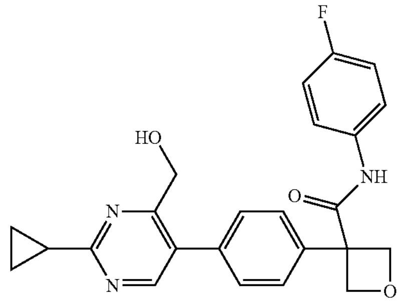 [SMILES: O=C(Nc1ccc(F)cc1)C1(c2ccc(-c3cnc(C4CC4)nc3CO)cc2)COC1] | 3-(4-(2-cyclopropyl-4-(hydroxymethyl)pyrimidin-5-yl)phenyl)-N-(4-fluorophenyl)oxetane-3-carboxamide | 420 |
| 139 | 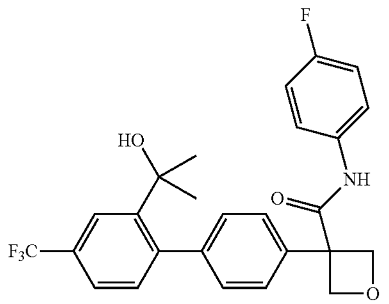 [SMILES: CC(C)(O)c1cc(C(F)(F)F)ccc1-c1ccc(C2(C(=O)Nc3ccc(F)cc3)COC2)cc1] | N-(4-fluorophenyl)-3-(2'-(2-hydroxypropan-2-yl)-4'-(trifluoromethyl)-[1,1'-biphenyl]-4-yl)oxetane-3-carboxamide | 474 |

Examples 140-148 in the following table were prepared in a similar fashion as Ex. 76 using intermediate I-155 (see Ex. 76 for preparation) and corresponding coupling alcohol partners.

| Ex. # | Structure | Chemical Name | Mass [M + H]+ |
|---|---|---|---|
| 140 | 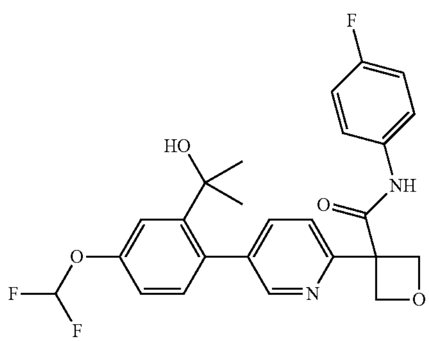 [SMILES: CC(C)(O)c1cc(OC(F)F)ccc1-c1ccc(C2(C(=O)Nc3ccc(F)cc3)COC2)nc1] | 3-(5-(4-(difluoromethoxy)-2-(2-hydroxypropan-2-yl)phenyl)pyridin-2-yl)-N-(4-fluorophenyl)oxetane-3-carboxamide | 473 |
| 141 | 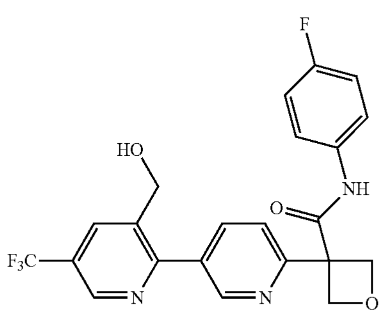 [SMILES: O=C(Nc1ccc(F)cc1)C1(c2ccc(-c3ncc(C(F)(F)F)cc3CO)cn2)COC1] | N-(4-fluorophenyl)-3-(3-(hydroxymethyl)-5-(trifluoromethyl)-[2,3'-bipyridin]-6'-yl)oxetane-3-carboxamide | 448 |

| Ex. # | Structure | Chemical Name | Mass [M + H]+ |
|---|---|---|---|
| 142 | 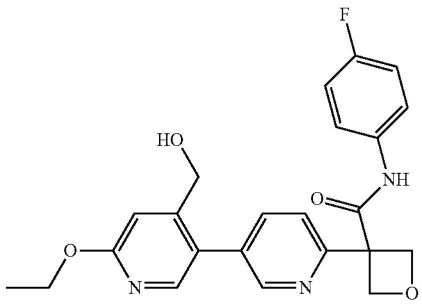 [SMILES: CCOc1cc(CO)c(-c2ccc(C3(C(=O)Nc4ccc(F)cc4)COC3)nc2)cn1] | 3-(6'-ethoxy-4'-(hydroxymethyl)-[3,3'-bipyridin]-6-yl)-N-(4-fluorophenyl)oxetane-3-carboxamide | 424 |
| 143 | 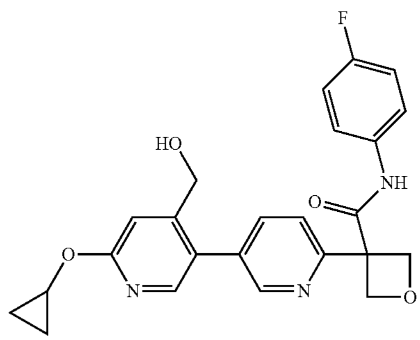 [SMILES: O=C(Nc1ccc(F)cc1)C1(c2ccc(-c3cnc(OC4CC4)cc3CO)cn2)COC1] | 3-(6'-cyclopropoxy-4'-(hydroxymethyl)-[3,3'-bipyridin]-6-yl)-N-(4-fluorophenyl)oxetane-3-carboxamide | 436 |
| 144 | 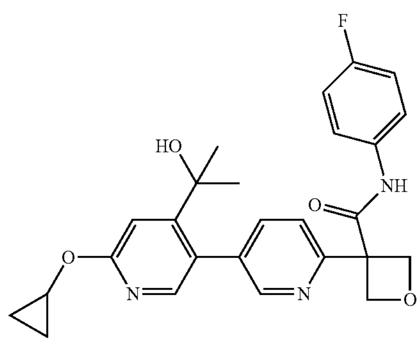 [SMILES: CC(C)(O)c1cc(OC2CC2)ncc1-c1ccc(C2(C(=O)Nc3ccc(F)cc3)COC2)nc1] | 3-(6'-cyclopropoxy-4'-(2-hydroxypropan-2-yl)-[3,3'-bipyridin]-6-yl)-N-(4-fluorophenyl)oxetane-3-carboxamide | 464 |
| 145 | 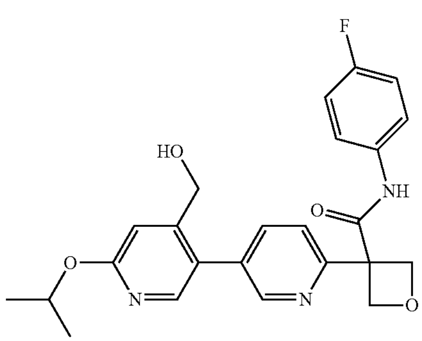 [SMILES: CC(C)Oc1cc(CO)c(-c2ccc(C3(C(=O)Nc4ccc(F)cc4)COC3)nc2)cn1] | N-(4-fluorophenyl)-3-(4'-(hydroxymethyl)-6'-isopropoxy-[3,3'-bipyridin]-6-yl)oxetane-3-carboxamide | 438 |

| Ex. # | Structure | Chemical Name | Mass [M + H]+ |
|---|---|---|---|
| 146 | 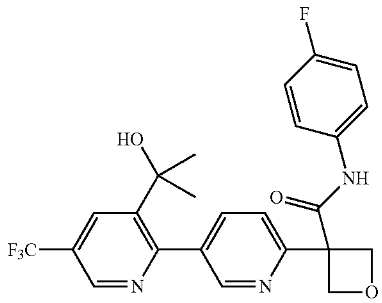 [SMILES: CC(C)(O)c1cc(C(F)(F)F)cnc1-c1ccc(C2(C(=O)Nc3ccc(F)cc3)COC2)nc1] | N-(4-fluorophenyl)-3-(3-(2-hydroxypropan-2-yl)-5-(trifluoromethyl)-[2,3'-bipyridin]-6'-yl)oxetane-3-carboxamide | 476 |
| 147 | 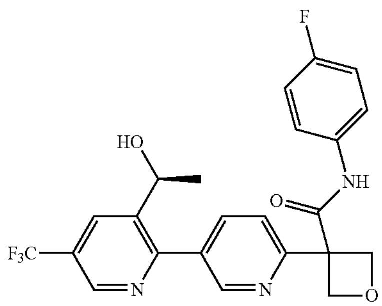 [SMILES: C[C@H](O)c1cc(C(F)(F)F)cnc1-c1ccc(C2(C(=O)Nc3ccc(F)cc3)COC2)nc1] | (S)-N-(4-fluorophenyl)-3-(3-(1-hydroxyethyl)-5-(trifluoromethyl)-[2,3'-bipyridin]-6'-yl)oxetane-3-carboxamide | 462 |
| 148 | 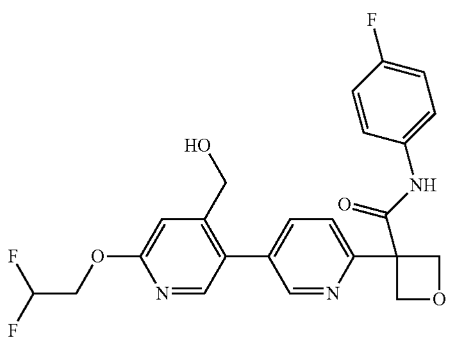 [SMILES: O=C(Nc1ccc(F)cc1)C1(c2ccc(-c3cnc(OCC(F)F)cc3CO)cn2)COC1] | 3-(6'-(2,2-difluoroethoxy)-4'-(hydroxymethyl)-[3,3'-bipyridin]-6-yl)-N-(4-fluorophenyl)oxetane-3-carboxamide | 460 |

Examples 149-151 in the following table were prepared in a similar fashion as Ex. 81.

| Ex. # | Structure | Chemical Name | Mass [M + H]+ |
|---|---|---|---|
| 149 | 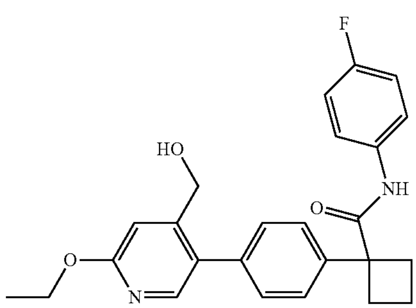 [SMILES: CCOc1cc(CO)c(-c2ccc(C3(C(=O)Nc4ccc(F)cc4)CCC3)cc2)cn1] | 1-(4-(6-ethoxy-4-(hydroxymethyl)pyridin-3-yl)phenyl)-N-(4-fluorophenyl)cyclobutane-1-carboxamide | 421 |

| Ex. # | Structure | Chemical Name | Mass [M + H]+ |
|---|---|---|---|
| 150 | 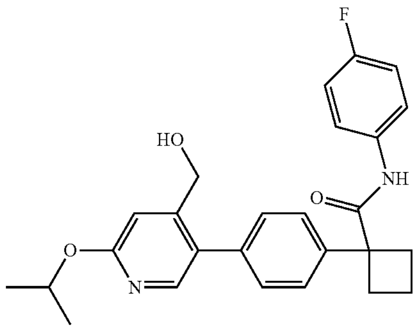 [SMILES: CC(C)Oc1cc(CO)c(-c2ccc(C3(C(=O)Nc4ccc(F)cc4)CCC3)cc2)cn1] | N-(4-fluorophenyl)-1-(4-(4-(hydroxymethyl)-6-isopropoxypyridin-3-yl)phenyl)cyclobutane-1-carboxamide | 435 |
| 151 | 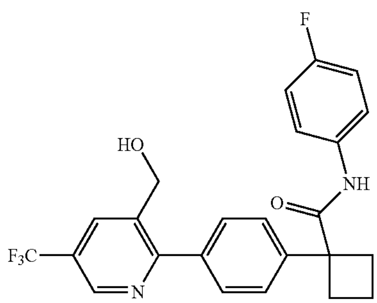 [SMILES: O=C(Nc1ccc(F)cc1)C1(c2ccc(-c3ncc(C(F)(F)F)cc3CO)cc2)CCC1] | N-(4-fluorophenyl)-1-(4-(3-(hydroxymethyl)-5-(trifluoromethyl)pyridin-2-yl)phenyl)cyclobutane-1-carboxamide | 445 |
Example 152: 3-fluoro-N-(4-fluorophenyl)-1-(4-(4-(hydroxymethyl)-6-(trifluoromethyl)pyridin-3-yl)phenyl)cyclobutane-1-carboxamide
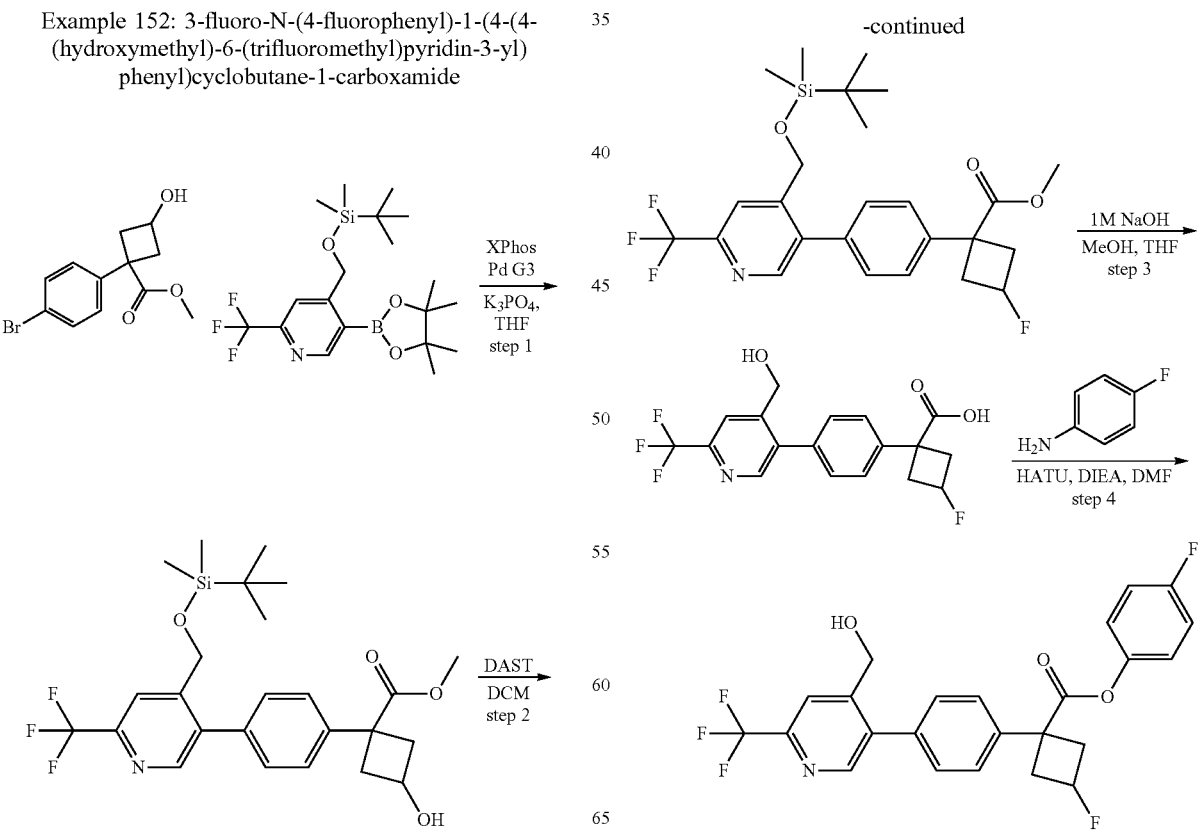

Step 1: methyl 1-(4-(4-(((tert-butyldimethylsilyl) oxy)methyl)-6-(trifluoromethyl)pyridin-3-yl)phenyl)-3-hydroxycyclobutane-1-carboxylate To a vial were added methyl 1-(4-bromophenyl)-3-hydroxycyclobutanecarboxylate (113 mg, 0.396 mmol), 4-(((tert-butyldimethylsilyl)oxy)-methyl)-5-(4,4,5,5-tetramethyl-1,3,2-dioxaborolan-2-yl)-2-(trifluoromethyl)pyridine (248 mg, 0.594 mmol), XPhos Pd G3 (33 mg, 0.04 mmol), THF (2000 µl) and $K_3PO_4$ (1000 µl, 1 mmol). The mixture was evacuated and backfilled with nitrogen for 4 times and heated at 60° C. for 1 h. The mixture was diluted with water and EtOAc. The aqueous layer was extracted with EtOAc 3 times. The combined organic layers were washed with brine, dried over $Na_2SO_4$, filtered and concentrated in vacuo to afford a residue, which was purified by column chromatography on silica gel to afford the title compound. MS (EI) m/z: 496 [M+H$^+$].

Step 2: methyl 1-(4-(4-(((tert-butyldimethylsilyl) oxy)methyl)-6-(trifluoromethyl)pyridin-3-yl)phenyl)-3-fluorocyclobutane-1-carboxylate A solution of methyl 1-(4-(4-(((tert-butyldimethylsilyl) oxy)methyl)-6-(trifluoromethyl)pyridin-3-yl)phenyl)-3-hydroxycyclobutanecarboxylate (147 mg, 0.297 mmol) in DCM (2500 µL) was treated with DAST (96 mg, 0.59 mmol) at 0° C. The mixture was stirred at RT for 3 h, then quenched with $NaHCO_3$ (sat.) and diluted with DCM. The organic phase was concentrated in vacuo and purified by column chromatography on silica gel to afford the title compound. MS (EI) m/z: 498 [M+H$^+$].

Step 3: 3-fluoro-1-(4-(4-(hydroxymethyl)-6-(trifluoromethyl)pyridin-3-yl)phenyl)cyclobutane-1-carboxylic acid To the vial containing methyl 1-(4-(4-(((tert-butyldimethylsilyl)oxy)methyl)-6-(trifluoromethyl)pyridin-3-yl)phenyl)-3-fluorocyclobutanecarboxylate (21 mg, 0.043 mmol) were added MeOH (100 µL, THF (300 µL) and NaOH (1M) (50 µL, 0.050 mmol). The mixture was stirred at RT for 18 h. The solvent was concentrated in vacuo to afford a residue, which was dissolved into 0.1 ml of water. The solution was adjusted to pH-3 with HCl (1 M), then concentrated in vacuo. The residue was dried by azeotropic evaporation with ACN twice and toluene once to afford the title compound, which was used in next step directly. MS (EI) m/z: 370 [M+H$^+$].

Step 4: 3-fluoro-N-(4-fluorophenyl)-1-(4-(4-(hydroxymethyl)-6-(trifluoromethyl)pyridin-3-yl)phenyl)cyclobutane-1-carboxamide To the vial containing 3-fluoro-1-(4-(4-(hydroxymethyl)-6-(trifluoromethyl)pyridin-3-yl)phenyl)cyclobutanecarboxylic acid (16 mg, 0.043 mmol), were added DMF (400 µL), 4-fluoroaniline (21 mg, 0.19 mmol), HATU (33 mg, 0.087 mmol) and DIEA (30 µl, 0.17 mmol). The mixture was stirred at RT for 15 min. The mixture was filtered and purified by reversed phase HPLC, eluting with water (0.1% TFA)-ACN to afford the title compound. $^1$H NMR (600 MHz, DMSO-d6) δ 9.71 (s, 1H), 8.61 (s, 1H), 8.02 (s, 1H), 7.69-7.60 (m, 2H), 7.56 (d, 2H), 7.50 (d, 2H), 7.19-7.08 (m, 2H), 5.65 (t, 1H), 5.17 (dp, 1H), 4.56 (d, 2H), 3.50-3.36 (m, 2H), 2.75-2.58 (m, 2H). MS (EI) m/z 463 [M+H$^+$].

Biological Assays
IDO1 Cellular Assay in HeLa Cells Stimulated with IFNγ

HeLa cells were cultured in complete HeLa culture medium (90% EMEM, 10% heat-inactivated fetal bovine serum) and expanded to about 1×10$^9$ cells. The cells were then collected and frozen down at 1×10$^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of 2×10$^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% $CO_2$ incubator. Afterwards, 12 µL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic IC$_{50}$ equation.

The biological activity data using the IDO1 cellular assay described above are summarized in the table below. Compounds disclosed herein generally have IC$_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific IC$_{50}$ activity data for the exemplified compounds disclosed herein is provided in the following table.
IDO1 Human Whole Blood Assay Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI using an Echo 555 acoustic liquid handler (Labcyte). LPS and IFNγ was prepared in RPMI to a 10× of final conc. (1000 ng/mL), final concentration is 100 ng/mL.

Human whole blood was drawn in sodium heparin coated tubes from healthy internal donors. 240 µL of blood was transferred to each of the wells of a v-bottom 96 well plate. 30 µL of compound was transferred from intermediate dilution plate, and incubated for 15 min. 30 µL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volume of Acetonitrile. The plates were centrifuged at 4000×G for 60 min. 20 μL of supernatant was carefully transferred to a 384 well plate contain 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. # | HeLa Cell Potency, $IC_{50}$ (nM) | Human Whole Blood Potency, $IC_{50}$ (nM) |
|---|---|---|
| 1 | 6.3 | |
| 2 | 16.1 | 1,850 |
| 3 | 2.3 | 128 |
| 4 | 50.1 | |
| 5 | 35.1 | |
| 6 | 2.2 | |
| 7 | 1.1 | 39 |
| 8 | 1.0 | 76 |
| 9 | 0.85 | |
| 10 | 1.4 | 82 |
| 11 | 2.7 | |
| 12 | 2.3 | 20 |
| 13 | 2.0 | 438 |
| 14 | 580 | |
| 15 | 495 | |
| 16 | 0.8 | 37 |
| 17 | 1.4 | 191 |
| 18 | 0.6 | 44 |
| 19 | 0.88 | 161 |
| 20 | 0.7 | 21 |
| 21 | 0.93 | 70 |
| 22 | 0.56 | 151 |
| 23 | 1.1 | 95 |
| 24 | 9.4 | |
| 25 | 38.3 | |
| 26 | 1.2 | 42 |
| 27 | 4.2 | 80 |
| 28 | 40.1 | |
| 29 | 5.8 | |
| 30 | 4.2 | |
| 31 | 0.72 | 117 |
| 32 | 2.4 | |
| 33 | 1.0 | 156 |
| 34 | 1.3 | 125 |
| 35 | 4.2 | |
| 36 | 0.94 | 238 |
| 37 | 1.0 | |
| 38 | 3.1 | |
| 39 | 0.85 | |
| 40 | 4.5 | |
| 41 | 4.1 | |
| 42 | 17.3 | |
| 43 | 10,000 | |
| 44 | 106.6 | |
| 45 | 3.2 | |
| 46 | 2.6 | |
| 47 | 808.8 | |
| 48 | 4.2 | |
| 49 | 5.4 | |
| 50 | 35.1 | 979 |
| 51 | 59.7 | |
| 52 | 59.7 | |
| 53 | 86.2 | |
| 54 | 217.0 | |
| 55 | 93.2 | |
| 56 | 11.7 | |
| 57 | 13.3 | 2,058 |
| 58 | 29.7 | |
| 59 | 163.3 | |
| 60 | 54.4 | |
| 61 | 1,469 | |
| 62 | 873.5 | |
| 63 | 3.7 | 95 |
| 64 | 2,837 | |
| 65 | 109.4 | |
| 66 | 165.8 | |
| 67 | 107.6 | |
| 68 | 185.4 | |
| 69 | 152.6 | |
| 70 | 5.4 | |
| 71 | 4.8 | |
| 72 | 5.5 | 3,024 |
| 73 | 51.3 | |
| 74 | 2.6 | 3,014 |
| 75 | 3,277 | |
| 76 | 5.3 | 110 |
| 77 | 2.9 | 17 |
| 78 | 3.6 | 22 |
| 79 | 0.56 | |
| 80 | 2.7 | 80 |
| 81 | 3.3 | 65 |
| 82 | 2.3 | 918 |
| 83 | 8.8 | |
| 84 | 7.8 | 88 |
| 85 | 6.0 | 343 |
| 86 | 2.9 | 273 |
| 87 | 7.4 | |
| 88 | 8.6 | 389 |
| 89 | 5.8 | |
| 90 | 49.1 | |
| 91 | 42.8 | |
| 92 | 96.3 | |
| 93 | 113.5 | |
| 94 | 5.0 | |
| 95 | 26.8 | |
| 96 | 4.8 | 434 |
| 97 | 2.1 | |
| 98 | 2.6 | 65 |
| 99 | 5.1 | |

-continued

| Ex. # | HeLa Cell Potency, IC$_{50}$ (nM) | Human Whole Blood Potency, IC$_{50}$ (nM) |
|---|---|---|
| 100 | 5.0 | 619 |
| 101 | 2.6 | 118 |
| 102 | 1.6 | 27 |
| 103 | 583.8 | |
| 104 | 56.8 | |
| 105 | 100.0 | |
| 106 | 42.3 | |
| 107 | 1.8 | 23 |
| 108 | 3.5 | |
| 109 | 4.5 | 28 |
| 110 | 1.6 | 51 |
| 111 | 1.9 | 40 |
| 112 | 1.4 | |
| 113 | 2.2 | 5 |
| 114 | 2.5 | 726 |
| 115 | 1.9 | 38 |
| 116 | 4.8 | 117 |
| 117 | 1.7 | 24 |
| 118 | 5.7 | 600 |
| 119a | 367.8 | |
| 119b | 1.3 | 76 |
| 119c | 69.2 | |
| 119d | 3.5 | 69 |
| 120 | 30.3 | |
| 121 | 1.6 | 14 |
| 122 | 2.0 | 248 |
| 123 | 2.2 | 414 |
| 124 | 3.4 | 639 |
| 125 | 1.5 | |
| 126 | 2.1 | 132 |
| 127 | 2.4 | 115 |
| 118 | 1.6 | 148 |
| 129 | 3.4 | 32 |
| 130 | 9.9 | |
| 131 | 2.8 | 22 |
| 132 | 2.0 | 16 |
| 133 | 1.5 | 28 |
| 134 | 1.5 | 87 |
| 135 | 2.6 | 65 |
| 136 | 1.7 | 129 |
| 137 | 1.6 | 147 |
| 138 | 15.3 | 261 |
| 139 | 2.0 | 128 |
| 140 | 3.0 | 7 |
| 141 | 9.4 | 177 |
| 142 | 2.5 | 67 |
| 143 | 2.4 | 126 |
| 144 | 2.2 | 28 |
| 145 | 1.7 | 55 |
| 146 | 4.2 | 60 |
| 147 | 6.0 | |
| 148 | 6.1 | 77 |
| 149 | 1.52 | 18 |
| 150 | 2.0 | 12 |
| 151 | 1.45 | 54 |
| 152 | 1.8 | 175 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

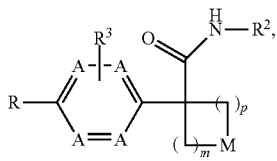

(I)

wherein:
n is 1;
p is 1;
each occurrence of A is —CH═;
M is selected from —O— and —S—;
$R^1$ is
  pyridinyl;
  wherein the pyridinyl is optionally substituted with 1-3 substituents independently selected from:
  (a) halogen,
  (b) —C$_{3-8}$ cycloalkyl, optionally substituted with OH,
  (c) —CN,
  (d) oxo,
  (e) —O—C$_{1-8}$ alkyl, optionally substituted with 1-5 halogens,
  (f) —O—C$_{3-8}$ cycloalkyl,
  (g) —C$_{1-8}$ alkyl, optionally substituted with 1-4 substituents independently selected from halogen, —OH, —NH$_2$, NHC(O)R$^c$ and —S(O)$_2$—C$_{1-8}$ alkyl, wherein R$^c$ is selected from —C$_{1-8}$ alkyl and —C$_{3-8}$ cycloalkyl,
  (h) —NH—S(O)$_2$—R$^c$, wherein R$^c$ is selected from —C$_{1-8}$ alkyl and —C$_{3-8}$ cycloalkyl,
  (i) —C(O)—R$^f$, R$^f$ is selected from —OH, —NH$_2$ and —NH—C$_{1-8}$ alkyl,
  (j) aryl, optionally substituted with 1-3 halogens, and
  (k) heterocyclyl, optionally substituted with 1-3 substituents independently selected from halogen and —C$_{1-8}$ alkyl;
$R^2$ is
  phenyl;
  wherein the phenyl is optionally substituted with 1-3 substituents independently selected from:
  (a) halogen,
  (b) —C$_{3-8}$ cycloalkyl,
  (c) —CN,
  (d) —O—C$_{1-8}$ alkyl, optionally substituted with 1-3 halogens and
  (e) —C$_{1-8}$ alkyl, optionally substituted with 1-3 substituents independently selected from halogen, —OH and —NH$_2$; and
$R^3$ is selected from H, halogen and —C$_{1-8}$ alkyl, optionally substituted with —OH.

2. The compound of claim 1, or a pharmaceutically acceptable salt thereof,
wherein:
M is —O—;
and
$R^3$ is H.

3. The compound of claim 1, or a pharmaceutically acceptable salt thereof, wherein:
$R^1$ is pyridinyl;
  wherein the pyridinyl is optionally substituted with 1-3 substituents independently selected from:
  (a) halogen,
  (b) cyclopropyl, optionally substituted with —OH,
  (c) cyclobutyl, optionally substituted with —OH, (d) —CN,
(e) oxo,
(f) —O—$C_{1-4}$ alkyl, optionally substituted with 1-3 halogens,
(g) —O-cyclopropyl,
(h) —$C_{1-4}$ alkyl, optionally substituted with 1-4 substituents independently selected from halogen and —OH, and
(i) phenyl, optionally substituted with 1-3 halogens.

4. The compound of claim 1, or a pharmaceutically acceptable salt thereof, wherein:
$R^2$ is phenyl;
wherein the phenyl is optionally substituted with 1-3 substituents independently selected from:
(a) halogen,
(b) —$C_{3-6}$ cycloalkyl,
(c) —CN,
(d) —O—$C_{1-6}$ alkyl, optionally substituted with 1-3 halogens, and
(e) —$C_{1-6}$ alkyl, optionally substituted with 1-3 substituents independently selected from halogen and —OH.

5. The compound of claim 1, or a pharmaceutically acceptable salt thereof, wherein:
$R^2$ is phenyl;
wherein the phenyl is-optionally substituted with 1-3 substituents independently selected from:
(a) halogen,
(b) —CN,
(c) —O—$C_{1-4}$ alkyl, optionally substituted with 1-3 halogens and
(d) —$C_{1-4}$ alkyl, optionally substituted with 1-3 halogens.

6. The compound of claim 1, or a pharmaceutically acceptable salt thereof, wherein:
M is —O—;
$R^1$ is
wherein the pyridinyl is optionally substituted with 1-3 substituents independently selected from:
(a) halogen,
(b) cyclopropyl, optionally substituted with —OH,
(c) —O—$C_{1-4}$ alkyl, optionally substituted with 1-3 halogens, and
(d) —$C_{1-4}$ alkyl, optionally substituted with 1-4 substituents independently selected from halogen and —OH;
and
$R^2$ is phenyl;
wherein the phenyl is optionally substituted with 1-3 substituents independently selected from:
(a) halogen,
(b) —CN,
(c) —O—$C_{1-4}$ alkyl, optionally substituted with 1-3 halogens and
(d) —$C_{1-4}$ alkyl, optionally substituted with 1-3 halogens.

7. The compound of claim 6, or a pharmaceutically acceptable salt thereof, wherein:
$R^1$ is pyridinyl;
wherein the pyridinyl is optionally substituted with 1-3 substituents independently selected from:
(a) halogen, and
(b) —$C_{1-4}$ alkyl, optionally substituted with 1-4 substituents independently selected from halogen and —OH; and $R^2$ is phenyl;
wherein the phenyl is optionally substituted with 1-3 halogens; and
$R^3$ is H.

8. The compound of claim 1 of formula (Ia), or a pharmaceutically acceptable salt thereof:

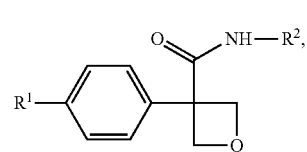

(Ia)

wherein:
$R^1$ is pyridinyl;
wherein the pyridinyl is optionally substituted with 1-3 substituents independently selected from:
(a) halogen,
(b) —O—$C_{1-4}$ alkyl, optionally substituted with 1-3 halogens,
(c) —O-cyclopropyl, and
(d) —$C_{1-4}$ alkyl, optionally substituted with 1-4 substituents independently selected from halogen and —OH; and
$R^2$ is phenyl, optionally substituted with 1-3 halogens.

9. The compound of claim 8, or a pharmaceutically acceptable salt thereof, wherein:
$R^1$ is pyridinyl, optionally substituted with 1-3 substituents independently selected from:
(a) halogen,
(b) —$CH_3$,
(c) —$CHF_2$,
(d) —$CF_3$, and
(e) —$C(CH_3)_2OH$; and
$R^2$ is phenyl, optionally substituted with 1-2 halogens.

10. The compound of claim 1 of formula (Ii), or a pharmaceutically acceptable salt thereof:

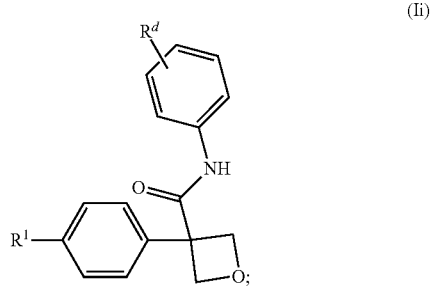

(Ii)

wherein:
$R^1$ is pyridinyl;
wherein the pyridinyl is optionally substituted with 1-3 substituents independently selected from:
(a) halogen,
(b) —CN,
(c) —O—$C_{1-4}$ alkyl, optionally substituted with 1-3 halogens,
(d) —O-cyclopropyl, and
(e) —$C_{1-4}$ alkyl, optionally substituted with 1-4 substituents independently selected from halogen and —OH; and R$^d$ is selected from:
(a) halogen,
(b) —CN,
(c) —O—C$_{1-3}$ alkyl, optionally substituted with 1-3 halogens, and
(d) C$_{1-3}$ alkyl, optionally substituted with 1-3 halogens.

11. The compound of claim 10, or a pharmaceutically acceptable salt thereof,
wherein:
R$^1$ is pyridinyl, optionally substituted with 1-3 substituents independently selected from:
(a) halogen,
(b) —CH$_3$,
(c) —CHF$_2$,
(d) —CF$_3$,
(e) —CH$_2$OH, and
(f) —C(CH$_3$)$_2$OH;
and
R$^d$ is selected from:
(a) a halogen selected from F, Cl and Br,
(b) —CH$_3$, and
(c) —CF$_3$.

12. The compound of claim 1, or a pharmaceutically acceptable salt thereof, selected from the group consisting of:
3-(4-(6-cyclopropylpyridin-3-yl)phenyl)-N-(4-fluorophenyl)oxetane-3-carboxamide,
3-(4-(6-cyclopropyl-4-fluoropyridin-3-yl)phenyl)-N-(4-fluorophenyl)oxetane-3-carboxamide,
3-(4-(6-cyclopropyl-4-methylpyridin-3-yl)phenyl)-N-(4-fluorophenyl)oxetane-3-carboxamide,
N-(4-fluorophenyl)-3-(4-(4-methyl-6-(trifluoromethyl)pyridin-3-yl)phenyl)oxetane-3-carboxamide,
3-(4-(6-(difluoromethoxy)-2,4-dimethylpyridin-3-yl)phenyl)-N-(4-fluorophenyl)oxetane-3-carboxamide,
3-(4-(6-(difluoromethoxy)-4-methylpyridin-3-yl)phenyl)-N-(4-fluorophenyl)oxetane-3-carboxamide,
N-(4-fluorophenyl)-3-(4-(4-(hydroxymethyl)-6-(trifluoromethyl)pyridin-3-yl)phenyl)oxetane-3-carboxamide,
N-(4-fluorophenyl)-3-(4-(4-(2-hydroxypropan-2-yl)-6-(trifluoromethyl)pyridin-3-yl)phenyl)oxetane-3-carboxamide,
3-[4-[6-(difluoromethoxy)-4-(hydroxymethyl)-3-pyridyl]phenyl]-N-(4-fluorophenyl)oxetane-3-carboxamide,
N-(4-fluorophenyl)-3-[4-[3-(2-hydroxyethyl)-5-(trifluoromethyl)-2-pyridyl]phenyl]oxetane-3-carboxamide,
(R or S)—N-(4-fluorophenyl)-3-(4-(4-(1-hydroxyethyl)-6-(trifluoromethyl)pyridin-3-yl)phenyl)oxetane-3-carboxamide,
3-[4-[6-(difluoromethoxy)-4-(1-hydroxy-1-methyl-ethyl)pyridin-1-ium-3-yl]phenyl]-N-(4-fluorophenyl)oxetane-3-carboxamide;
N-(4-chlorophenyl)-3-(4-(4-(2-hydroxypropan-2-yl)-6-(trifluoromethyl)pyridin-3-yl)phenyl)oxetane-3-carboxamide,
N-(4-chlorophenyl)-3-[4-[4-(hydroxymethyl)-6-(trifluoromethyl)-3-pyridyl]phenyl]oxetane-3-carboxamide,
N-(4-chlorophenyl)-3-[4-[6-(difluoromethoxy)-4-(hydroxymethyl)-3-pyridyl]phenyl]oxetane-3-carboxamide,
3-[4-[6-cyclopropyl-2-(hydroxmethyl)pyridin-1-ium-3-yl]phenyl]-N-(4-fluorophenyl)oxetane-3- carboamide,
N-(4-fluorophenyl)-3-[4-[6-(trifluoromethyl)pyridin-1-ium-3-yl]phenyl]oxetane-3-carboxamide,
N-(4-fluorophenyl)-3-[4-[2-(hydroxymethyl)-6-(trifluoromethyl)-3-pyridyl]phenyl]oxetane-3-carboxamide,
N-(4-fluorophenyl)-3-(4-(2-(2-hydroxypropan-2-yl)-6-(trifluoromethyl)pyridin-3-yl)phenyl)oxetane-3-carboxamide,
3-(4-(4-(fluoromethyl)-6-(trifluoromethyl)pyridin-3-yl)phenyl)-N-(4-fluorophenyl)oxetane-3-carboxamide,
3-(4-(4-(hydroxymethyl)-6-(trifluoromethyl)pyridin-3-yl)phenyl)-N-(4-(trifluoromethoxy)phenyl)oxetane-3-carboxamide,
N-(4-bromophenyl)-3-(4-(4-(hydroxymethyl)-6-(trifluoromethyl)pyridin-3-yl)phenyl)oxetane-3-carboxamide,
3-(4-(4-(hydroxymethyl)-6-(trifluoromethyl)pyridin-3-yl)phenyl)-N-(4-(trifluoromethyl)phenyl)oxetane-3-carboxamide,
N-(3,4-difluorophenyl)-3-(4-(4-(hydroxymethyl)-6-(trifluoromethyl)pyridin-3-yl)phenyl)oxetane-3-carboxamide,
N-(4-cyanophenyl)-3-(4-(4-(hydroxymethyl)-6-(trifluoromethyl)pyridin-3-yl)phenyl)oxetane-3-carboxamide,
N-(4-(difluoromethoxy)phenyl)-3-(4-(4-(hydroxymethyl)-6-(trifluoromethyl)pyridin-3-yl)phenyl)oxetane-3-carboxamide,
N-(4-fluorophenyl)-3-(4-(3-(hydroxymethyl)-5-(trifluoromethyl)pyridin-2-yl)phenyl)oxetane-3-carboxamide,
N-(4-fluorophenyl)-3-(4-(4-(1-hydroxycyclobutyl)-6-(trifluoromethyl)pyridin-3-yl)phenyl)oxetane-3-carboxamide,
N-(4-fluorophenyl)-3-(4-(4-(1-hydroxycyclopropyl)-6-(trifluoromethyl)pyridin-3-yl)phenyl)oxetane-3-carboxamide,
3-(4-(6-cyclopropoxy-4-(hydroxymethyl)pyridin-3-yl)phenyl)-N-(4-fluorophenyl)oxetane-3-carboxamide,
3-(4-(6-cyclopropoxy-4-(2-hydroxypropan-2-yl)pyridin-3-yl)phenyl)-N-(4-fluorophenyl)oxetane-3-carboxamide,
5-(4-(3-((4-flurophenyl)carbamoyl)oxetan-3-yl)phenyl)-N-methyl-2-(trifluoromethyl)isonicotinamide,
5-(4-(3-((4-flurophenyl)carbomoyl)oxetan-3-yl)phenyl)-2-(trifluoromethyl)isonicotinamide,
(R)-3-(4-(4-(1-amino-2,2,2-trifluoroethyl)-6-(trifluoromethyl)pyridin-3-yl)phenyl)-N-(4-fluorophenyl)oxetane-3-carboxamide,
(S)-3-(4-(4-(1-amino-2,2,2-trifluoroethyl)-6-(trifluoromethyl)pyridin-3-yl)phenyl)-N-(4-fluorophenyl)oxetane-3-carboxamide,
N-(4-fluorophenyl)-3-(4-(3-(2-hydroxypropan-2-yl)-5-(trifluoromethyl)pyridin-2-yl)phenyl)oxetane-3-carboxamide,
3-(4-(5-cyclopropoxy-3-(hydroxymethyl)pyridin-2-yl)phenyl)-N-(4-fluorophenyl)oxetane-3-carboxamide,
3-(4-(5-cyclopropoxy-3-(2-hydroxypropan-2-yl)pyridin-2-yl)phenyl)-N-(4-fluorophenyl)oxetane-3-carboxamide,
N-(4-fluorophenyl)-3-(4-(4-(hydroxymethyl)-6-isopropoxypyridin-3-yl)phenyl)oxetane-3-carboxamide,
3-(4-(6-(2,2-difluoroethoxy)-4-(hydroxymethyl)pyridin-3-yl)phenyl)-N-(4-fluorophenyl)oxetane-3-carboxamide,
N-(4-fluorophenyl)-3-(4-(4-(hydroxymethyl)-6-(2,2,2-trifluoroethoxy)pyridin-3-yl)phenyl)oxetane-3-carboxamide,
3-(3-fluoro-4-(4-(hydroxymethyl)-6-(trifluoromethyl)pyridin-3-yl)phenyl)-N-(4-fluorophenyl)oxetane-3-carboxamide,
3-(4-(6-ethoxy-4-(hydroxymethyl)pyridin-3-yl)phenyl)-N-(4-fluorophenyl)oxetane-3-carboxamide, and
N-(4-fluorophenyl)-3-(4-(3-(hydroxymethyl)-5-(trifluoromethyl)pyridin-2-yl)phenyl)oxetane-3-carboxamide.

13. A composition which comprises a pharmaceutically acceptable carrier and a compound of claim 1 or a pharmaceutically acceptable salt thereof.

14. A compound which is N-(4-fluorophenyl)-3-(4-(4-(2-hydroxypropan-2-yl)-6-(trifluoromethyl)pyridin-3yl)phenyl)oxetane-3 -carboxamide, or a pharmaceutically acceptable salt thereof.

15. The compound of claim 14 which is N-(4-fluorophenyl)-3-(4-(4-(2-hydroxypropan-2-yl)-6-(trifluoromethyl)pyridin-3yl)phenyl)oxetane-3-carboxamide.

16. The compound of claim 14 which is a pharmaceutically acceptable salt of N-(4-fluorophenyl)-3-(4-(4-(2-hydroxypropan-2-yl)-6-(trifluoromethyl)pyridin-3yl)phenyl)oxetane-3-carboxamide.

\* \* \* \* \*